(12) United States Patent
Dvorak et al.

(10) Patent No.: US 7,579,470 B2
(45) Date of Patent: Aug. 25, 2009

(54) FUSED HETEROCYCLIC COMPOUNDS

(75) Inventors: Curt A. Dvorak, San Diego, CA (US); Dale A. Rudolph, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 11/924,277

(22) Filed: Oct. 25, 2007

(65) Prior Publication Data

US 2008/0103132 A1    May 1, 2008

Related U.S. Application Data

(63) Continuation of application No. 10/941,664, filed on Sep. 15, 2004, now Pat. No. 7,402,680.

(60) Provisional application No. 60/552,673, filed on Mar. 11, 2004, provisional application No. 60/504,528, filed on Sep. 17, 2003.

(51) Int. Cl.
*C07D 417/02* (2006.01)
*A01N 43/42* (2006.01)

(52) U.S. Cl. .................. 546/113; 546/119; 514/300; 514/303

(58) Field of Classification Search .......... 546/113, 546/119
See application file for complete search history.

(56) References Cited

U.S. PATENT DOCUMENTS

| | | | |
|---|---|---|---|
| 3,992,544 | A | 11/1976 | Archibald et al. |
| 5,053,508 | A | 10/1991 | Schiehser et al. |
| 5,648,352 | A | 7/1997 | Bock et al. |
| 5,663,178 | A | 9/1997 | Audia et al. |
| 5,843,912 | A | 12/1998 | Hosmane et al. |
| 6,057,325 | A | 5/2000 | Kennis et al. |
| 6,177,443 | B1 | 1/2001 | Madsen et al. |
| 6,559,174 | B2 | 5/2003 | Lin et al. |
| 2003/0199542 | A1 | 10/2003 | Woods et al. |
| 2003/0199544 | A1 | 10/2003 | Woods et al. |
| 2005/0101594 | A1 | 5/2005 | Binch et al. |
| 2006/0100233 | A1 | 5/2006 | Villa et al. |
| 2006/0135508 | A1 | 6/2006 | Villa et al. |
| 2006/0241065 | A1 | 10/2006 | Hosmane et al. |

FOREIGN PATENT DOCUMENTS

| | | | |
|---|---|---|---|
| EP | 0086422 | A2 | 8/1983 |
| EP | 0086422 | B1 | 9/1987 |
| EP | 0905136 | A1 | 3/1999 |
| WO | WO 9414777 | A1 | 7/1994 |
| WO | WO 98/40385 | A1 | 9/1998 |
| WO | WO 02/066484 | A1 | 8/2002 |
| WO | 03101989 | * | 5/2003 |
| WO | WO 03/051797 | A2 | 6/2003 |
| WO | WO 03099822 | A2 | 12/2003 |
| WO | WO 2004/014374 | A1 | 2/2004 |
| WO | WO 2004013144 | A1 | 2/2004 |
| WO | 2004/094429 | * | 4/2004 |
| WO | WO 2005009387 | A2 | 2/2005 |
| WO | WO 2005/030776 | A1 | 4/2005 |

OTHER PUBLICATIONS

Radinov et al. STN Accession No. 988:111448, Abstract of Journal of Molecular Structure (1987), 158, 99-108.*
Abdel-Magid, A.F. et al.: Reductive Amination of Aldehydes and Ketones with Sodium Triacetoxyborohydride. Studies on Direct and Indirect Reductive Amination Procedures. J. Org. Chem. (1996) 61(11) 3849-3862.
Bourrain, S. et al.: Regioselective Rapid Analogue Syntheses of 1-Methyl-3,5-diarylpyrazoles via Palladium-catalysed Coupling to 3(5)-Pyrazolyl Nonaflates. Synlett. 2004, 5, 795-798.
Ghali, N.I. et al.: High-yielding Synthesis of Monoalkylhydrazines. J. Org. Chem. 1981, 46(26), 5413-5414.
Hoyer, D. et al.: Molecular, Pharmacological and Functional Diversity of 5-HT Receptors. Pharmacol. Biochem. Behav. 2002. 71(4), 533-554.
Lim, S. et al.: Reaction of Cyclohexanones Imines with Substituted Nitroolefins. New Synthesis of Tetrahydroindole Derivatives. Tetrahedron Lett. 1999, 40(22), 4177-4180.
Moriya, T. et al.: Studies of Seven-membered Heterocyclic Compounds Containing Nnitrogen. IX. The Synthesis of 5-Ethoxycarbonyl-1-azacycloheptan-4-one and Its Derivatives. Bull. Chem. Soc. Jpn. 1968, 41(1), 230-231. (for some reason the scan the chemists gave me is upside down in Adobe).
Oh-E, T. et al.: Palladium-Catalyzed Cross-Coupling Reaction of Organoboron Compounds with Organic Triflates. J. Org. Chem. 1993, 58(8), 2201-2208.
Roglans, A. et al.: Preparation of 3-Pyrrolidone and 4-Perhydroazepinone. Synth. Commun. 1992, 22(9), 1249-1258.
Roth, B.L. et al.: The Multiplicity of Serotonin Receptors: Uselessly Diverse Molecules or an Embarrassment of Riches? Neuroscientist 2000, 6(4), 252-262.
Sasatani, S. et al.: "Diisobutylaluminum Hydride A Novel Reagent for the Reduction of Oximes"; Tetrahedron Letters (1983) 24(43): 4711-4712.
Vidal, J. et al.: Electrophilic Amination: Preparation and Use of N-Boc-3-(4-cyanophenyl)oxaziridine, a New Reagent That Transfers a N-Boc Group to N- and C-Nucleophiles. J. Org. Chem. 1993, 58(18), 4791-4793.
Winters, G. et al.: Synthesis, in Vitro [3H]Prazosin Displacement, and in Vivo Activity of 3-Aryl-4,5,6,7-tetrahydropyrazolo[4,3-c]pyridines, a New Class of Antihypertensive Agents, J. Med. Chem. 1985, 28(7), 934-940.
PCT International Search Report dated Dec. 14, 2005 for International Application PCT/US2004/030190.

* cited by examiner

*Primary Examiner*—D. Margaret Seaman
*Assistant Examiner*—Nizal S Chandrakumar
(74) *Attorney, Agent, or Firm*—Micheal J. Atkins

(57) ABSTRACT

Certain fused pyrrole- and pyrazole-containing heterocyclic compounds are serotonin modulators useful in the treatment of serotonin-mediated diseases.

2 Claims, No Drawings

FUSED HETEROCYCLIC COMPOUNDS

This application is a continuation of parent application U.S. Ser. No. 10/941,664, filed on Sep. 15, 2004 now U.S. Pat. No. 7,402,680, which claims the benefit under 35 USC § 119(e) of the following provisional applications: U.S. Ser. No. 60/504,528 filed on Sep. 17, 2003 and U.S. Ser. No. 60/552,673 filed on Mar. 11, 2004. The complete disclosures of the aforementioned related U.S. patent applications are hereby incorporated herein by reference for all purposes.

FIELD OF THE INVENTION

There is provided by the present invention compounds that are serotonin receptor modulators. More particularly, there is provided by the present invention fused heterocyclic compounds that are serotonin receptor modulators useful for the treatment of disease states mediated by serotonin receptor activity.

BACKGROUND OF THE INVENTION

Serotonin (5-hydroxytryptamine, 5-HT) is a major neurotransmitter eliciting effects via a multiplicity of receptors. To date, at least fifteen different 5-HT receptors have been identified, largely as the result of cloning cDNA's, and these receptors have been grouped into seven families (5-$HT_1$ through 5-$HT_7$) (Hoyer, D. et al. *Pharmacol. Biochem. Behav.* (2002) 71, 533-554). Fourteen of the fifteen cloned 5-HT receptors are expressed in the brain. 5-HT is implicated in many disease states, particularly conditions of the central nervous system including; depression, anxiety, schizophrenia, eating disorders, obsessive compulsive disorder, learning and memory dysfunction, migraine, chronic pain, sensory perception, motor activity, temperature regulation, nociception, sexual behavior, hormone secretion and cognition. The identification of multiple 5-HT receptors has provided the opportunity to characterize existing therapeutic agents thought to act via the serotonergic system. Consequently, this has led to the realization that many drugs have non-selective properties (Roth, B. L. et al. *Neuroscientist* (2000) 6(4) 252-262). For example, the antipsychotic drugs, clozapine, chlorpromazine, haloperidol and olanzapine exhibit affinities for multiple serotonin receptors in addition to other families of receptors. Similar behavior has been noted for antidepressants, including imipramine, nortriptaline, fluoxetine and sertraline. Similarly, the anti-migraine agent sumatriptan exhibits high affinity for several serotonin receptors. While the lack of selectivity often contributes to a favorable therapeutic outcome, it can also cause undesirable and dose-limiting side effects (Stahl, S. M. *Essential Psychopharmacology*, 2$^{nd}$ ed., Cambridge University Press, Cambridge, U.K., 2000). Thus, the inhibition of serotonin and norepinephrine uptake together with 5-$HT_2$ receptor blockade is responsible for the therapeutic effects of the tricyclic antidepressants. In contrast, their blockade of histamine $H_1$, muscarinic and alpha-adrenergic receptors can lead to sedation, blurred vision and orthostatic hypertension respectively. Likewise, the atypical antipsychotics, including olanzapine and clozapine, are considered to have positive therapeutic effects attributable to their actions at 5-$HT_2$, $D_2$ and 5-$HT_7$ receptors. Conversely, their side effect liability is due to their affinities at a range of dopaminergic, serotonergic and adrenergic receptors.

More selective ligands therefore have the potential to ameliorate untoward pharmacologies and provide novel therapies. More importantly the ability to obtain compounds with known receptor selectivities affords the prospect to target multiple therapeutic mechanisms and improve clinical responses with a single drug.

SUMMARY OF THE INVENTION

The invention features a compound of formulae (I), (II) and (III):

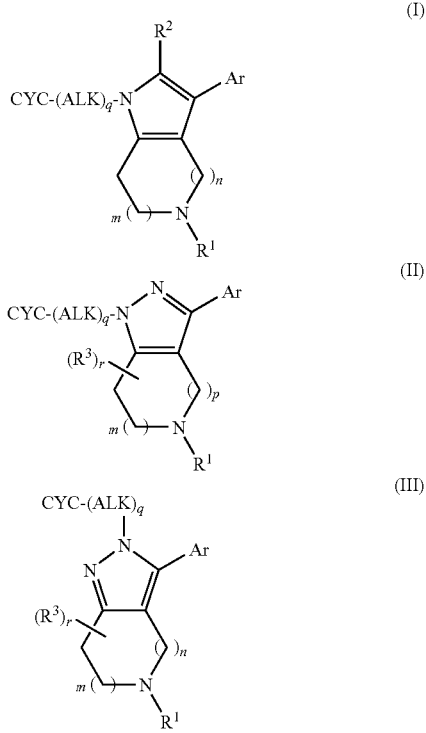

wherein
m is 0, 1 or 2;
n is 1, 2 or 3;
p is 1, 2 or 3, with the proviso that where m is 1, p is not 1;
m+n is less than or equal to 4;
m+p is less than or equal to 4;
q is 0 or 1;
r is 0, 1, 2, 3, 4, or 5;
$R^3$ is —$C_{1-4}$alkyl, allyl, propargyl, or benzyl, each optionally substituted with —$C_{1-3}$alkyl, —OH, or halo;
Ar is an aryl or heteroaryl ring selected from the group consisting of:
a) phenyl, optionally mono-, di- or tri-substituted with $R^r$ or di-substituted on adjacent carbons with —$OC_{1-4}$alkyleneO—, —$(CH_2)_{2-3}$NH—, —$(CH_2)_{1-2}$NH($CH_2$)—, —$(CH_2)_{2-3}$N($C_{1-4}$alkyl)- or —$(CH_2)_{1-2}$N($C_{1-4}$alkyl)($CH_2$)—;
$R^r$ is selected from the group consisting of —OH, —$C_{1-6}$alkyl, —$OC_{1-6}$alkyl, —$C_{2-6}$alkenyl, —$OC_{3-6}$alkenyl, —$C_{2-6}$alkynyl, —$OC_{3-6}$alkynyl, —CN, —$NO_2$, —N($R^y$)$R^z$ (wherein $R^y$ and $R^z$ are independently selected from H or $C_{1-6}$alkyl), —(C=O)N($R^y$)$R^z$, —(N—$R^t$)$COR^t$, —(N—$R^t$)$SO_2C_{1-6}$alkyl (wherein $R^t$ is H or $C_{1-6}$alkyl), —(C=O)$C_{1-6}$alkyl, —(S=(O)$_n$)—$C_{1-6}$alkyl (wherein n is selected from 0, 1 or 2), —$SO_2$N($R^y$)$R^z$, —$SCF_3$, halo, —$CF_3$, —$OCF_3$, —COOH and —$COOC_{1-6}$alkyl;

b) phenyl or pyridyl fused at two adjacent carbon ring members to a three membered hydrocarbon moiety to form a fused five membered aromatic ring, which moiety has one carbon atom replaced by >O, >S, >NH or >N($C_{1-4}$alkyl) and which moiety has up to one additional carbon atom optionally replaced by —N═, the fused rings optionally mono-, di- or tri-substituted with $R^r$;

c) phenyl fused at two adjacent ring members to a four membered hydrocarbon moiety to form a fused six membered aromatic ring, which moiety has one or two carbon atoms replaced by —N═, the fused rings optionally mono-, di- or tri-substituted with $R^r$;

d) naphthyl, optionally mono-, di- or tri-substituted with $R^r$;

e) a monocyclic aromatic hydrocarbon group having five ring atoms, having a carbon atom which is the point of attachment, having one carbon atom replaced by >O, >S, >NH or >N($C_{1-4}$alkyl), having up to one additional carbon atoms optionally replaced by —N═, optionally mono- or di-substituted with $R^r$ and optionally benzofused or pyridofused at two adjacent carbon atoms, where the benzofused or pyridofused moiety is optionally mono-, di-, or tri-substituted with $R^r$; and f) a monocyclic aromatic hydrocarbon group having six ring atoms, having a carbon atom which is the point of attachment, having one or two carbon atoms replaced by —N═, optionally mono- or di-substituted with $R^r$ and optionally benzofused or pyridofused at two adjacent carbon atoms, where the benzofused or pyridofused moiety is optionally mono- or di-substituted with $R^r$;

g) phenyl or pyridyl, substituted with a substituent selected from the group consisting of phenyl, pyridyl, thiophenyl, oxazolyl and tetrazolyl, where the resultant substituted moiety is optionally further mono-, di- or tri-substituted with $R^r$;

ALK is a branched or unbranched $C_{1-8}$alkylene, $C_{2-8}$alkenylene, $C_{2-8}$alkynylene or $C_{3-8}$cycloalkenylene, optionally mono-, di-, or tri-substituted with a substituent independently selected from the group consisting of: —OH, —O$C_{1-6}$alkyl, —O$C_{3-6}$cycloalkyl, —CN, —NO$_2$, —N($R^a$)$R^b$ (wherein $R^a$ and $R^b$ are independently selected from H, $C_{1-6}$alkyl or $C_{2-6}$alkenyl), —(C═O)N($R^a$)$R^b$, —(N—$R^c$)COR$^c$, —(N—$R^c$)SO$_2$$C_{1-6}$alkyl (wherein $R^c$ is H or $C_{1-6}$alkyl), —(C═O)$C_{1-6}$alkyl, —(S═(O)$_d$)—$C_{1-6}$alkyl (wherein d is selected from 0, 1 or 2), SO$_2$N($R^a$)$R^b$, —SCF$_3$, halo, —CF$_3$, —OCF$_3$, —COOH and —COO$C_{1-6}$alkyl;

CYC is hydrogen or a carbocyclic, heterocyclic, aryl or heteroaryl ring selected from the group consisting of:

i) phenyl, optionally mono-, di- or tri-substituted with $R^q$ or di-substituted on adjacent carbons with —O$C_{1-4}$alkyleneO—, —(CH$_2$)$_{2-3}$NH—, —(CH$_2$)$_{1-2}$NH(CH$_2$)—, —(CH$_2$)$_{2-3}$N($C_{1-4}$alkyl)- or —(CH$_2$)$_{1-2}$N($C_{1-4}$alkyl)(CH$_2$)—;

$R^q$ is selected from the group consisting of —OH, —$C_{1-6}$alkyl, —O$C_{1-6}$alkyl, —$C_{3-6}$cycloalkyl, —O$C_{3-6}$cycloalkyl, phenyl, —Ophenyl, benzyl, —Obenzyl, —CN, —NO$_2$, —N($R^a$)$R^b$ (wherein $R^a$ and $R^b$ are independently selected from H, $C_{1-6}$alkyl or $C_{2-6}$alkenyl, or $R^a$ and $R^b$ may be taken together with the nitrogen of attachment to form an otherwise aliphatic hydrocarbon ring, said ring having 5 to 7 members, optionally having one carbon replaced with >O, ═N—, >NH or >N($C_{1-4}$alkyl), optionally having one carbon substituted with —OH, and optionally having one or two unsaturated bonds in the ring), —(C═O)N($R^a$)$R^b$, —(N—$R^c$)COR$^c$, —(N—$R^c$)SO$_2$$C_{1-6}$alkyl (wherein $R^c$ is H or $C_{1-6}$alkyl or two $R^c$ in the same substituent may be taken together with the amide of attachment to form an otherwise aliphatic hydrocarbon ring, said ring having 4 to 6 members), —N—(SO$_2$$C_{1-6}$alkyl)$_2$, —(C═O)$C_{1-6}$alkyl, —(S═(O)$_d$)—$C_{1-6}$alkyl (wherein d is selected from 0, 1 or 2), —SO$_2$N($R^a$)$R^b$, —SCF$_3$, halo, —CF$_3$, —OCF$_3$, —COOH and —COO$C_{1-6}$alkyl;

ii) phenyl or pyridyl fused at two adjacent carbon ring members to a three membered hydrocarbon moiety to form a fused five membered aromatic ring, which moiety has one carbon atom replaced by >O, >S, >NH or >N($C_{1-4}$alkyl) and which moiety has up to one additional carbon atom optionally replaced by —N═, the fused rings optionally mono-, di- or tri-substituted with $R^q$;

iii) phenyl fused at two adjacent carbon ring members to a four membered hydrocarbon moiety to form a fused six membered aromatic ring, which moiety has one or two carbon atoms replaced by —N═, the fused rings optionally mono-, di- or tri-substituted with $R^q$;

iv) naphthyl, optionally mono-, di- or tri-substituted with $R^q$;

v) a monocyclic aromatic hydrocarbon group having five ring atoms, having a carbon atom which is the point of attachment, having one carbon atom replaced by >O, >S, >NH or >N($C_{1-4}$alkyl), having up to one additional carbon atoms optionally replaced by —N═, optionally mono- or di-substituted with $R^q$ and optionally benzofused or pyridofused at two adjacent carbon atoms, where the benzofused or pyridofused moiety is optionally mono-, di-, or tri-substituted with $R^q$;

vi) a monocyclic aromatic hydrocarbon group having six ring atoms, having a carbon atom which is the point of attachment, having one or two carbon atoms replaced by —N═, optionally mono- or di-substituted with $R^q$ and optionally benzofused or pyridofused at two adjacent carbon atoms, where the benzofused or pyridofused moiety is optionally mono- or di-substituted with $R^q$;

vii) a 3-8 membered non-aromatic carbocyclic or heterocyclic ring said ring having 0, 1 or 2 non-adjacent heteroatom members selected from O, S, —N═, >NH or >N$R^q$, having 0, 1 or 2 unsaturated bonds, having 0, 1 or 2 carbon members which is a carbonyl, optionally having one carbon member which forms a bridge, having 0 to 5 substituents $R^q$ and optionally benzofused or pyridofused at two adjacent carbon atoms where the benzofused or pyridofused moiety has 0, 1, 2 or 3 substituents $R^q$; and viii) a 4-7 membered non-aromatic carbocyclic or heterocyclic ring said ring having 0, 1 or 2 non-adjacent heteroatom members selected from O, S, —N═, >NH or >N$R^q$, having 0, 1 or 2 unsaturated bonds, having 0, 1 or 2 carbon members which is a carbonyl and optionally having one carbon member which forms a bridge, the heterocyclic ring fused at two adjacent carbon atoms forming a saturated bond or an adjacent carbon and nitrogen atom forming a saturated bond to a 4-7 membered carbocyclic or heterocyclic ring, having 0 or 1 possibly additional heteroatom member, not at the ring junction, selected from O, S, —N═, >NH or >N$R^q$, having 0, 1 or 2 unsaturated bonds, having 0, 1 or 2 carbon members which is a carbonyl and the fused rings having 0 to 5 substituents $R^q$;

$R^1$ is selected from the group consisting of H, $C_{1-7}$alkyl, $C_{2-7}$alkenyl, $C_{2-7}$alkynyl, $C_{3-7}$cycloalkyl, $C_{3-7}$cycloalkylC$_{1-7}$alkyl, C$_{3-7}$cycloalkenyl, C$_{3-7}$cycloalkenylC$_{1-7}$alkyl and benzo-fused C$_{4-7}$cycloalkyl, each optionally mono-, di-, or tri-substituted with R$^p$;

R$^p$ is selected from the group consisting of —OH, —OC$_{1-6}$alkyl, —C$_{3-6}$cycloalkyl, —OC$_{3-6}$cycloalkyl, —CN, —NO$_2$, phenyl, pyridyl, thienyl, furanyl, pyrrolyl, —N(R$^s$)R$^u$ (wherein R$^s$ and R$^u$ are independently selected from H or C$_{1-6}$alkyl, or may be taken together with the nitrogen of attachment to form an otherwise aliphatic hydrocarbon ring, said ring having 5 to 7 members, optionally having one carbon replaced with >O, =N—, >NH or >N(C$_{1-4}$alkyl) and optionally having one or two unsaturated bonds in the ring), —(C=O)N(R$^s$)R$^u$, —(N—R$^v$)COR$^v$, —(N—R$^v$)SO$_2$C$_{1-6}$alkyl (wherein R$^v$ is H or C$_{1-6}$alkyl or two R$^v$ in the same substituent may be taken together with the amide of attachment to form an otherwise aliphatic hydrocarbon ring, said ring having 4 to 6 members), —(C=O)C$_{1-6}$alkyl, —(S=(O)$_n$)—C$_{1-6}$alkyl (wherein n is selected from 0, 1 or 2), —SO$_2$N(R$^s$)R$^u$, —SCF$_3$, halo, —CF$_3$, —OCF$_3$, —COOH and —COOC$_{1-6}$alkyl, wherein the foregoing phenyl, pyridyl, thienyl, furanyl and pyrrolyl substituents are optionally mono-, di-, or tri-substituted with a substituent independently selected from the group consisting of: —OH, —C$_{1-6}$alkyl, —OC$_{1-6}$alkyl, —CN, —NO$_2$, —N(R$^a$)R$^b$ (wherein R$^a$ and R$^b$ are independently selected from H, C$_{1-6}$alkyl or C$_{2-6}$alkenyl), —(C=O)N(R$^a$)R$^b$, —(N—R$^c$)COR$^c$, —(N—R$^c$)SO$_2$C$_{1-6}$alkyl (wherein R$^c$ is H or C$_{1-6}$alkyl), —(C=O)C$_{1-6}$alkyl, —(S=(O)$_d$)—C$_{1-6}$alkyl (wherein d is selected from 0, 1 or 2), —SO$_2$N(R$^a$)R$^b$, —SCF$_3$, halo, —CF$_3$, —OCF$_3$, —COOH and —COOC$_{1-6}$alkyl;

R$^2$ is selected from the group consisting of H, C$_{1-7}$alkyl, C$_{2-7}$alkenyl, C$_{2-7}$alkynyl and C$_{3-7}$cycloalkyl;

and enantiomers, diastereomers, hydrates, solvates and pharmaceutically acceptable salts, esters and amides thereof.

Similarly, isomeric forms of the compounds of formulae (I), (II), and (III), and of their pharmaceutically acceptable salts, esters, and amides, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of a regioisomeric mixture.

The invention also features pharmaceutical compositions containing such compounds and methods of using such compositions in the treatment or prevention of disease states mediated by the serotonin receptors, particularly, 5-HT$_7$ and/or 5-HT$_2$ receptor subtypes.

DETAILED DESCRIPTION

Preferably, m is 1 or 2 and most preferably, m is 1.
Preferably, n is 1 or 2.
Preferably, p is 1 or 2.
Preferably, m+n is 2 or 3.
Preferably, m+p is 2 or 3.
Preferably, q is 1.
Preferably, r is 0, 1, or 2.
Preferably, r is 4.
Preferably R$^3$, optionally substituted, is selected from the group consisting of methyl, ethyl, propyl, isopropyl, butyl, allyl, propargyl, and benzyl.
Preferably, R$^3$ is methyl.

Preferably Ar, optionally substituted, is selected from the group consisting of:

a) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl, b) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, c) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl, d) naphthyl, e) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, f) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, [1,5], [1,6], [1,7], or [1,8]naphthyridin-2-, 3-, or 4-yl, [2,5], [2,6], [2,7], [2,8]naphthyridin-1-, 3-, or 4-yl, and g) biphenyl, 4-tetrazolylphenyl.

More preferably, Ar, optionally substituted, is selected from the group consisting of phenyl, pyridyl, thiophen-2-yl and thiophen-3-yl.

Specific Ar may be selected from the group consisting of phenyl, 2-methoxyphenyl, 3-methoxyphenyl, 4-methoxyphenyl, 2-methylphenyl, 3-methylphenyl, 4-methylphenyl, 4-ethylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-trifluoromethylphenyl, 3-trifluoromethylphenyl, 4-trifluoromethylphenyl, 3-trifluoromethoxyphenyl, 4-trifluoromethoxyphenyl, 3-cyanophenyl, 4-cyanophenyl, 3-acetylphenyl, 4-acetylphenyl, 3,4-difluorophenyl, 3,4-dichlorophenyl, 2,3-difluorophenyl, 2,3-dichlorophenyl, 2,4-difluorophenyl, 2,4-dichlorophenyl, 3-nitrophenyl, 4-nitrophenyl, 3-chloro-4-fluorophenyl, 3-fluoro-4-chlorophenyl, benzo[1,3]dioxol-4 or 5-yl, 3-hydroxyphenyl, 4-hydroxyphenyl, 4-hydroxy-2-methylphenyl, 4-hydroxy-3-fluorophenyl, 3,4-dihydroxyphenyl, 4-dimethylaminophenyl, 4-carbamoylphenyl, 4-fluoro-3-methylphenyl, furan-2-yl, furan-3-yl, thiophen-2-yl, thiophen-3-yl, 5-chlorothiophen-2-yl, 5-methylthiophen-2-yl, 5-chlorothiophen-3-yl, 5-methylthiophen-3-yl, 4'-chlorobiphenyl, and 4-tetrazolylphenyl.

Preferably, ALK, optionally substituted, is selected from the group consisting of methylene, ethylene, propylene, butylene, tert-butylene, pentylene, 1-ethylpropylene, 2-ethylpropylene, 2-ethylbutylene, isopropylene, but-3-enylene, isobutylene, 3-methylbutylene, allylene, and prop-2-ynylene.

Specific ALK may be selected from the group consisting of methylene, trifluoromethylmethylene, methoxycarbonylmethyl, methylcarbamoylmethyl, ethylene, propylene, 3-methoxycarbonyl propylene, 3-carboxy propylene, butylene, tert-butylene, 4-hydroxybutylene, 4-methoxycarbonyl butylene, 4-carboxy butylene, pentylene, 5-hydroxypentylene, 1-ethylpropylene, 2-ethylpropylene, 2-ethylbutylene, isopropylene, but-3-enylene, isobutylene, 3-methylbutylene, prop-2-ynylene, 2-dimethylaminoethylene, and 2-cyanoethylene.

Preferably CYC, optionally substituted, is hydrogen or is selected from the group consisting of:

i) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl, ii) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, iii) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl, iv) naphthyl, v) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, vi) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, [1,5], [1,6], [1,7], or [1,8]naphthyridin-2-, 3-, or 4-yl, [2,5], [2,6], [2,7], [2,8]naphthyridin-1-, 3-, or 4-yl, vii) cyclopropyl, cyclobutyl, cyclopentyl, cyclohexyl, cyclohexenyl, cycloheptyl, cyclooctyl, adamantyl, pyrrolinyl, pyrrolidinyl, pyrazolinyl, piperidinyl, homopiperidinyl, azepanyl, tetrahydrofuranyl, tetrahydropyranyl, piperazinyl, morpholinyl, thiomorpholinyl, piperidinonyl, indanyl, dihydroindolyl, oxindolyl, dihydropyrrolopyridinyl, and viii) bicyclo[4.1.0]heptane, octahydroindolyl, octahydroisoindolinyl, decahydroquinolinyl, decahydroisoquinolinyl, octahydropyrrolopyridinyl, and octahydropyrrolopyrrolidinyl.

More preferably, CYC, optionally substituted, is selected from the group consisting of hydrogen, phenyl, indolyl, benzthiazolyl, isoquinolyl, quinazolinyl, naphthalen-1 or 2-yl, thiophen-2-yl, thiophen-3-yl, furan-2-yl, furan-3-yl, pyridinyl, cyclobutyl, cyclopentyl, cyclohexyl, cycloheptyl, cyclooctyl, piperidin-2,3 or 4-yl, 2-pyrrolin-2, 3, 4 or 5-yl, 3-pyrrolin-2 or 3-yl, 2-pyrazolin-3, 4 or 5-yl, morpholin-2, 3, 5 or 6-yl, thiomorpholin-2, 3, 5 or 6-yl, piperazin-2, 3, 5 or 6-yl, pyrrolidin-2 or 3-yl, homopiperidinyl, adamantanyl, and octahydroindolyl.

Most preferably, CYC, optionally substituted, is selected from the group consisting of hydrogen, phenyl, pyridyl, cyclobutyl, cyclopentyl, cyclohexyl, thiophen-2-yl, thiophen-3-yl, tetrahydropyranyl, furan-2-yl, furan-3-yl and naphthalen-1 or 2-yl.

Specific CYC may be selected from the group consisting of hydrogen, phenyl, 2-methoxyphenyl, 3-methoxyphenyl, 4-methoxyphenyl, 2-methylphenyl, 3-methylphenyl, 4-methylphenyl, 4-ethylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-trifluoromethylphenyl, 3-trifluoromethylphenyl, 4-trifluoromethylphenyl, 3-trifluoromethoxyphenyl, 4-trifluoromethoxyphenyl, 2-cyanophenyl, 3-cyanophenyl, 4-cyanophenyl, 3-acetylphenyl, 4-acetylphenyl, 3,4-difluorophenyl, 3,4-dichlorophenyl, 2,3-difluorophenyl, 2,3-dichlorophenyl, 2,4-difluorophenyl, 2,4-dichlorophenyl, 2,6-difluorophenyl, 2,6-dichlorophenyl, 2,6-dimethylphenyl, 2,4,6-trifluorophenyl, 2,4,6-trichlorophenyl, 3,4,5-trimethoxyphenyl, cyclobutyl, cyclohexyl, cyclopentyl, 4-fluoro-3-methylphenyl, 3-nitrophenyl, 4-nitrophenyl, 4-methyl-3-fluorophenyl, 3,4-dimethylphenyl, 4-methoxy-3-fluorophenyl, 4-methoxy-2-methylphenyl, 3-aminophenyl, 4-aminophenyl, 4-carbomethoxyphenyl, 3-methanesulfonylamino-phenyl, 4-methanesulfonylamino-phenyl, 3-dimethanesulfonylamino-phenyl, 4-dimethanesulfonylamino-phenyl, thiophen-2-yl, thiophen-3-yl, 5-chlorothiophen-2-yl, benzo[1,3]dioxol-4 or 5-yl, tetrahydropyran-2,3 or 4-yl, furan-2-yl, furan-3-yl, 5-carboxyethyl-furan-2-yl, naphthalen-1 or 2-yl, 3,4-bisbenzyloxyphenyl, 2-hydroxyphenyl, 3-hydroxyphenyl, 4-hydroxyphenyl, 4-hydroxy-2-methylphenyl, 4-hydroxy-3-fluorophenyl and 3,4-dihydroxyphenyl.

Preferably, $R^1$ is selected from the group consisting of hydrogen, $C_{1-3}$alkyl, $C_{2-4}$alkenyl, $C_{2-4}$alkynyl, $C_{3-6}$cycloalkyl, $C_{3-6}$cycloalkyl$C_{1-3}$alkyl, $C_{5-6}$cycloalkenyl, benzofused $C_{5-6}$cycloalkyl, each optionally mono-, di-, or tri-substituted with $R^p$.

More preferably, $R^1$, optionally $R^p$ substituted, is selected from the group consisting of hydrogen, methyl, ethyl, propyl, and isopropyl.

Specific $R^1$ may be selected from the group consisting of hydrogen, methyl, ethyl, propyl, isopropyl, 3-hydroxypropyl, benzyl, 3,4-dimethoxybenzyl, methoxycarbonylmethyl, carbamoylmethyl, phenethyl, phenpropyl, and hydroxyethyl.

Preferably, $R^2$ is hydrogen, $C_{1-3}$alkyl, $C_{2-4}$alkenyl, $C_{2-4}$alkynyl, or $C_{3-6}$cycloalkyl.

More preferably, $R^2$ is hydrogen or methyl.

It is understood that some compounds referred to herein are chiral and/or have geometric isomeric centers, for example E- and Z-isomers. The present invention encompasses all such optical, including stereoisomers and racemic mixtures, diastereomers, and geometric isomers that possess the activity that characterizes the compounds of this invention. In addition, certain compounds referred to herein can exist in solvated as well as unsolvated forms. It is understood that this invention encompasses all such solvated and unsolvated forms that possess the activity that characterizes the compounds of this invention.

Compounds according to the present invention that have been modified to be detectable by some analytic technique are also within the scope of this invention. The compounds of the present invention may be labeled with radioactive elements such as $^{125}I$, $^{18}F$, $^{11}C$, $^{64}Cu$, and the like for use in imaging or for radioactive treatment of patients. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Preferably, compounds of the present invention labeled with $^{18}F$ or $^{11}C$ may be used as a positron emission tomography (PET) molecular probe for studying serotonin-mediated disorders. Another example of such compounds is an isotopically labeled compound, such as a deuterium and/or tritium labeled compound that may be used in reaction kinetic studies. The compounds described herein may be reacted with an appropriate functionalized radioactive reagents using conventional chemistry to provide radiolabeled compounds.

Pharmaceutically acceptable salts, esters, and amides include carboxylate salts (e.g., $C_{1-8}$alkyl, $C_{3-8}$cycloalkyl, aryl, $C_{2-10}$heteroaryl, or $C_{2-10}$ non-aromatic heterocyclic), amino addition salts, acid addition salts, esters, and amides that are within a reasonable benefit/risk ratio, pharmacologically effective and suitable for contact with the tissues of patients without undue toxicity, irritation, or allergic response. Representative addition salts for compounds of formula (I) displaying basic functionality include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. Representative addition salts for compounds of formula (I) displaying acidic functionality are those that form non-toxic base salts with such compounds. These salts may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1-19, which is incorporated herein by reference.

Representative pharmaceutically acceptable amides of the invention include those derived from ammonia, primary $C_{1-6}$ alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters.

Preferred compounds, which are fused pyrroles, are selected from the group consisting of:

| EX | CHEMICAL NAME |
|---|---|
| 1 | 1-Benzyl-3-(4-nitro-phenyl)-4,5,6,7-tetrahydro-1H-pyrrolo[3,2-c]pyridine; |
| 2 | 1-Benzyl-3-(3-chloro-4-fluoro-phenyl)-4,5,6,7-tetrahydro-1H-pyrrolo[3,2-c]pyridine; |
| 3 | 4-(1-Benzyl-4,5,6,7-tetrahydro-1H-pyrrolo[3,2-c]pyridin-3-yl)-phenol; |
| 4 | 1-Benzyl-3-(4-trifluoromethoxy-phenyl)-4,5,6,7-tetrahydro-1H-pyrrolo[3,2-c]pyridine; |
| 5 | 1-Benzyl-3-(5-chloro-thiophen-2-yl)-4,5,6,7-tetrahydro-1H-pyrrolo[3,2-c]pyridine; |
| 6 | 1-Benzyl-3-thiophen-2-yl-4,5,6,7-tetrahydro-1H-pyrrolo[3,2-c]pyridine; |
| 7 | 1-(3-Chloro-benzyl)-3-phenyl-4,5,6,7-tetrahydro-1H-pyrrolo[3,2-c]pyridine; |
| 8 | 1-Benzyl-3-(3-fluoro-phenyl)-4,5,6,7-tetrahydro-1H-pyrrolo[3,2-c]pyridine; |
| 9 | 3-(4-Chloro-phenyl)-1-(2-fluoro-benzyl)-4,5,6,7-tetrahydro-1H-pyrrolo[3,2-c]pyridine; |
| 10 | 1-(3-Chloro-benzyl)-3-(4-chloro-phenyl)-4,5,6,7-tetrahydro-1H-pyrrolo[3,2-c]pyridine; |
| 11 | 1-(2-Chloro-benzyl)-3-phenyl-4,5,6,7-tetrahydro-1H-pyrrolo[3,2-c]pyridine; |
| 12 | 1-(4-Chloro-benzyl)-3-(4-chloro-phenyl)-4,5,6,7-tetrahydro-1H-pyrrolo[3,2-c]pyridine; |
| 13 | 1-Benzyl-3-(2,4-dichloro-phenyl)-4,5,6,7-tetrahydro-1H-pyrrolo[3,2-c]pyridine; |
| 14 | 1-(4-Methoxy-benzyl)-3-phenyl-4,5,6,7-tetrahydro-1H-pyrrolo[3,2-c]pyridine; |
| 15 | 1-(2-Chloro-benzyl)-3-(4-chloro-phenyl)-4,5,6,7-tetrahydro-1H-pyrrolo[3,2-c]pyridine; |
| 16 | 1-(2,4-Dichloro-benzyl)-3-phenyl-4,5,6,7-tetrahydro-1H-pyrrolo[3,2-c]pyridine; |
| 17 | 1-Benzyl-2-methyl-3-phenyl-4,5,6,7-tetrahydro-1H-pyrrolo[3,2-c]pyridine; |
| 18 | 1-Benzyl-3-p-tolyl-4,5,6,7-tetrahydro-1H-pyrrolo[3,2-c]pyridine; |
| 19 | 1-Benzyl-3-(3,4-dichloro-phenyl)-4,5,6,7-tetrahydro-1H-pyrrolo[3,2-c]pyridine; |
| 20 | 3-Benzo[1,3]dioxol-5-yl-1-benzyl-4,5,6,7-tetrahydro-1H-pyrrolo[3,2-c]pyridine; |
| 21 | 1-Benzyl-3-(4-fluoro-phenyl)-4,5,6,7-tetrahydro-1H-pyrrolo[3,2-c]pyridine; |
| 22 | 1-Butyl-3-p-tolyl-4,5,6,7-tetrahydro-1H-pyrrolo[3,2-c]pyridine; |
| 23 | 1-Benzyl-3-(4-bromo-phenyl)-4,5,6,7-tetrahydro-1H-pyrrolo[3,2-c]pyridine; |
| 24 | 1-Benzyl-3-(4-trifluoromethyl-phenyl)-4,5,6,7-tetrahydro-1H-pyrrolo[3,2-c]pyridine; |
| 25 | 1-Benzyl-3-(4-chloro-phenyl)-4,5,6,7-tetrahydro-1H-pyrrolo[3,2-c]pyridine; |
| 26 | 1-Benzyl-3-phenyl-1,4,5,6,7,8-hexahydro-pyrrolo[2,3-d]azepine; |
| 27 | 1-Benzyl-3-(5-methyl-thiophen-2-yl)-4,5,6,7-tetrahydro-1H-pyrrolo[3,2-c]pyridine; |
| 28 | 1-Benzyl-3-(4-chloro-phenyl)-1,4,5,6,7,8-hexahydro-pyrrolo[2,3-d]azepine; |
| 29 | 1-Benzyl-3-(5-chloro-thiophen-2-yl)-1,4,5,6,7,8-hexahydro-pyrrolo[2,3-d]azepine; |
| 30 | 1-(4-Chloro-benzyl)-3-phenyl-4,5,6,7-tetrahydro-1H-pyrrolo[3,2-c]pyridine; |
| 31 | 1-Benzyl-3-phenyl-4,5,6,7-tetrahydro-1H-pyrrolo[3,2-c]pyridine; |
| 32 | 1-Benzyl-3-(3-chloro-phenyl)-1,4,5,6,7,8-hexahydro-pyrrolo[2,3-d]azepine; |
| 33 | 1-Benzyl-3-(3-chloro-phenyl)-4,5,6,7-tetrahydro-1H-pyrrolo[3,2-c]pyridine; |
| 34 | 1-Benzyl-3-(4-methoxy-phenyl)-4,5,6,7-tetrahydro-1H-pyrrolo[3,2-c]pyridine; |
| 35 | 1-Benzyl-3-(4-chloro-phenyl)-5-ethyl-4,5,6,7-tetrahydro-1H-pyrrolo[3,2-c]pyridine; |
| 36 | 1-Benzyl-3-(4-chloro-phenyl)-5-isopropyl-4,5,6,7-tetrahydro-1H-pyrrolo[3,2-c]pyridine; |
| 37 | 3-[1-Benzyl-3-(4-chloro-phenyl)-1,4,6,7-tetrahydro-pyrrolo[3,2-c]pyridin-5-yl]-propan-1-ol; |
| 38 | 1-Benzyl-3-(4-chloro-phenyl)-5-methyl-4,5,6,7-tetrahydro-1H-pyrrolo[3,2-c]pyridine; |
| 39 | 1-Benzyl-3-(3-chloro-phenyl)-5-methyl-4,5,6,7-tetrahydro-1H-pyrrolo[3,2-c]pyridine; |
| 40 | 1-Benzyl-3-(3-chloro-4-fluoro-phenyl)-5-methyl-4,5,6,7-tetrahydro-1H-pyrrolo[3,2-c]pyridine; |
| 41 | 1,5-Dibenzyl-3-phenyl-4,5,6,7-tetrahydro-1H-pyrrolo[3,2-c]pyridine; and |
| 42 | 1-Benzyl-5-isopropyl-3-phenyl-4,5,6,7-tetrahydro-1H-pyrrolo[3,2-c]pyridine. |

Preferred compounds, which are fused 1-substituted pyrazoles, are selected from the group consisting of:

| EX | CHEMICAL NAME |
|---|---|
| 43 | 1-Benzyl-3-(4-trifluoromethyl-phenyl)-1,4,5,6,7,8-hexahydro-1,2,6-triaza-azulene; |
| 44 | 1-Benzyl-3-phenyl-1,4,5,6,7,8-hexahydro-1,2,6-triaza-azulene; |
| 45 | 1-Benzyl-3-(2-fluoro-phenyl)-1,4,5,6,7,8-hexahydro-1,2,6-triaza-azulene; |
| 46 | 1-Benzyl-3-(3-fluoro-phenyl)-1,4,5,6,7,8-hexahydro-1,2,6-triaza-azulene; |
| 47 | 1-Benzyl-3-(4-fluoro-phenyl)-1,4,5,6,7,8-hexahydro-1,2,6-triaza-azulene; |
| 48 | 1-Benzyl-3-(2,3-difluoro-phenyl)-1,4,5,6,7,8-hexahydro-1,2,6-triaza-azulene; |
| 49 | 1-Benzyl-3-(3,4-dichloro-phenyl)-1,4,5,6,7,8-hexahydro-1,2,6-triaza-azulene; |
| 50 | 1-[4-(1-Benzyl-1,4,5,6,7,8-hexahydro-1,2,6-triaza-azulen-3-yl)-phenyl]-ethanone; |
| 51 | 1-Benzyl-3-(4-trifluoromethoxy-phenyl)-1,4,5,6,7,8-hexahydro-1,2,6-triaza-azulene; |

-continued

| EX | CHEMICAL NAME |
|---|---|
| 52 | 1-Benzyl-3-(3-chloro-phenyl)-1,4,5,6,7,8-hexahydro-1,2,6-triaza-azulene; |
| 53 | 3-(1-Benzyl-1,4,5,6,7,8-hexahydro-1,2,6-triaza-azulen-3-yl)-benzonitrile; |
| 54 | 4-(1-Benzyl-1,4,5,6,7,8-hexahydro-1,2,6-triaza-azulen-3-yl)-benzonitrile; |
| 55 | 1-(4-Chloro-benzyl)-3-phenyl-1,4,5,6,7,8-hexahydro-1,2,6-triaza-azulene; |
| 56 | 1-(4-Chloro-benzyl)-3-(4-chloro-phenyl)-1,4,5,6,7,8-hexahydro-1,2,6-triaza-azulene; |
| 57 | 1-Benzyl-3-phenyl-6-propyl-1,4,5,6,7,8-hexahydro-1,2,6-triaza-azulene; |
| 58 | 1-Benzyl-6-isopropyl-3-phenyl-1,4,5,6,7,8-hexahydro-1,2,6-triaza-azulene; |
| 59 | 1-Benzyl-3-(4-chloro-phenyl)-1,4,5,6,7,8-hexahydro-1,2,6-triaza-azulene; |
| 60 | 1-Benzyl-3-(4-chloro-phenyl)-1,4,5,6,7,8-hexahydro-1,2,5-triaza-azulene; |
| 61 | 3-(4-Chloro-phenyl)-1-methyl-1,4,5,6,7,8-hexahydro-1,2,6-triaza-azulene; |
| 63 | 3-(4-Chloro-phenyl)-1-ethyl-1,4,5,6,7,8-hexahydro-1,2,6-triaza-azulene; |
| 65 | 3-(4-Chloro-phenyl)-1-propyl-1,4,5,6,7,8-hexahydro-1,2,6-triaza-azulene; |
| 67 | 1-Butyl-3-(4-chloro-phenyl)-1,4,5,6,7,8-hexahydro-1,2,6-triaza-azulene; |
| 69 | 3-(4-Chloro-phenyl)-1-(2-cyclohexyl-ethyl)-1,4,5,6,7,8-hexahydro-1,2,6-triaza-azulene; |
| 71 | 3-(4-Chloro-phenyl)-1-phenethyl-1,4,5,6,7,8-hexahydro-1,2,6-triaza-azulene; |
| 73 | 3-(4-Chloro-phenyl)-1-(4-fluoro-3-methyl-benzyl)-1,4,5,6,7,8-hexahydro-1,2,6-triaza-azulene; |
| 74 | 3-(4-Chloro-phenyl)-1-(3-methyl-benzyl)-1,4,5,6,7,8-hexahydro-1,2,6-triaza-azulene; |
| 75 | 3-(4-Chloro-phenyl)-1-(4-fluoro-benzyl)-1,4,5,6,7,8-hexahydro-1,2,6-triaza-azulene; |
| 76 | 3-(4-Chloro-phenyl)-1-(3-fluoro-benzyl)-1,4,5,6,7,8-hexahydro-1,2,6-triaza-azulene; |
| 77 | 3-(4-Chloro-phenyl)-1-(4-methyl-benzyl)-1,4,5,6,7,8-hexahydro-1,2,6-triaza-azulene; |
| 78 | 3-(4-Chloro-phenyl)-1-(3,4-difluoro-benzyl)-1,4,5,6,7,8-hexahydro-1,2,6-triaza-azulene; |
| 79 | 3-(4-Chloro-phenyl)-1-(3-nitro-benzyl)-1,4,5,6,7,8-hexahydro-1,2,6-triaza-azulene; |
| 80 | 3-(4-Chloro-phenyl)-1-(3-fluoro-4-methyl-benzyl)-1,4,5,6,7,8-hexahydro-1,2,6-triaza-azulene; |
| 81 | 3-(4-Chloro-phenyl)-1-(3,4-dimethyl-benzyl)-1,4,5,6,7,8-hexahydro-1,2,6-triaza-azulene; |
| 85 | 5-[3-(4-Chloro-phenyl)-5,6,7,8-tetrahydro-4H-1,2,6-triaza-azulen-1-yl]-pentanoic acid methyl ester; |
| 86 | 5-[3-(4-Chloro-phenyl)-5,6,7,8-tetrahydro-4H-1,2,6-triaza-azulen-1-yl]-pentanoic acid; |
| 87 | 5-[3-(4-Chloro-phenyl)-5,6,7,8-tetrahydro-4H-1,2,6-triaza-azulen-1-yl]-pentan-1-ol; |
| 88 | 4-[3-(4-Chloro-phenyl)-5,6,7,8-tetrahydro-4H-1,2,6-triaza-azulen-1-yl]-butyric acid methyl ester; |
| 91 | 4-[3-(4-Chloro-phenyl)-5,6,7,8-tetrahydro-4H-1,2,6-triaza-azulen-1-yl]-butyric acid; |
| 93 | 4-[3-(4-Chloro-phenyl)-5,6,7,8-tetrahydro-4H-1,2,6-triaza-azulen-1-yl]-butan-1-ol; |
| 96 | 3-(4-Chloro-phenyl)-1-(3-fluoro-4-methoxy-benzyl)-1,4,5,6,7,8-hexahydro-1,2,6-triaza-azulene; |
| 98 | 3-(4-Chloro-phenyl)-1-(4-nitro-benzyl)-1,4,5,6,7,8-hexahydro-1,2,6-triaza-azulene; |
| 99 | 4-(3-Phenyl-5,6,7,8-tetrahydro-4H-1,2,6-triaza-azulen-1-ylmethyl)-phenylamine; |
| 100 | N-[4-(3-Phenyl-5,6,7,8-tetrahydro-4H-1,2,6-triaza-azulen-1-ylmethyl)-phenyl]-methanesulfonamide; |
| 101 | N,N-[4-(3-phenyl-5,6,7,8-tetrahydro-4H-1,2,6-triaza-azulen-1-ylmethyl)-phenyl]-dimethanesulfonamide; |
| 102 | 1-Benzyl-3-p-tolyl-1,4,5,6,7,8-hexahydro-1,2,6-triaza-azulene; |
| 103 | 3-(4-Chloro-phenyl)-1-thiophen-2-ylmethyl-1,4,5,6,7,8-hexahydro-1,2,6-triaza-azulene; |
| 104 | 1-Benzyl-3-thiophen-2-yl-1,4,5,6,7,8-hexahydro-1,2,6-triaza-azulene; |
| 105 | 3-(4-Chloro-phenyl)-1-(3-methoxy-benzyl)-1,4,5,6,7,8-hexahydro-1,2,6-triaza-azulene; |
| 106 | 3-(4-Chloro-phenyl)-1-(2-fluoro-benzyl)-1,4,5,6,7,8-hexahydro-1,2,6-triaza-azulene; |
| 107 | 3-(4-Chloro-phenyl)-1-(2-methyl-benzyl)-1,4,5,6,7,8-hexahydro-1,2,6-triaza-azulene; |
| 108 | 3-(4-Chloro-phenyl)-1-(2,4-difluoro-benzyl)-1,4,5,6,7,8-hexahydro-1,2,6-triaza-azulene; |
| 109 | 3-(4-Chloro-phenyl)-1-(2-methoxy-benzyl)-1,4,5,6,7,8-hexahydro-1,2,6-triaza-azulene; |
| 110 | 1-(2-Chloro-benzyl)-3-(4-chloro-phenyl)-1,4,5,6,7,8-hexahydro-1,2,6-triaza-azulene; |
| 111 | 1-But-3-enyl-3-(4-chloro-phenyl)-1,4,5,6,7,8-hexahydro-1,2,6-triaza-azulene; |
| 112 | 1-(2-Bromo-benzyl)-3-(4-chloro-phenyl)-1,4,5,6,7,8-hexahydro-1,2,6-triaza-azulene; |
| 113 | 1-(4-Bromo-benzyl)-3-(4-chloro-phenyl)-1,4,5,6,7,8-hexahydro-1,2,6-triaza-azulene; |
| 114 | 3-(4-Chloro-phenyl)-1-(2-ethyl-butyl)-1,4,5,6,7,8-hexahydro-1,2,6-triaza-azulene; |
| 115 | 3-(4-Chloro-phenyl)-1-(5-chloro-thiophen-2-ylmethyl)-1,4,5,6,7,8-hexahydro-1,2,6-triaza-azulene; |
| 116 | 1-(3-Bromo-benzyl)-3-(4-chloro-phenyl)-1,4,5,6,7,8-hexahydro-1,2,6-triaza-azulene; |
| 117 | 3-(4-Chloro-phenyl)-1-cyclohexylmethyl-1,4,5,6,7,8-hexahydro-1,2,6-triaza-azulene; |
| 118 | 3-(4-Chloro-phenyl)-1-isobutyl-1,4,5,6,7,8-hexahydro-1,2,6-triaza-azulene; |

-continued

| EX | CHEMICAL NAME |
|---|---|
| 119 | 1-Benzo[1,3]dioxol-5-ylmethyl-3-(4-chloro-phenyl)-1,4,5,6,7,8-hexahydro-1,2,6-triaza-azulene; |
| 120 | 3-(4-Chloro-phenyl)-1-(tetrahydro-pyran-4-ylmethyl)-1,4,5,6,7,8-hexahydro-1,2,6-triaza-azulene; |
| 121 | 3-(4-Chloro-phenyl)-1-(2,6-difluoro-benzyl)-1,4,5,6,7,8-hexahydro-1,2,6-triaza-azulene; |
| 123 | 3-(4-Chloro-phenyl)-1-(4-methoxy-benzyl)-1,4,5,6,7,8-hexahydro-1,2,6-triaza-azulene; |
| 124 | 3-(4-Chloro-phenyl)-1-(3-methyl-butyl)-1,4,5,6,7,8-hexahydro-1,2,6-triaza-azulene; |
| 125 | 3-(4-Chloro-phenyl)-1-(2-trifluoromethyl-benzyl)-1,4,5,6,7,8-hexahydro-1,2,6-triaza-azulene |
| 128 | 3-(4-Chloro-phenyl)-1-(4-methoxy-2-methyl-benzyl)-1,4,5,6,7,8-hexahydro-1,2,6-triaza-azulene; |
| 134 | 3-(4-Chloro-phenyl)-1-prop-2-ynyl-1,4,5,6,7,8-hexahydro-1,2,6-triaza-azulene; |
| 135 | 3-(4-Chloro-phenyl)-1-pentafluorophenylmethyl-1,4,5,6,7,8-hexahydro-1,2,6-triaza-azulene; |
| 137 | 3-(4-Chloro-phenyl)-1-(2,4,6-trifluoro-benzyl)-1,4,5,6,7,8-hexahydro-1,2,6-triaza-azulene; |
| 138 | 2-[3-(4-Chloro-phenyl)-5,6,7,8-tetrahydro-4H-1,2,6-triaza-azulen-1-ylmethyl]-benzonitrile; |
| 142 | 3-(4-Chloro-phenyl)-1-naphthalen-2-ylmethyl-1,4,5,6,7,8-hexahydro-1,2,6-triaza-azulene; |
| 144 | 5-[3-(4-Chloro-phenyl)-5,6,7,8-tetrahydro-4H-1,2,6-triaza-azulen-1-ylmethyl]-furan-2-carboxylic acid ethyl ester; |
| 145 | 3-(4-Chloro-phenyl)-1-naphthalen-1-ylmethyl-1,4,5,6,7,8-hexahydro-1,2,6-triaza-azulene; |
| 147 | [3-(4-Chloro-phenyl)-5,6,7,8-tetrahydro-4H-1,2,6-triaza-azulen-1-yl]-acetic acid methyl ester; |
| 148 | 2-[3-(4-Chloro-phenyl)-5,6,7,8-tetrahydro-4H-1,2,6-triaza-azulen-1-yl]-N-methyl-acetamide; |
| 150 | 3-(4-Chloro-phenyl)-1-(3,4,5-trimethoxy-benzyl)-1,4,5,6,7,8-hexahydro-1,2,6-triaza-azulene; |
| 152 | 3-(4-Chloro-phenyl)-1-(2,6-dimethyl-benzyl)-1,4,5,6,7,8-hexahydro-1,2,6-triaza-azulene; |
| 154 | 1-(3,4-Bis-benzyloxy-benzyl)-3-(4-chloro-phenyl)-1,4,5,6,7,8-hexahydro-1,2,6-triaza-azulene; |
| 156 | 3-[3-(4-Chloro-phenyl)-5,6,7,8-tetrahydro-4H-1,2,6-triaza-azulen-1-ylmethyl]-phenol; |
| 157 | 4-[3-(4-Chloro-phenyl)-5,6,7,8-tetrahydro-4H-1,2,6-triaza-azulen-1-ylmethyl]-phenol; |
| 158 | 4-[3-(4-Chloro-phenyl)-5,6,7,8-tetrahydro-4H-1,2,6-triaza-azulen-1-ylmethyl]-3-methyl-phenol; |
| 159 | 4-[3-(4-Chloro-phenyl)-5,6,7,8-tetrahydro-4H-1,2,6-triaza-azulen-1-ylmethyl]-benzene-1,2-diol; |
| 160 | 4-[3-(4-Chloro-phenyl)-5,6,7,8-tetrahydro-4H-1,2,6-triaza-azulen-1-ylmethyl]-2-fluoro-phenol; |
| 162 | 2-[3-(4-Chloro-phenyl)-5,6,7,8-tetrahydro-4H-1,2,6-triaza-azulen-1-ylmethyl]-phenol; |
| 165 | 1-Benzyl-3-(4-chloro-phenyl)-6-methyl-1,4,5,6,7,8-hexahydro-1,2,6-triaza-azulene; |
| 166 | 1-Benzyl-3-(4-chloro-phenyl)-6-ethyl-1,4,5,6,7,8-hexahydro-1,2,6-triaza-azulene; |
| 167 | 3-(4-Chloro-phenyl)-6-(3,4-dimethoxy-benzyl)-1,4,5,6,7,8-hexahydro-1,2,6-triaza-azulene; |
| 168 | 1-Butyl-3-(4-chloro-phenyl)-6-(3,4-dimethoxy-benzyl)-1,4,5,6,7,8-hexahydro-1,2,6-triaza-azulene; |
| 169 | 1-Benzyl-3-(4-chloro-phenyl)-6-(3,4-dimethoxy-benzyl)-1,4,5,6,7,8-hexahydro-1,2,6-triaza-azulene; |
| 170 | [1-Benzyl-3-(4-chloro-phenyl)-4,5,7,8-tetrahydro-1H-1,2,6-triaza-azulen-6-yl]-acetic acid methyl ester; |
| 171 | 2-[1-Benzyl-3-(4-chloro-phenyl)-4,5,7,8-tetrahydro-1H-1,2,6-triaza-azulen-6-yl]-ethanol; |
| 172 | 3-(4-Chloro-phenyl)-1-phenyl-1,4,5,6,7,8-hexahydro-1,2,6-triaza-azulene; |
| 173 | 3-(4-Chloro-phenyl)-1-(2-methyl-benzyl)-4,5,6,7,8,9-hexahydro-1H-1,2,6-triaza-cyclopentacyclooctene; |
| 174 | 3-(4-Chloro-phenyl)-1-(2-methyl-benzyl)-4,5,6,7,8,9-hexahydro-1H-1,2,7-triaza-cyclopentacyclooctene; |
| 175 | 3-(4-Chloro-phenyl)-1-(2-methyl-benzyl)-4,5,6,7-tetrahydro-1H-pyrazolo[3,4-c]pyridine; |
| 230 | {4-[3-(4-Chloro-phenyl)-5,6,7,8-tetrahydro-4H-1,2,6-triaza-azulen-1-ylmethyl]-phenyl}-methyl-amine; |
| 237 | 3-(4-Chloro-phenyl)-1-cyclobutyl-1,4,5,6,7,8-hexahydro-1,2,6-triaza-azulene; |
| 239 | 3-(4-Chloro-phenyl)-1-cyclohexyl-1,4,5,6,7,8-hexahydro-1,2,6-triaza-azulene; |
| 254 | 3-(4-Chloro-phenyl)-1-cycloheptyl-1,4,5,6,7,8-hexahydro-1,2,6-triaza-azulene; |
| 255 | 3-(4-Chloro-phenyl)-1-cyclooctyl-1,4,5,6,7,8-hexahydro-1,2,6-triaza-azulene; |

| EX | CHEMICAL NAME |
|---|---|
| 273 | 1-Benzyl-3-(4-chloro-phenyl)-1,4,5,6,7,8-hexahydro-1,2,6-triaza-azulene citrate salt; |
| 316 | 3-(4-Chloro-phenyl)-1-pyridin-4-ylmethyl-1,4,5,6,7,8-hexahydro-1,2,6-triaza-azulene; |
| 317 | 3-(4-Chloro-phenyl)-1-pyridin-2-ylmethyl-1,4,5,6,7,8-hexahydro-1,2,6-triaza-azulene; |
| 319 | 3-(4-Chloro-phenyl)-1-pyridin-3-ylmethyl-1,4,5,6,7,8-hexahydro-1,2,6-triaza-azulene; |
| 320 | 4-[3-(4-Chloro-phenyl)-5,6,7,8-tetrahydro-4H-1,2,6-triaza-azulen-1-ylmethyl]-benzoic acid methyl ester; |
| 321 | 3-(4-Chloro-phenyl)-1-(tetrahydro-pyran-4-yl)-1,4,5,6,7,8-hexahydro-1,2,6-triaza-azulene; |
| 322 | 3-(4-Chloro-phenyl)-1-(4-methyl-cyclohexyl)-1,4,5,6,7,8-hexahydro-1,2,6-triaza-azulene; |
| 323 | {2-[3-(4-Chloro-phenyl)-5,6,7,8-tetrahydro-4H-1,2,6-triaza-azulen-1-yl]-ethyl}-dimethyl-amine. |
| 324 | 3-(4-Chloro-phenyl)-1-(1-oxy-pyridin-2-ylmethyl)-1,4,5,6,7,8-hexahydro-1,2,6-triaza-azulene; |
| 325 | 2-[1-Benzyl-3-(4-chloro-phenyl)-4,5,7,8-tetrahydro-1H-1,2,6-triaza-azulen-6-yl]-acetamide; |
| 326 | 3-[3-(4-Chloro-phenyl)-5,6,7,8-tetrahydro-4H-1,2,6-triaza-azulen-1-yl]-propionitrile. |
| 332 | 1-(4-Chloro-benzyl)-3-(4-chloro-phenyl)-1,4,5,6,7,8-hexahydro-1,2,5-triaza-azulene; |
| 333 | 3-(4-Chloro-phenyl)-1-(4-methyl-benzyl)-1,4,5,6,7,8-hexahydro-1,2,5-triaza-azulene; |
| 334 | 3-(4-Chloro-phenyl)-1-(3,4-difluoro-benzyl)-1,4,5,6,7,8-hexahydro-1,2,5-triaza-azulene; |
| 335 | 3-(4-Chloro-phenyl)-1-(3-methyl-benzyl)-1,4,5,6,7,8-hexahydro-1,2,5-triaza-azulene; |
| 336 | 3-(4-Chloro-phenyl)-1-(3-fluoro-4-methyl-benzyl)-1,4,5,6,7,8-hexahydro-1,2,5-triaza-azulene; and |
| 337 | 3-(4-Chloro-phenyl)-1-(4-fluoro-3-methyl-benzyl)-1,4,5,6,7,8-hexahydro-1,2,5-triaza-azulene. |

Preferred compounds, which are fused 2-substituted pyrazoles, are selected from the group consisting of:

| EX | CHEMICAL NAME |
|---|---|
| 62 | 3-(4-Chloro-phenyl)-2-methyl-2,4,5,6,7,8-hexahydro-1,2,6-triaza-azulene; |
| 64 | 3-(4-Chloro-phenyl)-2-ethyl-2,4,5,6,7,8-hexahydro-1,2,6-triaza-azulene; |
| 66 | 3-(4-Chloro-phenyl)-2-propyl-2,4,5,6,7,8-hexahydro-1,2,6-triaza-azulene; |
| 68 | 2-Butyl-3-(4-chloro-phenyl)-2,4,5,6,7,8-hexahydro-1,2,6-triaza-azulene; |
| 70 | 3-(4-Chloro-phenyl)-2-(2-cyclohexyl-ethyl)-2,4,5,6,7,8-hexahydro-1,2,6-triaza-azulene; |
| 72 | 3-(4-Chloro-phenyl)-2-phenethyl-2,4,5,6,7,8-hexahydro-1,2,6-triaza-azulene; |
| 82 | 5-[3-(4-Chloro-phenyl)-5,6,7,8-tetrahydro-4H-1,2,6-triaza-azulen-2-yl]-pentanoic acid methyl ester; |
| 83 | 5-[3-(4-Chloro-phenyl)-5,6,7,8-tetrahydro-4H-1,2,6-triaza-azulen-2-yl]-pentanoic acid; |
| 84 | 5-[3-(4-Chloro-phenyl)-5,6,7,8-tetrahydro-4H-1,2,6-triaza-azulen-2-yl]-pentan-1-ol; |
| 89 | 4-[3-(4-Chloro-phenyl)-5,6,7,8-tetrahydro-4H-1,2,6-triaza-azulen-2-yl]-butyric acid methyl ester; |
| 90 | 4-[3-(4-Chloro-phenyl)-5,6,7,8-tetrahydro-4H-1,2,6-triaza-azulen-2-yl]-butyric acid; |
| 92 | 4-[3-(4-Chloro-phenyl)-5,6,7,8-tetrahydro-4H-1,2,6-triaza-azulen-2-yl]-butan-1-ol; |
| 94 | 3-(4-Chloro-phenyl)-2-(3,4-difluoro-benzyl)-2,4,5,6,7,8-hexahydro-1,2,6-triaza-azulene; |
| 95 | 3-(4-Chloro-phenyl)-2-(4-methyl-benzyl)-2,4,5,6,7,8-hexahydro-1,2,6-triaza-azulene; |
| 97 | 3-(4-Chloro-phenyl)-2-(3-fluoro-4-methoxy-benzyl)-2,4,5,6,7,8-hexahydro-1,2,6-triaza-azulene; |
| 122 | 3-(4-Chloro-phenyl)-2-cyclohexylmethyl-2,4,5,6,7,8-hexahydro-1,2,6-triaza-azulene; |
| 126 | 3-(4-Chloro-phenyl)-2-(2-methyl-benzyl)-2,4,5,6,7,8-hexahydro-1,2,6-triaza-azulene; |
| 127 | 2-Benzyl-3-(4-chloro-phenyl)-2,4,5,6,7,8-hexahydro-1,2,6-triaza-azulene; |
| 129 | 3-(4-Chloro-phenyl)-2-(2,4-difluoro-benzyl)-2,4,5,6,7,8-hexahydro-1,2,6-triaza-azulene; |
| 130 | 5-[3-(4-Chloro-phenyl)-5,6,7,8-tetrahydro-4H-1,2,6-triaza-azulen-2-ylmethyl]-furan-2-carboxylic acid ethyl ester; |
| 131 | 3-(4-Chloro-phenyl)-2-isobutyl-2,4,5,6,7,8-hexahydro-1,2,6-triaza-azulene; |
| 132 | 3-(4-Chloro-phenyl)-2-(2-methoxy-benzyl)-2,4,5,6,7,8-hexahydro-1,2,6-triaza-azulene; |
| 133 | 2-Benzyl-3-phenyl-2,4,5,6,7,8-hexahydro-1,2,6-triaza-azulene; |
| 136 | 3-(4-Chloro-phenyl)-2-thiophen-2-ylmethyl-2,4,5,6,7,8-hexahydro-1,2,6-triaza-azulene; |

-continued

| EX | CHEMICAL NAME |
|---|---|
| 139 | 3-(4-Chloro-phenyl)-2-(5-chloro-thiophen-2-ylmethyl)-2,4,5,6,7,8-hexahydro-1,2,6-triaza-azulene; |
| 140 | 3-(4-Chloro-phenyl)-2-(2,6-difluoro-benzyl)-2,4,5,6,7,8-hexahydro-1,2,6-triaza-azulene; |
| 141 | 3-(4-Chloro-phenyl)-2-(2-trifluoromethyl-benzyl)-2,4,5,6,7,8-hexahydro-1,2,6-triaza-azulene; |
| 143 | 3-(4-Chloro-phenyl)-2-(2-ethyl-butyl)-2,4,5,6,7,8-hexahydro-1,2,6-triaza-azulene; |
| 146 | 2-Benzo[1,3]dioxol-5-ylmethyl-3-(4-chloro-phenyl)-2,4,5,6,7,8-hexahydro-1,2,6-triaza-azulene; |
| 149 | 3-(4-Chloro-phenyl)-2-pentafluorophenylmethyl-2,4,5,6,7,8-hexahydro-1,2,6-triaza-azulene; |
| 151 | 3-(4-Chloro-phenyl)-2-naphthalen-1-ylmethyl-2,4,5,6,7,8-hexahydro-1,2,6-triaza-azulene; |
| 153 | 3-(4-Chloro-phenyl)-2-(3,4,5-trimethoxy-benzyl)-2,4,5,6,7,8-hexahydro-1,2,6-triaza-azulene; |
| 155 | 2-(3,4-Bis-benzyloxy-benzyl)-3-(4-chloro-phenyl)-2,4,5,6,7,8-hexahydro-1,2,6-triaza-azulene; |
| 161 | 4-[3-(4-Chloro-phenyl)-5,6,7,8-tetrahydro-4H-1,2,6-triaza-azulen-2-ylmethyl]-2-fluoro-phenol; |
| 163 | 4-[3-(4-Chloro-phenyl)-5,6,7,8-tetrahydro-4H-1,2,6-triaza-azulen-2-ylmethyl]-3-methyl-phenol; |
| 164 | 2-[3-(4-Chloro-phenyl)-5,6,7,8-tetrahydro-4H-1,2,6-triaza-azulen-2-ylmethyl]-phenol; |
| 176 | 2,3-Diphenyl-2,4,5,6,7,8-hexahydro-1,2,6-triaza-azulene; |
| 177 | 2-Cyclohexyl-3-phenyl-2,4,5,6,7,8-hexahydro-1,2,6-triaza-azulene; |
| 178 | 3-(4-Chloro-phenyl)-2-cyclohexyl-2,4,5,6,7,8-hexahydro-1,2,6-triaza-azulene; |
| 179 | 2-Cyclohexyl-3-(4-trifluoromethyl-phenyl)-2,4,5,6,7,8-hexahydro-1,2,6-triaza-azulene; |
| 180 | 2-Cyclopentyl-3-phenyl-2,4,5,6,7,8-hexahydro-1,2,6-triaza-azulene; |
| 181 | 3-(4-Chloro-phenyl)-2-cyclopentyl-2,4,5,6,7,8-hexahydro-1,2,6-triaza-azulene; |
| 182 | 2-Cyclopentyl-3-(4-fluoro-phenyl)-2,4,5,6,7,8-hexahydro-1,2,6-triaza-azulene; |
| 183 | 2-(1-Ethyl-propyl)-3-(3-fluoro-phenyl)-2,4,5,6,7,8-hexahydro-1,2,6-triaza-azulene; |
| 184 | 2-(1-Ethyl-propyl)-3-(4-fluoro-phenyl)-2,4,5,6,7,8-hexahydro-1,2,6-triaza-azulene; |
| 185 | 2-(1-Ethyl-propyl)-3-thiophen-3-yl-2,4,5,6,7,8-hexahydro-1,2,6-triaza-azulene; |
| 186 | 2-(1-Ethyl-propyl)-3-phenyl-2,4,5,6,7,8-hexahydro-1,2,6-triaza-azulene; |
| 187 | 3-(4-Chloro-phenyl)-2-(2,2,2-trifluoro-ethyl)-2,4,5,6,7,8-hexahydro-1,2,6-triaza-azulene; |
| 188 | 2-(2,2,2-Trifluoro-ethyl)-3-(4-trifluoromethyl-phenyl)-2,4,5,6,7,8-hexahydro-1,2,6-triaza-azulene; |
| 189 | 2-Isopropyl-3-phenyl-2,4,5,6,7,8-hexahydro-1,2,6-triaza-azulene; |
| 190 | 3-(4-Fluoro-phenyl)-2-isopropyl-2,4,5,6,7,8-hexahydro-1,2,6-triaza-azulene; |
| 191 | 2-(1-Ethyl-propyl)-3-thiophen-2-yl-2,4,5,6,7,8-hexahydro-1,2,6-triaza-azulene; |
| 192 | 2-Cyclopentyl-3-thiophen-3-yl-2,4,5,6,7,8-hexahydro-1,2,6-triaza-azulene; |
| 193 | 2-Ethyl-3-phenyl-2,4,5,6,7,8-hexahydro-1,2,6-triaza-azulene; |
| 194 | 2-Ethyl-3-(4-fluoro-phenyl)-2,4,5,6,7,8-hexahydro-1,2,6-triaza-azulene; |
| 195 | 2-Ethyl-3-thiophen-2-yl-2,4,5,6,7,8-hexahydro-1,2,6-triaza-azulene; |
| 196 | 2-(3-Chloro-phenyl)-3-phenyl-2,4,5,6,7,8-hexahydro-1,2,6-triaza-azulene; |
| 197 | 2-(3-Fluoro-phenyl)-3-phenyl-2,4,5,6,7,8-hexahydro-1,2,6-triaza-azulene; |
| 198 | 2-(2-Chloro-phenyl)-3-phenyl-2,4,5,6,7,8-hexahydro-1,2,6-triaza-azulene; |
| 199 | 2-Phenyl-3-thiophen-2-yl-2,4,5,6,7,8-hexahydro-1,2,6-triaza-azulene; |
| 200 | 3-(4-Fluoro-phenyl)-2-phenyl-2,4,5,6,7,8-hexahydro-1,2,6-triaza-azulene; |
| 201 | 3-(4-Chloro-phenyl)-2-phenyl-2,4,5,6,7,8-hexahydro-1,2,6-triaza-azulene; |
| 202 | 3-(3-Chloro-phenyl)-2-phenyl-2,4,5,6,7,8-hexahydro-1,2,6-triaza-azulene; |
| 203 | 2-Phenyl-3-p-tolyl-2,4,5,6,7,8-hexahydro-1,2,6-triaza-azulene; |
| 204 | 2,3-Diphenyl-4,5,6,7-tetrahydro-2H-pyrazolo[4,3-c]pyridine; |
| 205 | 3-Phenyl-2-(3-trifluoromethyl-phenyl)-2,4,5,6,7,8-hexahydro-1,2,6-triaza-azulene; |
| 206 | 3-(4-Methoxy-phenyl)-2-phenyl-2,4,5,6,7,8-hexahydro-1,2,6-triaza-azulene; |
| 207 | 2-(4-Chloro-phenyl)-3-phenyl-2,4,5,6,7,8-hexahydro-1,2,6-triaza-azulene; |
| 208 | 6-Methyl-2,3-diphenyl-2,4,5,6,7,8-hexahydro-1,2,6-triaza-azulene; |
| 209 | 2-Isopropyl-3-p-tolyl-2,4,5,6,7,8-hexahydro-1,2,6-triaza-azulene; |
| 210 | 3-(4-Ethyl-phenyl)-2-isopropyl-2,4,5,6,7,8-hexahydro-1,2,6-triaza-azulene; |
| 211 | 3-(4-Chloro-phenyl)-2-isopropyl-2,4,5,6,7,8-hexahydro-1,2,6-triaza-azulene; |
| 212 | 4-(2-Isopropyl-2,4,5,6,7,8-hexahydro-1,2,6-triaza-azulen-3-yl)-benzonitrile; |
| 213 | 2-Isopropyl-3-(4-trifluoromethyl-phenyl)-2,4,5,6,7,8-hexahydro-1,2,6-triaza-azulene; |
| 214 | 2-Ethyl-3-p-tolyl-2,4,5,6,7,8-hexahydro-1,2,6-triaza-azulene; |
| 215 | 2-tert-Butyl-3-phenyl-2,4,5,6,7,8-hexahydro-1,2,6-triaza-azulene; |
| 216 | 2-tert-Butyl-3-(4-fluoro-phenyl)-2,4,5,6,7,8-hexahydro-1,2,6-triaza-azulene; |
| 217 | 2-Cyclopentyl-3-p-tolyl-2,4,5,6,7,8-hexahydro-1,2,6-triaza-azulene; |
| 218 | 2-Cyclopentyl-3-(4-trifluoromethyl-phenyl)-2,4,5,6,7,8-hexahydro-1,2,6-triaza-azulene; |
| 219 | 3-(3-Chloro-phenyl)-2-cyclopentyl-2,4,5,6,7,8-hexahydro-1,2,6-triaza-azulene; |
| 220 | 2-Cyclopentyl-3-(4-methoxy-phenyl)-2,4,5,6,7,8-hexahydro-1,2,6-triaza-azulene; |
| 221 | 2-(3,3-Dimethyl-cyclopentyl)-3-phenyl-2,4,5,6,7,8-hexahydro-1,2,6-triaza-azulene; |
| 222 | 2-(3,3-Dimethyl-cyclopentyl)-3-(4-fluoro-phenyl)-2,4,5,6,7,8-hexahydro-1,2,6-triaza-azulene; |
| 223 | 3-(4-Chloro-phenyl)-2-(3,3-dimethyl-cyclopentyl)-2,4,5,6,7,8-hexahydro-1,2,6-triaza-azulene; |

-continued

| EX | CHEMICAL NAME |
|---|---|
| 224 | 2-Cyclohexyl-3-(4-fluoro-phenyl)-2,4,5,6,7,8-hexahydro-1,2,6-triaza-azulene; |
| 225 | 2-Cyclohexyl-3-(3,4-difluoro-phenyl)-2,4,5,6,7,8-hexahydro-1,2,6-triaza-azulene; |
| 226 | 2-Cyclohexyl-3-p-tolyl-2,4,5,6,7,8-hexahydro-1,2,6-triaza-azulene; |
| 227 | 2-Cyclohexyl-3-(4-methoxy-phenyl)-2,4,5,6,7,8-hexahydro-1,2,6-triaza-azulene; |
| 228 | 4-(2-Cyclohexyl-2,4,5,6,7,8-hexahydro-1,2,6-triaza-azulen-3-yl)-benzonitrile; |
| 229 | 3-(3-Chloro-phenyl)-2-cyclohexyl-2,4,5,6,7,8-hexahydro-1,2,6-triaza-azulene; |
| 231 | 3-(4-Fluoro-phenyl)-2-isopropyl-4,5,6,7-tetrahydro-2H-pyrazolo[4,3-c]pyridine; |
| 232 | 2-Cyclopentyl-3-furan-3-yl-2,4,5,6,7,8-hexahydro-1,2,6-triaza-azulene; |
| 233 | 2-Cyclopentyl-3-thiophen-2-yl-2,4,5,6,7,8-hexahydro-1,2,6-triaza-azulene; |
| 234 | 2-tert-Butyl-3-thiophen-3-yl-2,4,5,6,7,8-hexahydro-1,2,6-triaza-azulene; |
| 235 | 2-tert-Butyl-3-furan-3-yl-2,4,5,6,7,8-hexahydro-1,2,6-triaza-azulene; |
| 236 | 2-Cyclopentyl-3-(3,4-difluoro-phenyl)-2,4,5,6,7,8-hexahydro-1,2,6-triaza-azulene; |
| 238 | 3-(4-Chloro-phenyl)-2-cyclobutyl-2,4,5,6,7,8-hexahydro-1,2,6-triaza-azulene; |
| 240 | 2-tert-Butyl-3-thiophen-2-yl-2,4,5,6,7,8-hexahydro-1,2,6-triaza-azulene; |
| 241 | 3-(3-Chloro-4-fluoro-phenyl)-2-cyclopentyl-2,4,5,6,7,8-hexahydro-1,2,6-triaza-azulene; |
| 242 | 2-Isopropyl-3-(4-methoxy-phenyl)-2,4,5,6,7,8-hexahydro-1,2,6-triaza-azulene; |
| 243 | 2-Isopropyl-3-(4-trifluoromethoxy-phenyl)-2,4,5,6,7,8-hexahydro-1,2,6-triaza-azulene; |
| 244 | 2-Isopropyl-3-(4-isopropyl-phenyl)-2,4,5,6,7,8-hexahydro-1,2,6-triaza-azulene; |
| 245 | 3-(4-tert-Butyl-phenyl)-2-isopropyl-2,4,5,6,7,8-hexahydro-1,2,6-triaza-azulene; |
| 246 | 2-Isopropyl-3-m-tolyl-2,4,5,6,7,8-hexahydro-1,2,6-triaza-azulene; |
| 247 | 2-Isopropyl-3-o-tolyl-2,4,5,6,7,8-hexahydro-1,2,6-triaza-azulene; |
| 248 | 3-(3,4-Dichloro-phenyl)-2-isopropyl-2,4,5,6,7,8-hexahydro-1,2,6-triaza-azulene; |
| 249 | 2-Benzyl-3-(4-fluoro-phenyl)-2,4,5,6,7,8-hexahydro-1,2,6-triaza-azulene; |
| 250 | 2-Isopropyl-3-thiophen-2-yl-2,4,5,6,7,8-hexahydro-1,2,6-triaza-azulene; |
| 251 | 3-(2-Chloro-phenyl)-2-isopropyl-2,4,5,6,7,8-hexahydro-1,2,6-triaza-azulene; |
| 252 | 1-[4-(2-Isopropyl-2,4,5,6,7,8-hexahydro-1,2,6-triaza-azulen-3-yl)-phenyl]-ethanone; |
| 253 | 2-Isopropyl-3-(4-nitro-phenyl)-2,4,5,6,7,8-hexahydro-1,2,6-triaza-azulene; |
| 256 | 2-Benzyl-3-(4-chloro-phenyl)-2,4,5,6,7,8-hexahydro-1,2,5-triaza-azulene; |
| 257 | 2-Ethyl-3-(4-ethyl-phenyl)-2,4,5,6,7,8-hexahydro-1,2,6-triaza-azulene; |
| 258 | 4-(2-Ethyl-2,4,5,6,7,8-hexahydro-1,2,6-triaza-azulen-3-yl)-benzonitrile; |
| 259 | 3-(4-Fluoro-phenyl)-2-isopropyl-6-methyl-2,4,5,6,7,8-hexahydro-1,2,6-triaza-azulene; |
| 260 | 3-(4-Fluoro-phenyl)-2,6-diisopropyl-2,4,5,6,7,8-hexahydro-1,2,6-triaza-azulene; |
| 261 | 2-Ethyl-3-(4-isopropyl-phenyl)-2,4,5,6,7,8-hexahydro-1,2,6-triaza-azulene; |
| 262 | 2-Ethyl-3-(4-methoxy-phenyl)-2,4,5,6,7,8-hexahydro-1,2,6-triaza-azulene; |
| 263 | 2-Ethyl-3-(4-trifluoromethyl-phenyl)-2,4,5,6,7,8-hexahydro-1,2,6-triaza-azulene; |
| 264 | 2-Ethyl-3-o-tolyl-2,4,5,6,7,8-hexahydro-1,2,6-triaza-azulene; |
| 265 | 3-(2-Chloro-phenyl)-2-ethyl-2,4,5,6,7,8-hexahydro-1,2,6-triaza-azulene; |
| 266 | 2-Ethyl-3-(2-fluoro-phenyl)-2,4,5,6,7,8-hexahydro-1,2,6-triaza-azulene; |
| 267 | 3-(2,4-Dichloro-phenyl)-2-isopropyl-2,4,5,6,7,8-hexahydro-1,2,6-triaza-azulene; |
| 268 | [4-(2-Ethyl-2,4,5,6,7,8-hexahydro-1,2,6-triaza-azulen-3-yl)-phenyl]-dimethyl-amine; |
| 269 | 6-Benzyl-3-(4-fluoro-phenyl)-2-isopropyl-2,4,5,6,7,8-hexahydro-1,2,6-triaza-azulene; |
| 270 | 3-(4-Fluoro-phenyl)-2-isopropyl-6-(3-phenyl-propyl)-2,4,5,6,7,8-hexahydro-1,2,6-triaza-azulene; |
| 271 | 3-(4-Fluoro-phenyl)-2-isopropyl-6-phenethyl-2,4,5,6,7,8-hexahydro-1,2,6-triaza-azulene; and |
| 272 | 3-(4-Fluoro-phenyl)-2-isopropyl-4,5,7,8-tetrahydro-2H-1,2,6-triaza-azulene-6-carboxylic acid tert-butyl ester. |
| 274 | 3-(4'-Chloro-biphenyl-4-yl)-2-(2,2,2-trifluoro-ethyl)-2,4,5,6,7,8-hexahydro-1,2,6-triaza-azulene; |
| 275 | 3-(4'-Chloro-biphenyl-4-yl)-2-cyclopentyl-2,4,5,6,7,8-hexahydro-1,2,6-triaza-azulene; |
| 276 | 2-Cyclobutyl-3-phenyl-2,4,5,6,7,8-hexahydro-1,2,6-triaza-azulene; |
| 277 | 2-Cyclobutyl-3-(4-fluoro-phenyl)-2,4,5,6,7,8-hexahydro-1,2,6-triaza-azulene; |
| 278 | 2-Cyclobutyl-3-p-tolyl-2,4,5,6,7,8-hexahydro-1,2,6-triaza-azulene; |
| 279 | 2-Cyclobutyl-3-(4-trifluoromethyl-phenyl)-2,4,5,6,7,8-hexahydro-1,2,6-triaza-azulene; |
| 280 | 4-(2-Cyclobutyl-2,4,5,6,7,8-hexahydro-1,2,6-triaza-azulen-3-yl)-benzonitrile |
| 281 | 2-Cyclopropyl-3-phenyl-2,4,5,6,7,8-hexahydro-1,2,6-triaza-azulene; |
| 282 | 2-Cyclopropyl-3-(4-fluoro-phenyl)-2,4,5,6,7,8-hexahydro-1,2,6-triaza-azulene; |
| 283 | 2-(1-Ethyl-propyl)-3-(4-fluoro-3-methyl-phenyl)-2,4,5,6,7,8-hexahydro-1,2,6-triaza-azulene; |
| 284 | 2-Cyclopropyl-3-p-tolyl-2,4,5,6,7,8-hexahydro-1,2,6-triaza-azulene; |
| 285 | 2-Cyclopropyl-3-thiophen-3-yl-2,4,5,6,7,8-hexahydro-1,2,6-triaza-azulene; |
| 286 | 4-(2-Cyclopropyl-2,4,5,6,7,8-hexahydro-1,2,6-triaza-azulen-3-yl)-benzonitrile; |
| 287 | 6-Benzyl-2-isopropyl-3-phenyl-4,5,6,7-tetrahydro-2H-pyrazolo[3,4-c]pyridine; |
| 288 | 2-Isopropyl-3-phenyl-4,5,6,7-tetrahydro-2H-pyrazolo[3,4-c]pyridine; |

| EX | CHEMICAL NAME |
|---|---|
| 289 | 6-Benzyl-2-isopropyl-3-thiophen-3-yl-4,5,6,7-tetrahydro-2H-pyrazolo[3,4-c]pyridine; |
| 290 | 6-Benzyl-2-isopropyl-3-p-tolyl-4,5,6,7-tetrahydro-2H-pyrazolo[3,4-c]pyridine. |
| 291 | 6-Benzyl-3-(4-fluoro-phenyl)-2-isopropyl-4,5,6,7-tetrahydro-2H-pyrazolo[3,4-c]pyridine; |
| 292 | 3-(4-Fluoro-phenyl)-2-isopropyl-4,5,6,7-tetrahydro-2H-pyrazolo[3,4-c]pyridine; |
| 293 | 2-Isopropyl-3-p-tolyl-4,5,6,7-tetrahydro-2H-pyrazolo[3,4-c]pyridine; |
| 294 | 2-Cyclopentyl-3-(4-fluoro-phenyl)-5,5,7,7-tetramethyl-2,4,5,6,7,8-hexahydro-1,2,6-triaza-azulene; |
| 295 | 2-Cyclopentyl-5,5,7,7-tetramethyl-3-phenyl-2,4,5,6,7,8-hexahydro-1,2,6-triaza-azulene; |
| 296 | 2-Isopropyl-5,5,7,7-tetramethyl-3-phenyl-2,4,5,6,7,8-hexahydro-1,2,6-triaza-azulene; |
| 297 | 3-(4-Fluoro-phenyl)-2-isopropyl-5,5,7,7-tetramethyl-2,4,5,6,7,8-hexahydro-1,2,6-triaza-azulene; |
| 298 | 2-sec-Butyl-3-phenyl-2,4,5,6,7,8-hexahydro-1,2,6-triaza-azulene; |
| 299 | 2-sec-Butyl-3-(4-fluoro-phenyl)-2,4,5,6,7,8-hexahydro-1,2,6-triaza-azulene; |
| 300 | 2-sec-Butyl-3-p-tolyl-2,4,5,6,7,8-hexahydro-1,2,6-triaza-azulene; |
| 301 | 2-sec-Butyl-3-(4-trifluoromethyl-phenyl)-2,4,5,6,7,8-hexahydro-1,2,6-triaza-azulene; |
| 302 | 2-Cyclopentyl-3-(4-fluoro-phenyl)-6-methyl-2,4,5,6,7,8-hexahydro-1,2,6-triaza-azulene; |
| 303 | 4-(2-Isopropyl-2,4,5,6,7,8-hexahydro-1,2,6-triaza-azulen-3-yl)-benzamide; |
| 304 | 2-Isopropyl-3-[4-(1H-tetrazol-5-yl)-phenyl]-2,4,5,6,7,8-hexahydro-1,2,6-triaza-azulene; |
| 305 | 6-Benzyl-3-(4-fluoro-phenyl)-2-isopropyl-8-methyl-2,4,5,6,7,8-hexahydro-1,2,6-triaza-azulene; |
| 306 | 3-(4-Fluoro-phenyl)-2-isopropyl-8-methyl-2,4,5,6,7,8-hexahydro-1,2,6-triaza-azulene; |
| 307 | 3-(4-Fluoro-phenyl)-2-isopropyl-4-methyl-2,4,5,6,7,8-hexahydro-1,2,6-triaza-azulene; |
| 308 | 2-Cyclopentyl-3-(4-fluoro-phenyl)-7-methyl-2,4,5,6,7,8-hexahydro-1,2,6-triaza-azulene; |
| 309 | 2-Cyclopentyl-3-(4-fluoro-phenyl)-5-methyl-2,4,5,6,7,8-hexahydro-1,2,6-triaza-azulene; |
| 310 | 2-Cyclopentyl-7-methyl-3-p-tolyl-2,4,5,6,7,8-hexahydro-1,2,6-triaza-azulene; |
| 311 | 2-Isopropyl-7-methyl-3-phenyl-2,4,5,6,7,8-hexahydro-1,2,6-triaza-azulene; |
| 312 | 2-Isopropyl-5-methyl-3-phenyl-2,4,5,6,7,8-hexahydro-1,2,6-triaza-azulene; |
| 313 | 3-(4-Fluoro-phenyl)-2-isopropyl-7-methyl-2,4,5,6,7,8-hexahydro-1,2,6-triaza-azulene; |
| 314 | 3-(4-Fluoro-phenyl)-2-isopropyl-5-methyl-2,4,5,6,7,8-hexahydro-1,2,6-triaza-azulene; |
| 315 | 2-Isopropyl-7-methyl-3-p-tolyl-2,4,5,6,7,8-hexahydro-1,2,6-triaza-azulene; |
| 318 | 3-(4-Chloro-phenyl)-2-pyridin-2-ylmethyl-1,4,5,6,7,8-hexahydro-1,2,6-triaza-azulene; |
| 327 | 3-[3-(4-Chloro-phenyl)-5,6,7,8-tetrahydro-4H-1,2,6-triaza-azulen-2-yl]-propionitrile; |
| 328 | 3-(4-Chloro-phenyl)-2-cycloheptyl-2,4,5,6,7,8-hexahydro-1,2,6-triaza-azulene; |
| 329 | 3-(4-Chloro-phenyl)-2-cyclooctyl-2,4,5,6,7,8-hexahydro-1,2,6-triaza-azulene; |
| 330 | 3-(4-Chloro-phenyl)-2-(4-methyl-cyclohexyl)-2,4,5,6,7,8-hexahydro-1,2,6-triaza-azulene; |
| 331 | 2-Benzyl-3-(4-chloro-phenyl)-2,4,5,6-tetrahydro-pyrrolo[3,4-c]pyrazole; and |
| 338 | 3-(4-Fluoro-phenyl)-2-isopropyl-5,7-dimethyl-2,4,5,6,7,8-hexahydro-1,2,6-triaza-azulene. |

In another embodiment of the present invention, preferred compounds are selected from the group consisting of:

| EX | CHEMICAL NAME |
|---|---|
| 59 | 1-Benzyl-3-(4-chloro-phenyl)-1,4,5,6,7,8-hexahydro-1,2,6-triaza-azulene; |
| 74 | 3-(4-Chloro-phenyl)-1-(3-methyl-benzyl)-1,4,5,6,7,8-hexahydro-1,2,6-triaza-azulene; |
| 75 | 3-(4-Chloro-phenyl)-1-(4-fluoro-benzyl)-1,4,5,6,7,8-hexahydro-1,2,6-triaza-azulene; |
| 76 | 3-(4-Chloro-phenyl)-1-(3-fluoro-benzyl)-1,4,5,6,7,8-hexahydro-1,2,6-triaza-azulene; |
| 103 | 3-(4-Chloro-phenyl)-1-thiophen-2-ylmethyl-1,4,5,6,7,8-hexahydro-1,2,6-triaza-azulene; |
| 104 | 1-Benzyl-3-thiophen-2-yl-1,4,5,6,7,8-hexahydro-1,2,6-triaza-azulene; |
| 108 | 3-(4-Chloro-phenyl)-1-(2,4-difluoro-benzyl)-1,4,5,6,7,8-hexahydro-1,2,6-triaza-azulene; |
| 160 | 4-[3-(4-Chloro-phenyl)-5,6,7,8-tetrahydro-4H-1,2,6-triaza-azulen-1-ylmethyl]-2-fluoro-phenol; |
| 165 | 1-Benzyl-3-(4-chloro-phenyl)-6-methyl-1,4,5,6,7,8-hexahydro-1,2,6-triaza-azulene; |
| 166 | 1-Benzyl-3-(4-chloro-phenyl)-6-ethyl-1,4,5,6,7,8-hexahydro-1,2,6-triaza-azulene; |
| 214 | 2-Ethyl-3-p-tolyl-2,4,5,6,7,8-hexahydro-1,2,6-triaza-azulene; |
| 257 | 2-Ethyl-3-(4-ethyl-phenyl)-2,4,5,6,7,8-hexahydro-1,2,6-triaza-azulene; and |
| 273 | 1-Benzyl-3-(4-chloro-phenyl)-1,4,5,6,7,8-hexahydro-1,2,6-triaza-azulene citrate salt. |

In still another embodiment of the present invention, preferred compounds are selected from the group consisting of:

| EX | CHEMICAL NAME |
|---|---|
| 131 | 3-(4-Chloro-phenyl)-2-isobutyl-2,4,5,6,7,8-hexahydro-1,2,6-triaza-azulene; |
| 133 | 2-Benzyl-3-phenyl-2,4,5,6,7,8-hexahydro-1,2,6-triaza-azulene; |
| 177 | 2-Cyclohexyl-3-phenyl-2,4,5,6,7,8-hexahydro-1,2,6-triaza-azulene; |

-continued

| EX | CHEMICAL NAME |
|---|---|
| 178 | 3-(4-Chloro-phenyl)-2-cyclohexyl-2,4,5,6,7,8-hexahydro-1,2,6-triaza-azulene; |
| 181 | 3-(4-Chloro-phenyl)-2-cyclopentyl-2,4,5,6,7,8-hexahydro-1,2,6-triaza-azulene; |
| 182 | 2-Cyclopentyl-3-(4-fluoro-phenyl)-2,4,5,6,7,8-hexahydro-1,2,6-triaza-azulene; |
| 183 | 2-(1-Ethyl-propyl)-3-(3-fluoro-phenyl)-2,4,5,6,7,8-hexahydro-1,2,6-triaza-azulene; |
| 184 | 2-(1-Ethyl-propyl)-3-(4-fluoro-phenyl)-2,4,5,6,7,8-hexahydro-1,2,6-triaza-azulene; |
| 186 | 2-(1-Ethyl-propyl)-3-phenyl-2,4,5,6,7,8-hexahydro-1,2,6-triaza-azulene; |
| 191 | 2-(1-Ethyl-propyl)-3-thiophen-2-yl-2,4,5,6,7,8-hexahydro-1,2,6-triaza-azulene; |
| 215 | 2-tert-Butyl-3-phenyl-2,4,5,6,7,8-hexahydro-1,2,6-triaza-azulene; |
| 216 | 2-tert-Butyl-3-(4-fluoro-phenyl)-2,4,5,6,7,8-hexahydro-1,2,6-triaza-azulene; |
| 217 | 2-Cyclopentyl-3-p-tolyl-2,4,5,6,7,8-hexahydro-1,2,6-triaza-azulene; |
| 218 | 2-Cyclopentyl-3-(4-trifluoromethyl-phenyl)-2,4,5,6,7,8-hexahydro-1,2,6-triaza-azulene; |
| 220 | 2-Cyclopentyl-3-(4-methoxy-phenyl)-2,4,5,6,7,8-hexahydro-1,2,6-triaza-azulene; |
| 236 | 2-Cyclopentyl-3-(3,4-difluoro-phenyl)-2,4,5,6,7,8-hexahydro-1,2,6-triaza-azulene; |
| 238 | 3-(4-Chloro-phenyl)-2-cyclobutyl-2,4,5,6,7,8-hexahydro-1,2,6-triaza-azulene; |
| 241 | 3-(3-Chloro-4-fluoro-phenyl)-2-cyclopentyl-2,4,5,6,7,8-hexahydro-1,2,6-triaza-azulene; |
| 242 | 2-Isopropyl-3-(4-methoxy-phenyl)-2,4,5,6,7,8-hexahydro-1,2,6-triaza-azulene; |
| 277 | 2-Cyclobutyl-3-(4-fluoro-phenyl)-2,4,5,6,7,8-hexahydro-1,2,6-triaza-azulene; |
| 278 | 2-Cyclobutyl-3-p-tolyl-2,4,5,6,7,8-hexahydro-1,2,6-triaza-azulene; |
| 279 | 2-Cyclobutyl-3-(4-trifluoromethyl-phenyl)-2,4,5,6,7,8-hexahydro-1,2,6-triaza-azulene; |
| 284 | 2-Cyclopropyl-3-p-tolyl-2,4,5,6,7,8-hexahydro-1,2,6-triaza-azulene; |
| 300 | 2-sec-Butyl-3-p-tolyl-2,4,5,6,7,8-hexahydro-1,2,6-triaza-azulene; |
| 302 | 2-Cyclopentyl-3-(4-fluoro-phenyl)-6-methyl-2,4,5,6,7,8-hexahydro-1,2,6-triaza-azulene; |
| 306 | 3-(4-Fluoro-phenyl)-2-isopropyl-8-methyl-2,4,5,6,7,8-hexahydro-1,2,6-triaza-azulene; and |
| 310 | 2-Cyclopentyl-7-methyl-3-p-tolyl-2,4,5,6,7,8-hexahydro-1,2,6-triaza-azulene. |

In yet another embodiment of the present invention preferred compounds are selected from the group consisting of:

| EX | CHEMICAL NAME |
|---|---|
| 47 | 1-Benzyl-3-(4-fluoro-phenyl)-1,4,5,6,7,8-hexahydro-1,2,6-triaza-azulene; |
| 64 | 3-(4-Chloro-phenyl)-2-ethyl-2,4,5,6,7,8-hexahydro-1,2,6-triaza-azulene; |
| 118 | 3-(4-Chloro-phenyl)-1-isobutyl-1,4,5,6,7,8-hexahydro-1,2,6-triaza-azulene; |
| 180 | 2-Cyclopentyl-3-phenyl-2,4,5,6,7,8-hexahydro-1,2,6-triaza-azulene; |
| 190 | 3-(4-Fluoro-phenyl)-2-isopropyl-2,4,5,6,7,8-hexahydro-1,2,6-triaza-azulene; |
| 192 | 2-Cyclopentyl-3-thiophen-3-yl-2,4,5,6,7,8-hexahydro-1,2,6-triaza-azulene; |
| 209 | 2-Isopropyl-3-p-tolyl-2,4,5,6,7,8-hexahydro-1,2,6-triaza-azulene; |
| 210 | 3-(4-Ethyl-phenyl)-2-isopropyl-2,4,5,6,7,8-hexahydro-1,2,6-triaza-azulene; |
| 211 | 3-(4-Chloro-phenyl)-2-isopropyl-2,4,5,6,7,8-hexahydro-1,2,6-triaza-azulene; |
| 212 | 4-(2-Isopropyl-2,4,5,6,7,8-hexahydro-1,2,6-triaza-azulen-3-yl)-benzonitrile; |
| 213 | 2-Isopropyl-3-(4-trifluoromethyl-phenyl)-2,4,5,6,7,8-hexahydro-1,2,6-triaza-azulene; |
| 232 | 2-Cyclopentyl-3-furan-3-yl-2,4,5,6,7,8-hexahydro-1,2,6-triaza-azulene; |
| 233 | 2-Cyclopentyl-3-thiophen-2-yl-2,4,5,6,7,8-hexahydro-1,2,6-triaza-azulene; |
| 284 | 2-Cyclopropyl-3-p-tolyl-2,4,5,6,7,8-hexahydro-1,2,6-triaza-azulene; |
| 300 | 2-sec-Butyl-3-p-tolyl-2,4,5,6,7,8-hexahydro-1,2,6-triaza-azulene; and |
| 315 | 2-Isopropyl-7-methyl-3-p-tolyl-2,4,5,6,7,8-hexahydro-1,2,6-triaza-azulene. |

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

The fused heterocyclic compounds of formulas (I), (II), and (III) may be prepared by a number of reaction schemes. Access to compounds of formula (I) is described in Scheme 1. Preparation of compounds of formula (II) is described in Schemes 2, 3, 5, and 6. Synthesis of compounds of formula (III) is shown in Schemes 3 and 4. Persons skilled in the art will recognize that certain compounds are more advantageously produced by one scheme as compared to the other.

Scheme 1

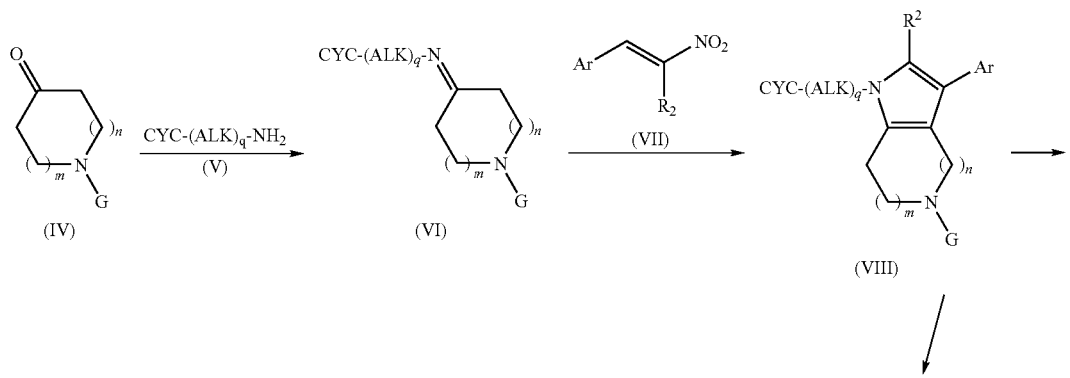

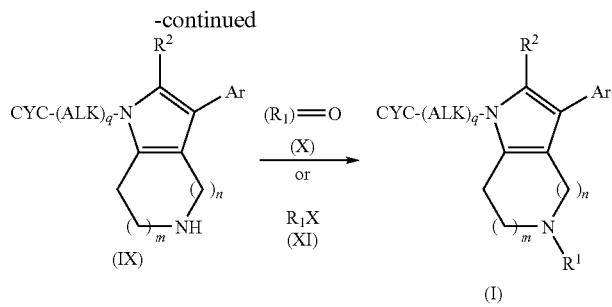

Referring to Scheme 1, compounds of formula (I) may be prepared from compounds of formula (IV). The amine moiety in compounds of formula (IV) can be suitably protected, shown by substituent G, as an alkyl or benzyl amine, amide, carbamate or other groups such as those described in "Protecting Groups In Organic Synthesis", $3^{rd}$ ed.; T. W. Greene and P. G. M. Wuts, John Wiley & Sons, 1999 (G is —$C_{1-6}$alkyl, —$COOC_{1-6}$alkyl, —(C=O)$C_{1-6}$alkyl, or benzyl unsubstituted or substituted with —$OC_{1-6}$alkyl or —$C_{1-6}$alkyl). A preferred protecting group would be the t-butyl carbamate (Boc) group. The carbonyl functional group of compound (IV) can be treated with a primary amine of type (V), in a suitable solvent like THF, toluene, benzene, methanol or ethanol at temperatures between 20 and 110° C. with removal of water by either Dean-Stark apparatus or by the addition of a dehydrating agent such as $SiO_2$, $MgSO_4$, $CuSO_4$, Ti(O-iPr)$_4$ or 4 Å molecular sieves to form the corresponding imines of type (VI). Preferred solvents are toluene and ethanol with preferred dehydrating agents being $SiO_2$ and 4 Å molecular sieves. One skilled in the art would recognize that the imines of type (VI) might exist as more than one tautomeric form. Compounds of type (VI) can then be treated with a nitro olefin of type (VII) to give pyrrole compounds of formula (VIII). One skilled in the art would recognize that imines of formula (VI), existing as more that one enamine tautomer, would give rise to regioisomers upon treatment with a nitro olefin of type (VII) depending on the structure of the compound of formula (IV). The protecting group on the nitrogen can either be removed using generally accepted methods or, depending on the type of group involved, can be converted directly to compounds of formula (I). More specifically, a group such as a t-butyl carbamate can be removed with an acid like trifluoroacetic acid or hydrochloric acid and the like in a solvent such as $CH_2Cl_2$, ethanol or methanol to afford compounds of formula (IX). It will be generally recognized that compounds of formula (IX) represent a subset of compounds of formula (I) wherein $R^1$ is equal to H. Compounds of formula (IX) and (I) may be converted to their corresponding salts using methods known to those skilled in the art.

Compounds such as (I) can be prepared from compounds of type (IX) using conventional synthetic methods such as alkylation or reductive amination. Thus, treatment of compounds of formula (IX) with a compound of formula (X) containing a carbonyl group in the presence of a reductant such as $NaBH_4$, $NaBH_3CN$, $NaBH(OAc)_3$ or hydrogen gas in the presence of a catalyst in a solvent such as $CH_2Cl_2$, DCE, THF, ethanol, methanol or similar will afford compounds of formula (I). One skilled in the art will recognize that the addition of acid to decrease the pH of the reaction mixture to less than pH 7 may be required. Examples of acids may include AcOH, Ti(O-iPr)$_4$, trifluoroacetic acid or hydrochloric acid and the like. In addition, compounds such as (IX) can be treated with an alkylating agent of type (XI). For example, treatment with an alkyl chloride, bromide, iodide, mesylate or tosylate (wherein X is Cl, Br, I, OMs, OTs, or the like) in solvent such as DMF, DMA, THF or ethanol and in the presence of a base like $NaHCO_3$, $Na_2CO_3$, $K_2CO_3$ or $Cs_2CO_3$ will give compounds of formula (I).

Scheme 2

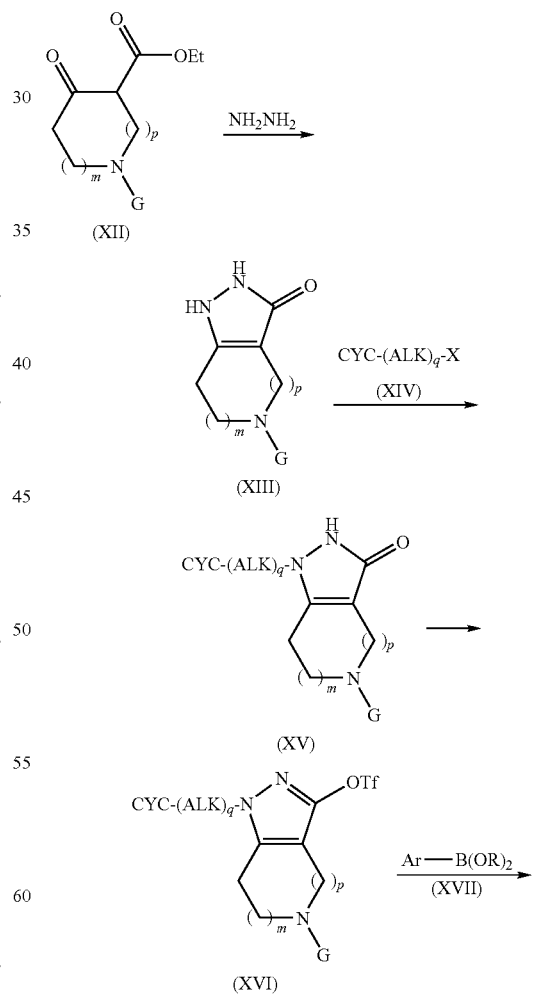

-continued

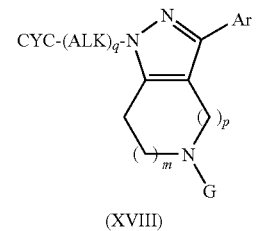

(XVIII)

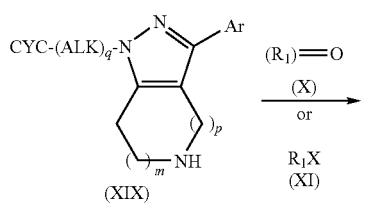

(XIX)

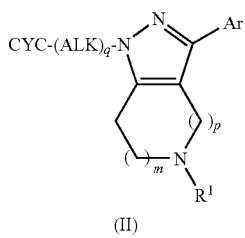

(II)

Referring to Scheme 2, compounds of formula (II) can be prepared from compounds of formula (XII). As in Scheme 1, the amine moiety in compounds of formula (XII) can be suitably protected, shown by substituent G, as an alkyl or benzyl amine, amide, carbamate or other groups such as those described in "Protecting Groups In Organic Synthesis", 3$^{rd}$ ed.; T. W. Greene and P. G. M. Wuts, John Wiley & Sons, 1999. A preferred protecting group would be the t-butyl carbamate (Boc) group. The condensation of hydrazine with compounds of formula (XII) in a solvent like methanol, ethanol, isopropanol or t-butyl alcohol at temperatures from 20 to 80° C. will form compounds of type (XIII). One skilled it the art will recognize that compounds of formula (XIII) may exist in more that one resonance form. More specifically, compounds of formula (XIII) are tautomeric with the corresponding 3-hydroxypyrazoles. Compounds such as (XIII) can be treated with an alkylating agent such as formula (XIV) to afford compounds of type (XV). For example, treatment with an alkyl or benzyl chloride, bromide, iodide, mesylate or tosylate (wherein X is Cl, Br, I, OMs, OTs, or the like) in DMF, DMA, THF or ethanol in the presence of a base like NaHCO$_3$, Na$_2$CO$_3$, K$_2$CO$_3$, NaH, potassium tert-butoxide, or Cs$_2$CO$_3$ will afford compounds of formula (XV). One skilled in the art will recognize that the alkylation of compounds of formula (XIII) may give rise to regioisomers. Compounds of type (XV) can be converted into a precursor for transition metal-catalyzed cross-coupling reactions, such as Stille, Suzuki, Negishi or other such coupling reactions known to one skilled in the art. For example, treatment with POCl$_3$, PCl$_3$, PCl$_5$, PBr$_3$ or POBr$_3$ can afford the corresponding 3-halopyrazoles. A preferred method would involve treatment with a triflating agent such as trifluoromethanesulfonic anhydride or N-phenyltrifluoromethanesulfonimide in DCE, CH$_2$Cl$_2$, THF or the like in the presence of a base like pyridine, triethylamine or diisopropylethylamine to provide pyrazole triflates of formula (XVI). Treatment of triflates of formula (XVI) with an organoboron compound of formula (XVII) in the presence of a catalyst like Pd(PPh$_3$)$_4$, PdCl$_2$(PPh$_3$)$_2$, PdCl$_2$(Po-tol$_3$)$_2$, PdCl$_2$(dppe) or PdCl$_2$(dppf) in a solvent such as THF, 1,4-dioxane, DMA, DMF, DME, toluene, toluene/ethanol, or toluene/H$_2$O mixtures, in the presence of a base such as Na$_2$CO$_3$, K$_2$CO$_3$, Cs$_2$CO$_3$, K$_3$PO$_4$, KF, CsF, KOAc or the like will afford compounds of formula (XVIII). Preferred catalysts are Pd(PPh$_3$)$_4$ and PdCl$_2$(dppf), with or without additives such as dppf and catalytic Bu$_4$NBr. Preferred solvents include THF, 1,4-dioxane, toluene, and toluene/H$_2$O mixtures with preferred bases being Na$_2$CO$_3$, K$_2$CO$_3$, Cs$_2$CO$_3$, and K$_3$PO$_4$. The protecting group on the nitrogen of compounds of formula (XVIII) may be removed using generally accepted methods, which one skilled in the art would recognize. More specifically, a group such as a t-butyl carbamate can be removed with an acid like trifluoroacetic acid or hydrochloric acid and the like in a solvent such as CH$_2$Cl$_2$, ethanol or methanol to afford compounds of formula (XIX). Compounds of formula (XIX) or (II) may be converted to their corresponding salts using methods known to those skilled in the art. For example, amines of formula (XIX) can be treated with citric acid in a solvent such as methanol to provide the corresponding citrate salt. It will be generally recognized that compounds of formula (XIX) represent a subset of compounds of formula (II) wherein R$^1$ is equal to H.

Compounds such as (II) can be prepared from compounds of type (XIX) using conventional synthetic methods such as alkylation or reductive amination. Thus, treatment of compounds of formula (XIX) with a compound of formula (X) containing a carbonyl group in the presence of a reductant such as NaBH$_4$, NaBH$_3$CN, NaBH(OAc)$_3$ or hydrogen gas in the presence of a catalyst in a solvent such as CH$_2$Cl$_2$, DCE, THF, ethanol, methanol or similar will afford compounds of formula (II). One skilled in the art will recognize that the addition of acid to decrease the pH of the reaction mixture to less than pH 7 may be required. Examples of acids may include AcOH, Ti(O-iPr)$_4$, trifluoroacetic acid or hydrochloric acid and the like. In addition, compounds such as (XIX) can be treated with an alkylating agent of type (XI). For example, treatment with an alkyl chloride, bromide, iodide, mesylate or tosylate (wherein X is Cl, Br, I, OMs, OTs, or the like) in solvent such as DMF, DMA, THF or ethanol and in the presence of a base like NaHCO$_3$, Na$_2$CO$_3$, K$_2$CO$_3$ or Cs$_2$CO$_3$ will give compounds of formula (II).

Scheme 3

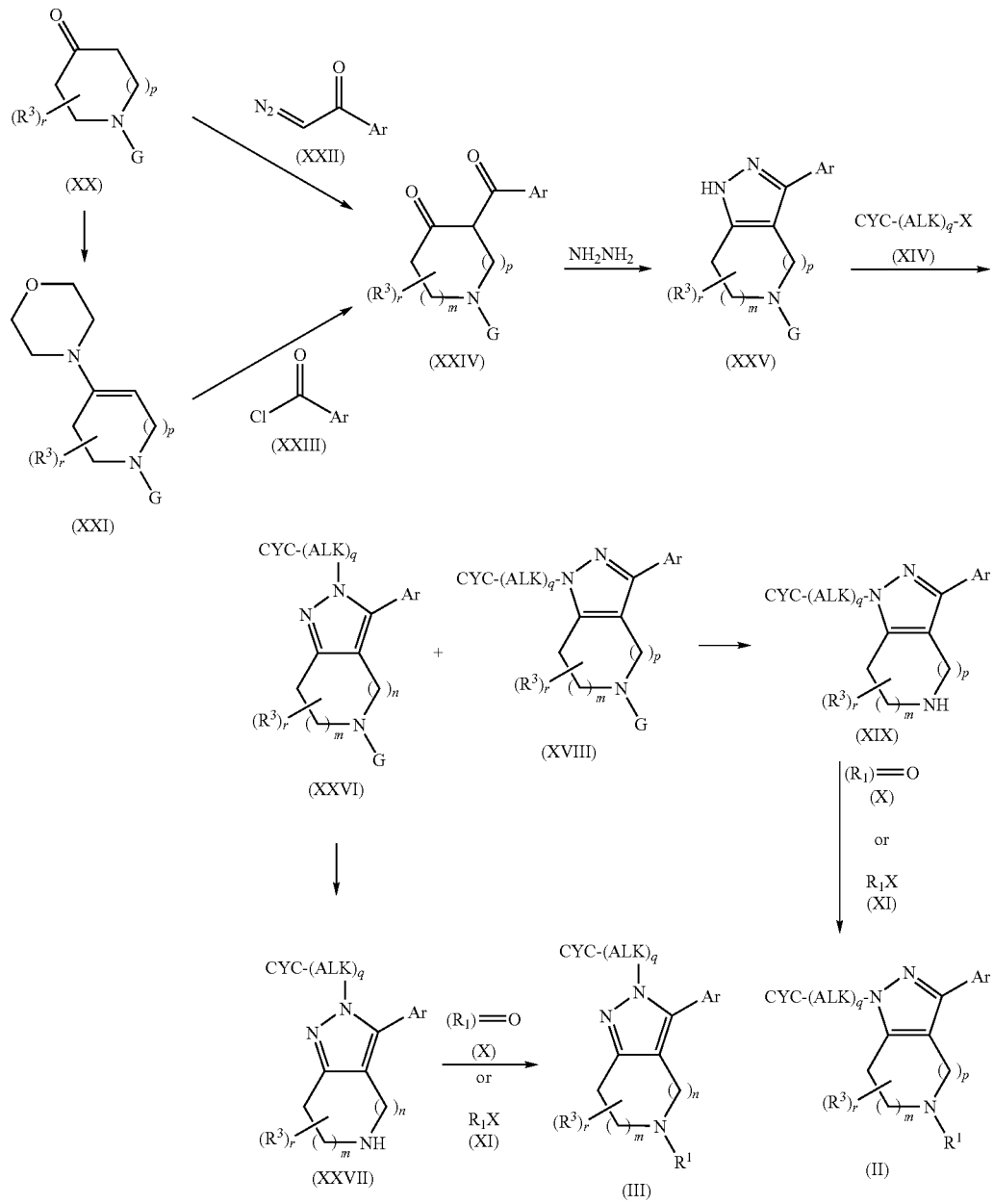

Referring to Scheme 3, compounds of formula (II), (III), (XXVII), and (XXVIII) can be prepared as described. The amine moiety in compounds of formula (XX) can be suitably protected, shown by substituent G, as an alkyl or benzyl amine, amide, carbamate or other groups such as those described in "Protecting Groups In Organic Synthesis", 3$^{rd}$ ed.; T. W. Greene and P. G. M. Wuts, John Wiley & Sons, 1999. A preferred protecting group would be the t-butyl carbamate (Boc) group. The carbonyl functional group of compound (XX) can be treated with a saturated secondary amine, such as morpholine, in a suitable solvent like toluene or benzene at temperatures between 20 and 110° C. with removal of water by a Dean-Stark apparatus with or without an acid catalyst such as TsOH, will afford the corresponding enamines of type (XXI). One skilled in the art would recognize that enamines of type (XXI) might exist as more that one enamine regioisomer depending on the structure of the compound of formula (XX). Treatment of enamines (XXI) with a benzoyl chloride will afford the diketone compounds of formula (XXIV). Additionally, the carbonyl functional group of compound (XX) can be treated with a diazoketone in the presence of a Lewis acid, such as BF$_3$, to give the diketone compounds (XXIV) directly. The condensation of hydrazine with compounds of formula (XXIV) in a solvent like methanol, ethanol, isopropanol or t-butyl alcohol at temperatures from 20 to 80° C. will form pyrazole compounds of type (XXV). Compounds such as (XXV) can be treated with an alkylating agent of formula (XIV). For example, treatment with an alkyl or benzyl chloride, bromide, iodide, mesylate or tosylate (wherein X is Cl, Br, I, OMs, OTs or the like) in DMF, DMA, THF or ethanol in the presence of a base like NaHCO$_3$, Na$_2$CO$_3$, NaH, potassium tert-butoxide, K$_2$CO$_3$ or Cs$_2$CO$_3$ will afford a mixture of compounds of formula (XXVI) and (XVIII). One skilled in art would recognize that a mixture of compounds of formula (XXVI) and (XVIII) may be separated by chromatographic or crystallization techniques. The protecting group on the nitrogen may be removed using generally accepted methods, which one skilled in the art would recognize. More specifically, a group such as a t-butyl carbamate can be removed from compounds of formula (XXVI) and (XVIII) with an acid like trifluoroacetic acid or hydrochloric acid and the like in a solvent such as CH$_2$Cl$_2$, ethanol or methanol to afford compounds of formula (XXVII) and (XIX) respectively. Compounds of formula (XXVII), (XIX), (II), or (111) may be converted to their corresponding salts using methods known to those skilled in the art. It will be generally recognized that compounds of formula (XXVII) and (XIX) represent subsets of compounds of formula (III) and (II) respectively, wherein R$^1$ is equal to H.

Compounds such as (II) and (III) can be prepared from compounds of formula (XIX) and (XXVII) respectively, using conventional synthetic methods such as alkylation or reductive amination. Thus, treatment of compounds of formula (XIX) with a compound of formula (X) containing a carbonyl group in the presence of a reductant such as NaBH$_4$, NaBH$_3$CN, NaBH(OAc)$_3$ or hydrogen gas in the presence of a catalyst in a solvent such as CH$_2$Cl$_2$, DCE, THF, ethanol, methanol or similar will afford compounds of formula (II). One skilled in the art will recognize that the addition of acid to decrease the pH of the reaction mixture to less than pH 7 may be required. Examples of acids may include AcOH, Ti(O-iPr)$_4$, trifluoroacetic acid or hydrochloric acid and the like. In addition, compounds such as (XIX) can be treated with an alkylating agent of type (XI). For example, treatment with an alkyl chloride, bromide, iodide, mesylate or tosylate (wherein X is Cl, Br, I, OMs, OTs, or the like) in solvent such as DMF, DMA, THF or ethanol in the presence of a base like NaHCO$_3$, Na$_2$CO$_3$, K$_2$CO$_3$ or Cs$_2$CO$_3$ will give compounds of formula (II).

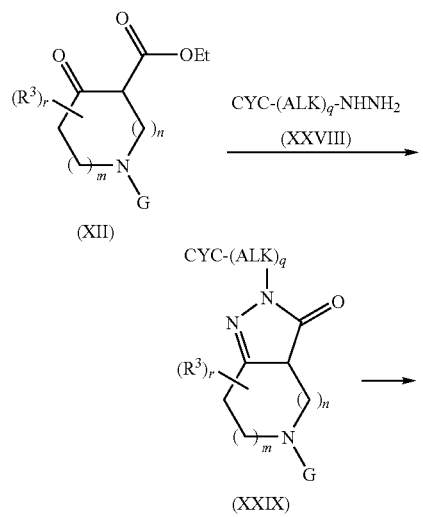

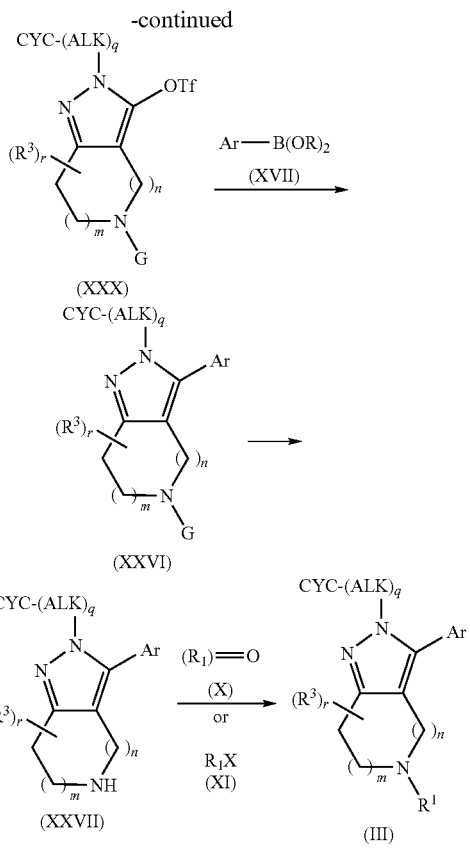

Referring to Scheme 4, compounds of formula (III) can be prepared as outlined. The amine moiety in compounds of formula (XII) can be suitably protected, shown by substituent G, as an alkyl or benzyl amine, amide, carbamate or other groups such as those described in "Protecting Groups In Organic Synthesis", 3$^{rd}$ ed.; T. W. Greene and P. G. M. Wuts, John Wiley & Sons, 1999. The condensation of an alkyl or aryl hydrazine of type (XXVIII), or the salt thereof, with compounds of formula (XII) in a solvent like methanol, ethanol, isopropanol or t-butyl alcohol at temperatures from 20 to 80° C. with or without a base such as NaHCO$_3$, Na$_2$CO$_3$, K$_2$CO$_3$, Cs$_2$CO$_3$, triethylamine or diisopropylethylamine will afford compounds of formula (XXIX). Preferred solvents are ethanol and t-butyl alcohol with preferred bases being triethylamine and diisopropylethylamine. Compounds of formula (XXIX) can be converted into a precursor for transition metal-catalyzed cross-coupling reactions, such as Stille, Suzuki, Negishi or other such coupling reactions known to one skilled in the art. For example, treatment with POCl$_3$, PCl$_3$, PCl$_5$, PBr$_3$ or POBr$_3$ can afford the corresponding 3-halopyrazoles. A preferred method would involve treatment with a triflating agent such as trifluoromethanesulfonic anhydride or N-phenyltrifluoromethanesulfonimide in DCE, CH$_2$Cl$_2$, THF or the like in the presence of a base like pyridine, triethylamine or diisopropylethylamine to provide pyrazole triflates of formula (XXX). Treatment of triflates of formula (XXX) with an organoboron compound of formula (XVII) in the presence of a catalyst like Pd(PPh$_3$)$_4$, PdCl$_2$(PPh$_3$)$_2$, PdCl$_2$(Po-tol$_3$)$_2$, PdCl$_2$(dppe) or PdCl$_2$(dppf) in a solvent such as THF, 1,4-dioxane, DMA, DMF, DME, toluene, toluene/ethanol, or toluene/H$_2$O mixtures, in the presence of a base such as Na$_2$CO$_3$, K$_2$CO$_3$, Cs$_2$CO$_3$, K$_3$PO$_4$, KF, CsF, KOAc or the like will afford compounds of formula (XXVI). Preferred catalysts are Pd(PPh$_3$)$_4$ and PdCl$_2$(dppf), with or without additives such as dppf and catalytic Bu$_4$NBr. Preferred solvents are THF, 1,4-dioxane, toluene, and toluene/H$_2$O mixtures with preferred bases being Na$_2$CO$_3$, K$_2$CO$_3$, Cs$_2$CO$_3$, and K$_3$PO$_4$. The protecting group on the nitrogen of compounds of formula (XXVI) may be removed using generally accepted methods, which one skilled in the art would recognize. More specifically, a group such as a t-butyl carbamate can be removed with an acid like trifluoroacetic acid or hydrochloric acid and the like in a solvent such as CH$_2$Cl$_2$, ethanol or methanol to afford compounds of formula (XXVII). Compounds of formula (XXVII) or (III) may be converted to their corresponding salts using methods known to those skilled in the art. It will be generally recognized that compounds of formula (XXVII) represent a subset of compounds of formula (III) wherein R$^1$ is equal to H.

Compounds such as (III) can be prepared from compounds of type (XXVII) using conventional synthetic methods such as alkylation or reductive amination. Thus, treatment of compounds of formula (XXVII) with a compound of formula (X) containing a carbonyl group in the presence of a reductant such as NaBH$_4$, NaBH$_3$CN, NaBH(OAc)$_3$ or hydrogen gas in the presence of a catalyst in a solvent such as CH$_2$Cl$_2$, DCE, THF, ethanol, methanol or similar will afford compounds of formula (III). One skilled in the art will recognize that the addition of acid to decrease the pH of the reaction mixture to less than pH 7 may be required. Examples of acids may include AcOH, Ti(O-iPr)$_4$, trifluoroacetic acid or hydrochloric acid and the like. In addition, compounds such as (XXVII) can be treated with an alkylating agent of type (XI). For example, treatment with an alkyl chloride, bromide, iodide, mesylate or tosylate (wherein X is Cl, Br, I, OMs, OTs, or the like) in solvent such as DMF, DMA, THF or ethanol in the presence of a base like NaHCO$_3$, Na$_2$CO$_3$, K$_2$CO$_3$ or Cs$_2$CO$_3$ will afford compounds of formula (III).

Scheme 5

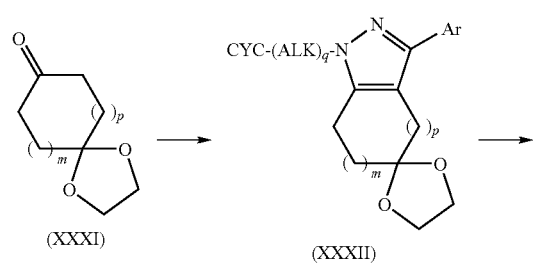

(XXXI)    (XXXII)

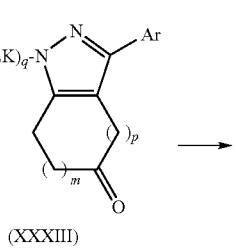

(XXXIII)

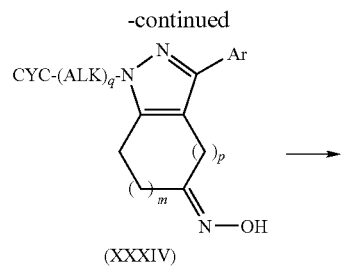

(XXXIV)

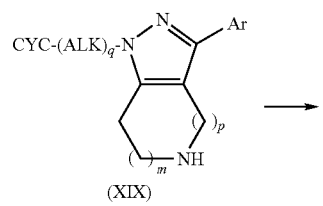

(XIX)

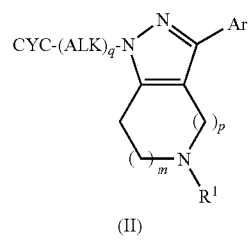

(II)

Referring to Scheme 5, in an alternative embodiment, compounds of formula (II) may be prepared from a ketone of formula (XXXI). A ketone of formula (XXXI) may be converted to the pyrazole of formula (XXXII) according to the procedure shown in Scheme 3 for the conversion of a compound of formula (XX) to a compound of formula (XVIII). A compound of formula (XXXIII) may be prepared from a compound of formula (XXXII) upon treatment with aqueous acid. For example, treatment of a compound of formula (XXXII) with HCl in aqueous THF at elevated temperatures will afford compounds of formula (XXXIII). A ketone of formula (XXXIII) may be converted to an oxime of formula (XXXIV) by treatment with hydroxylamine, preferably upon treatment with hydroxylamine in pyridine. Compounds of formula (XXXIV) may exist as a single isomer or mixture of stereoisomers. Treatment of an oxime of formula (XXXIV) with a hydride reducing agent can afford compounds of formula (XIX). In a preferred embodiment, the reducing agent is diisobutylaluminum hydride in CH$_2$Cl$_2$. Conversion of compounds of formula (XIX) to compounds of formula (II) can be effected using the methods described in Scheme 3.

Scheme 6

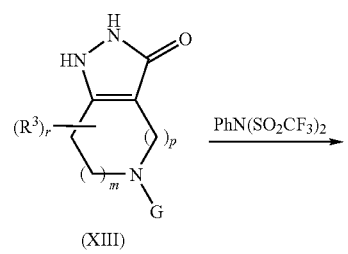

(XIII)

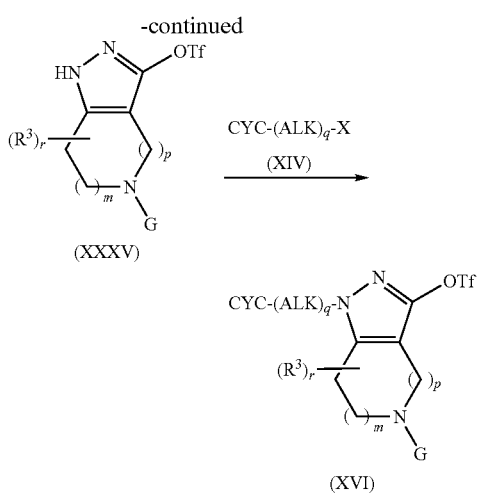

Referring to Scheme 6, in an alternative embodiment, compounds of formula (XIX) may also be prepared as outlined. The amine moiety in compounds of formula (XIII) can be suitably protected, shown by substituent G, as an alkyl or benzyl amine, amide, carbamate or other groups such as those described in "Protecting Groups In Organic Synthesis", $3^{rd}$ ed.; T. W. Greene and P. G. M. Wuts, John Wiley & Sons, 1999. Preferably, the sequence outlined in Scheme 6 may be employed for compounds where p=1, m=2, and G=t-butyl carbamoyl. Treatment of pyrazolones of formula (XIII) with a triflating agent such as N-phenyltrifluoromethanesulfonimide or trifluoromethanesulfonic anhydride in pyridine or another non-nucleophilic amine base gives pyrazole triflates of formula (XXXV). Compounds such as (XXXV) can be treated with an alkylating agent of formula (XIV). For example, treatment with an alkyl or benzyl chloride, bromide, iodide, mesylate or tosylate (wherein X is Cl, Br, I, OMs, OTs or the like) in DMF, DMA, THF or ethanol in the presence of a base like $NaHCO_3$, $Na_2CO_3$, NaH, $K_2CO_3$, $Cs_2CO_3$, or potassium tert-butoxide will afford compounds of formula (XVI). Preferably, alkylation is affected using alkylating agents such as benzyl bromide in the presence of a suitable base such as potassium tert-butoxide. Pyrazoles of formula (XVI) can be carried forward as described in Scheme 2 to provide compounds of formula (XIX) and (I).

The compounds of the present invention are serotonin receptor modulators, and as such, the compounds are useful in the treatment of serotonin-mediated disease states. Particularly, the compounds may be used in the treatment or prevention of CNS disorders, such as sleep disorders, depression/anxiety, generalized anxiety disorder, schizophrenia, bipolar disorders, psychotic disorders, obsessive-compulsive disorder, mood disorders, post-traumatic stress and other stress-related disorders, migraine, pain, eating disorders, obesity, sexual dysfunction, metabolic disturbances, hormonal imbalance, alcohol abuse, addictive disorders, nausea, inflammation, centrally mediated hypertension, sleep/wake disturbances, jetlag, and circadian rhythm abnormalities. The compounds may also be used in the treatment and prevention of hypotension, peripheral vascular disorders, cardiovascular shock, renal disorders, gastric motility, diarrhea, spastic colon, irritable bowel disorders, ischemias, septic shock, urinary incontinence, and other disorders related to the gastrointestinal and vascular systems. In addition, compounds of the present invention may be used in the treatment or prevention of a range of ocular disorders including glaucoma, optic neuritis, diabetic retinopathy, retinal edema, and age-related macular degeneration.

The compounds of the present invention are $5-HT_7$ modulators and many are $5-HT_7$ antagonists. As such, the compounds are useful in the treatment of $5-HT_7$-mediated disease states. Where the compounds possess substantial $5-HT_7$ antagonist activity, they may be particularly useful in the treatment or prevention of depression/anxiety, sleep/wake disturbances, jetlag, migraine, urinary incontinence, gastric motility, and irritable bowel disorders.

Many of the compounds of the present invention are $5-HT_2$ modulators and many are $5-HT_2$ antagonists. As such, the compounds are useful in the treatment of $5-HT_2$-mediated diseases and conditions. Where the compounds possess substantial $5-HT_2$ antagonist activity, they may be particularly useful in the treatment or prevention of depression/anxiety, generalized anxiety disorder, schizophrenia, bipolar disorders, psychotic disorders, obsessive-compulsive disorder, mood disorders, post-traumatic stress disorders, sleep disturbances, sexual dysfunction, eating disorders, migraine, addictive disorders, and peripheral vascular disorders.

It is anticipated that the compounds of the invention can be administered by oral or parenteral routes, including intravenous, intramuscular, intraperitoneal, subcutaneous, rectal and topical administration, and inhalation. For oral administration, the compounds of the invention will generally be provided in the form of tablets or capsules or as an aqueous solution or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate and lactose. Cornstarch and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the active ingredient is mixed with a solid diluent and soft gelatin capsules wherein the active ingredient is mixed with water or an oil such as peanut oil, liquid paraffin or olive oil. For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

| Protocol for Preparative Reversed-Phase HPLC | | |
|---|---|---|
| Gilson ® | | |
| Column: | YMC-Pack ODS-A, 5 µm, 75 × 30 mm | |
| Flow rate: | 25 mL/min | |
| Detection: | λ = 220 & 254 nm | |
| Gradient (acetonitrile/water, 0.05% trifluoroacetic acid) | | |
| 1) | 0.0 min | 15% acetonitrile/85% water |
| 2) | 20.0 min | 99% acetonitrile/1% water |

| Protocol for HPLC (Reversed-Phase) | | |
|---|---|---|
| Method A: | | |
| Hewlett Packard Series 1100 | | |
| Column: | Agilent ZORBAX ® Bonus RP, 5 µm, 4.6 × 250 mm | |
| Flow rate: | 1 mL/min | |
| Detection: | λ = 220 & 254 nm | |
| Gradient (acetonitrile/water, 0.05% trifluoroacetic acid) | | |
| 1) | 0.0 min | 1% acetonitrile/99% water |
| 2) | 20.0 min | 99% acetonitrile/1% water |
| Method B: | | |
| Hewlett Packard HPLC | | |
| Column: | Agilent ZORBAX ® Eclipse XDB-C8, 5 µm, 4.6 × 150 mm | |
| Flow rate: | 1 mL/min | |
| Detection: | λ = 220 & 254 nm | |
| Gradient (acetonitrile/water, 0.05% trifluoroacetic acid) | | |
| 1) | 0.0 min | 1% acetonitrile/99% water |
| 2) | 8.0 min | 99% acetonitrile/1% water |
| 3) | 12.0 min | 99% acetonitrile/1% water |

| Protocol for Preparative SFC | |
|---|---|
| Thar Technologies ® | |
| Column: | Chiracel AD, 10 µm, 250 × 20 mm |
| Flow rate: | 37 gm/min |
| Detection: | λ = 220 & 254 nm |
| Mobile phase: | Isocratic 30% IPA/70% CO$_2$ |
| Pressure: | 150 Bar |
| Temperature: | 35° C. |

| Protocol for Analytical SFC | |
|---|---|
| Jasco ® | |
| Column: | Chiracel AD, 10 µm, 250 × 4.6 mm |
| Flow rate: | 1 gm/min |
| Detection: | λ = 220 & 254 nm |
| Mobile phase: | Isocratic 30% IPA/70% CO$_2$ |
| Pressure: | 150 Bar |
| Temperature: | 35° C. |

Mass spectra were obtained on an Agilent series 1100 MSD using electrospray ionization (ESI) in either positive or negative modes as indicated.

Thin-layer chromatography was performed using Merck silica gel 60 $F_{254}$ 2.5 cm×7.5 cm 250 µm or 5.0 cm×10.0 cm 250 µm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

NMR spectra were obtained on either a Bruker model DPX400 (400 MHz), DPX500 (500 MHz), or DPX600 (600 MHz) spectrometer. The format of the $^1$H NMR data below is: chemical shift in ppm down field of the tetramethylsilane reference (multiplicity, coupling constant J in Hz, integration).

Example 1

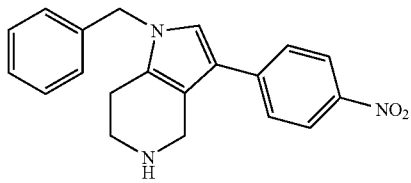

1-Benzyl-3-(4-nitro-phenyl)-4,5,6,7-tetrahydro-1H-pyrrolo[3,2-c]pyridine

Step A. 1-Benzyl-3-(4-nitro-phenyl)-1,4,6,7-tetrahydro-pyrrolo[3,2-c]pyridine-5-carboxylic acid tert-butyl ester. To a stirred solution of 4-oxo-piperidine-1-carboxylic acid tert-butyl ester (0.69 g) in toluene (5 mL) was added 378 µL of benzylamine. The mixture was stirred for 10 min and then 0.70 g of silica gel (SiO$_2$) was added. After stirring at RT for 8 h, 0.77 g of 1-nitro-4-(2-nitro-vinyl)-benzene in toluene (5 mL) was added and the mixture was stirred for 14 h at RT. The mixture was then filtered through diatomaceous earth and the filtrate was concentrated in vacuo. Chromatography on SiO$_2$ (8 to 20% EtOAc/hexanes) afforded 0.48 g of the desired compound. MS (ESI): exact mass calculated for C$_{25}$H$_{27}$N$_3$O$_4$, 433.20; found, m/z 434.2 [M+H]$^+$, 456.2 [M+Na]$^+$.

Step B. To a stirred solution of 0.20 g of the above compound in a 10:1 mixture of CH$_2$Cl$_2$/MeOH (6 mL) was added 1.9 mL of 1.0 M HCl in Et$_2$O. After stirring for 12 h at RT, a white solid had formed, which was collected by filtration to afford 0.11 g of the title compound. MS (ESI): exact mass calculated for C$_{20}$H$_{19}$N$_3$O$_2$, 333.15; found, m/z 334.2 [M+H]$^+$. $^1$H NMR (500 MHz, CD$_3$OD): 8.26-8.21 (m, 2H), 7.59-7.55 (m, 2H), 7.42 (s, 1H), 7.36 (t, J=7.4 Hz, 2H), 7.30 (t, J=7.4 Hz, 1 Hz), 7.20 (d, J=7.4 Hz, 2H), 5.19 (s, 2H), 4.44 (s, 2H), 3.53 (t, J=6.3 Hz, 2H), 2.89 (t, J=6.3 Hz, 2H).

Examples 2-25 were prepared according to the procedure described in Example 1, with alterations as noted.

Example 2

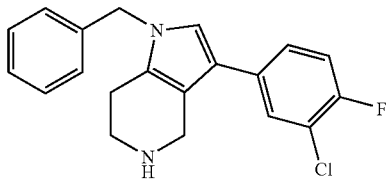

1-Benzyl-3-(3-chloro-4-fluoro-phenyl)-4,5,6,7-tetrahydro-1H-pyrrolo[3,2-c]pyridine The title compound (0.18 g) was prepared from 0.54 g of 4-oxo-piperidine-1-carboxylic acid tert-butyl ester, 293 µL of benzylamine, and 0.62 g of 2-chloro-1-fluoro-4-(2-nitro-vinyl)-benzene. MS (ESI): exact mass calculated for $C_{20}H_{18}ClFN_2$, 340.11; found, m/z 341.1 [M+H]$^+$, 343.2 [M+H]$^+$. $^1$H NMR (500 MHz, $CD_3OD$): 7.45-7.43 (m, 1H), 7.36-7.16 (m, 8H), 5.15 (s, 2H), 4.35 (s, 2H), 3.50 (t, J=6.3 Hz, 2H), 2.85 (t, J=6.3 Hz, 2H).

Example 3

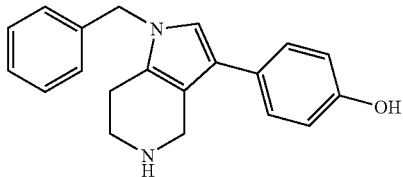

4-(1-Benzyl-4,5,6,7-tetrahydro-1H-pyrrolo[3,2-c]pyridin-3-yl)-phenol

The title compound (0.09 g) was prepared from 1.22 g of 4-oxo-piperidine-1-carboxylic acid tert-butyl ester, 856 µL of benzylamine, and 1.29 g of 4-(2-nitro-vinyl)-phenol, which was added in EtOH (12 mL). MS (ESI): exact mass calculated for $C_{20}H_{20}N_2O$, 304.16; found, m/z 305.2 [M+H]$^+$. $^1$H NMR (500 MHz, $CD_3OD$): 7.35-7.32 (m, 2H), 7.29-7.25 (m, 2H), 7.17-7.14 (m, 4H), 6.98 (s, 1H), 6.80-6.77 (m, 2H), 5.12 (s, 2H), 4.31 (s, 2H), 3.49 (t, J=6.3 Hz, 2H), 2.85 (t, J=6.3 Hz, 2H).

Example 4

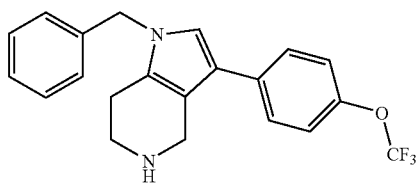

1-Benzyl-3-(4-trifluoromethoxy-phenyl)-4,5,6,7-tetrahydro-1H-pyrrolo[3,2-c]pyridine The title compound (0.28 g) was prepared from 0.50 g of 4-oxo-piperidine-1-carboxylic acid tert-butyl ester, 274 µL of benzylamine, and 0.59 g of 1-trifluoromethoxy-4-(2-nitro-vinyl)-benzene using $CH_2Cl_2$ as the solvent. MS (ESI): exact mass calculated for $C_{21}H_{19}F_3N_2O$, 372.14; found, m/z 373.2 [M+H]$^+$. $^1$H NMR (400 MHz, $CD_3OD$): 7.44-7.41 (m, 2H), 7.37-7.26 (m, 5H), 7.19-7.17 (m, 3H), 5.15 (s, 2H), 4.37 (s, 2H), 3.51 (t, J=6.3 Hz, 2H), 2.87 (t, J=6.3 Hz, 2H).

Example 5

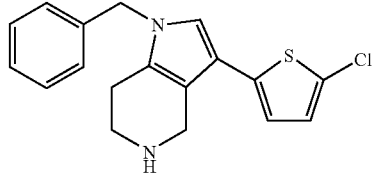

1-Benzyl-3-(5-chloro-thiophen-2-yl)-4,5,6,7-tetrahydro-1H-pyrrolo[3,2-c]pyridine The title compound (82.3 mg) was prepared from 0.56 g of 4-oxo-piperidine-1-carboxylic acid tert-butyl ester, 300 µL of benzylamine, and 0.53 g of 2-chloro-5-(2-nitro-vinyl)-thiophene. MS (ESI): exact mass calculated for $C_{18}H_{17}ClN_2S$, 328.08; found, m/z 329.1 [M+H]$^+$. $^1$H NMR (500 MHz, $CD_3OD$): 7.36-7.33 (m, 2H), 7.30-7.27 (m, 1H), 7.17-7.15 (m, 2H), 7.12 (s, 1H), 6.89 (d, J=3.8 Hz, 1H), 6.73 (d, J=3.8 Hz, 1H), 5.12 (s, 2H), 4.31 (s, 2H), 3.48 (t, J=6.3 Hz, 2H), 2.84 (t, J=6.3 Hz, 2H).

Example 6

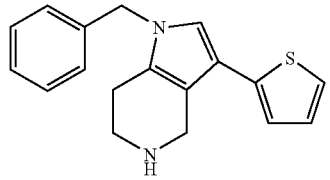

1-Benzyl-3-thiophen-2-yl-4,5,6,7-tetrahydro-1H-pyrrolo[3,2-c]pyridine

The title compound (136.8 mg) was prepared from 0.53 g of 4-oxo-piperidine-1-carboxylic acid tert-butyl ester, 300 µL of benzylamine, and 0.41 g of 2-(2-nitro-vinyl)-thiophene. MS (ESI): exact mass calculated for $C_{18}H_{18}N_2S$, 294.12; found, m/z 295.2 [M+H]$^+$. $^1$H NMR (500 MHz, $CD_3OD$): 7.36-7.32 (m, 2H), 7.30-7.26 (m, 1H), 7.22 (dd, J=5.2, 1.1 Hz, 1H), 7.18-7.15 (m, 2H), 7.12 (s, 1H), 7.02 (dd, J=5.2, 3.6 Hz, 1H), 6.94 (dd, J=3.6, 1.1 Hz, 1H), 5.13 (s, 2H), 4.34 (s, 2H), 3.49 (t, J=6.3 Hz, 2H), 2.85 (t, J=6.3 Hz, 2H).

Example 7

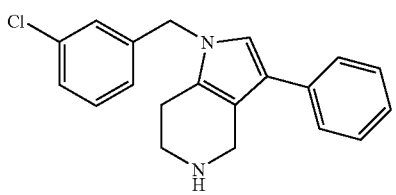

1-(3-Chloro-benzyl)-3-phenyl-4,5,6,7-tetrahydro-1H-pyrrolo[3,2-c]pyridine

The title compound (159.0 mg) was prepared from 0.55 g of 4-oxo-piperidine-1-carboxylic acid tert-butyl ester, 334 μL of 3-chlorobenzylamine, and 0.40 g of (2-nitro-vinyl)-benzene and without $SiO_2$. MS (ESI): exact mass calculated for $C_{20}H_{19}ClN_2$, 322.12; found, m/z 323.2 [M+H]$^+$. $^1$H NMR (500 MHz, CD$_3$OD): 7.38-7.32 (m, 5H), 7.31-7.28 (m, 1H), 7.23-7.19 (m, 1H), 7.17-7.16 (m, 1H), 7.13 (s, 1H), 7.12-7.10 (m, 1H), 5.16 (s, 2H), 4.37 (s, 2H), 3.52 (t, J=6.3 Hz, 2H), 2.86 (t, J=6.3 Hz, 2H).

Example 8

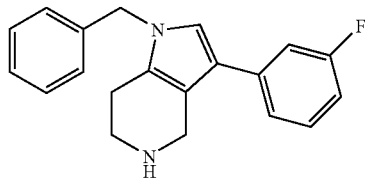

1-Benzyl-3-(3-fluoro-phenyl)-4,5,6,7-tetrahydro-1H-pyrrolo[3,2-c]pyridine

The title compound (282.6 mg) was prepared from 0.61 g of 4-oxo-piperidine-1-carboxylic acid tert-butyl ester, 330 μL of benzylamine, and 0.50 g of (2-nitro-vinyl)-3-fluorobenzene, using EtOH as the solvent and without $SiO_2$. MS (ESI): exact mass calculated for $C_{20}H_{19}FN_2$, 306.15; found, m/z 307.2 [M+H]$^+$. $^1$H NMR (500 MHz, CD$_3$OD): 7.38-7.32 (m, 3H), 7.30-7.26 (m, 1H), 7.20-7.14 (m, 4H), 7.10-7.06 (m, 1H), 6.95-6.90 (m, 1H), 5.15 (s, 2H), 4.36 (s, 2H), 3.50 (t, J=6.3 Hz, 2H), 2.86 (t, J=6.3 Hz, 2H).

Example 9

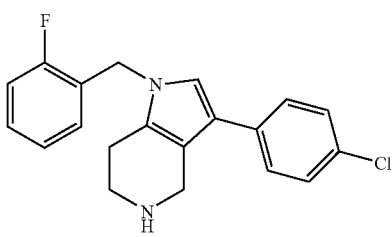

3-(4-Chloro-phenyl)-1-(2-fluoro-benzyl)-4,5,6,7-tetrahydro-1H-pyrrolo[3,2-c]pyridine The title compound (129.2 mg) was prepared from 0.49 g of 4-oxo-piperidine-1-carboxylic acid tert-butyl ester, 286 μL of 2-fluorobenzylamine, and 0.46 g of (2-nitro-vinyl)-4-chlorobenzene, replacing $SiO_2$ with crushed 4 Å molecular sieves. MS (ESI): exact mass calculated for $C_{20}H_{18}ClFN_2$, 340.11; found, m/z 341.1 [M+H]$^+$. $^1$H NMR (500 MHz, CD$_3$OD): 7.38-7.30 (m, 5H), 7.18-7.12 (m, 3H), 7.10-7.06 (m, 1H), 5.20 (s, 2H), 4.35-4.34 (m, 2H), 3.54 (t, J=6.3 Hz, 2H), 2.94 (t, J=6.3 Hz, 2H).

Example 10

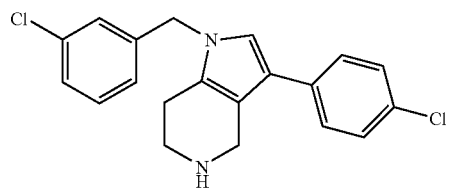

1-(3-Chloro-benzyl)-3-(4-chloro-phenyl)-4,5,6,7-tetrahydro-1H-pyrrolo[3,2-c]pyridine The title compound (212.8 mg) was prepared from 0.55 g of 4-oxo-piperidine-1-carboxylic acid tert-butyl ester, 340 μL of 3-chlorobenzylamine, and 0.51 g of (2-nitro-vinyl)-4-chlorobenzene, replacing $SiO_2$ with crushed 4 Å molecular sieves. MS (ESI): exact mass calculated for $C_{20}H_{18}Cl_2N_2$, 356.08; found, m/z 357.1 [M+H]$^+$. $^1$H NMR (500 MHz, CD$_3$OD): 7.38-7.28 (m, 6H), 7.18-7.15 (m, 2H), 7.12-7.09 (m, 1H), 5.16 (s, 2H), 4.36 (s, 2H), 3.52 (t, J=6.3 Hz, 2H), 2.86 (t, J=6.3 Hz, 2H).

Example 11

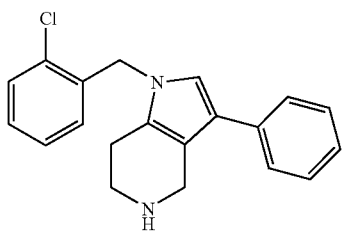

1-(2-Chloro-benzyl)-3-phenyl-4,5,6,7-tetrahydro-1H-pyrrolo[3,2-c]pyridine

The title compound (113.8 mg) was prepared from 0.55 g of 4-oxo-piperidine-1-carboxylic acid tert-butyl ester, 334 μL of 2-chlorobenzylamine, 0.40 g of (2-nitro-vinyl)-benzene, and without $SiO_2$. MS (ESI): exact mass calculated for $C_{20}H_{19}ClN_2$, 322.12; found, m/z 323.2 [M+H]$^+$. $^1$H NMR (500 MHz, CD$_3$OD): 7.46 (m, 1H), 7.37-7.26 (m, 6H), 7.22-

7.19 (m, 1H), 7.07 (s, 1H), 6.85-6.82 (m, 1H), 5.25 (s, 2H), 4.39 (s, 2H), 3.54 (t, J=6.3 Hz, 2H), 2.88 (t, J=6.3 Hz, 2H).

Example 12

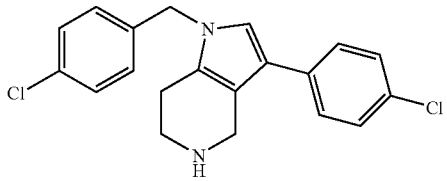

1-(4-Chloro-benzyl)-3-(4-chloro-phenyl)-4,5,6,7-tetrahydro-1H-pyrrolo[3,2-c]pyridine The title compound (260.2 mg) was prepared from 0.55 g of 4-oxo-piperidine-1-carboxylic acid tert-butyl ester, 340 µL of 4-chlorobenzylamine, and 0.51 g of (2-nitro-vinyl)-4-chlorobenzene. MS (ESI): exact mass calculated for $C_{20}H_{18}Cl_2N_2$, 356.08; found, m/z 357.1 [M+H]$^+$. $^1$H NMR (500 MHz, CD$_3$OD): 7.37-7.31 (m, 6H), 7.17-7.13 (m, 3H), 5.15 (s, 2H), 4.35 (s, 2H), 3.51 (t, J=6.3 Hz, 2H), 2.85 (t, J=6.3 Hz, 2H).

Example 13

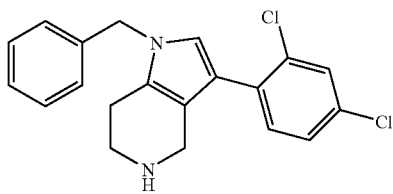

1-Benzyl-3-(2,4-dichloro-phenyl)-4,5,6,7-tetrahydro-1H-pyrrolo[3,2-c]pyridine

The title compound (454.6 mg) was prepared from 0.52 g of 4-oxo-piperidine-1-carboxylic acid tert-butyl ester, 280 µL of benzylamine, and 0.57 g of 2,4-dichloro-1-(2-nitro-vinyl)-benzene, using a 5:1 EtOH/toluene mixture as the solvent. MS (ESI): exact mass calculated for $C_{20}H_{18}Cl_2N_2$, 356.08; found, m/z 357.1 [M+H]$^+$. $^1$H NMR (500 MHz, CD$_3$OD): 7.53 (d, J=2.2 Hz, 1H), 7.36-7.32 (m, 3H), 7.30-7.28 (m, 2H), 7.20-7.17 (m, 2H), 7.04 (s, 1H), 5.16 (s, 2H), 4.13 (s, 2H), 3.50 (t, J=6.3 Hz, 2H), 2.88 (t, J=6.3 Hz, 2H).

Example 14

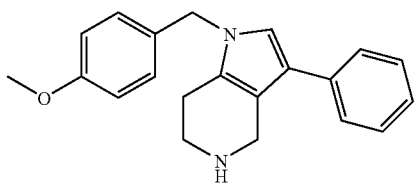

1-(4-Methoxy-benzyl)-3-phenyl-4,5,6,7-tetrahydro-1H-pyrrolo[3,2-c]pyridine

The title compound (0.19 g) was prepared from 1.51 g of 4-oxo-piperidine-1-carboxylic acid tert-butyl ester, 1.0 mL of 4-methoxybenzylamine, and 1.13 g of (2-nitro-vinyl)-benzene, using EtOH as the solvent and omitting SiO$_2$. MS (ESI): exact mass calculated for $C_{21}H_{22}N_2O$, 318.17; found, m/z 319.2 [M+H]$^+$. $^1$H NMR (500 MHz, CD$_3$OD): 7.39-7.30 (m, 4H), 7.20-7.15 (m, 1H), 7.14-7.11 (m, 2H), 7.08 (s, 1H), 6.90-6.87 (m, 2H), 5.05 (s, 2H), 4.34 (s, 2H), 3.50 (t, J=6.3 Hz, 2H), 2.88 (t, J=6.3 Hz, 2H).

Example 15

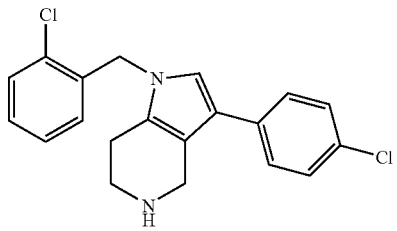

1-(2-Chloro-benzyl)-3-(4-chloro-phenyl)-4,5,6,7-tetrahydro-1H-pyrrolo[3,2-c]pyridine The title compound (149.9 mg) was prepared from 0.50 g of 4-oxo-piperidine-1-carboxylic acid tert-butyl ester, 304 µL of 2-chlorobenzylamine, and 0.46 g of (2-nitro-vinyl)-4-chlorobenzene, replacing SiO$_2$ with crushed 4 Å molecular sieves. MS (ESI): exact mass calculated for $C_{20}H_{18}Cl_2N_2$, 356.08; found, m/z 357.1 [M+H]$^+$. $^1$H NMR (500 MHz, CD$_3$OD): 7.58-7.56 (m, 1H), 7.47-7.45 (m, 1H), 7.37-7.26 (m, 5H), 7.10 (s, 1H), 6.85-6.82 (m, 1H), 5.25 (s, 2H), 4.38 (s, 2H), 3.53 (t, J=6.3 Hz, 2H), 2.88 (t, J=6.3 Hz, 2H).

Example 16

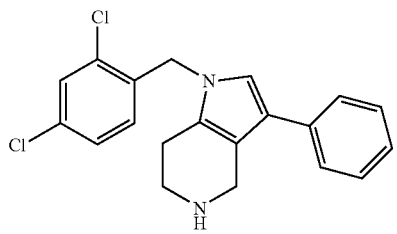

1-(2,4-Dichloro-benzyl)-3-phenyl-4,5,6,7-tetrahydro-1H-pyrrolo[3,2-c]pyridine

The title compound (0.43 g) was prepared from 0.55 g of 4-oxo-piperidine-1-carboxylic acid tert-butyl ester, 370 µL of 2,4-dichlorobenzylamine, and 0.41 g of (2-nitro-vinyl)-benzene, using EtOH as the solvent. MS (ESI): exact mass calculated for $C_{20}H_{18}Cl_2N_2$, 356.08; found, m/z 357.1 [M+H]$^+$. $^1$H NMR (500 MHz, CD$_3$OD): 7.55-7.50 (m, 2H), 7.37-7.29

(m, 4H), 7.22-7.18 (m, 1H), 7.07 (s, 1H), 6.77 (d, J=8.5 Hz, 1H), 5.23 (s, 2H), 4.38 (s, 2H), 3.54 (t, J=6.3 Hz, 2H), 2.86 (t, J=6.3 Hz, 2H).

Example 17

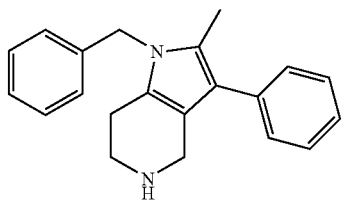

1-Benzyl-2-methyl-3-phenyl-4,5,6,7-tetrahydro-1H-pyrrolo[3,2-c]pyridine

The title compound (89.4 mg) was prepared from 0.51 g of 4-oxo-piperidine-1-carboxylic acid tert-butyl ester, 272 μL of benzylamine, and 0.41 g of (2-nitro-propenyl)-benzene. MS (ESI): exact mass calculated for $C_{21}H_{22}N_2$, 302.18; found, m/z 303.2 [M+H]$^+$. $^1$H NMR (400 MHz, CD$_3$OD): 7.41-7.36 (m, 2H), 7.35-7.30 (m, 2H), 7.28-7.21 (m, 4H), 7.05-7.01 (m, 2H), 5.16 (s, 2H), 4.18 (s, 2H), 3.52 (t, J=6.3 Hz, 2H), 2.89 (t, J=6.3 Hz, 2H).

Example 18

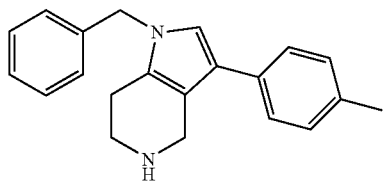

1-Benzyl-3-p-tolyl-4,5,6,7-tetrahydro-1H-pyrrolo[3,2-c]pyridine

The title compound (89.7 mg) was prepared from 0.51 g of 4-oxo-piperidine-1-carboxylic acid tert-butyl ester, 272 μL of benzylamine, and 0.41 g of 1-methyl-4-(2-nitro-vinyl)-benzene. MS (ESI): exact mass calculated for $C_{21}H_{22}N_2$, 302.18; found, m/z 303.2 [M+H]$^+$. $^1$H NMR (500 MHz, CD$_3$OD): 7.35-7.31 (m, 2H), 7.29-7.25 (m, 1H), 7.23-7.20 (m, 2H), 7.18-7.14 (m, 4H), 7.06 (s, 1H), 5.13 (s, 2H), 4.33 (s, 2H), 3.49 (t, J=6.3 Hz, 2H), 2.86 (t, J=6.3 Hz, 2H).

Example 19

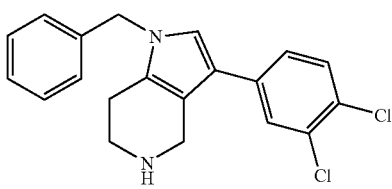

1-Benzyl-3-(3,4-dichloro-phenyl)-4,5,6,7-tetrahydro-1H-pyrrolo[3,2-c]pyridine

The title compound (228.2 mg) was prepared from 0.49 g of 4-oxo-piperidine-1-carboxylic acid tert-butyl ester, 268 μL of benzylamine, and 0.55 g of 1,2-dichloro-4-(2-nitro-vinyl)-benzene. MS (ESI): exact mass calculated for $C_{20}H_{18}Cl_2N_2$, 356.08; found, m/z 357.1 [M+H]$^+$. $^1$H NMR (400 MHz, CD$_3$OD): 7.51-7.47 (m, 2H), 7.36-7.32 (m, 2H), 7.32-7.25 (m, 2H), 7.22 (s, 1H), 7.19-7.15 (m, 2H), 5.15 (s, 2H), 4.35 (s, 2H), 3.50 (t, J=6.3 Hz, 2H), 2.85 (t, J=6.3 Hz, 2H).

Example 20

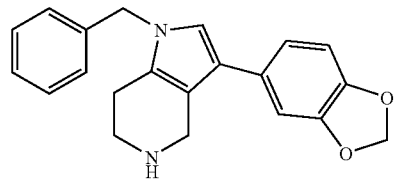

3-Benzo[1,3]dioxol-5-yl-1-benzyl-4,5,6,7-tetrahydro-1H-pyrrolo[3,2-c]pyridine

The title compound (306.0 mg) was prepared from 0.49 g of 4-oxo-piperidine-1-carboxylic acid tert-butyl ester, 268 μL of benzylamine, and 0.48 g of 5-(2-nitro-vinyl)-benzo[1,3]dioxole. MS (ESI): exact mass calculated for $C_{21}H_{20}N_2O_2$, 332.15; found, m/z 333.2 [M+H]$^+$. $^1$H NMR (400 MHz, CD$_3$OD): 7.36-7.30 (m, 2H), 7.29-7.24 (m, 1H), 7.18-7.14 (m, 2H), 7.01 (s, 1H), 6.85-6.75 (m, 3H), 5.93 (s, 2H), 5.12 (s, 2H), 4.31 (s, 2H), 3.49 (t, J=6.3 Hz, 2H), 2.85 (t, J=6.3 Hz, 2H).

Example 21

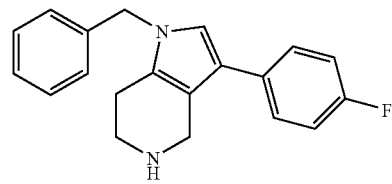

1-Benzyl-3-(4-fluoro-phenyl)-4,5,6,7-tetrahydro-1H-pyrrolo[3,2-c]pyridine

The title compound (706.2 mg) was prepared from 1.31 g of 4-oxo-piperidine-1-carboxylic acid tert-butyl ester, 700 μL of benzylamine, and 1.10 g of 1-fluoro-4-(2-nitro-vinyl)-benzene. MS (ESI): exact mass calculated for $C_{20}H_{19}FN_2$, 306.15; found, m/z 307.2 [M+H]$^+$. $^1$H NMR (500 MHz, CD$_3$OD): 7.36-7.25 (m, 5H), 7.18-7.15 (m, 2H), 7.11-7.05 (m, 3H), 5.13 (s, 2H), 4.33 (s, 2H), 3.50 (t, J=6.3 Hz, 2H), 2.86 (t, J=6.3 Hz, 2H).

Example 22

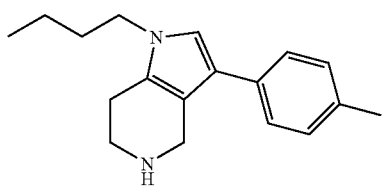

1-Butyl-3-p-tolyl-4,5,6,7-tetrahydro-1H-pyrrolo[3,2-c]pyridine

The title compound (292.8 mg) was prepared from 0.56 g of 4-oxo-piperidine-1-carboxylic acid tert-butyl ester, 260 μL of butylamine, and 0.45 g of 1-methyl-4-(2-nitro-vinyl)-benzene. MS (ESI): exact mass calculated for $C_{18}H_{24}N_2$, 268.19; found, m/z 269.2 [M+H]$^+$. $^1$H NMR (500 MHz, $CD_3OD$): 7.20-7.14 (m, 4H), 6.93 (s, 1H), 4.32 (s, 2H), 3.88 (t, J=7.1 Hz, 2H), 3.56 (t, J=6.0 Hz, 2H), 3.00 (t, J=6.0 Hz, 2H), 2.32 (s, 3H), 1.77-1.70 (m, 2H), 1.41-1.33 (m, 2H), 0.97 (t, J=7.4 Hz, 3H).

Example 23

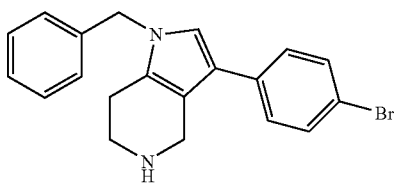

1-Benzyl-3-(4-bromo-phenyl)-4,5,6,7-tetrahydro-1H-pyrrolo[3,2-c]pyridine

The title compound (0.38 g) was prepared from 0.66 g of 4-oxo-piperidine-1-carboxylic acid tert-butyl ester, 300 μL of benzylamine, and 0.63 g of 1-bromo-4-(2-nitro-vinyl)-benzene. MS (ESI): exact mass calculated for $C_{20}H_{19}BrN_2$, 366.07; found, m/z 367.1 [M+H]$^+$. $^1$H NMR (500 MHz, $CD_3OD$): 7.51-7.48 (m, 2H), 7.36-7.32 (m, 2H), 7.30-7.25 (m, 3H), 7.19-7.16 (m, 2H), 5.14 (s, 2H), 4.35 (s, 2H), 3.50 (t, J=6.3 Hz, 2H), 2.87 (t, J=6.3 Hz, 2H).

Example 24

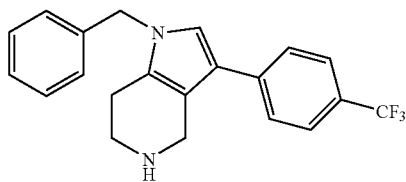

1-Benzyl-3-(4-trifluoromethyl-phenyl)-4,5,6,7-tetrahydro-1H-pyrrolo[3,2-c]pyridine The title compound (0.23 g) was prepared from 0.50 g of 4-oxo-piperidine-1-carboxylic acid tert-butyl ester, 274 μL of benzylamine, and 0.55 g of 1-trifluoromethyl-4-(2-nitro-vinyl)-benzene, using acetonitrile as the solvent. MS (ESI): exact mass calculated for $C_{21}H_{19}F_3N_2$, 356.16; m/z found, 357.2 [M+H]$^+$. $^1$H NMR (500 MHz, $CD_3OD$): 7.65-7.63 (m, 2H), 7.54-7.52 (m, 2H), 7.36-7.27 (m, 4H), 7.20-7.18 (m, 2H), 5.17 (s, 2H), 4.40 (s, 2H), 3.52 (t, J=6.3 Hz, 2H), 2.88 (t, J=6.3 Hz, 2H).

Example 25

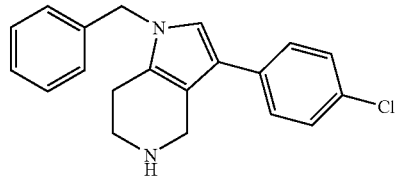

1-Benzyl-3-(4-chloro-phenyl)-4,5,6,7-tetrahydro-1H-pyrrolo[3,2-c]pyridine

The title compound (1.19 g) was prepared from 1.55 g of 4-oxo-piperidine-1-carboxylic acid tert-butyl ester, 850 μL of benzylamine, and 1.43 g of 1-chloro-4-(2-nitro-vinyl)-benzene, using a 1:1 mixture of EtOH/toluene as the solvent. MS (ESI): exact mass calculated for $C_{20}H_{20}Cl_2N_2$, 322.12; m/z found, 323.2 [M+H]$^+$, 325.2 [M+H]$^+$. $^1$H NMR (400 MHz, $CD_3OD$): 7.37-7.26 (m, 7H), 7.18-7.16 (m, 3H), 5.15 (s, 2H), 4.35 (s, 2H), 3.50 (t, J=6.3 Hz, 2H), 2.87 (t, J=6.3 Hz, 2H).

Example 26

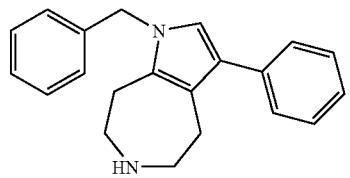

1-Benzyl-3-phenyl-1,4,5,6,7,8-hexahydro-pyrrolo[2,3-d]azepine

Step A. 1-Benzyl-3-phenyl-4,5,7,8-tetrahydro-1H-pyrrolo[2,3-d]azepine-6-carboxylic acid tert-butyl ester. A solution of the compound (0.53 g) from Example 59, Step B, and 272 μL of benzylamine in benzene (10 mL) was heated at reflux for 24 h using a Dean-Stark apparatus. The solvent was removed, the crude material was dissolved in toluene (10 mL), and 0.38 g of (2-nitro-vinyl)-benzene was added. The mixture was stirred for 24 h at RT and concentrated in vacuo. Chromatography on $SiO_2$ (1 to 20% EtOAc/hexanes) afforded 108.0 mg of the desired compound. MS (ESI): exact mass calculated for $C_{26}H_{30}N_2O_2$, 402.53; found, m/z 403.2 [M+H]$^+$.

Step B. To a stirred solution of the compound from Step A (108.0 mg) in $CH_2Cl_2$ (5 mL) was added TFA (1 mL). The mixture was stirred at RT for 12 h and then concentrated in vacuo. The residue was partitioned between $CH_2Cl_2$ (10 mL) and 1 M NaOH (10 mL). The layers were separated and the aqueous layer was extracted with $CH_2Cl_2$ (2×10 mL). The combined organic layers were concentrated. Chromatography on $SiO_2$ (5% 2 M $NH_3$ in MeOH/$CH_2Cl_2$) gave 66.5 mg of the title compound. MS (ESI): exact mass calculated for $C_{21}H_{22}N_2$, 302.41; found, m/z 303.2 [M+H]$^+$. $^1$H NMR (500 MHz, CDCl$_3$): 7.42-7.22 (m, 8H), 7.08 (m, 2H), 6.67 (s, 1H), 5.08 (s, 2H), 3.06-2.91 (m, 4H), 2.90-2.82 (m, 2H), 2.77-2.68 (m, 2H), 2.25 (br s, 1H).

Example 27

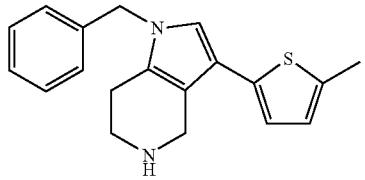

1-Benzyl-3-(5-methyl-thiophen-2-yl)-4,5,6,7-tetrahydro-1H-pyrrolo[3,2-c]pyridine Step A. 1-Benzyl-3-(5-methyl-thiophen-2-yl)-1,4,6,7-tetrahydro-pyrrolo[3,2-c]pyridine-5-carboxylic acid tert-butyl ester. A mixture of 4-oxo-piperidine-1-carboxylic acid tert-butyl ester (0.54 g) and 300 μL of benzylamine in toluene (10 mL) was heated at reflux for 6 h using a Dean-Stark apparatus. The solution was cooled to RT and 0.47 g of 2-methyl-5-(2-nitro-vinyl)-thiophene was added. The mixture was stirred for 16 h at RT and then was concentrated in vacuo. The residue was chromatographed on SiO$_2$ (1 to 30% EtOAc/ hexanes) to afford 281.9 mg of the desired compound. TLC (SiO$_2$, 33% EtOAc/hexanes): R$_f$=0.54

Step B. To a stirred solution of the compound from Step A (281.9 mg) in EtOH (10 mL) was added HCl (1 M in Et$_2$O, 5 mL). The resulting mixture was stirred at RT for 24 h and concentrated in vacuo. The residue was then partitioned between CH$_2$Cl$_2$ (10 mL) and 1 M NaOH (10 mL). The layers were separated and the aqueous layer was extracted with CH$_2$Cl$_2$ (2×10 mL). The combined organic layers were concentrated. Chromatography on SiO$_2$ (CH$_2$Cl$_2$ to 5% 2 M NH$_3$ in MeOH/CH$_2$Cl$_2$) gave 59.0 mg of the title compound. MS (ESI): exact mass calculated for $C_{19}H_{20}N_2S$, 308.13; found, m/z 309.2 [M+H]$^+$. $^1$H NMR (500 MHz, CDCl$_3$): 7.35-7.25 (m, 3H), 7.09-7.06 (m, 2H), 6.76 (s, 1H), 6.65-6.62 (m, 2H), 4.96 (s, 2H), 4.03 (s, 2H), 3.14 (t, J=5.8 Hz, 2H), 2.50 (t, J=5.8 Hz, 2H), 2.45 (s, 3H).

Example 28

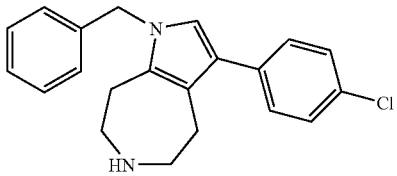

1-Benzyl-3-(4-chloro-phenyl)-1,4,5,6,7,8-hexahydro-pyrrolo[2,3-d]azepine

Step A. 1-Benzyl-3-(4-chloro-phenyl)-4,5,7,8-tetrahydro-1H-pyrrolo[2,3-d]azepine-6-carboxylic acid tert-butyl ester. The desired compound (54.2 mg) was prepared from the compound of Example 59, Step B (0.56 g), 280 μL of benzylamine, and 0.49 g of 1-chloro-4-(2-nitro-vinyl)-benzene as in Example 1, Step A. MS (ESI): exact mass calculated for $C_{26}H_{29}ClN_2O_2$, 436.19; found, m/z 437.2 [M+H]$^+$.

Step B. The above compound (54.2 mg) was converted to the title compound (19.2 mg) as in Example 27, Step B. MS (ESI): exact mass calculated for $C_{21}H_{21}ClN_2$, 336.14; found, m/z 337.1 [M+H]$^+$. $^1$H NMR (500 MHz, CDCl$_3$): 7.34-7.24 (m, 7H), 7.04 (d, J=7.1 Hz, 2H), 6.62 (s, 1H), 5.05 (s, 2H), 3.03-3.00 (m, 2H), 2.97-2.94 (m, 2H), 2.83-2.80 (m, 2H), 2.74-2.71 (m, 2H).

Example 29

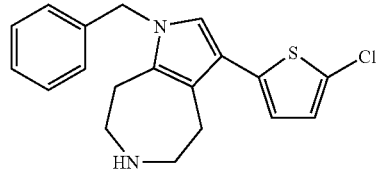

1-Benzyl-3-(5-chloro-thiophen-2-yl)-1,4,5,6,7,8-hexahydro-pyrrolo[2,3-d]azepine

Step A. 1-Benzyl-3-(5-chloro-thiophen-2-yl)-4,5,7,8-tetrahydro-1H-pyrrolo[2,3-d]azepine-6-carboxylic acid tert-butyl ester. The desired compound (124.5 mg) was prepared from the compound of Example 59, Step B (0.55 g), 280 μL of benzylamine, and 0.49 g of 2-chloro-5-(2-nitro-vinyl)-thiophene as in Example 1, Step A. MS (ESI): exact mass calculated for $C_{24}H_{27}ClN_2O_2S$, 442.15; found, m/z 443.2 [M+H]$^+$.

Step B. The above compound (124.5 mg) was converted to the title compound (30.7 mg) as in Example 27, Step B. MS (ESI): exact mass calculated for $C_{19}H_{19}ClN_2S$, 342.10; found, m/z 343.1 [M+H]$^+$. $^1$H NMR (500 MHz, CDCl$_3$): 7.35-7.31 (m, 2H), 7.29-7.25 (m, 1H), 7.04-7.00 (m, 2H), 6.82 (d, J=3.8 Hz, 1H), 6.66 (s, 1H), 6.64 (d, J=3.8 Hz, 1H), 5.02 (s, 2H), 3.06-3.03 (m, 2H), 2.97-2.93 (m, 2H), 2.88-2.84 (m, 2H), 2.72-2.68 (m, 2H).

Example 30

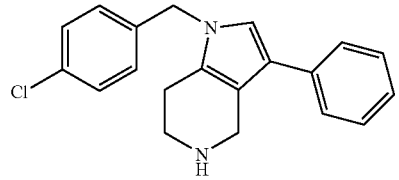

1-(4-Chloro-benzyl)-3-phenyl-4,5,6,7-tetrahydro-1H-pyrrolo[3,2-c]pyridine

Step A. 1-(4-Chloro-benzyl)-3-phenyl-1,4,6,7-tetrahydro-pyrrolo[3,2-c]pyridine-5-carboxylic acid tert-butyl ester. The desired compound (405.6 mg) was prepared from 0.53 g of 4-oxo-piperidine-1-carboxylic acid tert-butyl ester, 334 μL of 2-chlorobenzylamine, and 0.34 g of (2-nitro-vinyl)-benzene as in Example 1, Step A. MS (ESI): exact mass calculated for $C_{25}H_{27}ClN_2O_2$, 422.18; found, m/z 423.2 [M+H]$^+$.

Step B. The above compound (405.6 mg) was converted to the title compound (206.7 mg) as in Example 27, Step B, using MeOH as the solvent. The desired product was then treated with malic acid (75.0 mg) in EtOAc. The solids were collected by filtration to give the corresponding maleate salt. MS (ESI): exact mass calculated for $C_{20}H_{19}ClN_2$, 322.12; found, m/z 323.2 [M+H]$^+$. $^1$H NMR (500 MHz, CD$_3$OD): 7.37-7.32 (m, 6H), 7.22-7.18 (m, 1H), 7.16-7.13 (m, 2H), 7.12 (s, 1H), 6.24 (s, 2H), 5.14 (s, 2H), 4.35 (s, 2H), 3.51 (t, J=6.3 Hz, 2H), 2.84 (t, J=6.3 Hz, 2H).

Example 31

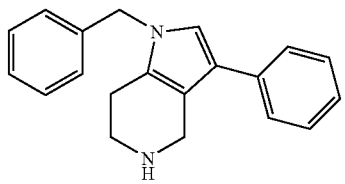

1-Benzyl-3-phenyl-4,5,6,7-tetrahydro-1H-pyrrolo[3,2-c]pyridine

Step A. 1-Benzyl-3-phenyl-1,4,6,7-tetrahydro-pyrrolo[3,2-c]pyridine-5-carboxylic acid tert-butyl ester. The desired compound (380.7 mg) was prepared from 0.51 g of 4-oxo-piperidine-1-carboxylic acid tert-butyl ester, 280 μL of benzylamine, and 0.39 g of (2-nitro-vinyl)-benzene as in Example 1, Step A. MS (ESI): exact mass calculated for $C_{25}H_{28}N_2O_2$, 388.22; found, m/z 389.2 [M+H]$^+$.

Step B. The above compound (0.37 g) was converted to the title compound (234.7 mg) as in Example 26, Step B. MS (ESI): exact mass calculated for $C_{20}H_{20}N_2$, 288.16; found, m/z 289.2 [M+H]$^+$. $^1$H NMR (500 MHz, CDCl$_3$): 7.27-7.23 (m, 6H), 7.22-7.17 (m, 1H), 7.12-7.07 (m, 1H), 7.03-6.99 (m, 2H), 6.77 (s, 1H), 4.93 (s, 2H), 3.98 (s, 2H), 3.07 (t, J=5.8 Hz, 2H), 2.48 (t, J=5.8 Hz, 2H).

Example 32

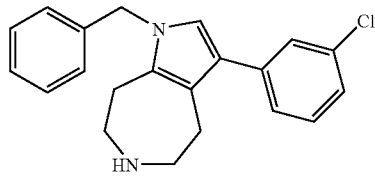

1-Benzyl-3-(3-chloro-phenyl)-1,4,5,6,7,8-hexahydro-pyrrolo[2,3-d]azepine

To a solution of the compound from Example 59, Step B (0.51 g) in toluene (5 mL) was added 280 μL of benzylamine and 0.8 mL of Ti(OiPr)$_4$. The resulting mixture was stirred for 3 h at RT. 1-Chloro-3-(2-nitro-vinyl)-benzene (0.46 g) was then added in one portion and stirring was continued for an additional 16 h at RT. The mixture was poured into water and filtered through diatomaceous earth. The aqueous filtrate was extracted with EtOAc (3×20 mL) and the combined organic layers were concentrated in vacuo. Chromatography on SiO$_2$ (1 to 35% EtOAc/hexanes) afforded 106.7 mg of 1-benzyl-3-(3-chloro-phenyl)-4,5,7,8-tetrahydro-1H-pyrrolo[2,3-d]azepine-6-carboxylic acid tert-butyl ester. This compound was then converted to the title compound (19.1 mg) as in Example 27, Step B, using 10:1 CH$_2$Cl$_2$/MeOH as the solvent. MS (ESI): exact mass calculated for $C_{21}H_{21}ClN_2$, 336.14; found, m/z 337.2 [M+H]$^+$. $^1$H NMR (500 MHz, CDCl$_3$): 7.36-7.30 (m, 3H), 7.29-7.25 (m, 2H), 7.23-7.17 (m, 2H), 7.05-7.02 (m, 2H), 6.64 (s, 1H), 5.05 (s, 2H), 3.01-2.98 (m, 2H), 2.94-2.91 (m, 2H), 2.82-2.97 (m, 2H), 2.71-2.68 (m, 2H).

Example 33

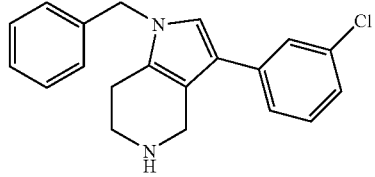

1-Benzyl-3-(3-chloro-phenyl)-4,5,6,7-tetrahydro-1H-pyrrolo[3,2-c]pyridine

The title compound (193.3 mg) was prepared from 0.50 g of 4-oxo-piperidine-1-carboxylic acid tert-butyl ester, 260 μL of benzylamine, and 0.45 g of 1-chloro-3-(2-nitro-vinyl)-benzene as in Example 9. MS (ESI): exact mass calculated for $C_{20}H_{19}ClN_2$, 322.12; found, m/z 323.2 [M+H]$^+$. $^1$H NMR (500 MHz, CDCl$_3$): 7.36-7.20 (m, 6H), 7.14-7.07 (m, 3H), 6.81 (s, 1H), 5.01 (s, 2H), 4.04 (s, 2H), 3.14 (t, J=5.8 Hz, 2H), 2.51 (t, J=5.8 Hz, 2H).

Example 34

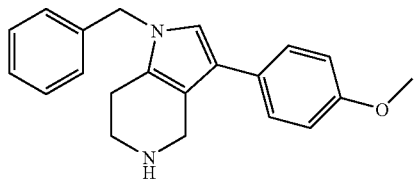

1-Benzyl-3-(4-methoxy-phenyl)-4,5,6,7-tetrahydro-1H-pyrrolo[3,2-c]pyridine

Step A. 1-Benzyl-3-(4-methoxy-phenyl)-1,4,6,7-tetrahydro-pyrrolo[3,2-c]pyridine-5-carboxylic acid tert-butyl ester. To a solution of 0.50 g of 4-oxo-piperidine-1-carboxylic acid tert-butyl ester and 260 μL of benzylamine in toluene (5 mL) was added 0.48 g of MgSO$_4$ and 16.7 mg of Bu$_2$SnCl$_2$. After 1 h, 0.45 g of 1-methoxy-4-(2-nitro-vinyl)-benzene was added and the mixture was stirred for 16 h at RT. The mixture was then diluted with water (80 mL) and extracted with EtOAc (3×15 mL) and the combined organic layers were concentrated in vacuo. Chromatography on SiO$_2$ (1 to 20% EtOAc/hexanes) afforded 0.38 g of the desired compound. MS (ESI): exact mass calculated for $C_{26}H_{30}N_2O_3$, 418.23; found, m/z 419.2 [M+H]$^+$.

Step B. The above compound (0.47 g) was converted to the title compound (275.2 mg) as in Example 26, Step B. MS (ESI): exact mass calculated for $C_{21}H_{22}N_2O$, 318.17; found, m/z 319.2 [M+H]$^+$. $^1$H NMR (400 MHz, CDCl$_3$): 7.35-7.24 (m, 5H), 7.12-7.08 (m, 2H), 6.90-6.86 (m, 2H), 6.74 (s, 1H), 4.99 (s, 2H), 4.04 (s, 2H), 3.81 (s, 3H), 3.16 (t, J=5.8 Hz, 2H), 2.53 (t, J=5.8 Hz, 2H).

Example 35

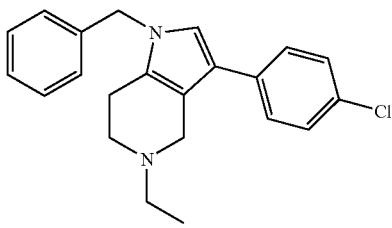

1-Benzyl-3-(4-chloro-phenyl)-5-ethyl-4,5,6,7-tetrahydro-1H-pyrrolo[3,2-c]pyridine To a solution of 1-benzyl-3-(4-chloro-phenyl)-4,5,6,7-tetrahydro-1H-pyrrolo[3,2-c]pyridine (Example 25; 0.11 g) in 1,2-dichloroethane (5 mL) was added 18 μL of acetic acid, 26 μL of acetaldehyde, and 0.10 g of NaBH(OAc)$_3$. The mixture was stirred at RT for 15 h. The mixture was diluted with CH$_2$Cl$_2$ and washed with satd. aq. NaHCO$_3$ (2×). The combined organic layers were dried over Na$_2$SO$_4$, filtered, and concentrated in vacuo. Chromatography on SiO$_2$ (1% 2 M NH$_3$ in MeOH/CH$_2$Cl$_2$) afforded 0.02 g of the title compound. The product was dissolved in Et$_2$O and treated with excess 1.0 M HCl in Et$_2$O to afford 0.02 g of the corresponding HCl salt. MS (ESI): exact mass calculated for $C_{22}H_{23}ClN_2$, 350.15; found, m/z 351.2 [M+H]$^+$, 353.2 [M+H]$^+$. $^1$H NMR (500 MHz, CD$_3$OD): 7.37-7.27 (m, 7H), 7.19-7.17 (m, 3H), 5.17-5.13 (m, 2H), 4.48-4.37 (m, 2H), 3.85-3.76 (m, 2H), 3.45-3.23 (m, 2H), 3.00-2.84 (m, 2H), 1.38 (t, J=7.1 Hz, 3H).

Example 36

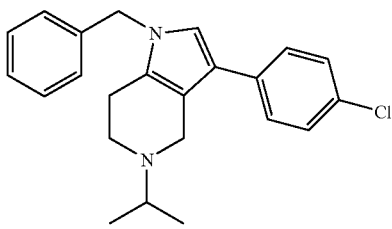

1-Benzyl-3-(4-chloro-phenyl)-5-isopropyl-4,5,6,7-tetrahydro-1H-pyrrolo[3,2-c]pyridine The title compound (0.1 g) was prepared from 1-benzyl-3-(4-chloro-phenyl)-4,5,6,7-tetrahydro-1H-pyrrolo[3,2-c]pyridine (Example 25; 0.10 g) and 32 μL of acetone as in Example 35. MS (ESI): exact mass calculated for $C_{23}H_{25}ClN_2$, 364.17; found, m/z 365.2 [M+H]$^+$, 367.2 [M+H]$^+$. $^1$H NMR (500 MHz, CD$_3$OD): 7.37-7.27 (m, 7H), 7.21-7.17 (m, 3H), 5.15 (d, J=5.2 Hz, 2H), 4.58-4.54 (m, 1H), 4.28-4.25 (m, 1H), 3.78-3.65 (m, 2H), 3.45-3.35 (m, 1H), 3.03-2.85 (m, 2H), 1.42 (t, J=6.6 Hz, 6H).

Example 37

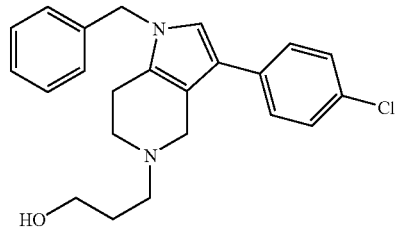

3-[1-Benzyl-3-(4-chloro-phenyl)-1,4,6,7-tetrahydro-pyrrolo[3,2-c]pyridin-5-yl]-propan-1-ol To a solution of 1-benzyl-3-(4-chloro-phenyl)-4,5,6,7-tetrahydro-1H-pyrrolo[3,2-c]pyridine (Example 25; 0.51 g) in DMF (14 mL) was added 1.39 g of Cs$_2$CO$_3$ and 142 μL of 3-bromo-1-propanol. The mixture was stirred at RT for 12 h and then was diluted with water. The aqueous layer was extracted with Et$_2$O and the combined organic layers were dried over Na$_2$SO$_4$, filtered, and concentrated in vacuo. Chromatography on SiO$_2$ (2% 2 M NH$_3$ in MeOH/CH$_2$Cl$_2$) afforded 0.15 g of the title compound. The product was dissolved in Et$_2$O and treated with excess 1.0 M HCl in Et$_2$O to afford 0.16 g the corresponding HCl salt. MS (ESI): exact mass calculated for $C_{23}H_{25}ClN_2O$, 380.17; found, m/z 381.2 [M+H]$^+$, 383.2 [M+H]$^+$. $^1$H NMR (500 MHz, CD$_3$OD): 7.37-7.27 (m, 7H), 7.19-7.17 (m, 3H), 5.15 (s, 2H), 4.47 (br s, 2H), 3.93-3.25 (m, 6H), 2.94-2.93 (m, 2H), 2.01-1.96 (m, 2H).

Example 38

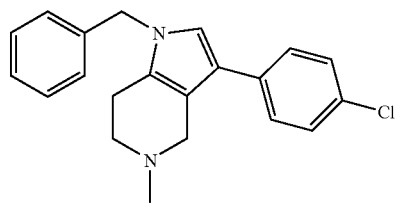

1-Benzyl-3-(4-chloro-phenyl)-5-methyl-4,5,6,7-tetrahydro-1H-pyrrolo[3,2-c]pyridine Step A. 1-Benzyl-3-(4-chloro-phenyl)-1,4,6,7-tetrahydro-pyrrolo[3,2-c]pyridine-5-carboxylic acid ethyl ester. To a stirred solution of 3.0 g of 4-oxo-piperidine-1-carboxylic acid ethyl ester in benzene (35 mL) was added 1.91 mL of benzylamine. The mixture was heated at reflux for 24 h using a Dean-Stark apparatus. The solvent was removed to give a pale yellow oil. A portion of the crude product (0.50 g) was dissolved in toluene (4 mL) and 0.35 g of 1-chloro-4-(2-nitro-vinyl)-benzene was added, followed by 0.7 g of 4 Å molecular sieves. The resulting mixture was stirred for 12 h at RT. The mixture was then filtered through diatomaceous earth and the filtrate was washed with satd. aq. NH$_4$Cl (3×). The combined organic extracts were dried over Na₂SO₄, filtered, and concentrated in vacuo. Chromatography on SiO₂ (8% EtOAc/hexanes) afforded 0.25 g the title compound. TLC (SiO₂, 25% EtOAc/hexanes): $R_f$=0.34. MS (ESI): exact mass calculated for $C_{23}H_{23}ClN_2O_2$, 394.14; found, m/z 395.2 [M+H]⁺, 397.2 [M+H]⁺, 417.1 [M+Na]⁺.

Step B. To a stirred solution of the above compound (0.25 g) in toluene (20 mL) was added 571 μL of sodium bis(2-methoxyethoxy)aluminum hydride (Red-Al, 1.5 M in toluene). The mixture was stirred for 48 h at RT and then was quenched by the addition of satd. aq. potassium sodium tartrate. The organic layer was separated and dried over Na₂SO₄, filtered, and concentrated in vacuo to give 0.16 g of the title compound. TLC (SiO₂, 10% MeOH/EtOAc): $R_f$=0.14. MS (ESI): exact mass calculated for $C_{21}H_{21}ClN_2$, 336.14; found, m/z 337.2 [M+H]⁺, 339.2 [M+H]⁺. ¹H NMR (500 MHz, CDCl₃): 7.31-7.24 (m, 7H), 7.07-7.06 (m, 2H), 6.76 (s, 1H), 4.98 (s, 2H), 3.56 (s, 2H), 2.72 (t, J=6.3 Hz, 2H), 2.60 (t, J=6.3 Hz, 2H).

Example 39

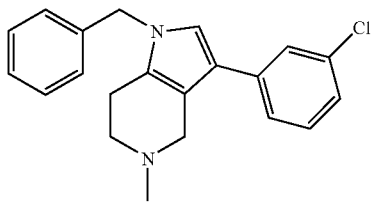

1-Benzyl-3-(3-chloro-phenyl)-5-methyl-4,5,6,7-tetrahydro-1H-pyrrolo[3,2-c]pyridine The title compound (0.34 g) was prepared from 3.0 g of 4-oxo-piperidine-1-carboxylic acid ethyl ester, 1.91 mL of benzylamine, and 1.2 g of 1-chloro-3-(2-nitro-vinyl)-benzene as in Example 38. TLC (SiO₂, 2% NH₃ in MeOH/EtOAc): $R_f$=0.25. MS (ESI): exact mass calculated for $C_{21}H_{21}ClN_2$, 336.14; found, m/z 337.2 [M+H]⁺, 339.2 [M+H]⁺. ¹H NMR (500 MHz, CD₃OD): 7.36-7.32 (m, 4H), 7.30-7.25 (m, 2H), 7.21-7.16 (m, 4H), 5.15 (s, 2H), 4.41 (s, 2H), 3.53 (t, J=6.3 Hz, 2H), 2.98 (s, 3H), 2.91 (t, J=6.3 Hz, 2H), 2.82-2.70 (m, 4H).

Example 40

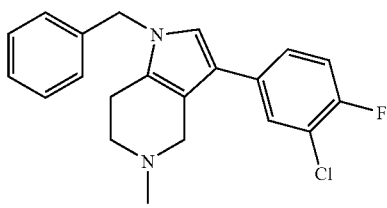

1-Benzyl-3-(3-chloro-4-fluoro-phenyl)-5-methyl-4,5,6,7-tetrahydro-1H-pyrrolo[3,2-c]pyridine The title compound (0.03 g) was prepared from 1-benzyl-3-(3-chloro-4-fluoro-phenyl)-4,5,6,7-tetrahydro-1H-pyrrolo[3,2-c]pyridine (Example 2) and paraformaldehyde as in Example 35. The product was then dissolved in 1/1 EtOAc/CH₂Cl₂ and treated with 0.03 g (0.15 mmol) of citric acid to afford 0.05 g of the corresponding citrate salt. MS (ESI): exact mass calculated for $C_{21}H_{20}ClFN_2$, 354.13; found, m/z 355.1 [M+H]⁺, 357.2 [M+H]⁺. ¹H NMR (500 MHz, CD₃OD): 7.44-7.22 (m, 1H), 7.34 (t, J=7.7 Hz, 2H), 7.30-7.26 (m, 2H), 7.22 (t, J=9.1 Hz, 1H), 7.19-7.13 (m, 3H), 5.14 (s, 2H), 4.36 (s, 2H), 3.50 (t, J=5.8 Hz, 2H), 2.96 (s, 3H), 2.89 (t, J=5.8, 2H), 2.82-2.71 (m, 4H).

Example 41

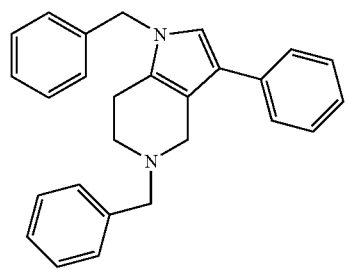

1,5-Dibenzyl-3-phenyl-4,5,6,7-tetrahydro-1H-pyrrolo[3,2-c]pyridine

To a stirred solution of 0.46 mL of 1-benzyl-piperidin-4-one in absolute EtOH (5 mL) was added 0.27 mL of benzylamine. After 3 h, the solvent was removed in vacuo. The residue was diluted with absolute EtOH (5 mL) and 0.37 g of (2-nitro-vinyl)-benzene was added in one portion. The mixture was stirred at RT for 16 h, filtered through diatomaceous earth, and the filtrate was concentrated. Chromatography on SiO₂ (1 to 20% EtOAc/hexanes) afforded 0.48 g of the title compound. MS (ESI): exact mass calculated for $C_{27}H_{26}N_2$, 378.21; found, m/z 379.2 [M+H]⁺. ¹H NMR (500 MHz, CDCl₃): 7.40-7.22 (m, 12H), 7.18-7.10 (m, 3H), 6.80 (s, 1H), 4.99 (s, 2H), 3.78 (br m, 2H), 3.75 (s, 2H), 2.79-2.74 (m, 2H), 2.59-2.55 (m, 2H).

Example 42

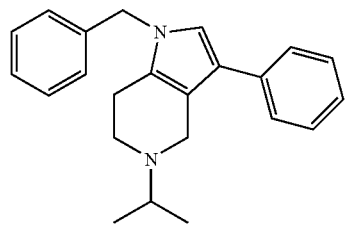

1-Benzyl-5-isopropyl-3-phenyl-4,5,6,7-tetrahydro-1H-pyrrolo[3,2-c]pyridine

The title compound (111.0 mg) was prepared from 372 μL of 1-isopropyl-piperidin-4-one, 270 μL of benzylamine, and 0.38 g of (2-nitro-vinyl)-benzene as in Example 41. The product was diluted with EtOAc and malic acid (39.0 mg) was added. The solids that formed were collected by filtration to give the title compound as a maleate salt. MS (ESI): exact mass calculated for $C_{23}H_{26}N_2$, 330.21; found, m/z 331.2 [M+H]$^+$. $^1$H NMR (500 MHz, CD$_3$OD): 7.38-7.33 (m, 6H), 7.30-7.27 (m, 1H), 7.23-7.19 (m, 3H), 7.14 (s, 1H), 6.25 (s, 2H), 5.15 (s, 2H), 3.74-3.66 (m, 1H), 2.96-2.91 (br m, 2H), 1.41 (d, J=6.6 Hz, 6H).

Example 43

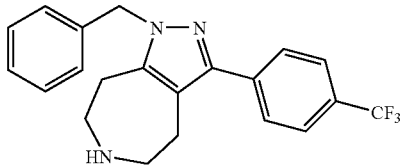

1-Benzyl-3-(4-trifluoromethyl-phenyl)-1,4,5,6,7,8-hexahydro-1,2,6-triaza-azulene Step A. 3-Oxo-2,3,4,5,7,8-hexahydro-1H-1,2,6-triaza-azulene-6-carboxylic acid tert-butyl ester. To a solution of 5-oxo-azepane-1,4-dicarboxylic acid 1-tert-butyl ester 4-ethyl ester (Example 59, Step A; 8.29 g) in 80 mL of EtOH was added 1.5 mL of hydrazine hydrate. The solution was heated at reflux for 2 days and then was cooled to RT. The solvent volume was reduced to ca. 20 mL and the resulting solution was stored at −15° C. for 16 h. Water was added and the solids were collected by filtration, washed with water, and dried to give 4.99 g of the desired compound as a white crystalline solid. MS (ESI): exact mass calculated for $C_{12}H_{19}N_3O_3$, 253.14; found, m/z 254.1 [M+H]$^+$.

Step B. 1-Benzyl-3-oxo-2,3,4,5,7,8-hexahydro-1H-1,2,6-triaza-azulene-6-carboxylic acid tert-butyl ester. To a stirred solution of 1.16 g the compound from step A in 15 mL of DMF was added 1.80 g of Cs$_2$CO$_3$. The suspension was stirred at RT for 20 min. Benzyl bromide (0.6 mL) was added and the mixture was stirred at RT for an additional 12 h. The mixture was diluted with water and extracted with Et$_2$O. The combined organic layers were washed with water, brine, dried over Na$_2$SO$_4$, and concentrated to afford 1.77 g of a colorless semi-solid. Chromatography on SiO$_2$ (15 to 50% EtOAc/hexanes) over 1 h gave 1.21 g of the desired compound as a mixture of mono-benzylated isomers. TLC (SiO$_2$, 50% EtOAc/hexanes): $R_f$=0.34. MS (ESI): exact mass calculated for $C_{19}H_{25}N_3O_3$, 343.19; found, m/z 344.2 [M+H]$^+$, 366.2 [M+Na]$^+$.

Step C. 1-Benzyl-3-trifluoromethanesulfonyloxy-4,5,7,8-tetrahydro-1H-1,2,6-triaza-azulene-6-carboxylic acid tert-butyl ester. To a stirred solution of the above mixture of regioisomers (1.21 g) in 35 mL of CH$_2$Cl$_2$ was added 1.93 mL of i-Pr$_2$NEt and 1.58 g of N-phenyltrifluoromethane-sulfonimide. The mixture was heated at reflux for 12 h and then was cooled and concentrated in vacuo. Chromatography on SiO$_2$ (5 to 20% EtOAc/hexanes) afforded 0.63 g of the desired compound. TLC (SiO$_2$, 25% EtOAc/hexanes): $R_f$=0.37. MS (ESI): exact mass calculated for $C_{20}H_{24}F_3N_3O_5S$, 475.14; found, m/z 476.2 [M+H]$^+$. Also, 0.68 g of the undesired mono-benzylated 3-benzyloxy-4,5,7,8-tetrahydro-1H-1,2,6-triaza-azulene-6-carboxylic acid tert-butyl ester was obtained.

Step D. 1-Benzyl-3-(4-trifluoromethyl-phenyl)-4,5,7,8-tetrahydro-1H-1,2,6-triaza-azulene-6-carboxylic acid tert-butyl ester. To a solution of the compound from step C (0.17 g) in 5 mL of THF was added 0.12 g of K$_3$PO$_4$, 0.08 g of 4-trifluoromethylphenylboronic acid and 0.03 g of PdCl$_2$dppf. The mixture was heated at reflux for 12 h. The mixture was cooled, filtered through diatomaceous earth, and concentrated in vacuo. Chromatography on SiO$_2$ (5 to 40% EtOAc/hexanes) afforded 0.05 g of the desired compound. TLC (SiO$_2$, 25% EtOAc/hexanes): $R_f$=0.49.

Step E. 1-Benzyl-3-(4-trifluoromethyl-phenyl)-1,4,5,6,7,8-hexahydro-1,2,6-triaza-azulene. To a stirred solution of the compound from step D (0.05 g) in 2 mL of CH$_2$Cl$_2$ was added 2.0 mL of TFA. The mixture was stirred at RT for 2 h and concentrated in vacuo. The crude product was re-dissolved in CH$_2$Cl$_2$ and treated with Dowex® 550A resin. After stirring for 2 h, the mixture was filtered and concentrated in vacuo to afford 0.04 g of the title compound. The product was dissolved in Et$_2$O and treated with excess 1.0 M HCl in Et$_2$O for 30 min. The solvent was removed in vacuo to afford 0.05 g of the corresponding HCl salt. MS (ESI): exact mass calculated for $C_{21}H_{20}F_3N_3$, 371.16; found, m/z 372.2 [M+H]$^+$. $^1$H NMR (500 MHz, CD$_3$OD): 7.78-7.74 (m, 4H), 7.37-7.28 (m, 3H), 7.20 (t, J=6.9 Hz, 2H), 5.46 (br s, 2H), 4.65 (br s, 1H), 3.40-3.37 (m, 3H), 3.17-3.10 (m, 4H).

The title compounds of Examples 44-53 were prepared according to the general procedure indicated by Example 43, Steps D and E, unless otherwise noted.

Example 44

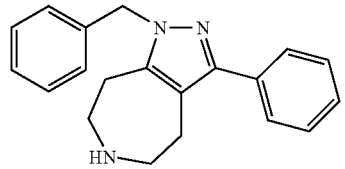

1-Benzyl-3-phenyl-1,4,5,6,7,8-hexahydro-1,2,6-triaza-azulene

The title compound (0.07 g) was prepared from the compound of Example 43, Step C (0.16 g), and 0.05 g of phenylboronic acid. MS (ESI): exact mass calculated for $C_{20}H_{21}N_3$, 303.17; found, m/z 304.2 [M+H]$^+$. $^1$H NMR (500 MHz, CD$_3$OD): 7.56-7.54 (m, 2H), 7.51-7.43 (m, 3H), 7.39-7.36 (m, 2H), 7.33-7.29 (m, 1H), 7.21 (d, J=6.9 Hz, 2H), 5.50 (s, 2H), 3.43-3.38 (m, 4H), 3.22-3.20 (m, 2H), 3.12-3.10 (m, 2H).

Example 45

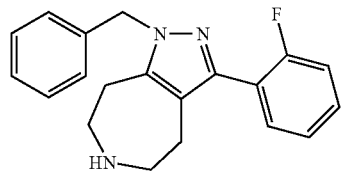

1-Benzyl-3-(2-fluoro-phenyl)-1,4,5,6,7,8-hexahydro-1,2,6-triaza-azulene

The title compound (0.06 g) was prepared from the compound of Example 43, Step C (0.31 g), and 0.10 g of 2-fluorophenylboronic acid, using 1,4-dioxane as the solvent. MS (ESI): exact mass calculated for $C_{20}H_{20}FN_3$, 321.16; found, m/z 322.2 [M+H]$^+$. $^1$H NMR (500 MHz, CD$_3$OD): 7.52-7.46

(m, 2H), 7.38-7.18 (m, 7H), 5.46 (s, 2H), 3.38-3.33 (m, 4H), 3.17-3.15 (m, 2H), 2.91-2.89 (m, 2H).

Example 46

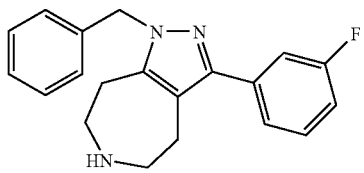

1-Benzyl-3-(3-fluoro-phenyl)-1,4,5,6,7,8-hexahydro-1,2,6-triaza-azulene

The title compound (0.07 g) was prepared from the compound of Example 43, Step C (0.30 g), and 0.10 g of 3-fluorophenylboronic acid, using 1,4-dioxane as the solvent. MS (ESI): exact mass calculated for $C_{20}H_{20}FN_3$, 321.16; found, m/z 322.2 [M+H]$^+$. $^1$H NMR (400 MHz, CD$_3$OD): 7.52-7.47 (m, 1H), 7.38-7.27 (m, 5H), 7.20-7.13 (m, 3H), 5.47 (s, 2H), 3.43-3.34 (m, 4H), 3.23-3.06 (m, 4H).

Example 47

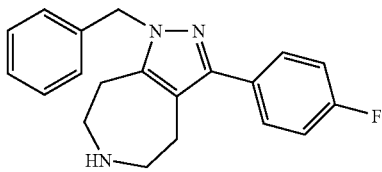

1-Benzyl-3-(4-fluoro-phenyl)-1,4,5,6,7,8-hexahydro-1,2,6-triaza-azulene

The title compound (0.07 g) was prepared from the compound of Example 43, Step C (0.22 g), and 0.20 g of 4-fluorophenylboronic acid, adding 9.1 mg of dppf and using 1,4-dioxane as the solvent. MS (ESI): exact mass calculated for $C_{20}H_{20}FN_3$, 321.16; found, m/z 322.2 [M+H]$^+$. $^1$H NMR (500 MHz, CDCl$_3$): 7.54-7.51 (m, 2H), 7.33-7.30 (m, 2H), 7.28-7.24 (m, 1H), 7.12-7.07 (m, 4H), 5.35 (s, 2H), 2.98-2.95 (m, 2H), 2.94-2.92 (m, 2H), 2.80-2.77 (m, 2H), 2.76-2.74 (m, 2H).

Example 48

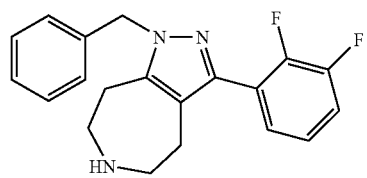

1-Benzyl-3-(2,3-difluoro-phenyl)-1,4,5,6,7,8-hexahydro-1,2,6-triaza-azulene

The title compound (0.05 g) was prepared from the compound of Example 43, Step C (0.30 g), and 0.11 g of 3,4-difluorophenylboronic acid, using 1,4-dioxane as the solvent. MS (ESI): exact mass calculated for $C_{20}H_{19}F_2N_3$, 339.15; found, m/z 340.2 [M+H]$^+$. $^1$H NMR (500 MHz, CD$_3$OD): 7.37-7.26 (m, 6H), 7.21-7.18 (m, 2H), 5.46 (s, 2H), 3.38-3.34 (m, 4H), 3.18-3.16 (m, 2H), 2.92-2.90 (m, 2H).

Example 49

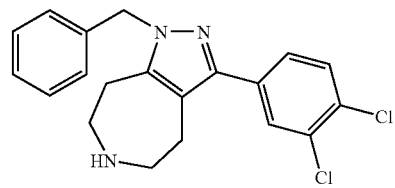

1-Benzyl-3-(3,4-dichloro-phenyl)-1,4,5,6,7,8-hexahydro-1,2,6-triaza-azulene

The title compound (0.02 g) was prepared from the compound of Example 43, Step C (0.17 g), and 0.08 g of 3,4-dichlorophenylboronic acid. MS (ESI): exact mass calculated for $C_{20}H_{19}Cl_2N_3$, 371.10; found, m/z 372.1 [M+H]$^+$, 374.1 [M+H]$^+$, 376.1 [M+H]$^+$. $^1$H NMR (500 MHz, CD$_3$OD): 7.78-7.74 (m, 4H), 7.37-7.28 (m, 3H), 7.21-7.18 (m, 2H), 5.46-5.45 (m, 2H), 3.40-3.30 (m, 4H), 3.17-3.10 (m, 4H).

Example 50

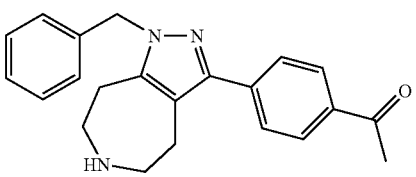

1-[4-(1-Benzyl-1,4,5,6,7,8-hexahydro-1,2,6-triaza-azulen-3-yl)-phenyl]-ethanone

The title compound (0.02 g) was prepared from the compound of Example 43, Step C (0.20 g), and 0.08 g of 4-acetylphenylboronic acid, using 1,4-dioxane as the solvent. MS (ESI): exact mass calculated for $C_{22}H_{23}N_3O$, 345.18; found, m/z 346.2 [M+H]$^+$. $^1$H NMR (500 MHz, CD$_3$OD): 8.10-8.09 (m, 2H), 7.71-7.70 (m, 2H), 7.38-7.19 (m, 5H), 5.48 (s, 2H), 3.40 (br s, 4H), 3.28-3.10 (m, 4H), 2.64 (s, 3H).

Example 51

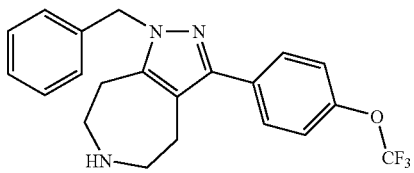

1-Benzyl-3-(4-trifluoromethoxy-phenyl)-1,4,5,6,7,8-hexahydro-1,2,6-triaza-azulene The title compound (0.03 g) was prepared from the compound of Example 43, Step C (0.26 g), and 0.13 g of 4-trifluoromethoxyphenylboronic acid, using 1,4-dioxane as the solvent. MS (ESI): exact mass calculated for $C_{21}H_{20}F_3N_3O$, 387.16; found, m/z 388.1 [M+H]$^+$. $^1$H NMR (500 MHz, CD$_3$OD): 7.67-7.63 (m, 2H), 7.39-7.28 (m, 5H), 7.20-7.17 (m, 2H), 5.44 (s, 2H), 3.39-3.36 (m, 2H), 3.32-3.30 (m, 2H), 3.15-3.06 (m, 4H).

Example 52

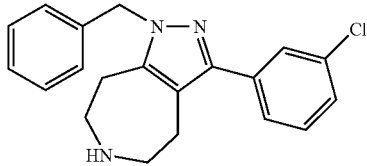

1-Benzyl-3-(3-chloro-phenyl)-1,4,5,6,7,8-hexahydro-1,2,6-triaza-azulene

The title compound (0.04 g) was prepared from the compound of Example 43, Step C (0.20 g), and 0.07 g of 3-chlorophenylboronic acid, using 1,4-dioxane as the solvent. MS (ESI): exact mass calculated for $C_{20}H_{20}ClN_3$, 337.13; found, m/z 338.1 [M+H]$^+$, 340.1 [M+H]$^+$. $^1$H NMR (400 MHz, CD$_3$OD): 7.56 (br s, 1H), 7.47-7.29 (m, 6H), 7.29-7.19 (m, 2H), 5.44 (s, 2H), 3.38-3.36 (m, 2H), 3.32-3.30 (m, 2H), 3.19-3.06 (m, 4H).

Example 53

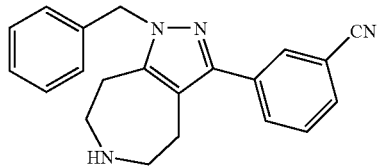

3-(1-Benzyl-1,4,5,6,7,8-hexahydro-1,2,6-triaza-azulen-3-yl)-benzonitrile

The title compound (0.04 g) was prepared from the compound of Example 43, Step C (0.30 g), and 0.10 g of 3-cyanophenylboronic acid, using 1,4-dioxane as the solvent. MS (ESI): exact mass calculated for $C_{21}H_{20}N_4$, 328.17; found, m/z 329.2 [M+H]$^+$. $^1$H NMR (500 MHz, CD$_3$OD): 7.91-7.86 (m, 2H), 7.76-7.75 (m, 1H), 7.65 (t, J=7.7 Hz, 1H), 7.37-7.20 (m, 3H), 7.19-7.18 (m, 2H), 5.45 (s, 2H), 3.39-3.37 (m, 4H), 3.17-3.08 (m, 4H).

Example 54

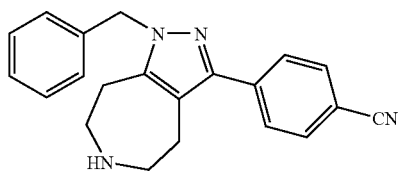

4-(1-Benzyl-1,4,5,6,7,8-hexahydro-1,2,6-triaza-azulen-3-yl)-benzonitrile

To a solution of 1-benzyl-3-trifluoromethanesulfonyloxy-4,5,7,8-tetrahydro-1H-1,2,6-triaza-azulene-6-carboxylic acid tert-butyl ester (Example 43, Step C, 0.30 g) in 9 mL of 1,4-dioxane was added 0.20 g of K$_3$PO$_4$, 0.10 g of 4-cyanophenylboronic acid, and 0.05 g of PdCl$_2$dppf. The mixture was heated at reflux for 72 h. The mixture was filtered through diatomaceous earth and concentrated in vacuo to give 0.33 g of an orange solid. Chromatography on SiO$_2$ (5 to 30% EtOAc/hexanes) afforded 0.21 g of a 7:1 mixture of 1-benzyl-3-(4-cyano-phenyl)-4,5,7,8-tetrahydro-1H-1,2,6-triaza-azulene-6-carboxylic acid tert-butyl ester and a side product, 1-benzyl-4,5,7,8-tetrahydro-1H-1,2,6-triaza-azulene-6-carboxylic acid tert-butyl ester. The mixture of compounds (0.21 g) was dissolved in 7 mL CH$_2$Cl$_2$ and 7 mL of TFA was added. The mixture was stirred at RT for 1 h and concentrated in vacuo. The crude product was dissolved in CH$_2$Cl$_2$ and treated with Dowex® 550A resin. After stirring for 2 h, the mixture was filtered and concentrated in vacuo. Chromatography using a C$_{18}$ reverse phase column afforded 0.14 g of the title compound as its TFA salt. MS (ESI): exact mass calculated for $C_{21}H_{20}N_4$, 328.17; found, m/z 329.1 [M+H]$^+$, 351.1 [M+Na]$^+$. $^1$H NMR (500 MHz, CD$_3$OD): 7.83-7.81 (m, 2H), 7.76-7.74 (m, 2H), 7.36-7.28 (m, 3H), 7.19-7.17 (m, 2H), 5.46 (s, 2H), 3.39-3.37 (m, 4H), 3.15-3.09 (m, 4H).

Example 55

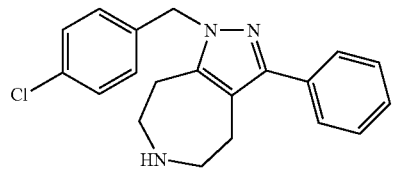

1-(4-Chloro-benzyl)-3-phenyl-1,4,5,6,7,8-hexahydro-1,2,6-triaza-azulene

Step A. 1-(4-Chloro-benzyl)-3-phenyl-4,5,7,8-tetrahydro-1H-1,2,6-triaza-azulene-6-carboxylic acid tert-butyl ester. To a solution of 0.13 g of 1-(4-chloro-benzyl)-3-trifluoromethanesulfonyl-4,5,7,8-tetrahydro-1H-1,2,6-triaza-azulene-6-carboxylic acid tert-butyl ester, prepared as in Example 43, Steps A through C, in 3 mL of THF was added 300 µL of water, 0.11 g of K$_2$CO$_3$, 44.9 mg of phenylboronic acid, and 20.0 mg of PdCl$_2$dppf. The mixture was heated at 100° C. for 18 h. The mixture was filtered through diatomaceous earth and concentrated in vacuo. Chromatography on SiO$_2$ (hexanes to 45% EtOAc/hexanes) afforded 16.1 mg of the desired compound. MS (ESI): exact mass calculated for C$_{25}$H$_{28}$ClN$_3$O$_2$, 437.19; found, m/z 438.2 [M+H]$^+$.

Step B. The above compound (16.1 mg) was converted to the title compound (7.1 mg) as in Example 26, Step B. MS (ESI): exact mass calculated for C$_{20}$H$_{20}$ClN$_3$, 337.13; found, m/z 338.1 [M+H]$^+$. $^1$H NMR (500 MHz, CDCl$_3$): 7.57-7.54 (m, 2H), 7.44-7.40 (m, 2H), 7.35-7.31 (m, 1H), 7.30-7.26 (m, 3H), 7.04 (d, J=8.5 Hz, 2H), 5.32 (s, 2H), 2.99-2.93 (m, 4H), 2.85-2.82 (m, 2H), 2.77-2.73 (m, 2H), 1.97 (br s, 1H).

Example 56

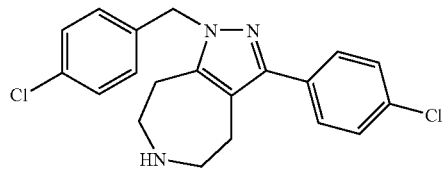

1-(4-Chloro-benzyl)-3-(4-chloro-phenyl)-1,4,5,6,7,8-hexahydro-1,2,6-triaza-azulene Step A. 1-(4-Chloro-benzyl)-3-(4-chloro-phenyl)-4,5,7,8-tetrahydro-1H-1,2,6-triaza-azulene-6-carboxylic acid tert-butyl ester. To a solution of 142.7 mg of 1-(4-chloro-benzyl)-3-trifluoromethanesulfonyl-4,5,7,8-tetrahydro-1H-1,2,6-triaza-azulene-6-carboxylic acid tert-butyl ester, prepared as in Example 43, Steps A through C, in 3 mL of THF was added 0.17 g of K$_3$PO$_4$, 54.9 mg of 4-chlorophenylboronic acid, and 22.1 mg of PdCl$_2$dppf. The mixture was heated at reflux for 48 h. The mixture was filtered through diatomaceous earth, rinsing with toluene, and the filtrate was concentrated in vacuo. Chromatography on SiO$_2$ (hexanes to 75% EtOAc/hexanes) afforded 6.7 mg of the desired compound. MS (ESI): exact mass calculated for C$_{25}$H$_{27}$Cl$_2$N$_3$O$_2$, 471.15; found, m/z 472.1 [M+H]$^+$.

Step B. The above compound (6.7 mg) was converted to the title compound (5.0 mg) as in Example 26, Step B. MS (ESI): exact mass calculated for C$_{20}$H$_{19}$Cl$_2$N$_3$, 371.10; found, m/z 372.1 [M+H]$^+$. $^1$H NMR (500 MHz, CDCl$_3$): 7.48 (d, J=8.5 Hz, 2H), 7.38 (d, J=8.5 Hz, 2H), 7.29 (d, J=8.5 Hz, 2H), 7.03 (d, J=8.5 Hz, 2H), 5.30 (s, 2H), 3.02-2.96 (m, 4H), 2.84-2.80 (m, 2H), 2.79-2.76 (m, 2H).

Example 57

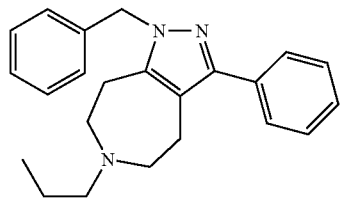

1-Benzyl-3-phenyl-6-propyl-1,4,5,6,7,8-hexahydro-1,2,6-triaza-azulene

The title compound (0.05 g) was prepared from 1-benzyl-3-phenyl-1,4,5,6,7,8-hexahydro-1,2,6-triaza-azulene (Example 44, 0.09 g) and 23 µL of propionaldehyde as in Example 35. MS (ESI): exact mass calculated for C$_{23}$H$_{27}$N$_3$, 345.22; found, m/z 346.3 [M+H]$^+$. $^1$H NMR (400 MHz, CD$_3$OD): 7.56-7.54 (m, 2H), 7.47-7.28 (m, 6H), 7.21-7.19 (m, 2H), 5.44 (s, 2H), 3.70-3.66 (m, 2H), 3.41-3.07 (m, 8H), 1.86-1.76 (m, 2H), 1.03 (t, J=7.3 Hz, 3H).

Example 58

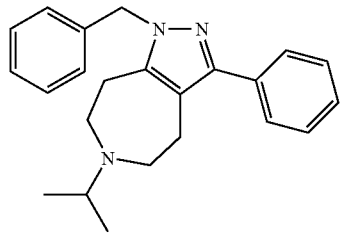

1-Benzyl-6-isopropyl-3-phenyl-1,4,5,6,7,8-hexahydro-1,2,6-triaza-azulene

The title compound (0.03 g) was prepared from 1-benzyl-3-phenyl-1,4,5,6,7,8-hexahydro-1,2,6-triaza-azulene (Example 44, 0.07 g) and 22 µL of acetone as in Example 35. MS (ESI): exact mass calculated for C$_{23}$H$_{27}$N$_3$, 345.22; found, m/z 346.3 [M+H]$^+$. $^1$H NMR (500 MHz, CD$_3$OD): 7.57-7.52 (m, 2H), 7.50-7.27 (m, 6H), 7.22-7.20 (m, 2H), 5.47 (s, 2H), 3.77-3.61 (m, 3H), 3.29-3.28 (m, 3H), 3.24-3.08 (m, 3H), 1.40 (d, J=6.0 Hz, 6H).

Example 59

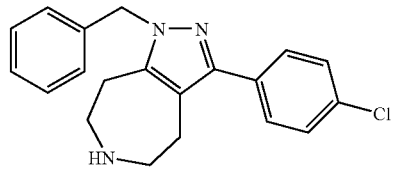

1-Benzyl-3-(4-chloro-phenyl)-1,4,5,6,7,8-hexahydro-1,2,6-triaza-azulene

Step A. 5-Oxo-azepane-1,4-dicarboxylic acid 1-tert-butyl ester 4-ethyl ester. A solution of 4-oxo-piperidine-1-carboxylic acid tert-butyl ester (35 mmol, 7.0 g) in anhydrous $Et_2O$ (50 mL) was stirred in a 200 mL 3-neck flask equipped with two addition funnels. The solution was cooled to −25° C. Ethyl diazoacetate (46.5 mmol, 4.89 mL) in anhydrous $Et_2O$ (10 mL) and $BF_3.OEt_2$ (36.7 mmol, 4.65 mL) in anhydrous $Et_2O$ (10 mL) were simultaneously but independently added to the solution over 90 min. The mixture was stirred for an additional 1 h and was slowly warmed to RT. Then, 30% aq. $K_2CO_3$ was added dropwise to the mixture until gas evolution ceased. The organic layer was separated, dried over $Na_2SO_4$, and concentrated. The residue was purified via chromatography ($SiO_2$, 5 to 20% EtOAc/hexanes) to yield the desired compound (7.5 g).

Step B. 4-Oxo-azepane-1-carboxylic acid tert-butyl ester. To a solution of the product of Step A in 1,4-dioxane (50 mL) was added 1 N NaOH (40.83 mmol, 40.83 mL). The mixture was allowed to stir at rt overnight. The solution was then acidified to pH 4-5 with 3 N HCl. The mixture was extracted with $Et_2O$ followed by $CH_2Cl_2$ until TLC showed no product remaining in the aqueous layer. The combined organic layers were dried over $Na_2SO_4$ and concentrated in vacuo to yield the desired compound (7.46 g). MS (ESI): exact mass calculated for $C_{11}H_{19}NO_3$, 213.14; found, m/z 236.2 $[M+Na]^+$.

Step C. 3-(4-Chloro-phenyl)-4,5,7,8-tetrahydro-1H-1,2,6-triaza-azulene-6-carboxylic acid tert-butyl ester. p-Toluenesulfonic acid (0.033 mg, 0.18 mmol) and morpholine (3.4 mL, 38 mmol) were added to a solution of the product of step B (7.46 g, 35.0 mmol) in benzene (15 mL). The reaction mixture was heated at reflux for 20 h using a Dean-Stark trap. The reaction mixture was cooled to RT and concentrated in vacuo to afford the intermediate enamine, which was used without further purification. To a 0° C. solution of the enamine in $CH_2Cl_2$ (30 mL) was added triethylamine (27.5 mmol, 3.80 mL) followed by a solution of 4-chlorobenzoyl chloride (27.5 mmol, 3.50 mL) in $CH_2Cl_2$ (10 mL). The reaction mixture was allowed to warm to RT and was stirred for 16 h. The mixture was poured over water and the layers were separated. The organic layer was dried over $Na_2SO_4$ and concentrated. The resulting oil was diluted with EtOH (120 mL), cooled to 0° C., and treated with hydrazine (75 mmol, 2.4 mL). The reaction mixture was allowed to warm to RT and was stirred for 16 h. The mixture was concentrated and the residue was purified by SFC purification to yield the desired compound (1.2 g). MS (ESI): exact mass calculated for $C_{18}H_{22}ClN_3O_2$, 347.14; found, m/z 346.0 $[M−H]^−$. $^1$H NMR (500 MHz, $CD_3OD$): 7.40-7.35 (m, 4H), 3.62-3.59 (m, 2H), 3.54-3.51 (m, 2H), 2.96-2.93 (m, 2H), 2.81-2.77 (m, 2H), 1.20 (s, 9H). The reaction sequence also yielded 3-(4-chloro-phenyl)-4,6,7,8-tetrahydro-1H-1,2,5-triaza-azulene-5-carboxylic acid tert-butyl ester (1.5 g). MS (ESI): exact mass calculated for $C_{18}H_{22}ClN_3O_2$, 347.14; found, m/z 346.0 $[M−H]^−$. $^1$H NMR (500 MHz, $CD_3OD$): 7.65. (d, J=8.2 Hz, 1H), 7.47-7.41 (m, 3H), 4.67-4.45 (m, 2H), 3.71-3.65 (m, 2H), 2.90-2.89 (m, 2H), 1.90-1.87 (m, 2H), 1.18 (s, 9H).

Step D. 1-Benzyl-3-(4-chloro-phenyl)-1,4,5,6,7,8-hexahydro-1,2,6-triaza-azulene-6-carboxylic acid tert-butyl ester. To a 0° C. solution of the product from Step C (0.10 g, 0.29 mmol) in DMF (2 mL) was added NaH (60% dispersion in oil, 92 mg, 2.3 mmol). The solution was allowed to warm to RT over 1 h, and, benzyl chloride (2.3 mmol) was then added. The reaction mixture was stirred for 16 h and then concentrated. The residue was diluted with water and extracted with $CH_2Cl_2$. The organic layer was washed with brine, dried over $Na_2SO_4$, and concentrated. The crude product was purified via $SiO_2$ chromatography to give the desired ester, which was carried directly into the next step. Also obtained was 2-benzyl-3-(4-chloro-phenyl)-4,5,7,8-tetrahydro-2H-1,2,6-triaza-azulene-6-carboxylic acid tert-butyl ester. MS (ESI): exact mass calculated for $C_{25}H_{28}ClN_3O_2$, 437.19; found, m/z 438.4 $[M+H]^+$. $^1$H NMR (500 MHz, $CDCl_3$): 7.50-7.48 (m, 2H), 7.40-7.38, (m, 2H), 7.33-7.26 (m, 3H), 7.13-7.11 (m, 2H), 5.33 (s, 2H), 3.55-3.51 (m, 4H), 2.86-2.77 (m, 4H), 1.47 (s, 9H).

Step E. The product from Step D was dissolved in 9:1 $CH_2Cl_2/MeOH$ (4 mL). An excess of 1 N HCl in $Et_2O$ was added and the resulting mixture was stirred for 2 h. The progress of the reaction was monitored by MS until no more starting material was evident. The reaction mixture was concentrated to obtain the desired product (51 mg). MS (ESI): exact mass calculated for $C_{20}H_{20}ClN_3$, 337.13; found, m/z 338.2 $[M+H]^+$. $^1$H NMR (500 MHz, $CD_3OD$): 7.56-7.53 (m, 2H), 7.51-7.48 (m, 2H), 7.38-7.29 (m, 3H), 7.20-7.19 (m, 2H), 5.48 (s, 2H), 3.42-3.37 (m, 4H), 3.20-3.18 (m, 2H), 3.10-3.08 (m, 2H).

An alternative method as outlined in Scheme 5 is shown below:

Step F. 3-(4-Chloro-phenyl)-1,4,6,7-tetrahydro-indazol-5-[1,3]dioxolane. The desired compound (5.0 g) was prepared from 5.0 g of 1,4-dioxa-spiro[4.5]decan-8-one, 4.5 mL of 4-chloro-benzoyl chloride and 3.0 mL of hydrazine according to the procedure outlined in Step C above. $^1$H NMR (500 MHz, $CDCl_3$): 7.53-7.50 (m, 2H), 7.36-7.33 (m, 2H), 4.02 (s, 4H), 2.91 (s, 2H), 2.89 (t, J=6.6 Hz, 2H), 2.01 (t, J=6.6 Hz, 2H).

Step G. 1-Benzyl-3-(4-chloro-phenyl)-1,4,6,7-tetrahydro-indazol-5-[1,3]dioxolane. The desired compound (3.93 g) was prepared from 4.0 g of the compound from step F as outlined in Step D, using benzyl bromide (1.9 mL) in place of benzyl chloride and $K_2CO_3$ (6.1 g) in place of NaH. $^1$H NMR (500 MHz, $CDCl_3$): 7.67-7.64 (m, 2H), 7.39-7.27 (m, 5H), 7.21-7.18 (m, 2H), 5.29 (s, 2H), 4.05-3.98 (m, 4H), 2.95 (s, 2H), 2.71 (t, J=6.6 Hz, 2H), 1.98 (t, J=6.6 Hz, 2H).

Step H. 1-Benzyl-3-(4-chloro-phenyl)-1,4,6,7-tetrahydro-indazol-5-one oxime. A solution of 3.87 g of the compound from step G in 80 mL of THF with 5 mL of 1 M HCl was heated at reflux for 16 h. The volatiles were removed in vacuo and water was added (300 mL). The mixture was adjusted to pH 9 by the addition of 1 M NaOH and then was extracted with $CH_2Cl_2$. The combined extracts were washed with brine and the solvent was removed in vacuo to provide 1-benzyl-3-(4-chloro-phenyl)-1,4,6,7-tetrahydro-indazol-5-one. This product (3.13 g) was treated with hydroxylamine hydrochloride (3.0 g) in 20 mL of pyridine. The reaction mixture was stirred at RT for 14 h then was diluted with water (300 mL), and stirred an additional hour. The mixture was filtered on paper and the solids were washed with EtOAc and dried in vacuo to afford 2.48 g of the desired compound. $^1$H NMR (500 MHz, acetone-$d_6$): 10.24 (s, 1H), 7.30-7.26 (m, 2H), 7.06-7.02 (m, 2H), 6.91-9.87 (m, 2H), 6.85-6.81 (m, 1H), 6.77-6.73 (m, 2H), 4.87 (s, 2H), 3.21 (s, 2H), 2.31 (t, J=6.6 Hz, 2H), 2.09 (t, J=6.6 Hz, 2H).

Step I. 1-Benzyl-3-(4-chloro-phenyl)-1,4,5,6,7,8-hexahydro-1,2,6-triaza-azulene. A solution of the compound from step H (78.2 mg) in 15 mL of $CH_2Cl_2$ was cooled to 0° C. and diisobutylaluminum hydride (1.5 M in toluene, 0.75 mL) was added. The solution was allowed to warm to RT and was stirred for 12 h. Water (0.2 mL) and NaF (0.40 g) were added and the mixture was stirred for 1 h. The mixture was filtered through diatomaceous earth and the filtrate was concentrated to afford 66.7 mg of a mixture of the title compound and 1-benzyl-3-(4-chloro-phenyl)-1,4,5,6,7,8-hexahydro-1,2,5-triaza-azulene. MS (ESI): exact mass calculated for $C_{20}H_{20}ClN_3$, 337.13; found, m/z 338.0 $[M+H]^+$.

Example 60 through 102 were prepared using the procedures described in Example 59, Steps D and E, unless otherwise noted.

Example 60

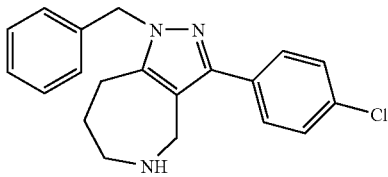

1-Benzyl-3-(4-chloro-phenyl)-1,4,5,6,7,8-hexahydro-1,2,5-triaza-azulene

The title compound (0.068 g) was prepared as in Example 59, Steps D and E, starting with 3-(4-chloro-phenyl)-4,6,7,8-tetrahydro-1H-1,2,5-triaza-azulene-5-carboxylic acid tert-butyl ester (0.1 g), the isomer from Example 59, Step C. The reaction sequence also yielded 2-benzyl-3-(4-chloro-phenyl)-2,6,7,8-tetrahydro-4H-1,2,5-triaza-azulene-5-carboxylic acid tert-butyl ester. MS (ESI): exact mass calculated for $C_{20}H_{20}ClN_3$, 337.13; found, m/z 338.2 $[M+H]^+$. $^1$H NMR (500 MHz, $CD_3OD$): 7.51-7.30 (m, 4H), 7.37-7.29 (m, 3H), 7.29-7.21 (m, 3H), 5.45 (s, 2H), 4.32 (s, 2H), 3.53-3.50 (m, 2H), 3.06-3.03 (m, 2H), 2.04-1.99 (m, 2H).

Example 61

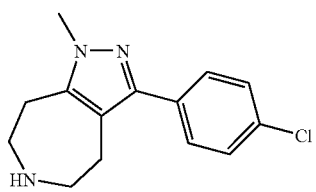

3-(4-Chloro-phenyl)-1-methyl-1,4,5,6,7,8-hexahydro-1,2,6-triaza-azulene

The title compound (0.028 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using methyl iodide (0.21 mL) in place of benzyl chloride. The reaction sequence also yielded 3-(4-chloro-phenyl)-2-methyl-4,5,7,8-tetrahydro-2H-1,2,6-triaza-azulene-6-carboxylic acid tert-butyl ester in the alkylation step. MS (ESI): exact mass calculated for $C_{14}H_{16}ClN_3$, 261.10; found, m/z 262.1 $[M+H]^+$. $^1$H NMR (500 MHz, $CD_3OD$): 7.69-7.65 (m, 4H), 4.07 (s, 3H), 3.69-3.67 (m, 2H), 3.58-3.56 (m, 2H), 3.44-3.42 (m, 2H), 3.05-3.04 (m, 2H).

Example 62

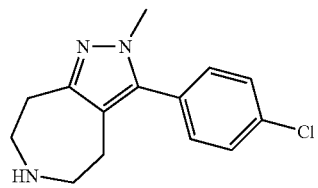

3-(4-Chloro-phenyl)-2-methyl-2,4,5,6,7,8-hexahydro-1,2,6-triaza-azulene

The title compound (0.011 g) was prepared from 3-(4-chloro-phenyl)-2-methyl-4,5,7,8-tetrahydro-2H-1,2,6-triaza-azulene-6-carboxylic acid tert-butyl ester (Example 61) according to Example 59, Step E. MS (ESI): exact mass calculated for $C_{14}H_{16}ClN_3$, 261.10; found, m/z 262.1 $[M+H]^+$. $^1$H NMR (500 MHz, $CD_3OD$): 7.48-7.45 (m, 2H), 7.28-7.26 (m, 2H), 3.60 (s, 3H), 3.31-3.29 (m, 2H), 3.21 (m, 2H), 3.04-3.02 (m, 2H), 2.72-2.70 (m, 2H).

Example 63

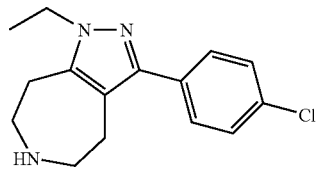

3-(4-Chloro-phenyl)-1-ethyl-1,4,5,6,7,8-hexahydro-1,2,6-triaza-azulene

The title compound (0.035 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using ethyl iodide (0.27 mL) in place of benzyl chloride. The reaction sequence also yielded 3-(4-chloro-phenyl)-2-ethyl-4,5,7,8-tetrahydro-2H-1,2,6-triaza-azulene-6-carboxylic acid tert-butyl ester in the alkylation step. MS (ESI): exact mass calculated for $C_{15}H_{18}ClN_3$, 275.12; found, m/z 276.1 $[M+H]^+$. $^1$H NMR (500 MHz, $CD_3OD$): 7.39-7.34 (m, 4H), 7.11 (q, J=7.3 Hz, 2H), 3.38-3.36 (m, 2H), 3.27-3.24 (m, 2H), 3.15-3.13 (m, 2H), 2.94-2.92 (m, 2H), 1.30 (t, J=7.3 Hz, 3H).

Example 64

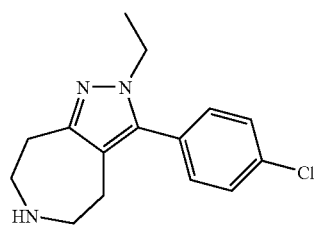

3-(4-Chloro-phenyl)-2-ethyl-2,4,5,6,7,8-hexahydro-1,2,6-triaza-azulene

The title compound (0.021 g) was prepared from 3-(4-chloro-phenyl)-2-ethyl-4,5,7,8-tetrahydro-2H-1,2,6-triaza-azulene-6-carboxylic acid tert-butyl ester (Example 63) according to Example 59, Step E. MS (ESI): exact mass calculated for $C_{15}H_{18}ClN_3$, 275.12; found, m/z 276.2 [M+H]$^+$. $^1$H NMR (500 MHz, CD$_3$OD): 7.46 (d, J=8.6 Hz, 2H), 7.24 (d, J=8.6 Hz, 2H), 3.90 (q, J=7.2 Hz, 2H), 3.31-3.29 (m, 2H), 3.20-3.19 (m, 2H), 3.06-3.04 (m, 2H), 2.69-2.67 (m, 2H), 1.17 (t, J=7.2 Hz, 3H).

Example 65

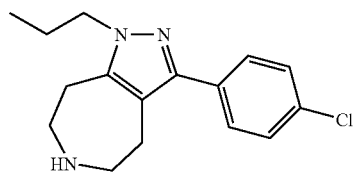

3-(4-Chloro-phenyl)-1-propyl-1,4,5,6,7,8-hexahydro-1,2,6-triaza-azulene

The title compound (0.031 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 1-iodopropane (0.33 mL) in place of benzyl chloride. The reaction sequence also yielded 3-(4-chloro-phenyl)-2-propyl-4,5,7,8-tetrahydro-2H-1,2,6-triaza-azulene-6-carboxylic acid tert-butyl ester in the alkylation step. MS (ESI): exact mass calculated for $C_{16}H_{20}ClN_3$, 289.13; found, m/z 290.2 [M+H]$^+$. $^1$H NMR (500 MHz, CD$_3$OD): 7.39-7.35 (m, 4H), 4.03 (t, J=7.2 Hz, 2H), 3.37-3.35 (m, 2H), 3.27-3.24 (m, 2H), 3.15-3.13 (m, 2H), 2.95-2.93 (m, 2H), 1.76-1.69 (m, 2H), 0.84 (t, J=7.4 Hz, 3H).

Example 66

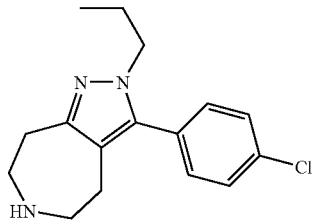

3-(4-Chloro-phenyl)-2-propyl-2,4,5,6,7,8-hexahydro-1,2,6-triaza-azulene

The title compound (0.016 g) was prepared from 3-(4-chloro-phenyl)-2-propyl-4,5,7,8-tetrahydro-2H-1,2,6-triaza-azulene-6-carboxylic acid tert-butyl ester (Example 65) according to Example 59, Step E. MS (ESI): exact mass calculated for $C_{16}H_{20}ClN_3$, 289.13; found, m/z 290.2 [M+H]$^+$. $^1$H NMR (500 MHz, CD$_3$OD): 7.45 (d, J=8.5 Hz, 2H), 7.23 (d, J=8.5 Hz, 2H), 3.83 (d, J=7.2 Hz, 2H), 3.30-3.28 (m, 2H), 3.20-3.19 (m, 2H), 3.05-3.03 (m, 2H), 2.68-2.66 (m, 2H), 1.62-1.18 (m, 2H), 0.65 (t, J=7.4 Hz, 3H).

Example 67

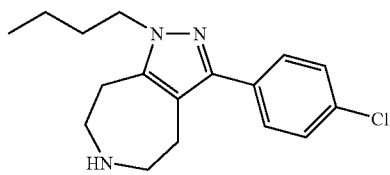

1-Butyl-3-(4-chloro-phenyl)-1,4,5,6,7,8-hexahydro-1,2,6-triaza-azulene

The title compound (0.033 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 1-iodobutane (0.038 mL) in place of benzyl chloride. The reaction sequence also yielded 2-butyl-3-(4-chloro-phenyl)-4,5,7,8-tetrahydro-2H-1,2,6-triaza-azulene-6-carboxylic acid tert-butyl ester in the alkylation step. MS (ESI): exact mass calculated for $C_{17}H_{22}ClN_3$, 303.15; found, m/z 304.2 [M+H]$^+$. $^1$H NMR (500 MHz, CD$_3$OD): 7.39-7.34 (m, 4H), 4.07 (t, J=7.2 Hz, 2H), 3.37-3.35 (m, 2H), 3.27-3.25 (m, 2H), 3.14-3.12 (m, 2H), 2.95-2.92 (m, 2H), 1.69-1.66 (m, 2H), 1.22-1.20 (m, 2H), 0.86 (t, J=7.4 Hz, 3H).

Example 68

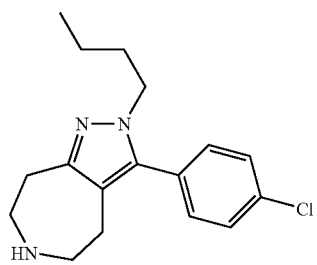

2-Butyl-3-(4-chloro-phenyl)-2,4,5,6,7,8-hexahydro-1,2,6-triaza-azulene

The title compound (0.018 g) was prepared from 2-butyl-3-(4-chloro-phenyl)-4,5,7,8-tetrahydro-2H-1,2,6-triaza-azulene-6-carboxylic acid tert-butyl ester (Example 67) according to Example 59, Step E. MS (ESI): exact mass calculated for $C_{17}H_{22}ClN_3$ 303.15; found, m/z 304.2 [M+H]$^+$. $^1$H NMR (500 MHz, CD$_3$OD): 7.46 (d, J=8.4 Hz, 2H), 7.25 (d, J=8.4 Hz, 2H), 3.91-3.88 (m, 2H), 3.32-3.30 (m, 2H), 3.21-3.19 (m, 2H), 3.07-3.05 (m, 2H), 2.70-2.68 (m, 2H), 1.58-1.52 (m, 2H), 1.06-1.03 (m, 2H), 0.68 (t, J=7.4 Hz, 3H).

Example 69

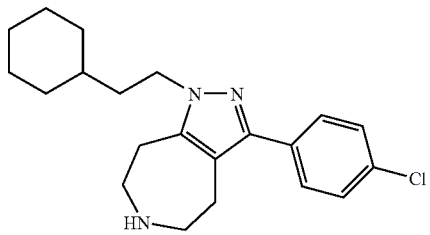

3-(4-Chloro-phenyl)-1-(2-cyclohexyl-ethyl)-1,4,5,6,
7,8-hexahydro-1,2,6-triaza-azulene The title compound (0.056 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 1-bromo-2-cyclohexylethane (0.053 mL) in place of benzyl chloride. The reaction sequence also yielded 3-(4-chloro-phenyl)-2-(2-cyclohexyl-ethyl)-4,5,7,8-tetrahydro-2H-1,2,6-triaza-azulene-6-carboxylic acid tert-butyl ester in the alkylation step. MS (ESI): exact mass calculated for $C_{21}H_{28}ClN_3$, 357.20; found, m/z 358.2 [M+H]$^+$. $^1$H NMR (500 MHz, CD$_3$OD): 7.46-7.34 (m, 4H), 4.08 (t, J=7.6 Hz, 2H), 3.37-3.35 (m, 2H), 3.27-3.25 (m, 2H), 3.13-3.11 (m, 2H), 2.94-2.92 (m, 2H), 1.68-1.20 (m, 7H), 1.18-1.05 (m, 4H), 0.93-0.86 (m, 2H).

Example 70

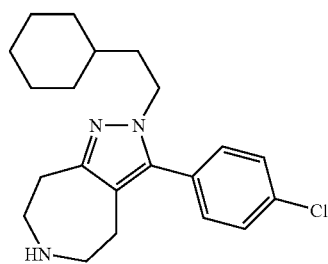

3-(4-Chloro-phenyl)-2-(2-cyclohexyl-ethyl)-2,4,5,6,
7,8-hexahydro-1,2,6-triaza-azulene The title compound (0.026 g) was prepared from 3-(4-chloro-phenyl)-2-(2-cyclohexyl-ethyl)-4,5,7,8-tetrahydro-2H-1,2,6-triaza-azulene-6-carboxylic acid tert-butyl ester (Example 69) according to Example 59, Step E. MS (ESI): exact mass calculated for $C_{21}H_{28}ClN_3$, 357.20; found, m/z 358.2 [M+H]$^+$. $^1$H NMR (500 MHz, CD$_3$OD): 7.46 (d, J=8.5 Hz, 2H), 7.23 (d, J=8.5 Hz, 2H), 3.90 (t, J=7.3 Hz, 2H), 3.30-3.28 (m, 2H), 3.20-3.19 (m, 2H), 3.05-3.03 (m, 2H), 2.69-2.67 (m, 2H), 1.48-1.41 (m, 5H), 1.36-1.33 (m, 2H), 1.03-1.00 (m, 3H), 0.95-0.89 (m, 1H), 0.81-0.67 (m, 2H).

Example 71

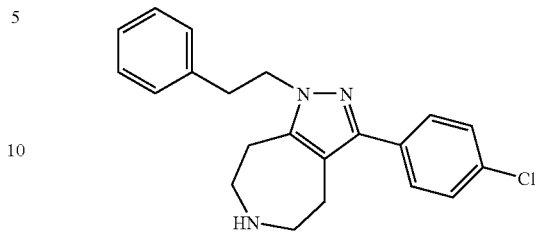

3-(4-Chloro-phenyl)-1-phenethyl-1,4,5,6,7,8-
hexahydro-1,2,6-triaza-azulene

The title compound (0.048 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using (2-chloroethyl)benzene (0.045 mL) in place of benzyl chloride. The reaction sequence also yielded 3-(4-chloro-phenyl)-2-phenethyl-4,5,7,8-tetrahydro-2H-1,2,6-triaza-azulene-6-carboxylic acid tert-butyl ester in the alkylation step. MS (ESI): exact mass calculated for $C_{21}H_{22}ClN_3$, 351.15; found, m/z 352.2 [M+H]$^+$. $^1$H NMR (500 MHz, CD$_3$OD): 7.52-7.47 (m, 4H), 7.28-7.21 (m, 3H), 7.03-7.01 (m, 2H), 4.39 (t, J=6.4 Hz, 2H), 3.20-3.18 (m, 2H), 3.13-3.10 (m, 2H), 2.95-2.93 (m, 2H), 2.91-2.89 (m, 2H), 2.69-2.67 (m, 2H).

Example 72

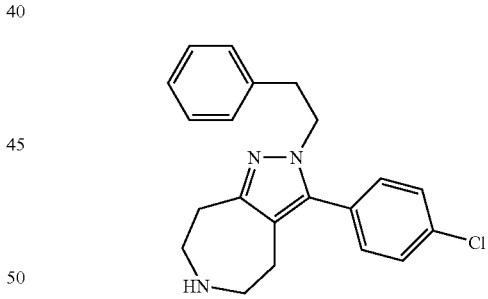

3-(4-Chloro-phenyl)-2-phenethyl-2,4,5,6,7,8-
hexahydro-1,2,6-triaza-azulene

The title compound (0.020 g) was prepared from 3-(4-chloro-phenyl)-2-phenethyl-4,5,7,8-tetrahydro-2H-1,2,6-triaza-azulene-6-carboxylic acid tert-butyl ester (Example 71) according to Example 59, Step E. MS (ESI): exact mass calculated for $C_{21}H_{22}ClN_3$, 351.15; found, m/z 352.2 [M+H]$^+$. $^1$H NMR (500 MHz, CD$_3$OD): 7.38-7.36 (m, 2H), 7.19-7.14 (m, 3H), 6.83-6.79 (m, 4H), 4.14 (t, J=6.7 Hz, 2H), 3.41-3.39 (m, 2H), 3.26-3.24 (m, 2H), 3.19-3.17 (m, 2H), 3.01-2.98 (m, 2H), 2.69-2.67 (m, 2H).

Example 73

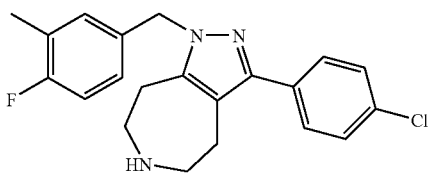

3-(4-Chloro-phenyl)-1-(4-fluoro-3-methyl-benzyl)-1,4,5,6,7,8-hexahydro-1,2,6-triaza-azulene The title compound (0.002 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 4-fluoro-3-methylbenzyl bromide (0.09 g) in place of benzyl chloride. MS (ESI): exact mass calculated for $C_{21}H_{21}ClFN_3$, 369.14; found, m/z 370.1 [M+H]$^+$. $^1$H NMR (500 MHz, CD$_3$OD): 7.49-7.47 (m, 2H), 7.45-7.42 (m, 2H), 7.07-7.01 (m, 1H), 7.00-6.95 (m, 1H), 6.95-6.90 (m, 1H), 5.31 (s, 2H), 2.97-2.91 (m, 4H), 2.89-2.84 (m, 2H), 2.82-2.77 (m, 2H), 2.22 (s, 3H).

Example 74

3-(4-Chloro-phenyl)-1-(3-methyl-benzyl)-1,4,5,6,7,8-hexahydro-1,2,6-triaza-azulene The title compound (0.004 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 3-methylbenzyl chloride (0.6 mL) in place of benzyl chloride. MS (ESI): exact mass calculated for $C_{21}H_{22}ClN_3$, 351.15; found, m/z 352.2 [M+H]$^+$. $^1$H NMR (500 MHz, CD$_3$OD): 7.31-7.26 (m, 2H), 7.26-7.21 (m, 2H), 6.99 (t, J=7.5 Hz, 1H), 6.88 (d, J=7.1 Hz, 1H), 6.76 (s, 1H), 6.67 (d, J=7.1 Hz, 1H), 5.13 (s, 2H), 2.79-2.73 (m, 4H), 2.69-2.65 (m, 2H), 2.63-2.60 (m, 2H), 2.09 (s, 3H).

Example 75

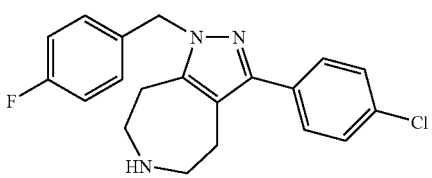

3-(4-Chloro-phenyl)-1-(4-fluoro-benzyl)-1,4,5,6,7,8-hexahydro-1,2,6-triaza-azulene The title compound (0.003 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 4-fluorobenzyl chloride (0.5 mL) in place of benzyl chloride. MS (ESI): exact mass calculated for $C_{20}H_{19}ClFN_3$, 355.13; found, m/z 356.2 [M+H]$^+$. $^1$H NMR (500 MHz, CD$_3$OD): 7.40-7.37 (m, 2H), 7.35-7.32 (m, 2H), 7.08-7.04 (m, 2H), 6.98-6.94 (m, 2H), 5.26 (s, 2H), 2.89-2.86 (m, 4H), 2.80-2.78 (m, 2H), 2.73-2.70 (m, 2H).

Example 76

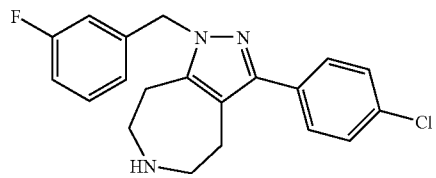

3-(4-Chloro-phenyl)-1-(3-fluoro-benzyl)-1,4,5,6,7,8-hexahydro-1,2,6-triaza-azulene The title compound (0.01 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 3-fluorobenzyl chloride (0.5 mL) in place of benzyl chloride. MS (ESI): exact mass calculated for $C_{20}H_{19}ClFN_3$, 355.13; found, m/z 356.1 [M+H]$^+$. $^1$H NMR (500 MHz, CD$_3$OD): 7.42-7.37 (m, 2H), 7.35-7.32 (m, 2H), 7.28-7.21 (m, 1H), 6.93-6.88 (m, 1H), 6.84 (d, J=7.7 Hz, 1H), 6.75-6.71 (m, 1H), 5.29 (s, 2H), 2.89-2.85 (m, 4H), 2.79-2.76 (m, 2H), 2.74-2.70 (m, 2H).

Example 77

3-(4-Chloro-phenyl)-1-(4-methyl-benzyl)-1,4,5,6,7,8-hexahydro-1,2,6-triaza-azulene The title compound (0.013 g) was prepared from 3-(4-chloro-phenyl)-4,5,7,8-tetrahydro-1H-1,2,6-triaza-azulene-6-carboxylic acid tert-butyl ester (Example 59, Step C, 0.74 g) using 4-methylbenzyl chloride (0.45 g) in place of benzyl chloride. The reaction sequence also yielded 3-(4-chloro-phenyl)-2-(4-methyl-benzyl)-4,5,7,8-tetrahydro-2H-1,2,6-triaza-azulene-6-carboxylic acid tert-butyl ester in the alkylation step. MS (ESI): exact mass calculated for $C_{21}H_{22}ClN_3$, 351.15; found, m/z 352.2 [M+H]$^+$. $^1$H NMR (500 MHz, CD$_3$OD): 7.39-7.36 (m, 2H), 7.34-7.31 (m, 2H), 7.03 (d, J=8.0 Hz, 2H), 6.90 (d, J=8.0 Hz, 2H), 5.21 (s, 2H), 2.83-2.67 (m, 4H), 2.75-2.72 (m, 2H), 2.69-2.67 (m, 2H), 2.20 (s, 3H).

Example 78

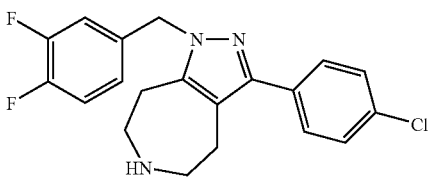

3-(4-Chloro-phenyl)-1-(3,4-difluoro-benzyl)-1,4,5,6,7,8-hexahydro-1,2,6-triaza-azulene The title compound (0.002 g) was prepared from 3-(4-chloro-phenyl)-4,5,7,8-tetrahydro-1H-1,2,6-triaza-azulene-6-carboxylic acid tert-butyl ester (Example 59, Step C, 0.07 g) using 3,4-difluorobenzyl bromide (0.4 mL) in place of benzyl chloride. The reaction sequence also yielded 3-(4-chloro-phenyl)-2-(3,4-difluoro-benzyl)-4,5,7,8-tetrahydro-2H-1,2,6-triaza-azulene-6-carboxylic acid tert-butyl ester in the alkylation step. MS (ESI): exact mass calculated for $C_{20}H_{18}ClF_2N_3$, 373.12; found, m/z 374.1 [M+H]$^+$. $^1$H NMR (500 MHz, CD$_3$OD): 7.41-7.38 (m, 2H), 7.36-7.33 (m, 2H), 7.22-7.20 (m, 1H), 7.07-7.02 (m, 1H), 6.96-6.92 (m, 1H), 5.26 (s, 2H), 3.06-3.02 (m, 4H), 2.94-2.91 (m, 2H), 2.87-2.84 (m, 2H).

Example 79

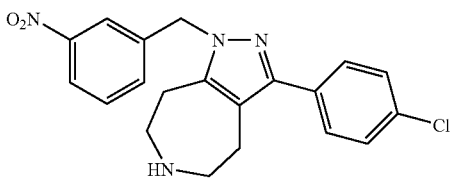

3-(4-Chloro-phenyl)-1-(3-nitro-benzyl)-1,4,5,6,7,8-hexahydro-1,2,6-triaza-azulene The title compound (0.005 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 3-nitrobenzyl bromide (0.09 g) in place of benzyl chloride and Cs$_2$CO$_3$ (0.2 g) in place of NaH. MS (ESI): exact mass calculated for $C_{20}H_{19}ClN_4O_2$, 382.12; found, m/z 383.1 [M+H]$^+$. $^1$H NMR (500 MHz, CD$_3$OD): 8.07-8.05 (m, 1H), 7.91-7.87 (m, 1H), 7.50 (t, J=7.9 Hz, 1H), 7.44-7.38 (m, 3H), 7.36-7.33 (m, 2H), 5.41 (s, 2H), 2.88-2.85 (m, 4H), 2.82-2.79 (m, 2H), 2.73-2.71 (m, 2H).

Example 80

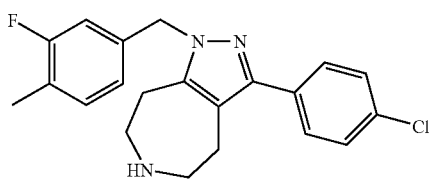

3-(4-Chloro-phenyl)-1-(3-fluoro-4-methyl-benzyl)-1,4,5,6,7,8-hexahydro-1,2,6-triaza-azulene The title compound (0.003 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 3-fluoro-4-methylbenzyl bromide (0.9 g) in place of benzyl chloride. MS (ESI): exact mass calculated for $C_{21}H_{21}ClFN_3$, 369.14; found, m/z 370.1 [M+H]$^+$. $^1$H NMR (500 MHz, CD$_3$OD): 7.50-7.47 (m, 2H), 7.44-7.42 (m, 2H), 7.19 (t, J=7.6 Hz, 1H), 6.84-6.81 (m, 1H), 6.78-6.75 (m, 1H), 5.33 (s, 2H), 2.95-2.92 (m, 4H), 2.87-2.84 (m, 2H), 2.81-2.78 (m, 2H), 2.22 (s, 3H).

Example 81

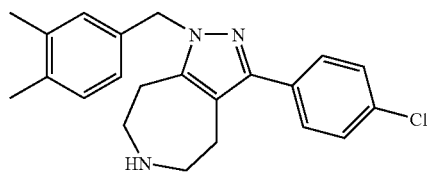

3-(4-Chloro-phenyl)-1-(3,4-dimethyl-benzyl)-1,4,5,6,7,8-hexahydro-1,2,6-triaza-azulene The title compound (0.003 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using 3,4-dimethylbenzyl chloride (0.6 mL) in place of benzyl chloride. MS (ESI): exact mass calculated for $C_{22}H_{24}ClN_3$, 365.17; found, m/z 366.2 [M+H]$^+$. $^1$H NMR (500 MHz, CD$_3$OD): 7.40-7.38 (m, 2H), 7.35-7.32 (m, 2H), 6.98-6.96 (m, 1H), 6.90-6.86 (m, 1H), 6.72-6.69 (m, 1H), 5.30 (s, 1H), 5.19 (s, 1H), 2.90-2.87 (m, 2H), 2.86-2.82 (m, 2H), 2.77-2.73 (m, 2H), 2.72-2.68 (m, 2H), 2.21 (s, 3H), 2.17 (s, 3H).

Example 82

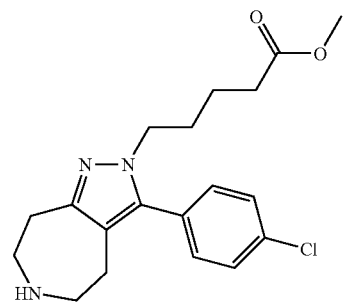

5-[3-(4-Chloro-phenyl)-5,6,7,8-tetrahydro-4H-1,2,6-triaza-azulen-2-yl]-pentanoic acid methyl ester The title compound (0.0042 g) was prepared from 3-(4-chloro-phenyl)-4,5,7,8-tetrahydro-1H-1,2,6-triaza-azulene-6-carboxylic acid tert-butyl ester (Example 59, Step C, 0.15 g) using methyl 5-chlorovalerate (0.90 mL) in place of benzyl chloride. The reaction sequence also yielded 3-(4-chloro-phenyl)-1-(4-methoxycarbonyl-butyl)-4,5,7,8-tetrahydro-1H-1,2,6-triaza-azulene-6-carboxylic acid tert-butyl ester in the alkylation step. MS (ESI): exact mass calculated for $C_{19}H_{24}ClN_3O_2$, 361.16; found, m/z 362.2 [M+H]+. 1H NMR (500 MHz, CD3OD): 7.54-7.51 (m, 2H), 7.31-7.29 (m, 2H), 3.95 (t, J=7.0 Hz, 2H), 3.60 (s, 3H), 3.03-3.01 (m, 2H), 2.93-2.91 (m, 4H), 2.56-2.53 (m, 2H), 2.16 (t, J=7.4 Hz, 2H), 1.67-1.62 (m, 2H), 1.41-1.38 (m, 2H).

Example 83

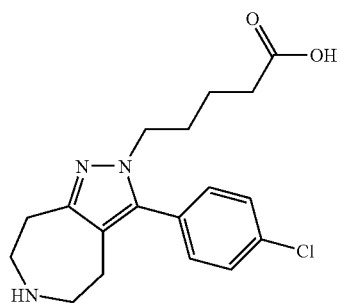

5-[3-(4-Chloro-phenyl)-5,6,7,8-tetrahydro-4H-1,2,6-triaza-azulen-2-yl]-pentanoic acid 5-[3-(4-Chloro-phenyl)-5,6,7,8-tetrahydro-4H-1,2,6-triaza-azulen-2-yl]-pentanoic acid methyl ester (Example 82, 0.009 g) was dissolved in 1 mL of 9:1 THF/MeOH and treated with 2 mL of 1 M NaOH. After stirring at RT for 5 h, the solvent was removed in vacuo. The aqueous residue was acidified with 1 mL of 1 N HCl and the mixture was extracted with EtOAc (3×). The combined organic layers were dried over Na2SO4, concentrated, and dried on a vacuum line. The residue was then dissolved in 1 mL of 9:1 CH2Cl2/MeOH and treated with 3 mL of 1 N HCl in Et2O. After 4 h, the volatiles were removed in vacuo. The crude oil was purified by preparative TLC (9:1 CH2Cl2/2 M NH3 in MeOH) to afford 0.002 g of the title compound. MS (ESI): exact mass calculated for $C_{18}H_{22}ClN_3O_2$, 347.14; found, m/z 348.1 [M+H]+. 1H NMR (500 MHz, CD3OD): 7.55-7.53 (m, 4H), 7.35-7.32 (m, 2H), 3.98 (t, J=7.0 Hz, 2H), 3.38-3.35 (m, 2H), 3.28-3.26 (m, 2H), 3.13-3.10 (m, 2H), 2.77-2.74 (m, 2H), 2.09-2.06 (m, 2H), 1.71-1.66 (m, 2H), 1.41-1.37 (m, 2H).

Example 84

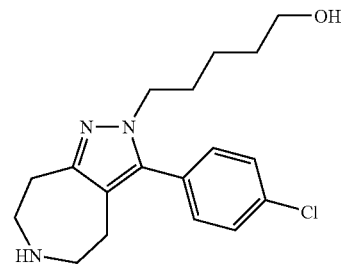

5-[3-(4-Chloro-phenyl)-5,6,7,8-tetrahydro-4H-1,2,6-triaza-azulen-2-yl]-pentan-1-ol 5-[3-(4-Chloro-phenyl)-5,6,7,8-tetrahydro-4H-1,2,6-triaza-azulen-2-yl]-pentanoic acid methyl ester (Example 82, 0.009 g) was dissolved in 9:1 Et2O/CH2Cl2 (3 mL) and the solution was added slowly to a stirred suspension of lithium aluminum hydride (2 mg) in 5 mL of anhydrous Et2O. After stirring at RT for 6 h, the reaction was quenched with 2 mL of water. The mixture was treated with 2 mL of 1 N NaOH, followed by another 2 mL of water. The mixture was then filtered through diatomaceous earth. The organic layer was separated, dried over MgSO4, and concentrated. After further drying via vacuum line, the resulting oil was dissolved in 2 mL of 9:1 CH2Cl2/MeOH and treated with 3 mL of 1 N HCl in Et2O. After 4 h, the volatiles were removed in vacuo. The crude oil was purified by preparative TLC (9:1 CH2Cl2/2 M NH3 in MeOH) to afford 0.001 g of the title compound as a colorless oil. MS (ESI): exact mass calculated for $C_{18}H_{24}ClN_3O$, 333.16; found, m/z 334.2 [M+H]+. 1H NMR (500 MHz, CD3OD): 7.54-7.52 (m, 2H), 7.32-7.30 (m, 2H), 3.95 (t, J=7.1 Hz, 2H), 3.44 (t, J=6.6 Hz, 2H), 3.13-3.09 (m, 2H), 3.03-3.00 (m, 2H), 2.98-2.95 (m, 2H), 2.61-2.58 (m, 2H), 1.70-1.64 (m, 2H), 1.40-1.35 (m, 2H), 1.20-1.16 (m, 2H).

Example 85

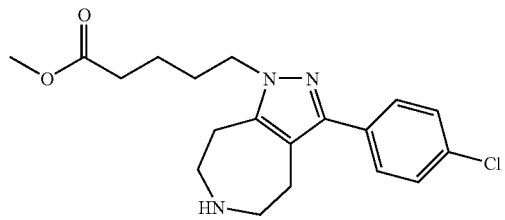

5-[3-(4-Chloro-phenyl)-5,6,7,8-tetrahydro-4H-1,2,6-triaza-azulen-1-yl]-pentanoic acid methyl ester The title compound (0.0051 g) was prepared from 3-(4-chloro-phenyl)-1-(4-methoxycarbonyl-butyl)-4,5,7,8-tetrahydro-1H-1,2,6-triaza-azulene-6-carboxylic acid tert-butyl ester (Example 82) according to Example 59, Step E. MS (ESI): exact mass calculated for $C_{19}H_{24}ClN_3O_2$, 361.16; found, m/z 362.2 [M+H]+. 1H NMR (500 MHz, CD3OD): 7.45-7.40 (m, 4H), 4.13 (t, J=7.0 Hz, 2H), 3.63 (s, 3H), 3.04-3.03 (m, 2H), 2.97-2.95 (m, 4H), 2.79-2.76 (m, 2H), 2.34 (t, J=7.4 Hz, 2H), 1.81-1.77 (m, 2H), 1.61-1.58 (m, 2H).

Example 86

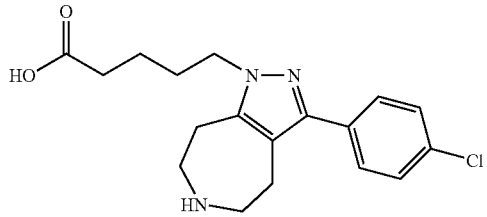

5-[3-(4-Chloro-phenyl)-5,6,7,8-tetrahydro-4H-1,2,6-triaza-azulen-1-yl]-pentanoic acid.

5-[3-(4-Chloro-phenyl)-5,6,7,8-tetrahydro-4H-1,2,6-triaza-azulen-1-yl]-pentanoic acid methyl ester (Example 85, 0.014 g) was hydrolyzed and de-protected as in Example 83 to afford the title compound (0.0014 g). MS (ESI): exact mass calculated for $C_{18}H_{22}ClN_3O_2$, 347.14; found, m/z 348.0 [M+H]$^+$. $^1$H NMR (500 MHz, CD$_3$OD): 7.49-7.43 (m, 4H), 4.18 (t, J=7.0 Hz, 2H), 3.45-3.43 (m, 2H), 3.25-3.22 (m, 2H), 3.17-3.16 (m, 2H), 3.04-3.01 (m, 2H), 2.28-2.24 (m, 2H), 1.84-1.82 (m, 2H), 1.60-1.57 (m, 2H).

Example 87

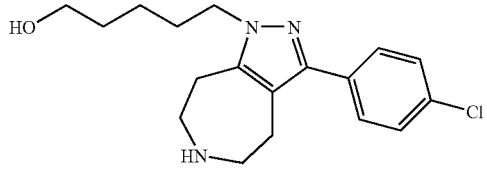

5-[3-(4-Chloro-phenyl)-5,6,7,8-tetrahydro-4H-1,2,6-triaza-azulen-1-yl]-pentan-1-ol 5-[3-(4-Chloro-phenyl)-5,6,7,8-tetrahydro-4H-1,2,6-triaza-azulen-1-yl]-pentanoic acid methyl ester (Example 85, 0.015 g) was reduced as in Example 84 to afford the title compound (0.0063 g) as a colorless oil. MS (ESI): exact mass calculated for $C_{18}H_{24}ClN_3O$, 333.16; found, m/z 334.1 [M+H]$^+$. $^1$H NMR (500 MHz, CD$_3$OD): 7.45-7.40 (m, 4H), 4.13 (t, J=7.2 Hz, 2H), 3.53 (t, J=6.4 Hz, 2H), 3.04-3.01 (m, 2H), 2.97-2.92 (m, 4H), 2.78-2.75 (m, 2H), 1.82-1.75 (m, 2H), 1.57-1.51 (m, 2H), 1.41-1.34 (m, 2H).

Example 88

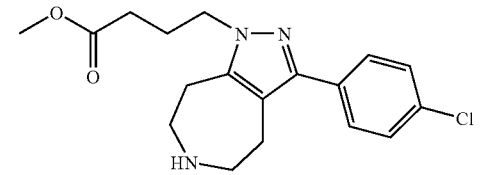

4-[3-(4-Chloro-phenyl)-5,6,7,8-tetrahydro-4H-1,2,6-triaza-azulen-1-yl]-butyric acid methyl ester The title compound (0.003 g) was prepared from 3-(4-chloro-phenyl)-4,5,7,8-tetrahydro-1H-1,2,6-triaza-azulene-6-carboxylic acid tert-butyl ester (Example 59, Step C, 0.1 g) using methyl 4-chlorobutyrate (0.8 mL) in place of benzyl chloride. The reaction sequence also yielded 3-(4-chloro-phenyl)-2-(3-methoxycarbonyl-propyl)-4,5,7,8-tetrahydro-2H-1,2,6-triaza-azulene-6-carboxylic acid tert-butyl ester in the alkylation step. MS (ESI): exact mass calculated for $C_{18}H_{22}ClN_3O_2$, 347.14; found, m/z 348.1 [M+H]$^+$. $^1$H NMR (500 MHz, CD$_3$OD): 7.37-7.31 (m, 4H), 4.07 (t, J=6.6 Hz, 2H), 3.52 (s, 3H), 2.97-2.94 (m, 2H), 2.88-2.84 (m, 4H), 2.70-2.66 (m, 2H), 2.25 (t, J=6.6 Hz, 2H), 1.98-1.95 (m, 2H).

Example 89

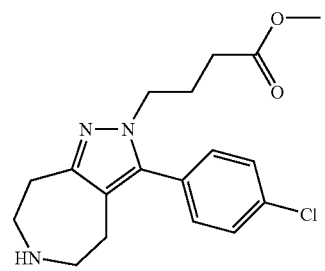

4-[3-(4-Chloro-phenyl)-5,6,7,8-tetrahydro-4H-1,2,6-triaza-azulen-2-yl]-butyric acid methyl ester The title compound (0.003 g) was prepared from 3-(4-chloro-phenyl)-2-(3-methoxycarbonyl-propyl)-4,5,7,8-tetrahydro-2H-1,2,6-triaza-azulene-6-carboxylic acid tert-butyl ester (Example 88) according to Example 59, Step E. MS (ESI): exact mass calculated for $C_{18}H_{22}ClN_3O_2$, 347.14; found, m/z 348.2 [M+H]$^+$. $^1$H NMR (400 MHz, CD$_3$OD): 7.45-7.42 (m, 2H), 7.23-7.20 (m, 2H), 3.91 (t, J=6.9 Hz, 2H), 3.44 (s, 3H), 3.04-3.00 (m, 2H), 2.93-2.86 (m, 4H), 2.52-2.49 (m, 2H), 2.07 (t, J=7.0 Hz, 2H), 1.88-1.80 (m, 2H).

Example 90

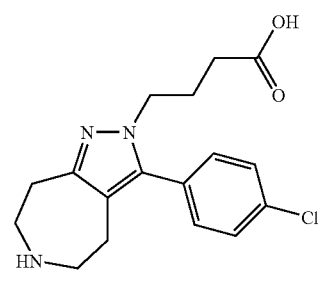

4-[3-(4-Chloro-phenyl)-5,6,7,8-tetrahydro-4H-1,2,6-triaza-azulen-2-yl]-butyric acid 4-[3-(4-Chloro-phenyl)-5,6,7,8-tetrahydro-4H-1,2,6-triaza-azulen-2-yl]-butyric acid methyl ester (Example 89, 0.006 g) was hydrolyzed as in Example 83 to afford the title compound (0.005 g). MS (ESI): exact mass calculated for $C_{17}H_{20}ClN_3O_2$, 333.12; found, m/z 334.1 [M+H]$^+$. $^1$H NMR (400 MHz, CD$_3$OD): 7.55-7.52 (m, 2H), 7.35-7.33 (m, 2H), 3.98 (t, J=6.8 Hz, 2H), 3.12-3.09 (m, 2H), 3.03-2.96 (m, 4H), 2.62-2.59 (m, 2H), 2.03-1.97 (m, 4H).

Example 91

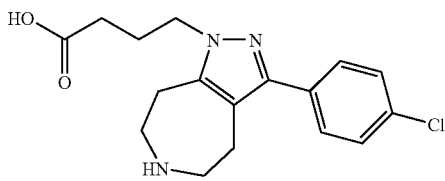

4-[3-(4-Chloro-phenyl)-5,6,7,8-tetrahydro-4H-1,2,6-triaza-azulen-1-yl]-butyric acid 4-[3-(4-Chloro-phenyl)-5,6,7,8-tetrahydro-4H-1,2,6-triaza-azulen-1-yl]-butyric acid methyl ester (Example 88, 0.009 g) was hydrolyzed as in Example 83 to afford the title compound (0.003 g). MS (ESI): exact mass calculated for $C_{17}H_{20}ClN_3O_2$, 333.12; found, m/z 334.1 [M+H]$^+$, m/z 332.0 [M−H]$^−$. $^1$H NMR (400 MHz, CD$_3$OD): 7.46-7.44 (m, 4H), 4.17 (t, J=7.1 Hz, 2H), 3.11-3.08 (m, 2H), 3.05-2.98 (m, 4H), 2.83-2.79 (m, 2H), 2.18-2.15 (m, 2H), 2.07-2.03 (m, 2H).

Example 92

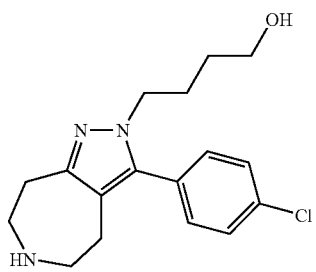

4-[3-(4-Chloro-phenyl)-5,6,7,8-tetrahydro-4H-1,2,6-triaza-azulen-2-yl]-butan-1-ol 4-[3-(4-Chloro-phenyl)-5,6,7,8-tetrahydro-4H-1,2,6-triaza-azulen-2-yl]-butyric acid methyl ester (Example 89, 0.006 g) was reduced as in Example 84 to afford the title compound as a white solid (0.001 g). MS (ESI): exact mass calculated for $C_{17}H_{22}ClN_3O$, 319.15; found, m/z 320.2 [M+H]$^+$. $^1$H NMR (400 MHz, CD$_3$OD): 7.45-7.41 (m, 2H), 7.22-7.20 (m, 2H), 3.89-3.84 (m, 2H), 3.32-3.29 (m, 2H), 2.94-2.91 (m, 2H), 2.85-2.81 (m, 4H), 2.47-2.43 (m, 2H), 1.63-1.58 (m, 2H), 1.24-1.17 (m, 2H).

Example 93

4-[3-(4-Chloro-phenyl)-5,6,7,8-tetrahydro-4H-1,2,6-triaza-azulen-1-yl]-butan-1-ol 4-[3-(4-Chloro-phenyl)-5,6,7,8-tetrahydro-4H-1,2,6-triaza-azulen-1-yl]-butyric acid methyl ester (Example 88, 0.02 g) was reduced and de-protected as in Example 84 to afford the title compound as a white solid (0.007 g). MS (ESI): exact mass calculated for $C_{17}H_{22}ClN_3O$, 319.15; found, m/z 320.2 [M+H]$^+$. $^1$H NMR (400 MHz, CD$_3$OD): 7.36-7.31 (m, 4H), 4.05 (t, J=7.2 Hz, 2H), 3.45 (t, J=6.4 Hz, 2H), 2.96-2.94 (m, 2H), 2.89-2.84 (m, 4H), 2.70-2.66 (m, 2H), 1.77-1.68 (m, 2H), 1.46-1.39 (m, 2H).

Example 94

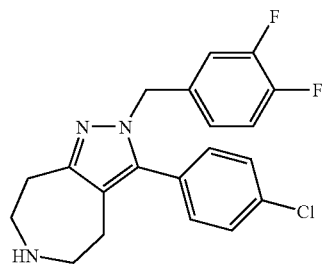

3-(4-Chloro-phenyl)-2-(3,4-difluoro-benzyl)-2,4,5,6,7,8-hexahydro-1,2,6-triaza-azulene The title compound (0.001 g) was prepared from 3-(4-chloro-phenyl)-2-(3,4-difluoro-benzyl)-4,5,7,8-tetrahydro-2H-1,2,6-triaza-azulene-6-carboxylic acid tert-butyl ester (Example 78) according to Example 59, Step E. MS (ESI): exact mass calculated for $C_{20}H_{18}ClF_2N_3$, 373.12; found, m/z 374.1 [M+H]$^+$. $^1$H NMR (500 MHz, CD$_3$OD): 7.41-7.36 (m, 2H), 7.15-7.10 (m, 2H), 7.07-7.01 (m, 1H), 6.77-6.72 (m, 1H), 6.65-6.62 (m, 1H), 5.06 (s, 2H), 3.17-3.15 (m, 2H), 09-3.05 (m, 2H), 2.99-2.97 (m, 2H), 2.62-2.59 (m, 2H).

Example 95

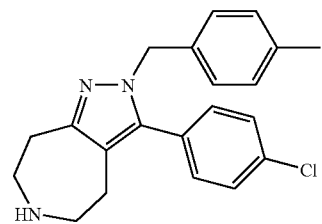

3-(4-Chloro-phenyl)-2-(4-methyl-benzyl)-2,4,5,6,7,8-hexahydro-1,2,6-triaza-azulene The title compound (0.005 g) was prepared from 3-(4-chloro-phenyl)-2-(4-methyl-benzyl)-4,5,7,8-tetrahydro-2H-1,2,6-triaza-azulene-6-carboxylic acid tert-butyl ester (Example 77) according to Example 59, Step E. MS (ESI): exact mass calculated for $C_{21}H_{22}ClN_3$, 351.15; found, m/z 352.2 [M+H]$^+$. $^1$H NMR (500 MHz, CD$_3$OD): 7.36-7.33 (m, 2H), 7.10-7.01 (m, 2H), 6.95 (d, J=7.8 Hz, 2H), 6.69 (d, J=8.0 Hz, 2H), 5.01 (s, 2H), 2.92-2.90 (m, 2H), 2.83-2.80 (m, 4H), 2.46-2.43 (m, 2H), 2.16 (s, 3H).

Example 96

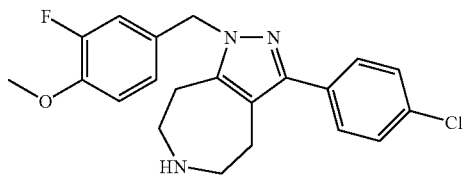

3-(4-Chloro-phenyl)-1-(3-fluoro-4-methoxy-benzyl)-1,4,5,6,7,8-hexahydro-1,2,6-triaza-azulene The title compound (0.021 g) was prepared from 3-(4-chloro-phenyl)-4,5,7,8-tetrahydro-1H-1,2,6-triaza-azulene-6-carboxylic acid tert-butyl ester (Example 59, Step C, 0.35 g) using 3-fluoro-4-methoxybenzyl bromide (0.25 g) in place of benzyl chloride. The reaction sequence also provided 3-(4-chloro-phenyl)-2-(3-fluoro-4-methoxy-benzyl)-4,5,7,8-tetrahydro-2H-1,2,6-triaza-azulene-6-carboxylic acid tert-butyl ester in the alkylation step. MS (ESI): exact mass calculated for $C_{21}H_{21}ClFN_3O$, 385.14; found, m/z 386.1 [M+H]$^+$. $^1$H NMR (500 MHz, CD$_3$OD): 7.50-7.47 (m, 2H), 7.47-7.42 (m, 2H), 7.06-7.02 (m, 1H), 6.90-6.86 (m, 2H), 5.29 (s, 2H), 3.84 (s, 3H), 3.35-3.29 (m, 2H), 2.94-2.92 (m, 4H), 2.88-2.85 (m, 2H), 2.80-2.77 (m, 2H). $^{13}$C NMR (125 MHz, CD$_3$OD): 154.2, 152.2, 149.1, 148.1, 143.5, 134.2, 132.9, 131.1, 131.0, 130.5, 129.1, 123.3, 118.7, 115.0, 114.8, 114.4, 56.2, 52.4, 49.9, 28.8, 27.3.

Example 97

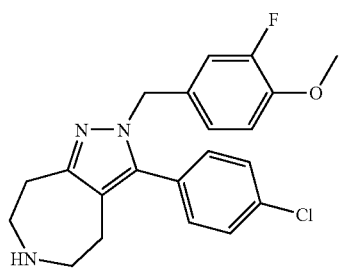

3-(4-Chloro-phenyl)-2-(3-fluoro-4-methoxy-benzyl)-2,4,5,6,7,8-hexahydro-1,2,6-triaza-azulene The title compound (0.017 g) was prepared from 3-(4-chloro-phenyl)-2-(3-fluoro-4-methoxy-benzyl)-4,5,7,8-tetrahydro-2H-1,2,6-triaza-azulene-6-carboxylic acid tert-butyl ester (Example 96) according to Example 59, Step E. MS (ESI): exact mass calculated for $C_{21}H_{21}ClFN_3O$, 385.14; found, m/z 386.0 [M+H]$^+$. $^1$H NMR (500 MHz, CD$_3$OD): 7.48-7.45 (m, 2H), 7.21-7.18 (m, 2H), 6.95-6.92 (m, 1H), 6.67-6.63 (m, 2H), 5.08 (s, 2H), 3.81 (s, 3H), 3.31-3.30 (m, 2H), 3.01-2.98 (m, 2H), 2.94-2.88 (m, 4H), 2.55-2.52 (m, 2H). $^{13}$C NMR (125 MHz, CD$_3$OD): 154.9, 153.8, 153.0, 148.9, 142.5, 136.6, 133.0, 132.1, 130.5, 130.0, 129.4, 124.3, 120.7, 116.0, 115.8, 115.1, 57.1, 53.3, 51.3, 32.7, 28.0.

Example 98

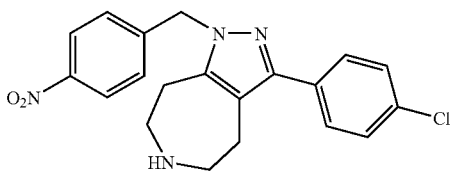

3-(4-Chloro-phenyl)-1-(4-nitro-benzyl)-1,4,5,6,7,8-hexahydro-1,2,6-triaza-azulene The title compound (0.004 g) was prepared from 3-(4-chloro-phenyl)-4,5,7,8-tetrahydro-1H-1,2,6-triaza-azulene-6-carboxylic acid tert-butyl ester (Example 59, Step C, 0.3 g) using 4-nitrobenzyl bromide (0.3 g) in place of benzyl chloride. MS (ESI): exact mass calculated for $C_{20}H_{19}ClN_4O_2$, 382.12; found, m/z 383.1 [M+H]$^+$. $^1$H NMR (400 MHz, CD$_3$OD): 8.23-8.19 (m, 2H), 7.51-7.47 (m, 2H), 7.45-7.47 (m, 2H), 7.32 (d, J=8.6 Hz, 2H), 5.52 (s, 2H), 2.98-2.95 (m, 4H), 2.89-2.85 (m, 2H), 2.83-2.79 (m, 2H).

Example 99

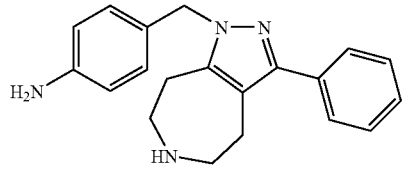

4-(3-Phenyl-5,6,7,8-tetrahydro-4H-1,2,6-triaza-azulen-1-ylmethyl)-phenylamine 3-(4-Chloro-phenyl)-1-(4-nitro-benzyl)-4,5,7,8-tetrahydro-1H-1,2,6-triaza-azulene-6-carboxylic acid tert-butyl ester (Example 98, 70 mg) was dissolved in 25 mL of anhydrous EtOH and treated with 10% palladium on carbon (20 mg). The mixture was subjected to hydrogen for 4 h at 30 psi. The mixture was filtered through diatomaceous earth. The filtrate was concentrated and dried via vacuum line to afford 55 mg of 1-(4-amino-benzyl)-3-phenyl-4,5,7,8-tetrahydro-1H-1,2,6-triaza-azulene-6-carboxylic acid tert-butyl ester. The intermediate aniline was then dissolved in 1 mL of MeOH and treated with 5 mL of 1 N HCl in Et$_2$O. After 6 h, the volatiles were removed in vacuo. The resulting yellow semi-solid was purified by preparative TLC (9:1 CH$_2$Cl$_2$/2 M NH$_3$ in MeOH) to afford 0.007 g of the title compound as a light yellow solid. MS (ESI): exact mass calculated for $C_{20}H_{22}N_4$, 318.18; found, m/z 319.2 [M+H]$^+$. $^1$H NMR (500 MHz, CD$_3$OD): 7.50-7.47 (m, 2H), 7.44-7.41 (m, 2H), 7.37-

7.34 (m, 1H), 6.94-6.90 (m, 2H), 6.68-6.65 (m, 2H), 5.23 (s, 2H), 3.11-3.06 (m, 4H), 2.99-2.96 (m, 2H), 2.91-2.88 (m, 2H).

Example 100

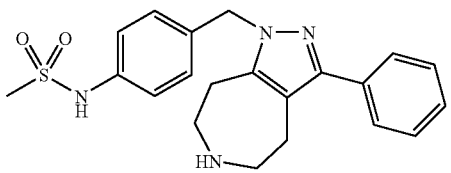

N-[4-(3-Phenyl-5,6,7,8-tetrahydro-4H-1,2,6-triaza-azulen-1-ylmethyl)-phenyl]-methanesulfonamide To a solution of 0.022 g of 1-(4-amino-benzyl)-3-phenyl-4,5,7,8-tetrahydro-1H-1,2,6-triaza-azulene-6-carboxylic acid tert-butyl ester (Example 99) in DMF (1 mL) was added 1 equivalent of triethylamine. After 5 min, 1 equivalent of methanesulfonyl chloride was added and the mixture was stirred overnight. The reaction was quenched with water and extracted with EtOAc (3×). The combined organic layers were dried over $Na_2SO_4$ and concentrated. The resulting oil was purified by preparative TLC (50% EtOAc/hexanes) to give 1-(4-methanesulfonylamino-benzyl)-3-phenyl-4,5,7,8-tetrahydro-1H-1,2,6-triaza-azulene-6-carboxylic acid tert-butyl ester. This mono-mesylate was then dissolved in 9:1 $CH_2Cl_2$/MeOH (2 mL) and treated with 3 mL of 1 N HCl in $Et_2O$. After 6 h, the volatiles were removed in vacuo. The resulting oil was purified by preparative TLC (9:1 $CH_2Cl_2$/2 M $NH_3$ in MeOH) to afford 0.004 g of the title compound as a white solid. MS (ESI): exact mass calculated for $C_{21}H_{24}N_4O_2S$, 396.16; found, m/z 397.1 $[M+H]^+$. $^1$H NMR (500 MHz, $CD_3OD$): 7.50-7.47 (m, 2H), 7.42 (t, J=7.7 Hz, 2H), 7.37-7.34 (m, 1H), 7.22-7.20 (m, 2H), 7.13-7.10 (m, 2H), 5.34 (s, 2H), 2.97-2.93 (m, 4H), 2.92 (s, 3H), 2.90-2.87 (m, 2H), 2.82-2.78 (m, 2H).

Example 101

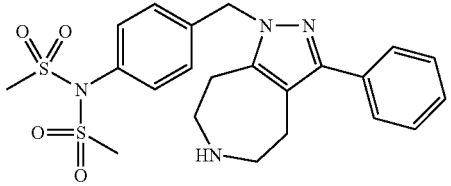

N,N-[4-(3-phenyl-5,6,7,8-tetrahydro-4H-1,2,6-triaza-azulen-1-ylmethyl)-phenyl]-dimethane-sulfonamide 1-(4-Amino-benzyl)-3-phenyl-4,5,7,8-tetrahydro-1H-1,2,6-triaza-azulene-6-carboxylic acid tert-butyl ester (Example 99, 0.05 mmol) was dissolved in 1 mL of DMF and treated with 1 equivalent of triethylamine. After 5 min, 1.5 equivalents of methanesulfonyl chloride were added and the mixture was stirred overnight. The reaction was quenched with water and extracted with EtOAc (3×). The combined organic layers were dried over $Na_2SO_4$ and concentrated. The resulting oil was purified by preparative TLC (50% EtOAc/hexanes) to provide 1-(4-dimethanesulfonylamino-benzyl)-3-phenyl-4,5,7,8-tetrahydro-1H-1,2,6-triaza-azulene-6-carboxylic acid tert-butyl ester. The intermediate was then dissolved in 2 mL of 9:1 $CH_2Cl_2$/MeOH and treated with 3 mL of 1 N HCl in $Et_2O$. After 6 h, the volatiles were removed in vacuo. The crude oil was purified by preparative TLC (9:1 $CH_2Cl_2$/2 M $NH_3$ in MeOH) to afford 0.006 g of the title compound as an off-white solid. MS (ESI): exact mass calculated for $C_{22}H_{26}N_4O_4S_2$, 474.14; found, m/z 475.1 $[M+H]^+$. $^1$H NMR (500 MHz, $CD_3OD$): 7.50-7.47 (m, 2H), 7.44-7.40 (m, 2H), 7.37-7.35 (m, 1H), 7.22-7.20 (m, 2H), 7.13-7.11 (m, 2H), 5.34 (s, 2H), 2.97-2.94 (m, 4H), 2.92 (s, 6H), 2.89-2.87 (m, 2H), 2.82-2.80 (m, 2H).

Example 102

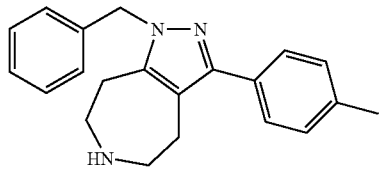

1-Benzyl-3-p-tolyl-1,4,5,6,7,8-hexahydro-1,2,6-triaza-azulene

The title compound (0.2 g) was prepared from 4-oxo-azepane-1-carboxylic acid tert-butyl ester (Example 59, Step B; 10 mmol) as in Example 59, Steps C through E, using 4-methyl-benzoyl chloride (11 mmol) in place of 4-chloro-benzoyl chloride. MS (ESI): exact mass calculated for $C_{21}H_{23}N_3$, 317.19; found, m/z 318.2 $[M+H]^+$. $^1$H NMR (500 MHz, $CD_3OD$): 7.34-7.33 (m, 2H), 7.29-7.26 (m, 2H), 7.24-7.21 (m, 3H), 7.10-7.09 (m, 2H), 5.40 (s, 2H), 3.33-3.27 (m, 4H), 3.11-3.09 (m, 2H), 3.00-2.98 (m, 2H), 2.30 (s, 3H).

Example 103

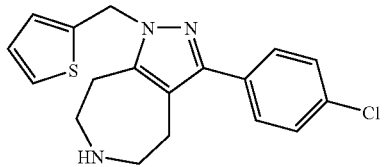

3-(4-Chloro-phenyl)-1-thiophen-2-ylmethyl-1,4,5,6,7,8-hexahydro-1,2,6-triaza-azulene Step A. 1-(4-Chlorophenyl)-2-diazo-ethanone. To a solution of diazomethane (33.2 mmol) in $Et_2O$ (70 mL) was added triethylamine (33.2 mmol). The mixture was cooled to 0° C., and 4-chlorobenzoyl chloride (30 mmol) in $Et_2O$ (30 mL) was added slowly. The mixture was then warmed to RT and stirred for 1 h. After filtration of the mixture, the clear filtrate was concentrated to provide the crude desired compound (5.4 g).

Step B. 3-(4-Chloro-phenyl)-4,5,7,8-tetrahydro-1H-1,2,6-triaza-azulene-6-carboxylic acid tert-butyl ester. To a 0° C. mixture of 4-oxo-piperidine 1-carboxylic acid tert-butyl ester (20 mmol) in Et$_2$O (150 mL) was added a solution of BF$_3$·Et$_2$O (30 mmol) in Et$_2$O (150 mL) followed by a solution of the product from Step A (21 mmol) in Et$_2$O (150 mL). After the addition was complete, the mixture was warmed to 25° C. and stirred for 1 h. Satd. aq. NaHCO$_3$ (200 mL) was added, and the layers were separated. The organic layer was concentrated, and the resulting residue was diluted with MeOH (100 mL). Hydrazine (3 mL) was added and the mixture was stirred at 25° C. for 16 h. Purification by flash chromatography (EtOAc/CH$_2$Cl$_2$) provided the desired compound (1.8 g).

Step C. The product from Step B (0.2 mmol) was mixed with 2-chloromethyl-thiophene (0.3 mmol) in DMF (2 mL), and Cs$_2$CO$_3$ (0.3 mmol) was then added. The mixture was stirred at 25° C. for 16 h. After concentration and purification by SiO$_2$ chromatography (EtOAc/hexanes), 3-(4-chloro-phenyl)-1-thiophen-2-ylmethyl-1,4,5,6,7,8-hexahydro-1,2,6-triaza-azulene was obtained. The intermediate was treated with TFA (1 mL) in CH$_2$Cl$_2$ (10 mL) for 4 h. After concentration of the reaction mixture, the title compound was obtained (0.029 g). The reaction sequence also provided 3-(4-chloro-phenyl)-2-thiophen-2-ylmethyl-4,5,7,8-tetrahydro-2H-1,2,6-triaza-azulene-6-carboxylic acid tert-butyl ester in the alkylation step. MS (ESI): exact mass calculated for C$_{18}$H$_{18}$ClN$_3$O, 343.09; found, m/z 344.1 [M+H]$^+$. $^1$H NMR (500 MHz, CD$_3$OD): 7.46-7.44 (m, 2H), 7.41-7.39 (m, 2H), 7.29 (dd, J=5.1, 1.1 Hz, 1H), 7.00 (dd, J=3.5. 1.1 Hz, 1H), 6.91 (dd, J=5.1, 3.5 Hz, 1H), 5.52 (s, 2H), 3.36-3.34 (m, 2H), 3.30-3.28 (m, 2H), 3.24-3.18 (m, 2H), 2.99-2.97 (m, 2H).

Example 104 through 155 were prepared using the procedure described in Example 103 unless otherwise noted.

Example 104

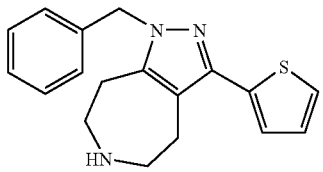

1-Benzyl-3-thiophen-2-yl-1,4,5,6,7,8-hexahydro-1,2,6-triaza-azulene

The title compound (28 mg) was prepared from 3-thiophen-2-yl-4,5,7,8-tetrahydro-1H-1,2,6-triaza-azulene-6-carboxylic acid tert-butyl ester as described in Example 103, using thiophene-2-carbonyl chloride (5 mmol) in place of 4-chlorobenzoyl chloride, and benzyl chloride (0.3 mmol) in place of 2-chloromethyl-thiophene. MS (ESI): exact mass calculated for C$_{18}$H$_{19}$N$_3$S, 309.13; found, m/z 310.1 [M+H]$^+$. $^1$H NMR (500 MHz, CD$_3$OD): 7.27-7.01 (m, 8H), 5.28 (s, 2H), 3.26-3.24 (br m, 2H), 3.18-3.16 (br m, 2H), 3.11-3.09 (br m, 2H), 2.96-2.94 (br m, 2H).

Example 105

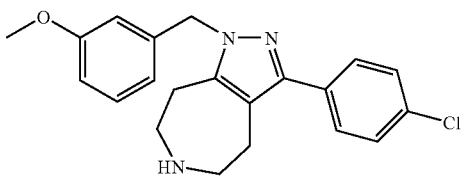

3-(4-Chloro-phenyl)-1-(3-methoxy-benzyl)-1,4,5,6,7,8-hexahydro-1,2,6-triaza-azulene The title compound (0.095 g) was prepared from 3-(4-chloro-phenyl)-4,5,7,8-tetrahydro-1H-1,2,6-triaza-azulene-6-carboxylic acid tert-butyl ester (Example 103, Step B; 1 mmol) using 3-methoxy-benzyl chloride (1.5 mmol) in place of 2-chloromethyl-thiophene. MS (ESI): exact mass calculated for C$_{21}$H$_{22}$ClN$_3$O, 367.15; found, m/z 368.1 [M+H]$^+$. $^1$H NMR (500 MHz, CD$_3$OD): 7.60 (d, J=8.5 Hz, 2H), 7.56 (d, J=8.5 Hz, 2H), 7.32 (d, J=7.9 Hz, 1H), 6.92 (dd, J=8.2, 2.1 Hz, 1H), 6.84 (s, 1H), 6.80 (d, J=8.2 Hz, 1H), 5.57 (s, 2H), 3.79 (s, 3H), 3.48-3.46 (br m, 2H), 3.44-3.42 (br m, 2H), 3.33-3.31 (br m, 2H), 3.16-3.14 (br m, 2H).

Example 106

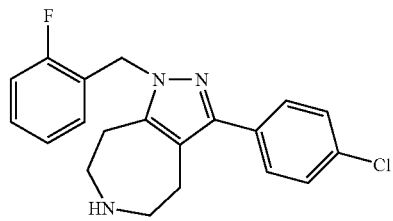

3-(4-Chloro-phenyl)-1-(2-fluoro-benzyl)-1,4,5,6,7,8-hexahydro-1,2,6-triaza-azulene The title compound (0.042 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 2-fluorobenzyl chloride (0.3 mmol) in place of 2-chloromethyl-thiophene. MS (ESI): exact mass calculated for C$_{20}$H$_{19}$ClFN$_3$, 355.13; found, m/z 356.2 [M+H]$^+$. $^1$H NMR (500 MHz, CD$_3$OD): 7.55-7.48 (br m, 4H), 7.39-3.37 (br m, 1H), 7.20-7.14 (m, 3H), 5.54 (s, 2H), 3.48-3.46 (br m, 2H), 3.40-3.38 (br m, 2H), 3.31-3.29 (br m, 2H), 3.13-3.11 (br m, 2H).

Example 107

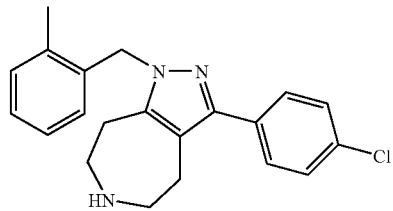

3-(4-Chloro-phenyl)-1-(2-methyl-benzyl)-1,4,5,6,7,8-hexahydro-1,2,6-triaza-azulene The title compound (0.03 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 2-methylbenzyl chloride (0.3 mmol) in place of 2-chloromethyl-thiophene. The reaction sequence also yielded 3-(4-chloro-phenyl)-2-(2-methyl-benzyl)-4,5,7,8-tetrahydro-2H-1,2,6-triaza-azulene-6-carboxylic acid tert-butyl ester in the alkylation step. MS (ESI): exact mass calculated for C$_{21}$H$_{22}$ClN$_3$, 351.15; found, m/z 352.2 [M+H]$^+$. $^1$H NMR (400 MHz, CD$_3$OD): 7.56 (d, J=8.5 Hz, 2H), 7.49

(d, J=8.5 Hz, 2H), 7.23-7.15 (m, 3H), 6.58 (d, J=7.5, 1H), 5.50 (s, 2H), 3.42-3.39 (br m, 4H), 3.15-3.12 (br m, 4H), 2.40 (s, 3H).

Example 108

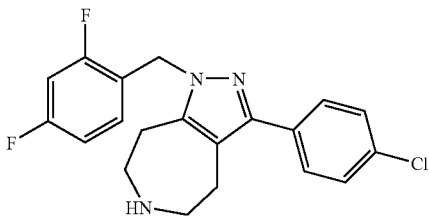

3-(4-Chloro-phenyl)-1-(2,4-difluoro-benzyl)-1,4,5,6,7,8-hexahydro-1,2,6-triaza-azulene The title compound (0.030 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 2,4-difluorobenzyl bromide (0.3 mmol) in place of 2-chloromethyl-thiophene. The reaction sequence also yielded 3-(4-chloro-phenyl)-2-(2,4-difluoro-benzyl)-4,5,7,8-tetrahydro-2H-1,2,6-triaza-azulene-6-carboxylic acid tert-butyl ester in the alkylation step. MS (ESI): exact mass calculated for $C_{20}H_{18}ClF_2N_3$, 373.12; found, m/z 374.1 [M+H]$^+$. $^1$H NMR (400 MHz, CD$_3$OD): 7.52-7.49 (br m, 4H), 7.27-7.24 (br m, 1H), 7.01-6.99 (br m, 2H), 5.52 (s, 2H), 3.51-3.49 (br m, 2H), 3.43-3.40 (br m, 2H), 3.34-3.31 (br m, 2H), 3.11-3.09 (br m, 2H).

Example 109

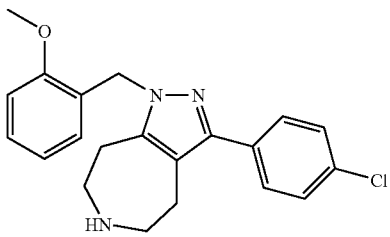

3-(4-Chloro-phenyl)-1-(2-methoxy-benzyl)-1,4,5,6,7,8-hexahydro-1,2,6-triaza-azulene The title compound (0.06 g) was prepared from 3-(4-chloro-phenyl)-4,5,7,8-tetrahydro-1H-1,2,6-triaza-azulene-6-carboxylic acid tert-butyl ester (Example 103, Step B; 0.3 mmol) using 2-methoxybenzyl chloride (0.3 mmol) in place of 2-chloromethyl-thiophene. The reaction sequence also yielded 3-(4-chloro-phenyl)-2-(2-methoxy-benzyl)-4,5,7,8-tetrahydro-2H-1,2,6-triaza-azulene-6-carboxylic acid tert-butyl ester in the alkylation step. MS (ESI): exact mass calculated for $C_{21}H_{22}ClN_3O$, 367.15; found, m/z 368.1 [M+H]$^+$. $^1$H NMR (500 MHz, CDCl$_3$): 7.45-7.43 (m, 2H), 7.30-7.27 (m, 2H), 7.18-7.17 (m, 1H), 6.80-6.77 (m, 2H), 6.61-6.59 (m, 1H), 5.26 (s, 2H), 3.80 (s, 3H), 2.92-2.86 (m, 4H), 2.74-2.69 (m, 4H).

Example 110

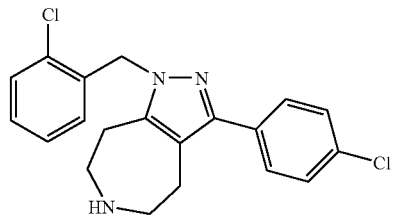

1-(2-Chloro-benzyl)-3-(4-chloro-phenyl)-1,4,5,6,7,8-hexahydro-1,2,6-triaza-azulene The title compound (0.01 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 2-chlorobenzyl chloride (0.3 mmol) in place of 2-chloromethyl-thiophene. MS (ESI): exact mass calculated for $C_{17}H_{22}ClN_3O$, 371.10; found, m/z 372.1 [M+H]$^+$. $^1$H NMR (500 MHz, CD$_3$OD): 7.43-7.41 (m, 2H), 7.32-7.30 (m, 2H), 7.32 (d, J=8.6 Hz, 2H), 6.76 (d, J=8.6 Hz, 2H), 5.23 (s, 2H), 2.94-2.91 (br m, 4H), 2.79-7.77 (br m, 2H), 2.73-7.71 (br m, 2H).

Example 111

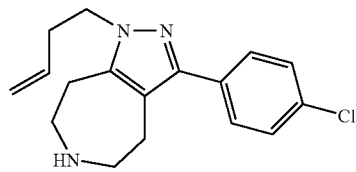

1-But-3-enyl-3-(4-chloro-phenyl)-1,4,5,6,7,8-hexahydro-1,2,6-triaza-azulene

The title compound (0.028 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 1-but-3-enyl chloride (0.3 mmol) in place of 2-chloromethyl-thiophene. MS (ESI): exact mass calculated for $C_{17}H_{22}ClN_3O$, 301.13; found, m/z 302.1 [M+H]$^+$. $^1$H NMR (500 MHz, CDCl$_3$): 7.40-7.37 (m, 2H), 7.31-7.28 (m, 2H), 6.75-6.67 (m, 1H), 5.02-5.00 (br m, 2H), 4.07 (t, J=7.3 Hz, 2H), 2.99-2.97 (br m, 2H), 2.91-2.89 (br m, 2H), 2.80-2.78 (br m, 2H), 2.71-2.69 (br m, 2H), 2.48 (q, J=7.3 Hz, 2H).

Example 112

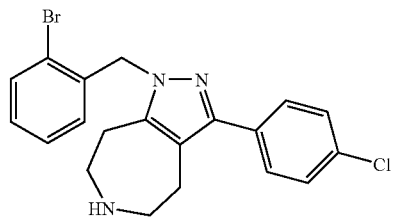

1-(2-Bromo-benzyl)-3-(4-chloro-phenyl)-1,4,5,6,7,8-hexahydro-1,2,6-triaza-azulene The title compound (0.035 g) was prepared from 3-(4-chloro-phenyl)-4,5,7,8-tetrahydro-1H-1,2,6-triaza-azulene- 6-carboxylic acid tert-butyl ester (Example 103, Step B; 0.2 mmol) using 2-bromobenzyl bromide (0.3 mmol) in place of 2-chloromethyl-thiophene. MS (ESI): exact mass calculated for $C_{20}H_{19}BrClN_3$, 415.05; found, m/z 418.0 [M+H]$^+$. $^1$H NMR (500 MHz, CD$_3$OD): 7.69 (d, J=7.8 Hz, 1H), 7.53-7.27 (m, 6H), 6.78 (d, J=7.8 Hz, 1H), 5.58 (s, 2H), 3.50-3.48 (br m, 4H), 3.19-3.17 (br m, 4H).

Example 113

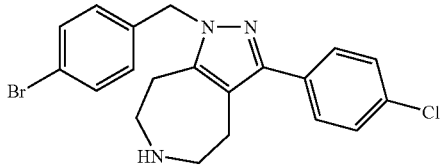

1-(4-Bromo-benzyl)-3-(4-chloro-phenyl)-1,4,5,6,7,8-hexahydro-1,2,6-triaza-azulene The title compound (0.032 g) was prepared from 3-(4-chloro-phenyl)-4,5,7,8-tetrahydro-1H-1,2,6-triaza-azulene-6-carboxylic acid tert-butyl ester (Example 103, Step B; 0.3 mmol) using 4-bromobenzyl bromide (0.3 mmol) in place of 2-chloromethyl-thiophene. MS (ESI): exact mass calculated for $C_{20}H_{19}BrClN_3$, 415.05; found, m/z 418.0 [M+H]$^+$. $^1$H NMR (500 MHz, CD$_3$OD): 7.48-7.40 (m, 6H), 6.92 (d, J=8.4 Hz, 2H), 5.28 (s, 2H), 3.32-3.30 (br m, 4H), 3.03-3.01 (br m, 4H).

Example 114

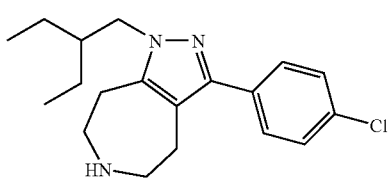

3-(4-Chloro-phenyl)-1-(2-ethyl-butyl)-1,4,5,6,7,8-hexahydro-1,2,6-triaza-azulene The title compound (0.010 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 1-bromo-2-ethyl-butane (0.3 mmol) in place of 2-chloromethyl-thiophene. The reaction sequence also yielded 3-(4-chloro-phenyl)-2-(2-ethyl-butyl)-4,5,7,8-tetrahydro-2H-1,2,6-triaza-azulene-6-carboxylic acid tert-butyl ester in the alkylation step. MS (ESI): exact mass calculated for $C_{19}H_{26}ClN_3$, 331.18; found, m/z 332.3 [M+H]$^+$. $^1$H NMR (400 MHz, CD$_3$OD): 7.50-7.48 (br m, 4H), 4.11-4.09 (br m, 2H), 3.71-3.69 (br m, 2H), 3.33-3.31 (br m, 2H), 3.26-3.24 (br m, 2H), 3.06-3.04 (br m, 2H), 1.91-1.89 (m, 1H), 1.36-1.34 (m, 4H), 0.93 (t, J=7.3 Hz, 6H).

Example 115

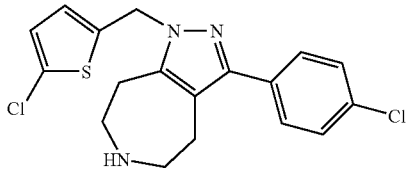

3-(4-Chloro-phenyl)-1-(5-chloro-thiophen-2-ylmethyl)-1,4,5,6,7,8-hexahydro-1,2,6-triaza-azulene The title compound (0.029 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 5-chloro-thiophen-2-ylmethyl chloride (0.3 mmol) in place of 2-chloromethyl-thiophene. The reaction sequence also yielded 3-(4-chloro-phenyl)-2-(5-chloro-thiophen-2-ylmethyl)-4,5,7,8-tetrahydro-2H-1,2,6-triaza-azulene-6-carboxylic acid tert-butyl ester in the alkylation step. MS (ESI): exact mass calculated for $C_{18}H_{17}Cl_2N_3S$, 377.05; found, m/z 378.0 [M+H]$^+$. $^1$H NMR (500 MHz, CD$_3$OD): 7.54-7.51 (m, 2H), 7.49-7.46 (m, 2H), 3.91 (d, J=3.8 Hz, 1H), 6.86 (d, J=3.8 Hz, 1H), 5.51 (s, 2H), 3.45-3.44 (m, 2H), 3.38-3.61 (m, 2H), 3.27-3.25 (m, 2H), 3.07-3.05 (m, 2H).

Example 116

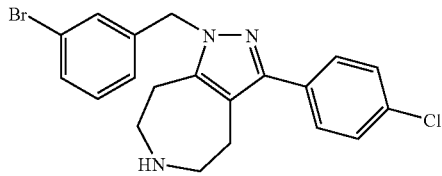

1-(3-Bromo-benzyl)-3-(4-chloro-phenyl)-1,4,5,6,7,8-hexahydro-1,2,6-triaza-azulene The title compound (0.04 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 3-bromobenzyl chloride (0.3 mmol) in place of 2-chloromethyl-thiophene. MS (ESI): exact mass calculated for $C_{20}H_{19}BrClN_3$, 415.05; found, m/z 416.0 [M+H]$^+$. $^1$H NMR (500 MHz, CD$_3$OD): 7.50-6.86 (m, 8H), 5.36 (s, 2H), 3.30-3.27 (br m, 4H), 3.06-3.04 (m, 4H).

Example 117

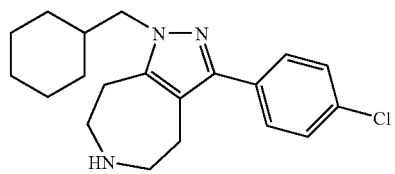

3-(4-Chloro-phenyl)-1-cyclohexylmethyl-1,4,5,6,7,8-hexahydro-1,2,6-triaza-azulene The title compound (0.09 g) was prepared from 3-(4-chloro-phenyl)-4,5,7,8-tetrahydro-1H-1,2,6-triaza-azulene- 6-carboxylic acid tert-butyl ester (Example 103, Step B; 170 mg) using cyclohexylmethyl bromide (2 mmol) in place of 2-chloromethyl-thiophene. The reaction sequence also yielded 3-(4-chloro-phenyl)-2-cyclohexylmethyl-4,5,7,8-tetrahydro-2H-1,2,6-triaza-azulene-6-carboxylic acid tert-butyl ester in the alkylation step. MS (ESI): exact mass calculated for $C_{20}H_{26}ClN_3$, 343.18; found, m/z 344.3 [M+H]$^+$. $^1$H NMR (500 MHz, CD$_3$OD): 7.37 (d, J=6.6 Hz, 2H), 7.32 (d, J=6.6 Hz, 2H), 3.94 (d, J=7.3 Hz, 2H), 3.44-3.40 (br m, 2H), 3.35-3.32 (br m, 2H), 3.17-3.14 (br m, 2H), 3.01-2.99 (br m, 2H), 1.74-1.53 (m, 4H), 1.52 (d, J=11.2 Hz, 2H), 1.17-1.10 (m, 3H), 0.94-0.90 (m, 2H).

Example 118

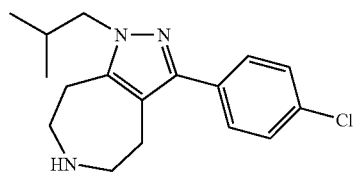

3-(4-Chloro-phenyl)-1-isobutyl-1,4,5,6,7,8-hexahydro-1,2,6-triaza-azulene

The title compound (0.031 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using isobutyl bromide (0.3 mmol) in place of 2-chloromethyl-thiophene. The reaction sequence also yielded 3-(4-chloro-phenyl)-2-isobutyl-4,5,7,8-tetrahydro-2H-1,2,6-triaza-azulene-6-carboxylic acid tert-butyl ester from the alkylation step. MS (ESI): exact mass calculated for $C_{17}H_{22}ClN_3$, 303.15; found, m/z 304.1 [M+H]$^+$. $^1$H NMR (500 MHz, CD$_3$OD): 7.64 (d, J=6.6 Hz, 2H), 7.56 (d, J=6.6 Hz, 2H), 4.20 (d, J=7.4 Hz, 2H), 3.72-3.69 (br m, 2H), 3.62-3.60 (br m, 2H), 3.44-3.42 (br m, 2H), 3.29-3.27 (br m, 2H), 2.35 (m, 1H), 1.14 (d, J=6.7 Hz, 6H).

Example 119

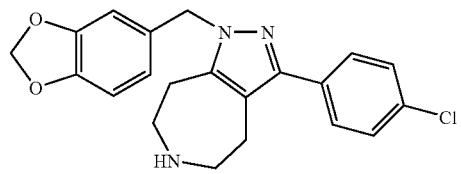

1-Benzo[1,3]dioxol-5-ylmethyl-3-(4-chloro-phenyl)-1,4,5,6,7,8-hexahydro-1,2,6-triaza-azulene The title compound (0.035 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using benzo[1,3]dioxol-5-ylmethyl chloride (0.3 mmol) in place of 2-chloromethyl-thiophene. The reaction sequence also yielded 2-benzo[1,3]dioxol-5-ylmethyl-3-(4-chloro-phenyl)-4,5,7,8-tetrahydro-2H-1,2,6-triaza-azulene-6-carboxylic acid tert-butyl ester in the alkylation step. MS (ESI): exact mass calculated for $C_{21}H_{20}ClN_3O_2$, 381.12; found, m/z 382.1 [M+H]$^+$. $^1$H NMR (500 MHz, CD$_3$OD): 7.39-7.32 (m, 4H), 6.67-6.65 (m, 1H), 6.54-6.61 (m, 2H), 5.81 (s, 2H), 5.16 (s, 2H), 2.81-2.79 (m, 4H), 2.76-2.74 (m, 2H), 2.68-2.66 (m, 2H).

Example 120

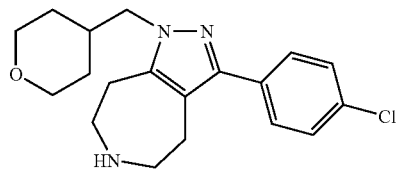

3-(4-Chloro-phenyl)-1-(tetrahydro-pyran-4-ylmethyl)-1,4,5,6,7,8-hexahydro-1,2,6-triaza-azulene The title compound was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using toluene-4-sulfonic acid tetrahydro-pyran-4-ylmethyl ester (0.3 mmol) in place of 2-chloromethyl-thiophene. The title compound was obtained as a 2:1 mixture (25 mg) with 3-(4-chloro-phenyl)-2-(tetrahydro-pyran-4-ylmethyl)-2,4,5,6,7,8-hexahydro-1,2,6-triaza-azulene. Data for the mixture: MS (ESI): exact mass calculated for $C_{19}H_{24}ClN_3O$, 345.16; found, m/z 346.1 [M+H]$^+$. $^1$H NMR (500 MHz, CD$_3$OD): 7.47-7.23 (m, 4H), 4.10-3.78 (m, 4H), 3.37-3.14 (m, 8H), 3.06-2.67 (m, 2H), 2.02-1.93 (m, 1H), 1.42-0.97 (m, 4H).

Example 121

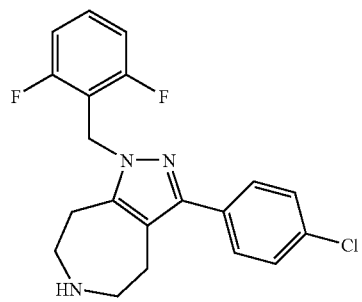

3-(4-Chloro-phenyl)-1-(2,6-difluoro-benzyl)-1,4,5,6,7,8-hexahydro-1,2,6-triaza-azulene The title compound (0.07 g) was prepared from 3-(4-chloro-phenyl)-4,5,7,8-tetrahydro-1H-1,2,6-triaza-azulene-6-carboxylic acid tert-butyl ester (Example 103, Step B; 1 mmol) using 2,6-difluorobenzyl chloride (1.5 mmol) in place of 2-chloromethyl-thiophene. The reaction sequence also yielded 3-(4-chloro-phenyl)-2-(2,6-difluoro-benzyl)-4,5,7,8-tetrahydro-2H-1,2,6-triaza-azulene-6-carboxylic acid tert-butyl ester in the alkylation step. MS (ESI): exact mass calculated for $C_{20}H_{18}ClF_2N_3$, 373.12; found, m/z 374.1 [M+H]$^+$. $^1$H NMR (500 MHz, CD$_3$OD): 7.34-7.30 (m, 5H), 6.93-6.90 (m, 2H), 5.34 (s, 2H), 3.59-3.57 (m, 2H), 3.39-3.37 (m, 4H), 2.94-2.92 (m, 2H).

Example 122

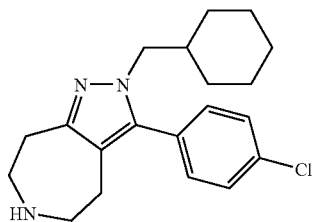

3-(4-Chloro-phenyl)-2-cyclohexylmethyl-2,4,5,6,7,8-hexahydro-1,2,6-triaza-azulene The title compound (0.06 g) was prepared from 3-(4-chloro-phenyl)-2-cyclohexyl methyl-4,5,7,8-tetrahydro-2H-1,2,6-triaza-azulene-6-carboxylic acid tert-butyl ester (Example 117) according to the deprotection method in Example 103, Step C. MS (ESI): exact mass calculated for $C_{20}H_{26}ClN_3$, 343.18; found, m/z 344.2 [M+H]$^+$. $^1$H NMR (500 MHz, CD$_3$OD): 7.39 (d, J=8.5 Hz, 2H), 7.31 (d, J=8.5 Hz, 2H), 4.10 (d, J=7.3 Hz, 2H), 3.49-3.47 (br m, 2H), 3.37-3.35 (br m, 2H), 3.21-3.19 (br m, 2H), 3.03-3.01 (br m, 2H), 1.88-1.61 (m, 4H), 1.52-1.49 (m, 2H), 1.17-1.10 (m, 3H), 0.94-0.90 (m, 2H).

Example 123

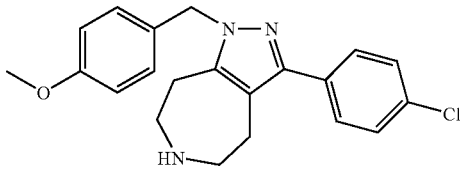

3-(4-Chloro-phenyl)-1-(4-methoxy-benzyl)-1,4,5,6,7,8-hexahydro-1,2,6-triaza-azulene The title compound (0.1 g) was prepared from 3-(4-chloro-phenyl)-4,5,7,8-tetrahydro-1H-1,2,6-triaza-azulene-6-carboxylic acid tert-butyl ester (Example 103, Step B; 1 mmol) using 4-methoxybenzyl chloride (1.5 mmol) in place of 2-chloromethyl-thiophene. MS (ESI): exact mass calculated for $C_{21}H_{22}ClN_3O$, 367.15; found, m/z 368.1 [M+H]$^+$. $^1$H NMR (400 MHz, CD$_3$OD): 7.41-7.39 (m, 2H), 7.31 (d, J=7.7 Hz, 2H), 6.70 (d, J=7.7 Hz, 2H), 5.36 (s, 2H), 3.60 (s, 3H), 3.33-3.31 (br m, 2H), 3.21-3.19 (br m, 2H), 3.18-3.16 (br m, 2H), 2.96-2.94 (br m, 2H).

Example 124

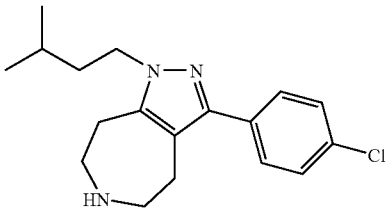

3-(4-Chloro-phenyl)-1-(3-methyl-butyl)-1,4,5,6,7,8-hexahydro-1,2,6-triaza-azulene The title compound (0.030 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 1-bromo-3-methyl-butane (0.3 mmol) in place of 2-chloromethyl-thiophene. MS (ESI): exact mass calculated for $C_{18}H_{24}ClN_3$, 317.17; found, m/z 318.3 [M+H]$^+$. $^1$H NMR (400 MHz, CD$_3$OD): 7.56-7.54 (m, 4H), 4.34 (s, 2H), 3.57-3.55 (br m, 2H), 3.44-3.42 (br m, 2H), 3.40-3.38 (br m, 2H), 3.29-3.27 (br m, 2H), 1.79-1.77 (br m, 1H), 1.02 (d, J=4.5 Hz, 6H).

Example 125

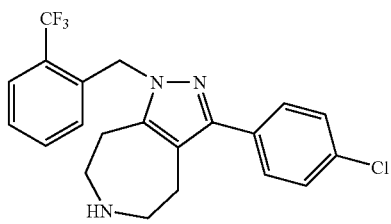

3-(4-Chloro-phenyl)-1-(2-trifluoromethyl-benzyl)-1,4,5,6,7,8-hexahydro-1,2,6-triaza-azulene The title compound (0.04 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 2-trifluoromethylbenzyl bromide (0.3 mmol) in place of 2-chloromethyl-thiophene. The reaction sequence also yielded 3-(4-chloro-phenyl)-2-(2-trifluoromethyl-benzyl)-4,5,7,8-tetrahydro-2H-1,2,6-triaza-azulene-6-carboxylic acid tert-butyl ester in the alkylation step. MS (ESI): exact mass calculated for $C_{21}H_{19}ClF_3N_3$, 405.12; found, m/z 406.1 [M+H]$^+$. $^1$H NMR (400 MHz, CD$_3$OD): 7.45 (d, J=7.7 Hz, 2H), 7.25-7.24 (br m, 3H), 7.18-7.16 (br m, 3H), 6.46-6.44 (br m, 1H), 5.43-5.41 (s, 2H), 3.14-3.11 (br m, 4H), 2.89-2.87 (br m, 4H).

Example 126

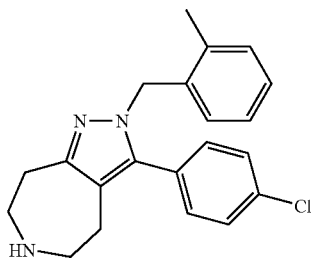

3-(4-Chloro-phenyl)-2-(2-methyl-benzyl)-2,4,5,6,7,8-hexahydro-1,2,6-triaza-azulene The title compound (0.020 g) was prepared from 3-(4-chloro-phenyl)-2-(2-methyl-benzyl)-4,5,7,8-tetrahydro-2H-1,2,6-triaza-azulene-6-carboxylic acid tert-butyl ester (Example 107) according to the deprotection method in Example 103, Step C. MS (ESI): exact mass calculated for $C_{21}H_{22}ClN_3$, 351.15; found, m/z 352.2 [M+H]$^+$. $^1$H NMR (400 MHz, CD$_3$OD): 7.47 (d, J=8.4 Hz, 2H), 7.24 (d, J=8.4 Hz, 2H), 7.15 (m, 3H), 6.60 (d, J=7.6 Hz, 1H), 5.23 (s, 2H), 3.46-3.44 (m, 2H), 3.36-3.34 (m, 2H), 3.21-3.19 (m, 2H), 2.89-2.87 (m, 2H), 2.13 (s, 3H).

Example 127

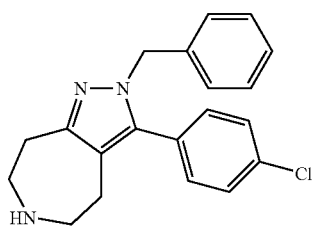

2-Benzyl-3-(4-chloro-phenyl)-2,4,5,6,7,8-hexahydro-1,2,6-triaza-azulene

The title compound (0.018 g) was prepared from 2-benzyl-3-(4-chloro-phenyl)-4,5,7,8-tetrahydro-2H-1,2,6-triaza-azulene-6-carboxylic acid tert-butyl ester (Example 59, Step D) according to the deprotection method in Example 103, Step C. MS (ESI): exact mass calculated for $C_{20}H_{20}ClN_3$, 337.13; found, m/z 338.1 [M+H]$^+$. $^1$H NMR (500 MHz, CD$_3$OD): 7.30-7.28 (m, 2H), 7.20-7.15 (m, 3H), 7.03-7.01 (m, 2H), 6.91-6.89 (m, 2H), 5.06 (s, 2H), 3.03-3.01 (m, 2H), 2.94-2.90 (m, 4H), 2.51-2.49 (m, 2H).

Example 128

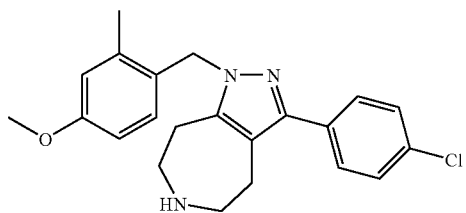

3-(4-Chloro-phenyl)-1-(4-methoxy-2-methyl-benzyl)-1,4,5,6,7,8-hexahydro-1,2,6-triaza-azulene To a solution of 3-(4-chloro-phenyl)-4,5,7,8-tetrahydro-1H-1,2,6-triaza-azulene-6-carboxylic acid tert-butyl ester (Example 103, Step B; 0.4 mmol) in toluene (3 mL) was added 4-methoxy-2-methyl-benzyl chloride (0.9 mmol) and cyanomethylene-tri-n-butylphosphorane (1 mmol). The mixture was heated at 110° C. for 16 h. After concentration and purification (SiO$_2$, EtOAc/hexanes), 3-(4-chloro-phenyl)-1-(4-methoxy-2-methyl-benzyl)-1,4,5,6,7,8-hexahydro-1,2,6-triaza-azulene-6-carboxylic acid tert-butyl ester was obtained (54 mg). The other regioisomer, 3-(4-chloro-phenyl)-2-(4-methoxy-2-methyl-benzyl)-1,4,5,6,7,8-hexahydro-1,2,6-triaza-azulene-6-carboxylic acid tert-butyl ester, was also obtained (86 mg). 3-(4-Chloro-phenyl)-1-(4-methoxy-2-methyl-benzyl)-1,4,5,6,7,8-hexahydro-1,2,6-triaza-azulene-6-carboxylic acid tert-butyl ester (20 mg) was treated with TFA (1 mL) in CH$_2$Cl$_2$ (10 mL) for 4 h. After concentration of the reaction mixture, the title compound was obtained (0.02 g). MS (ESI): exact mass calculated for $C_{22}H_{24}ClN_3O$, 381.16; found, m/z 382.1 [M+H]$^+$. $^1$H NMR (500 MHz, CD$_3$OD):

7.39-7.37 (m, 2H), 7.34-7.32 (m, 2H), 6.68-6.66 (br m, 1H), 6.54-6.52 (br m, 1H), 6.37 (d, J=8.3 Hz, 1H), 5.21 (s, 2H), 2.81-2.79 (m, 4H), 2.71-2.69 (m, 4H).

Example 129

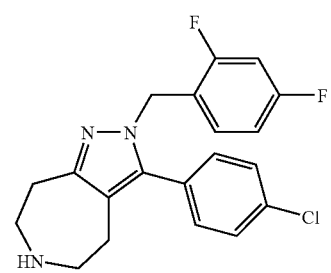

3-(4-Chloro-phenyl)-2-(2,4-difluoro-benzyl)-2,4,5,6,7,8-hexahydro-1,2,6-triaza-azulene The title compound (0.016 g) was prepared from 3-(4-chloro-phenyl)-2-(2,4-difluoro-benzyl)-4,5,7,8-tetrahydro-2H-1,2,6-triaza-azulene-6-carboxylic acid tert-butyl ester (Example 108; 0.2 mmol) according to the deprotection method in Example 103, Step C. MS (ESI): exact mass calculated for $C_{20}H_{18}ClF_2N_3$, 373.12; found, m/z 374.1 [M+H]$^+$. $^1$H NMR (400 MHz, CD$_3$OD): 7.54 (d, J=8.0 Hz, 2H), 7.49 (d, J=8.0 Hz, 2H), 6.96-6.88 (m, 3H), 5.27 (s, 2H), 3.46-3.44 (br m, 2H), 3.34-3.32 (br m, 2H), 3.23-3.21 (br m, 2H), 2.86-2.84 (br m, 2H).

Example 130

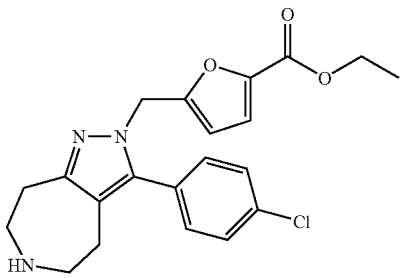

5-[3-(4-Chloro-phenyl)-5,6,7,8-tetrahydro-4H-1,2,6-triaza-azulen-2-ylmethyl]-furan-2-carboxylic acid ethyl ester The title compound (0.008 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 5-chloro-furan-2-carboxylic acid ethyl ester (0.3 mmol) in place of 2-chloromethyl-thiophene. The reaction sequence also provided 3-(4-chloro-phenyl)-1-(5-ethoxycarbonyl-furan-2-ylmethyl)-4,5,7,8-tetrahydro-1H-1,2,6-triaza-azulene-6-carboxylic acid tert-butyl ester in the alkylation step. MS (ESI): exact mass calculated for $C_{21}H_{22}ClN_3O_3$, 399.13; found, m/z 400.2 [M+H]$^+$. $^1$H NMR (500 MHz, CD$_3$OD): 7.44 (d, J=8.4 Hz, 2H), 7.30 (d, J=8.4 Hz, 2H), 7.00 (d, J=3.5 Hz, 1H), 6.21 (d, J=3.5 Hz, 1H), 5.09

(s, 2H), 4.21 (q, J=7.1 Hz, 2H), 3.21-3.19 (m, 2H), 3.11-3.09 (m, 2H), 2.96-2.94 (m, 2H), 2.61-2.59 (m, 2H), 1.24 (t, J=7.1 Hz, 2H).

Example 131

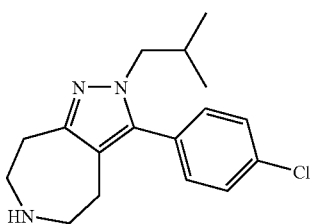

3-(4-Chloro-phenyl)-2-isobutyl-2,4,5,6,7,8-hexahydro-1,2,6-triaza-azulene

The title compound (0.010 g) was prepared from 3-(4-chloro-phenyl)-2-isobutyl-4,5,7,8-tetrahydro-2H-1,2,6-triaza-azulene-6-carboxylic acid tert-butyl ester (Example 118, Step C) according to the deprotection method from Example 103, Step C. MS (ESI): exact mass calculated for $C_{17}H_{22}ClN_3$, 303.15; found, m/z 304.1 [M+H]$^+$. $^1$H NMR (400 MHz, CD$_3$OD): 7.58-7.56 (m, 2H), 7.37-7.34 (m, 2H), 3.81 (d, J=7.5 Hz, 2H), 3.42-3.40 (m, 2H), 3.34-3.30 (m, 2H), 3.18-3.15 (m, 2H), 2.81-2.78 (m, 2H), 2.02-2.00 (m, 1H), 0.74 (d, J=6.7 Hz, 6H).

Example 132

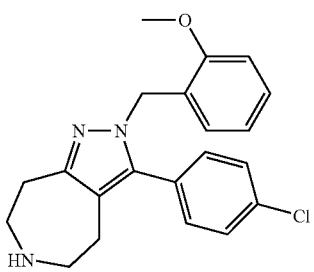

3-(4-Chloro-phenyl)-2-(2-methoxy-benzyl)-2,4,5,6,7,8-hexahydro-1,2,6-triaza-azulene The title compound (0.040 g) was prepared from 3-(4-chloro-phenyl)-2-(2-methoxy-benzyl)-4,5,7,8-tetrahydro-2H-1,2,6-triaza-azulene-6-carboxylic acid tert-butyl ester (Example 109) according to the deprotection method in Example 103, Step C. MS (ESI): exact mass calculated for $C_{21}H_{22}ClN_3O_3$, 399.13; found, m/z 368.2 [M+H]$^+$. $^1$H NMR (500 MHz, CDCl$_3$): 7.26 (d, J=6.5 Hz, 2H), 7.12 (t, J=7.6 Hz, 1H), 7.03 (d, J=6.5 Hz, 2H), 6.80 (t, J=7.6 Hz, 1H), 6.71 (d, J=7.6 Hz, 1H), 6.62 (d, J=7.6 Hz, 1H), 5.08 (s, 2H), 2.99-2.97 (m, 2H), 2.89-2.87 (m, 4H), 2.49-2.47 (m, 2H).

Example 133

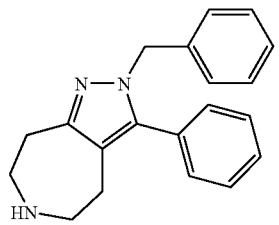

2-Benzyl-3-phenyl-2,4,5,6,7,8-hexahydro-1,2,6-triaza-azulene

To a solution of 2-benzyl-3-(4-chloro-phenyl)-4,5,7,8-tetrahydro-2H-1,2,6-triaza-azulene-6-carboxylic acid tert-butyl ester (0.1 mmol) (Example 59, Step D) in THF (25 mL) was added lithium aluminum hydride (100 mg). The mixture was heated at reflux for 4 h. Water (1 mL) was added, the mixture was filtered, and the filtrate was concentrated. After purification (SiO$_2$, EtOAc/hexanes), 2-benzyl-3-phenyl-2,4,5,6,7,8-hexahydro-1,2,6-triaza-azulene-6-carboxylic acid tert-butyl ester was obtained. The intermediate was diluted with CH$_2$Cl$_2$ (5 mL) and TFA (1 mL) was added. The reaction mixture was stirred at RT for 4 h. The reaction mixture was concentrated to obtain the title compound (0.018 g). MS (ESI): exact mass calculated for $C_{20}H_{21}N_3$, 303.17; found, m/z 304.3 [M+H]$^+$. $^1$H NMR (400 MHz, CD$_3$OD): 7.38-7.35 (m, 3H), 7.19-7.18 (m, 3H), 7.12-7.10 (m, 2H), 5.13 (s, 2H), 3.35-3.21 (br m, 6H), 3.34-3.30 (br m, 2H), 2.81-2.79 (br m, 2H).

Example 134

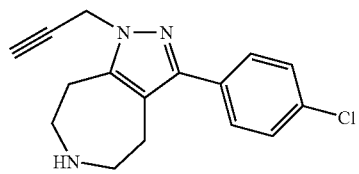

3-(4-Chloro-phenyl)-1-prop-2-ynyl-1,4,5,6,7,8-hexahydro-1,2,6-triaza-azulene

The title compound (0.014 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 2-propynyl chloride (0.3 mmol) in place of 2-chloromethyl-thiophene. MS (ESI): exact mass calculated for $C_{16}H_{16}ClN_3$, 285.10; found, m/z 286.2 [M+H]$^+$. $^1$H NMR (500 MHz, CD$_3$OD): 7.38-7.32 (m, 4H), 7.13 (t, J=6.4 Hz, 1H), 5.48 (d, J=6.4 Hz, 2H), 2.93-2.91 (m, 4H), 2.84-2.81 (m, 2H), 2.68-2.65 (m, 2H).

Example 135

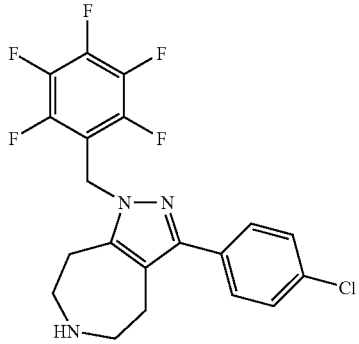

3-(4-Chloro-phenyl)-1-pentafluorophenylmethyl-1,4,5,6,7,8-hexahydro-1,2,6-triaza-azulene The title compound (0.02 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using pentafluorophenylmethyl chloride (0.3 mmol) in place of 2-chloromethyl-thiophene. The reaction sequence also yielded 3-(4-chloro-phenyl)-2-pentafluorophenylmethyl-4,5,7,8-tetrahydro-2H-1,2,6-triaza-azulene-6-carboxylic acid tert-butyl ester in the alkylation step. MS (ESI): exact mass calculated for $C_{20}H_{15}ClF_5N_3$, 427.09; found, m/z 428.1 [M+H]$^+$. $^1$H NMR (500 MHz, CD$_3$OD): 7.30 (br s, 4H), 5.34 (s, 2H), 3.01 (br s, 4H), 2.90-2.88 (m, 2H), 2.71-2.69 (m, 2H).

Example 136

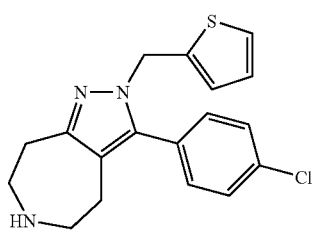

3-(4-Chloro-phenyl)-2-thiophen-2-ylmethyl-2,4,5,6,7,8-hexahydro-1,2,6-triaza-azulene The title compound (0.010 g) was prepared from 3-(4-chloro-phenyl)-2-thiophen-2-ylmethyl-4,5,7,8-tetrahydro-2H-1,2,6-triaza-azulene-6-carboxylic acid tert-butyl ester according to the method in Example 103. MS (ESI): exact mass calculated for $C_{18}H_{18}ClN_3S$, 343.09; found, m/z 344.1 [M+H]$^+$. $^1$H NMR (500 MHz, CD$_3$OD): 7.60-7.58 (m, 2H), 7.38-7.35 (m, 2H), 7.32 (dd, J=5.1, 1.1 Hz, 1H), 6.92 (dd, J=5.1, 3.5 Hz, 1H), 6.78 (dd, J=3.5, 1.1 Hz, 1H), 5.41 (s, 2H), 3.47-3.45 (m, 2H), 3.37-3.35 (m, 2H), 3.23-3.21 (m, 2H), 2.85-2.83 (m, 2H).

Example 137

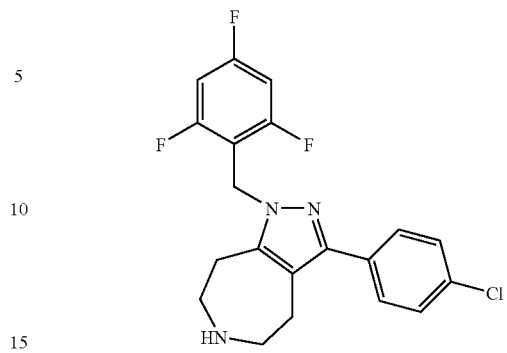

3-(4-Chloro-phenyl)-1-(2,4,6-trifluoro-benzyl)-1,4,5,6,7,8-hexahydro-1,2,6-triaza-azulene The title compound (0.027 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 2,4,6-trifluorobenzyl chloride (0.3 mmol) in place of 2-chloromethyl-thiophene. MS (ESI): exact mass calculated for $C_{20}H_{17}ClF_3N_3$, 391.11; found, m/z 392.1 [M+H]$^+$. $^1$H NMR (500 MHz, CD$_3$OD): 7.30-7.26 (m, 4H), 6.80-6.78 (br m, 2H), 5.25 (s, 2H), 2.94-2.92 (m, 4H), 2.82-2.80 (m, 2H), 2.66-2.62 (m, 2H).

Example 138

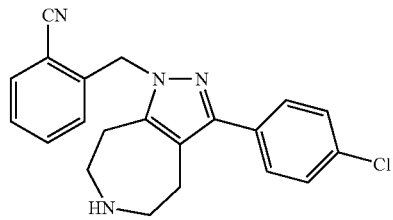

2-[3-(4-Chloro-phenyl)-5,6,7,8-tetrahydro-4H-1,2,6-triaza-azulen-1-ylmethyl]-benzonitrile The title compound (0.032 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 2-chloro-benzonitrile (0.3 mmol) in place of 2-chloromethyl-thiophene. MS (ESI): exact mass calculated for $C_{21}H_{19}ClN_4$, 362.13; found, m/z 363.2 [M+H]$^+$. $^1$H NMR (400 MHz, CD$_3$OD): 7.81 (d, J=7.6 Hz, 1H), 7.68-7.66 (br m, 1H), 7.54-7.51 (m, 3H), 7.46 (d, J=8.4 Hz, 2H), 7.23 (d, J=7.6 Hz, 1H), 5.64 (s, 2H), 3.51-3.49 (br m, 2H), 3.43-3.41 (br m, 2H), 3.31-3.29 (br m, 2H), 3.13-3.11 (br m, 2H).

Example 139

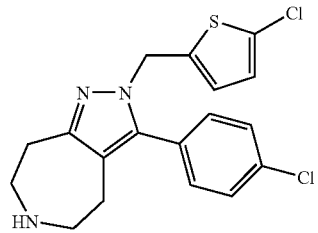

3-(4-Chloro-phenyl)-2-(5-chloro-thiophen-2-ylmethyl)-2,4,5,6,7,8-hexahydro-1,2,6-triaza-azulene The title compound (0.009 g) was prepared from 3-(4-chloro-phenyl)-2-(5-chloro-thiophen-2-ylmethyl)-4,5,7,8-tetrahydro-2H-1,2,6-triaza-azulene-6-carboxylic acid tert-butyl ester (Example 115) according to the deprotection method in Example 103, Step C. MS (ESI): exact mass calculated for $C_{18}H_{17}Cl_2N_3S$, 377.05; found, m/z 378.0 [M+H]+. 1H NMR (500 MHz, $CD_3OD$): 7.47-7.44 (m, 2H), 7.22-7.20 (m, 2H), 6.65 (d, J=3.8 Hz, 1H), 6.44 (d, J=3.8 Hz, 1H), 5.17 (s, 2H), 3.32-3.30 (m, 2H), 3.21-3.19 (m, 2H), 3.07-3.05 (m, 2H), 2.70-2.68 (m, 2H).

Example 140

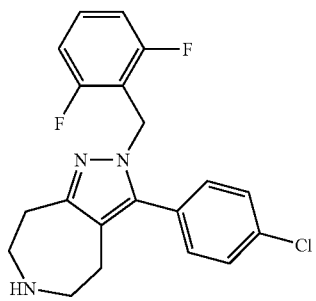

3-(4-Chloro-phenyl)-2-(2,6-difluoro-benzyl)-2,4,5,6,7,8-hexahydro-1,2,6-triaza-azulene The title compound (0.036 g) was prepared from 3-(4-chloro-phenyl)-2-(2,6-difluoro-benzyl)-4,5,7,8-tetrahydro-2H-1,2,6-triaza-azulene-6-carboxylic acid tert-butyl ester (Example 121, Step C) according to the deprotection method in Example 103, Step C. MS (ESI): exact mass calculated for $C_{20}H_{18}ClF_2N_3$, 373.12; found, m/z 374.2 [M+H]+. 1H NMR (500 MHz, $CD_3OD$): 7.44-7.42 (m, 2H), 7.27-7.23 (m, 3H), 6.79 (m, 2H), 5.14 (s, 2H), 3.27-3.25 (m, 2H), 3.21-3.18 (m, 2H), 3.02-3.00 (m, 2H), 2.69-2.67 (m, 2H).

Example 141

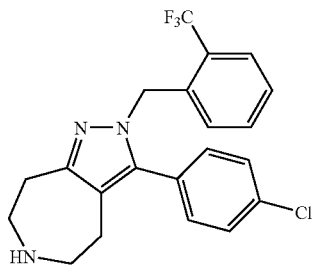

3-(4-Chloro-phenyl)-2-(2-trifluoromethyl-benzyl)-2,4,5,6,7,8-hexahydro-1,2,6-triaza-azulene The title compound (0.021 g) was prepared from 3-(4-chloro-phenyl)-2-(2-trifluoromethyl-benzyl)-4,5,7,8-tetrahydro-2H-1,2,6-triaza-azulene-6-carboxylic acid tert-butyl ester (Example 125) according to the deprotection method in Example 103, Step C. MS (ESI): exact mass calculated for $C_{21}H_{19}ClF_3N_3$, 405.12; found, m/z 406.1 [M+H]+. 1H NMR (400 MHz, $CD_3OD$): 7.69 (d, J=7.8 Hz, 1H), 7.59 (t, J=7.2 Hz, 1H), 7.53-7.46 (m, 3H), 7.27 (d, J=8.1 Hz, 2H), 6.83 (d, J=7.2 Hz, 1H), 5.47 (s, 2H), 3.51-3.49 (br m, 2H), 3.42-3.40 (br m, 2H), 3.31-3.29 (br m, 2H), 2.94-2.92 (br m, 2H).

Example 142

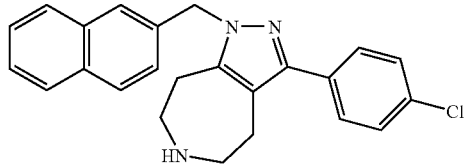

3-(4-Chloro-phenyl)-1-naphthalen-2-ylmethyl-1,4,5,6,7,8-hexahydro-1,2,6-triaza-azulene The title compound (0.043 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using naphthalen-2-ylmethyl chloride (0.3 mmol) in place of 2-chloromethyl-thiophene. MS (ESI): exact mass calculated for $C_{24}H_{22}ClN_3$, 387.15; found, m/z 388.1 [M+H]+. 1H NMR (500 MHz, $CDCl_3$): 7.74-7.69 (m, 3H), 7.45-7.38 (m, 5H), 7.34-7.32 (m, 1H), 7.18-7.16 (m, 2H), 5.43 (s, 2H), 3.04 (m, 2H), 2.99-2.97 (m, 2H), 2.87-2.85 (m, 4H).

Example 143

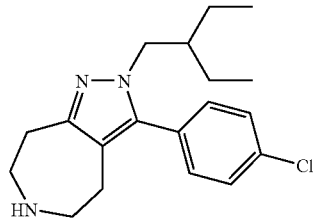

3-(4-Chloro-phenyl)-2-(2-ethyl-butyl)-2,4,5,6,7,8-hexahydro-1,2,6-triaza-azulene The title compound (0.012 g) was prepared from 3-(4-chloro-phenyl)-2-(2-ethyl-butyl)-4,5,7,8-tetrahydro-2H-1,2,6-triaza-azulene-6-carboxylic acid tert-butyl ester (Example 114) according to the deprotection method in Example 103, Step C. MS (ESI): exact mass calculated for $C_{19}H_{26}ClN_3$, 331.18; found, m/z 332.2 [M+H]+. 1H NMR (400 MHz, $CD_3OD$): 7.50-7.25 (br m, 4H), 3.76-3.74 (m, 2H), 3.33-3.31 (br m, 2H), 3.22-3.20 (br m, 2H), 3.09-3.07 (br m, 2H), 2.73-2.71 (br m, 2H), 1.56-1.54 (m, 1H), 1.16-1.14 (m, 4H), 0.82-0.55 (m, 6H).

Example 144

5-[3-(4-Chloro-phenyl)-5,6,7,8-tetrahydro-4H-1,2,6-triaza-azulen-1-ylmethyl]-furan-2-carboxylic acid ethyl ester The title compound (0.017 g) was prepared from 3-(4-chloro-phenyl)-1-(5-ethoxycarbonyl-furan-2-ylmethyl)-4,5,7,8-tetrahydro-1H-1,2,6-triaza-azulene-6-carboxylic acid tert-butyl ester (Example 130) according to the deprotection method in Example 103, Step C. MS (ESI): exact mass calculated for $C_{21}H_{22}ClN_3O_3$, 399.13; found, m/z 400.1 [M+H]$^+$. $^1$H NMR (500 MHz, CD$_3$OD): 7.37-7.32 (m, 4H), 7.06 (d, J=3.5 Hz, 1H), 6.41 (d, J=3.5 Hz, 1H), 5.34 (s, 2H), 4.21 (q, J=7.1 Hz, 2H), 3.26-3.24 (m, 2H), 3.19-3.17 (m, 2H), 3.13-3.11 (m, 2H), 2.86-2.84 (m, 2H), 1.24 (t, J=7.1 Hz, 2H).

Example 145

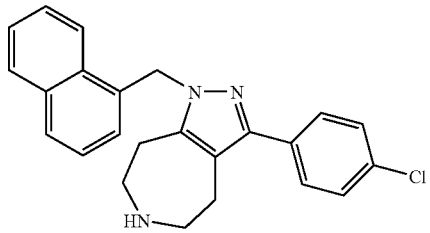

3-(4-Chloro-phenyl)-1-naphthalen-1-ylmethyl-1,4,5,6,7,8-hexahydro-1,2,6-triaza-azulene The title compound (0.015 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 1-naphthalen-methyl chloride (0.3 mmol) in place of 2-chloromethyl-thiophene. The reaction sequence also provided 3-(4-chloro-phenyl)-2-naphthalen-1-ylmethyl-4,5,7,8-tetrahydro-2H-1,2,6-triaza-azulene-6-carboxylic acid tert-butyl ester in the alkylation step. MS (ESI): exact mass calculated for $C_{24}H_{22}ClN_3$, 387.15; found, m/z 388.1 [M+H]$^+$. $^1$H NMR (500 MHz, CD$_3$OD): 7.79-7.18 (m, 11H), 5.74 (d, J=7.3 Hz, 2H), 3.42 (s, 2H), 3.21-3.19 (br m, 2H), 3.10-3.08 (br m, 2H), 2.92-2.90 (br m, 2H), 2.84-2.82 (br m, 2H).

Example 146

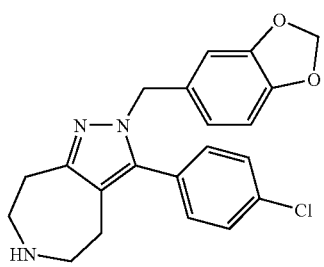

2-Benzo[1,3]dioxol-5-ylmethyl-3-(4-chloro-phenyl)-2,4,5,6,7,8-hexahydro-1,2,6-triaza-azulene The title compound (0.021 g) was prepared from 2-benzo[1,3]dioxol-5-ylmethyl-3-(4-chloro-phenyl)-4,5,7,8-tetrahydro-2H-1,2,6-triaza-azulene-6-carboxylic acid tert-butyl ester (Example 119) according to the deprotection method in Example 103, Step C. MS (ESI): exact mass calculated for $C_{21}H_{20}ClN_3O_2$, 381.12; found, m/z 382.0 [M+H]$^+$. $^1$H NMR (500 MHz, CD$_3$OD): 7.37-7.34 (m, 2H), 7.11-7.10 (m, 2H), 6.57 (d, J=7.9 Hz, 1H), 6.31-6.29 (m, 2H), 5.79 (s, 2H), 4.95 (s, 2H), 3.55-3.40 (m, 1H), 2.82-2.80 (m, 5H), 2.42-2.41 (m, 2H).

Example 147

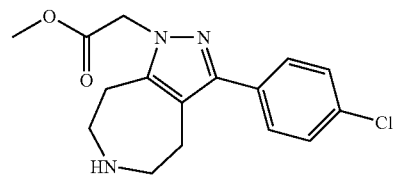

[3-(4-Chloro-phenyl)-5,6,7,8-tetrahydro-4H-1,2,6-triaza-azulen-1-yl]-acetic acid methyl ester The title compound (0.09 g) was prepared from 3-(4-chloro-phenyl)-4,5,7,8-tetrahydro-1H-1,2,6-triaza-azulene-6-carboxylic acid tert-butyl ester (Example 103, Step B; 1 mmol) using 2-bromoacetic acid methyl ester (1.5 mmol) in place of 2-chloromethyl-thiophene. MS (ESI): exact mass calculated for $C_{16}H_{18}ClN_3O_2$, 319.11; found, m/z 320.2 [M+H]$^+$. $^1$H NMR (500 MHz, CD$_3$OD): 7.31 (d, J=8.1 Hz, 2H), 7.26 (d, J=8.1 Hz, 2H), 4.93 (s, 2H), 3.56 (s, 3H), 3.27-3.25 (br m, 2H), 3.19-3.17 (br m, 2H), 3.04-3.03 (br m, 2H), 2.90-2.88 (br m, 2H).

Example 148

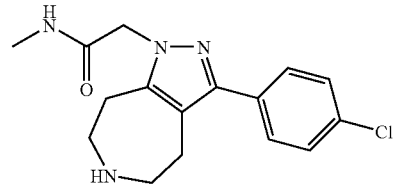

2-[3-(4-Chloro-phenyl)-5,6,7,8-tetrahydro-4H-1,2,6-triaza-azulen-1-yl]-N-methyl-acetamide To a solution of 3-(4-chloro-phenyl)-1-methylcarbamoyl-methyl-4,5,7,8-tetrahydro-1H-1,2,6-triaza-azulene-6-carboxylic acid tert-butyl ester (44 mg) (Example 147) in THF (0.5 mL) was added 8% aq. NaOH (0.3 mL). The mixture was stirred at RT for 16 h, and then was acidified with 1 N HCl (0.5 mL). The mixture was extracted with CH$_2$Cl$_2$ (2×2 mL). The combined organic layers were washed with brine, dried over Na$_2$SO$_4$, and concentrated. The residue was diluted with CH$_3$CN (0.5 mL) and treated with DCC (26 mg) and HOBt (18 mg). After 2 h at RT, a solution of methylamine hydrochloride (70 mg) in H$_2$O (0.3 mL) was added. The mixture was stirred at RT for 16 h. Concentration of the reaction mixture and purification of the residue by SiO$_2$ chromatography (EtOAc/hexanes) gave 3-(4-chloro-phenyl)-1-methylcarbamoyl methyl-4,5,7,8-tetrahydro-1H-1,2,6-triaza-azulene-6-carboxylic acid tert-butyl ester. The intermediate was treated with TFA (1 mL) in CH$_2$Cl$_2$ (10 mL) for 4 h, and the solution was concentrated to obtain the title compound (0.015 g). MS (ESI): exact mass calculated for $C_{16}H_{19}ClN_4O$, 318.12; found, m/z 319.1 [M+H]$^+$. $^1$H NMR (500 MHz, CD$_3$OD): 7.41-7.32 (m, 4H), 5.94 (br s, 1H), 4.70 (s, 2H), 2.98-2.90 (m, 4H), 2.77-2.71 (m, 7H).

Example 149

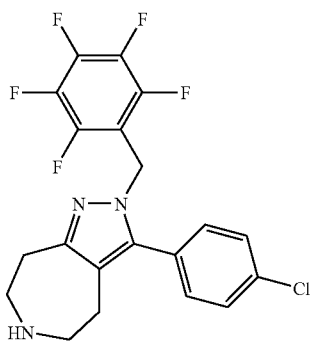

3-(4-Chloro-phenyl)-2-pentafluorophenylmethyl-2,4,
5,6,7,8-hexahydro-1,2,6-triaza-azulene The title compound (0.016 g) was prepared from 3-(4-chloro-phenyl)-2-pentafluorophenyl methyl-4,5,7,8-tetrahydro-2H-1,2,6-triaza-azulene-6-carboxylic acid tert-butyl ester (Example 135) according to the deprotection method in Example 103, Step C. MS (ESI): exact mass calculated for $C_{20}H_{15}ClF_5N_3$, 427.09; found, m/z 428.1 [M+H]$^+$. $^1$H NMR (500 MHz, CD$_3$OD): 7.45-7.43 (m, 2H), 7.26-7.23 (m, 2H), 5.15 (s, 2H), 2.91-2.89 (m, 2H), 2.83-2.81 (m, 2H), 2.79-2.77 (m, 2H), 2.46-2.44 (m, 2H).

Example 150

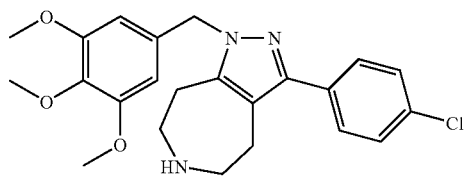

3-(4-Chloro-phenyl)-1-(3,4,5-trimethoxy-benzyl)-1,
4,5,6,7,8-hexahydro-1,2,6-triaza-azulene The title compound (0.006 g) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 3,4,5-trimethoxybenzyl chloride (0.3 mmol) in place of 2-chloromethyl-thiophene. The reaction sequence also yielded 3-(4-chloro-phenyl)-2-(3,4,5-trimethoxy-benzyl)-4,5,7,8-tetrahydro-2H-1,2,6-triaza-azulene-6-carboxylic acid tert-butyl ester in the alkylation step. MS (ESI): exact mass calculated for $C_{23}H_{26}ClN_3O_3$, 427.17; found, m/z 428.1 [M+H]$^+$. $^1$H NMR (500 MHz, CD$_3$OD): 7.51-7.49 (m, 2H), 7.46-7.44 (m, 2H), 6.44 (s, 2H), 5.32 (s, 2H), 3.78 (s, 6H), 3.74 (s, 3H), 2.95-2.89 (m, 6H), 2.81-2.79 (m, 2H).

Example 151

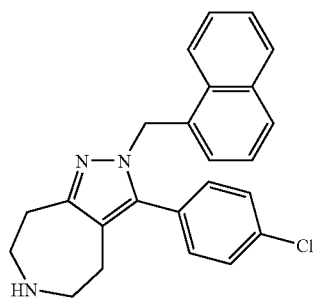

3-(4-Chloro-phenyl)-2-naphthalen-1-ylmethyl-2,4,5,
6,7,8-hexahydro-1,2,6-triaza-azulene The title compound (0.015 g) was prepared from 3-(4-chloro-phenyl)-2-naphthalen-1-ylmethyl-4,5,7,8-tetrahydro-2H-1,2,6-triaza-azulene-6-carboxylic acid tert-butyl ester (Example 145) according to the deprotection method in Example 103, Step C. MS (ESI): exact mass calculated for $C_{24}H_{22}ClN_3$, 387.15; found, m/z 388.2 [M+H]$^+$. $^1$H NMR (500 MHz, CDCl$_3$): 7.78-7.75 (m, 2H), 7.67 (d, J=8.3 Hz, 1H), 7.41-7.39 (m, 2H), 7.00 (td, J=8.0, 1.0 Hz, 1H), 7.21-7.19 (m, 2H), 7.02-7.01 (m, 2H), 6.69-6.67 (dd, J=7.1, 1.0 Hz, 1H), 5.56 (s, 2H), 3.31-3.29 (m, 2H), 2.90-2.88 (m, 4H), 2.49-2.47 (m, 2H).

Example 152

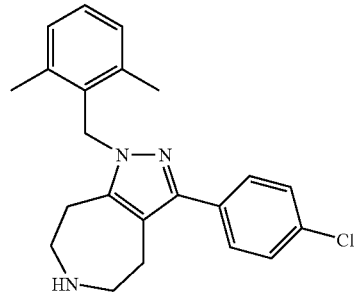

3-(4-Chloro-phenyl)-1-(2,6-dimethyl-benzyl)-1,4,5,
6,7,8-hexahydro-1,2,6-triaza-azulene The title compound (0.018 g) was prepared from 3-(4-chloro-phenyl)-4,5,7,8-tetrahydro-1H-1,2,6-triaza-azulene-6-carboxylic acid tert-butyl ester (Example 103, step B; 0.2 mmol) using 2,6-dimethylbenzyl chloride (0.3 mmol) in place of 2-chloromethyl-thiophene. MS (ESI): exact mass calculated for $C_{22}H_{24}ClN_3$, 365.17; found, m/z 366.2 [M+H]$^+$. $^1$H NMR (500 MHz, CD$_3$OD): 7.48-7.45 (m, 4H), 7.17-7.15 (br m, 1H), 7.11-7.09 (m, 2H), 5.51 (s, 2H), 3.43-3.41 (br m, 2H), 3.39-3.37 (br m, 2H), 3.31-3.29 (br m, 2H), 3.10-3.08 (br m, 2H), 2.31 (s, 3H).

Example 153

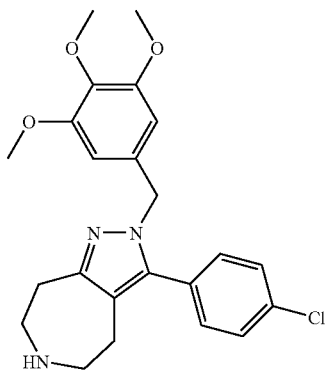

3-(4-Chloro-phenyl)-2-(3,4,5-trimethoxy-benzyl)-2,4,5,6,7,8-hexahydro-1,2,6-triaza-azulene The title compound (25 mg) was prepared from 3-(4-chloro-phenyl)-2-(3,4,5-trimethoxy-benzyl)-4,5,7,8-tetrahydro-2H-1,2,6-triaza-azulene-6-carboxylic acid tert-butyl ester (Example 150) according to the deprotection method in Example 103, Step C. MS (ESI): exact mass calculated for $C_{23}H_{26}ClN_3O_3$, 427.17; found, m/z 428.1 [M+H]$^+$. $^1$H NMR (500 MHz, CD$_3$OD): 7.39-7.36 (m, 2H), 7.13-7.11 (m, 2H), 6.07 (s, 2H), 5.00 (s, 2H), 3.59 (s, 9H), 2.90-2.70 (m, 6H), 2.46-2.44 (m, 2H).

Example 154

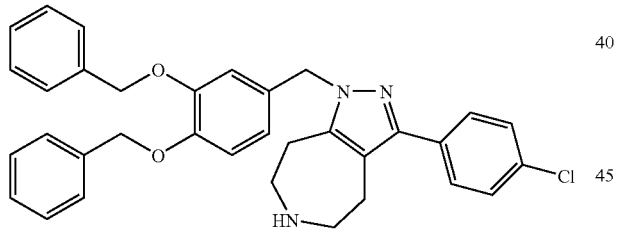

1-(3,4-Bis-benzyloxy-benzyl)-3-(4-chloro-phenyl)-1,4,5,6,7,8-hexahydro-1,2,6-triaza-azulene The title compound (22 mg) was prepared from 3-(4-chloro-phenyl)-4,5,7,8-tetrahydro-1H-1,2,6-triaza-azulene-6-carboxylic acid tert-butyl ester (Example 103, Step B; 0.2 mmol) using 3,4-bis(benzyloxy)benzyl chloride (0.3 mmol) in place of 2-chloromethyl-thiophene. The reaction sequence also provided 2-(3,4-bis-benzyloxy-benzyl)-3-(4-chloro-phenyl)-4,5,7,8-tetrahydro-2H-1,2,6-triaza-azulene-6-carboxylic acid tert-butyl ester in the alkylation step. MS (ESI): exact mass calculated for $C_{34}H_{32}ClN_3O_2$, 549.22; found, m/z 550.1 [M+H]$^+$. $^1$H NMR (500 MHz, CD$_3$OD): 7.36-7.16 (m, 14H), 6.86 (d, J=8.3 Hz, 1H), 6.65 (d, J=1.9 Hz, 1H), 6.56 (dd, J=8.3, 1.9 Hz, 1H), 5.13 (s, 2H), 4.99 (s, 2H), 4.97 (s, 2H), 2.78-2.76 (m, 2H), 2.73-2.71 (m, 2H), 2.65 (m, 4H).

Example 155

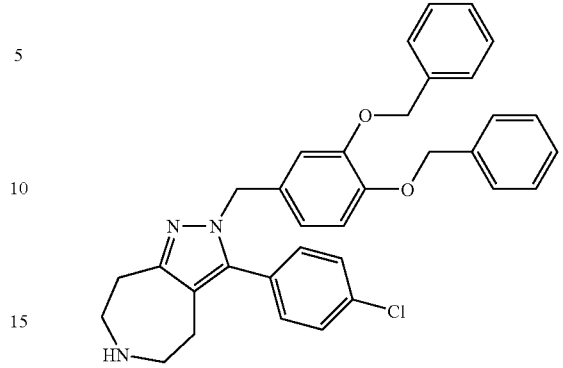

2-(3,4-Bis-benzyloxy-benzyl)-3-(4-chloro-phenyl)-2,4,5,6,7,8-hexahydro-1,2,6-triaza-azulene The title compound (20 mg) was prepared from 2-(3,4-bis-benzyloxy-benzyl)-3-(4-chloro-phenyl)-4,5,7,8-tetrahydro-2H-1,2,6-triaza-azulene-6-carboxylic acid tert-butyl ester (Example 154) according to the deprotection method in Example 103, Step C. MS (ESI): exact mass calculated for $C_{34}H_{32}ClN_3O_2$, 549.22; found, m/z 550.1 [M+H]$^+$. $^1$H NMR (500 MHz, CD$_3$OD): 7.43-7.30 (m, 12H), 7.07-7.05 (m, 2H), 6.89-6.87 (m, 1H), 6.47-6.46 (m, 2H), 5.09 (s, 2H), 5.04 (s, 2H), 5.01 (s, 2H), 2.99-2.97 (m, 2H), 2.93-2.91 (m, 2H), 2.88-2.86 (m, 2H), 2.52-2.50 (m, 2H).

Example 156

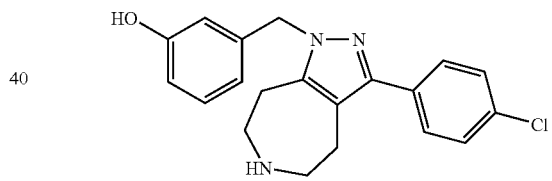

3-[3-(4-Chloro-phenyl)-5,6,7,8-tetrahydro-4H-1,2,6-triaza-azulen-1-ylmethyl]-phenol A solution of 3-(4-chloro-phenyl)-1-(3-methoxy-benzyl)-1,4,5,6,7,8-hexahydro-1,2,6-triaza-azulene (Example 105, 0.1 mmol) in CH$_2$Cl$_2$ (5 mL) was cooled to 0° C., and 1 M BBr$_3$ in CH$_2$Cl$_2$ (0.5 mL) was added. The mixture was allowed to warm to 25° C. After 2 h, satd. aq. NaHCO$_3$ (5 mL) was added. The layers were separated, and the aqueous layer was extracted with EtOAc (2×5 mL). The combined organic layers were dried over Na$_2$SO$_4$ and concentrated. Purification by flash chromatography (2 M NH$_3$ in MeOH/CH$_2$Cl$_2$) provided the title compound (10 mg). MS (ESI): exact mass calculated for $C_{20}H_{20}ClN_3O$, 353.13; found, m/z 354.1 [M+H]$^+$. $^1$H NMR (500 MHz, CD$_3$OD): 7.40-7.38 (m, 2H), 7.35-7.32 (m, 2H), 7.03 (t, J=7.9 Hz, 1H), 6.57 (dd, J=8.1, 2.0 Hz, 1H), 6.49 (d, J=8.1 Hz, 1H), 6.39-6.37 (br m, 1H), 5.20 (s, 2H), 2.81-2.78 (br m, 4H), 2.74-2.72 (br m, 2H), 2.70-2.68 (br m, 2H).

Example 157

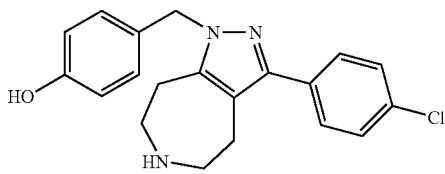

4-[3-(4-Chloro-phenyl)-5,6,7,8-tetrahydro-4H-1,2,6-triaza-azulen-1-ylmethyl]-phenol The title compound (10 mg) was prepared from (4-chlorophenyl)-1-(4-methoxy-benzyl)-1,4,5,6,7,8-hexahydro-1,2,6-triaza-azulene-6-carboxylic acid tert-butyl ester (Example 123, 0.1 mmol) as in Example 156. MS (ESI): exact mass calculated for $C_{20}H_{20}ClN_3O$, 353.13; found, m/z 354.1 [M+H]$^+$. $^1$H NMR (500 MHz, CD$_3$OD): 7.39-7.37 (m, 2H), 7.34-7.31 (m, 2H), 6.89-6.86 (m, 2H), 6.64-6.61 (m, 2H), 5.16 (s, 2H), 2.77-2.75 (br m, 6H), 2.67-2.65 (br m, 2H).

Example 158

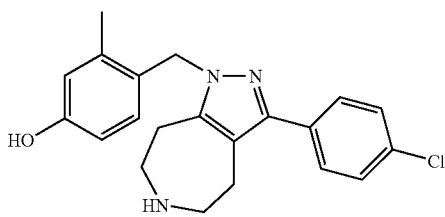

4-[3-(4-Chloro-phenyl)-5,6,7,8-tetrahydro-4H-1,2,6-triaza-azulen-1-ylmethyl]-3-methyl-phenol The title compound (8 mg) was prepared from (4-chlorophenyl)-1-(4-methoxy-2-methyl-benzyl)-1,4,5,6,7,8-hexahydro-1,2,6-triaza-azulene-6-carboxylic acid tert-butyl ester (Example 128, 34 mg) as in Example 156. MS (ESI): exact mass calculated for $C_{21}H_{22}ClN_3O$, 367.15; found, m/z 368.0 [M+H]$^+$. $^1$H NMR (500 MHz, CD$_3$OD): 7.39-7.37 (m, 2H), 7.33-7.32 (m, 2H), 6.54-6.52 (br m, 1H), 6.41-6.39 (br m, 1H), 6.28 (d, J=8.3 Hz, 1H), 5.17 (s, 2H), 2.83-2.78 (m, 4H), 2.71-2.67 (m, 2H).

Example 159

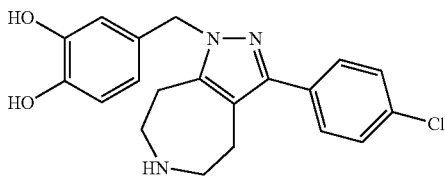

4-[3-(4-Chloro-phenyl)-5,6,7,8-tetrahydro-4H-1,2,6-triaza-azulen-1-ylmethyl]-benzene-1,2-diol A solution of 1-(3,4-bis-benzyloxy-benzyl)-3-(4-chlorophenyl)-1,4,5,6,7,8-hexahydro-1,2,6-triaza-azulene-carboxylic acid tert-butyl ester (Example 154, 0.1 mmol) in CH$_2$Cl$_2$ (5 mL) was cooled to 0° C., and 1 M BBr$_3$ in CH$_2$Cl$_2$ (0.5 mL) was added. The mixture was allowed to warm to RT and was stirred at RT for 1 h. The precipitate that had formed was collected by filtration, washed with water, and dried under vacuum to provide the title compound (25 mg). MS (ESI): exact mass calculated for $C_{20}H_{20}ClN_3O_2$, 369.12; found, m/z 370.0 [M+H]$^+$. $^1$H NMR (500 MHz, CD$_3$OD): 7.44-7.42 (m, 4H), 7.39-7.37 (m, 2H), 6.63 (d, J=8.1 Hz, 1H), 6.50 (d, J=2.1 Hz, 1H), 6.45 (dd, J=8.1, 2.1 Hz, 1H), 5.18 (s, 2H), 3.29-3.25 (m, 4H), 3.06-3.04 (m, 2H), 2.97-2.95 (m, 2H).

Example 160

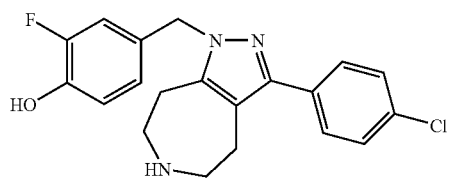

4-[3-(4-Chloro-phenyl)-5,6,7,8-tetrahydro-4H-1,2,6-triaza-azulen-1-ylmethyl]-2-fluoro-phenol BBr$_3$ (0.13 mL) was added slowly to a 0° C. solution of 0.022 g of 3-(4-chloro-phenyl)-1-(3-fluoro-4-methoxy-benzyl)-1,4,5,6,7,8-hexahydro-1,2,6-triaza-azulene (Example 96) in CH$_2$Cl$_2$ (20 mL). After 1 h, the mixture was warmed to RT and stirred for 18 h. The reaction was then cooled back to 0° C. and quenched by the addition of 5 mL of satd. aq. NaHCO$_3$. The aqueous layer was extracted with methanolic CH$_2$Cl$_2$ (2×). The combined organic layers were dried over Na$_2$SO$_4$ and concentrated. The crude oil was purified by preparative TLC (9:1 CH$_2$Cl$_2$/2 M NH$_3$ in MeOH) to afford the title compound (0.016 g) as a tan solid. MS (ESI): exact mass calculated for $C_{20}H_{19}ClFN_3O$, 371.12; found, m/z 372.1 [M+H]$^+$. $^1$H NMR (400 MHz, CD$_3$OD): 7.50-7.42 (m, 4H), 6.86-6.79 (m, 3H), 5.26 (s, 2H), 3.31-3.26 (m, 2H), 2.96-2.95 (m, 4H), 2.90-2.87 (m, 2H), 2.81-2.79 (m, 2H). $^{13}$C NMR (100 MHz, CD$_3$OD): 154.2, 151.8, 149.6, 146.1, 146.0, 143.8, 134.8, 133.4, 131.1, 130.3, 130.2, 129.7, 124.0, 119.1, 115.6, 115.4, 53.1, 50.4, 29.0, 27.5.

Example 161

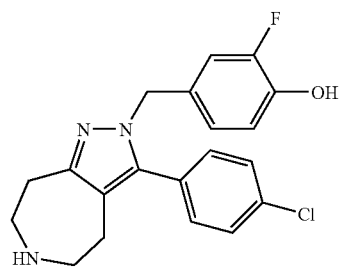

4-[3-(4-Chloro-phenyl)-5,6,7,8-tetrahydro-4H-1,2,6-triaza-azulen-2-ylmethyl]-2-fluoro-phenol 3-(4-Chloro-phenyl)-2-(3-fluoro-4-methoxy-benzyl)-2,4,5,6,7,8-hexahydro-1,2,6-triaza-azulene (Example 97, 0.12 g) was de-methylated as in Example 160 to afford the title compound (0.027 g) as an off-white solid. MS (ESI): exact mass calculated for $C_{20}H_{19}ClFN_3O$, 371.12; found, m/z 372.0

[M+H]+. 1H NMR (500 MHz, CD3OD): 7.48-7.44 (m, 2H), 7.21-7.18 (m, 2H), 6.75 (t, J=8.6 Hz, 1H), 6.61-6.58 (m, 1H), 6.53-6.50 (m 1H), 5.04 (s, 2H), 3.31-3.30 (m, 2H), 3.01-2.99 (m, 2H), 2.94-2.88 (m, 4H), 2.55-2.52 (m, 2H). 13C NMR (125 MHz, CD3OD): 154.2, 153.7, 152.3, 146.5, 146.4, 142.4, 136.6, 133.1, 130.6, 130.5, 130.1, 124.5, 120.7, 119.2, 116.0, 115.9, 53.4, 51.2, 32.6, 28.0.

Example 162

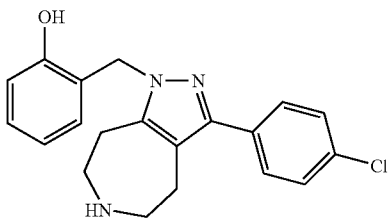

2-[3-(4-Chloro-phenyl)-5,6,7,8-tetrahydro-4H-1,2,6-triaza-azulen-1-ylmethyl]-phenol The title compound (13 mg) was prepared from 3-(4-chloro-phenyl)-1-(2-methoxy-benzyl)-1,4,5,6,7,8-hexahydro-1,2,6-triaza-azulene-6-carboxylic acid tert-butyl ester (Example 109, 0.1 mmol) as in Example 156. MS (ESI): exact mass calculated for $C_{20}H_{20}ClN_3O$, 353.13; found, m/z 354.2 [M+H]+. 1H NMR (500 MHz, CDCl3): 7.37 (d, J=6.5 Hz, 2H), 7.33 (d, J=6.5 Hz, 2H), 7.19 (t, J=7.6 Hz, 1H), 7.10 (d, J=7.6 Hz, 1H), 6.91 (d, J=7.6 Hz, 1H), 6.62 (t, J=7.6 Hz, 1H), 5.12 (s, 2H), 2.91-2.80 (br m, 6H), 2.68-2.66 (m, 2H).

Example 163

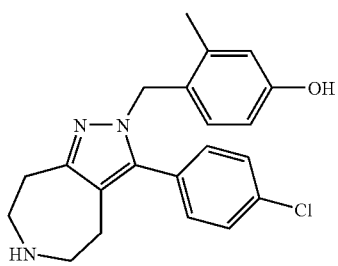

4-[3-(4-Chloro-phenyl)-5,6,7,8-tetrahydro-4H-1,2,6-triaza-azulen-2-ylmethyl]-3-methyl-phenol The title compound (14 mg) was prepared from (4-chloro-phenyl)-2-(4-methoxy-2-methyl-benzyl)-1,4,5,6,7,8-hexahydro-1,2,6-triaza-azulene-6-carboxylic acid tert-butyl ester (Example 128, 42 mg) as in Example 156. MS (ESI): exact mass calculated for $C_{21}H_{22}ClN_3O$, 367.15; found, m/z 368.1 [M+H]+. 1H NMR (500 MHz, CD3OD): 7.33-7.30 (m, 2H), 7.07-7.06 (m, 2H), 6.43 (d, J=2.3 Hz, 1H), 6.36 (dd, J=8.4, 2.3 Hz, 1H), 6.30 (d, J=8.4 Hz, 1H), 4.96 (s, 2H), 2.89-2.86 (m, 2H), 2.82-2.77 (m, 4H), 2.44 (m, 2H), 1.89 (s, 3H).

Example 164

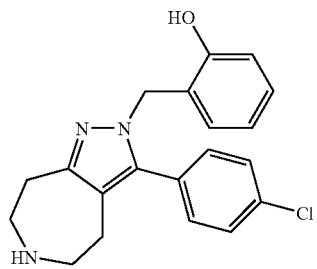

2-[3-(4-Chloro-phenyl)-5,6,7,8-tetrahydro-4H-1,2,6-triaza-azulen-2-ylmethyl]-phenol The title compound (8 mg) was prepared from 3-(4-chloro-phenyl)-2-(2-methoxy-benzyl)-1,4,5,6,7,8-hexahydro-1,2,6-triaza-azulene-6-carboxylic acid tert-butyl ester (Example 132, 30 mg) as in Example 156. MS (ESI): exact mass calculated for $C_{20}H_{20}ClN_3O$, 353.13; found, m/z 354.1 [M+H]+. 1H NMR (500 MHz, CDCl3): 7.62 (d, J=6.5 Hz, 2H), 7.36-7.34 (m, 3H), 7.13 (d, J=8.0 Hz, 1H), 7.00 (d, J=8.0 Hz, 1H), 6.82 (t, J=8.0 Hz, 1H), 5.08 (s, 2H), 3.11-3.00 (br m, 6H), 2.60-2.58 (m, 2H).

Example 165

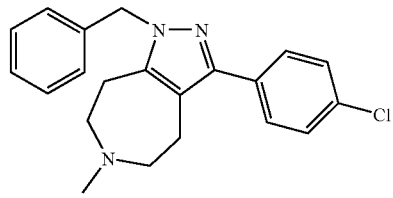

1-Benzyl-3-(4-chloro-phenyl)-6-methyl-1,4,5,6,7,8-hexahydro-1,2,6-triaza-azulene To a solution of 1-benzyl-3-(4-chloro-phenyl)-1,4,5,6,7,8-hexahydro-1,2,6-triaza-azulene (Example 59, Step E; 0.1 mmol) in 1,2-dichloroethane (5 mL) was added acetic acid (0.2 mmol), formaldehyde (37% water solution, 0.037 mL), and NaBH(OAc)3 (0.2 mmol). The mixture was stirred at RT for 15 h. The mixture was diluted with CH2Cl2 and washed with satd. aq. NaHCO3 (2×). The combined organic layers were dried over Na2SO4, filtered, and concentrated in vacuo. Chromatography on SiO2 (2 M NH3 in MeOH/CH2Cl2) afforded 0.015 g of the title compound. MS (ESI): exact mass calculated for $C_{21}H_{22}ClN_3$, 351.15; found, m/z 352.2 [M+H]+. 1H NMR (400 MHz, CDCl3): 7.45-7.42 (m, 2H), 7.32-7.29 (m, 2H), 7.26-7.19 (m, 3H), 7.03-7.01 (br m, 2H), 5.27 (s, 2H), 2.75-2.68 (m, 4H), 2.64-2.58 (m, 4H), 2.36 (s, 3H).

Examples 166 through 169 were synthesized using the procedure described in Example 165 unless otherwise noted.

Example 166

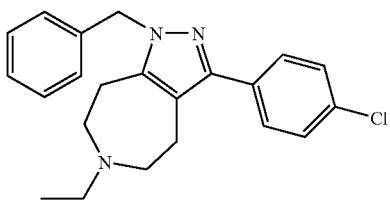

1-Benzyl-3-(4-chloro-phenyl)-6-ethyl-1,4,5,6,7,8-hexahydro-1,2,6-triaza-azulene

The title compound (18 mg) was prepared using acetaldehyde (0.2 mmol) in place of formaldehyde. MS (ESI): exact mass calculated for $C_{22}H_{24}ClN_3$, 365.17; found, m/z 366.2 [M+H]$^+$. $^1$H NMR (400 MHz, CDCl$_3$): 7.45-7.43 (m, 2H), 7.31-7.29 (m, 2H), 7.26-7.19 (m, 3H), 7.03-7.01 (br m, 2H), 5.26 (s, 2H), 2.74-2.71 (m, 10H), 1.01 (t, J=7.1 Hz, 3H).

Example 167

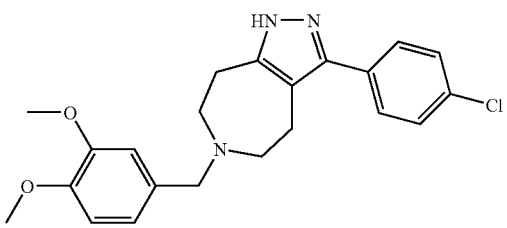

3-(4-Chloro-phenyl)-6-(3,4-dimethoxy-benzyl)-1,4,5,6,7,8-hexahydro-1,2,6-triaza-azulene To a solution of 3-(4-chloro-phenyl)-4,5,7,8-tetrahydro-1H-1,2,6-triaza-azulene-6-carboxylic acid tert-butyl ester (Example 59, Step C, 0.1 mmol) in CH$_2$Cl$_2$ (5 mL) was added TFA (1 mL). The mixture was stirred at RT for 16 h. After concentration, the intermediate 3-(4-chloro-phenyl)-1,4,5,6,7,8-hexahydro-1,2,6-triaza-azulene was obtained. The intermediate (0.1 mmol) was converted to the title compound (16 mg) according to the procedure described in Example 165 using 3,4-dimethoxy-benzaldehyde (0.2 mmol) in place of formaldehyde. MS (ESI): exact mass calculated for $C_{22}H_{24}ClN_3O_2$, 397.16; found, m/z 398.2 [M+H]$^+$. $^1$H NMR (500 MHz, CD$_3$OD): 7.38-7.35 (br m, 4H), 7.91 (d, J=1.8 Hz, 1H), 6.82-6.80 (dd, J=8.1, 1.8 Hz, 1H), 6.76-6.74 (d, J=8.1 Hz, 1H), 3.83-3.80 (s, 6H), 2.84-2.82 (m, 4H), 2.71-2.69 (m, 4H).

Example 168

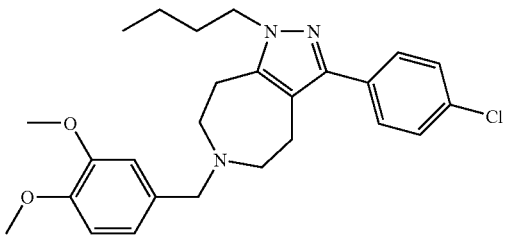

1-Butyl-3-(4-chloro-phenyl)-6-(3,4-dimethoxy-benzyl)-1,4,5,6,7,8-hexahydro-1,2,6-triaza-azulene The title compound (8 mg) was prepared from 1-butyl-3-(4-chloro-phenyl)-1,4,5,6,7,8-hexahydro-1,2,6-triaza-azulene (Example 67, 14 mg) using 3,4-dimethoxy-benzaldehyde (0.2 mmol) in place of formaldehyde. MS (ESI): exact mass calculated for $C_{26}H_{32}ClN_3O_2$, 453.22; found, m/z 454.2 [M+H]$^+$. $^1$H NMR (400 MHz, CDCl$_3$): 7.38 (d, J=8.4 Hz, 2H), 7.28 (d, J=8.4 Hz, 2H), 7.20 (s, 1H), 6.91-6.90 (br m, 1H), 6.81 (d, J=8.2 Hz, 1H), 6.75 (d, J=8.2 Hz, 1H), 3.98 (t, J=7.3 Hz, 2H), 3.82 (d, J=7.0 Hz, 6H), 3.66 (s, 2H), 2.78-2.72 (br m, 8H), 1.67 (m, 2H), 1.27 (m, 2H), 0.86 (t, J=7.3 Hz, 6H).

Example 169

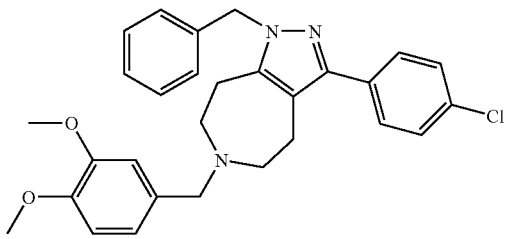

1-Benzyl-3-(4-chloro-phenyl)-6-(3,4-dimethoxy-benzyl)-1,4,5,6,7,8-hexahydro-1,2,6-triaza-azulene The title compound was prepared (12 mg) from 1-benzyl-3-(4-chloro-phenyl)-1,4,5,6,7,8-hexahydro-1,2,6-triaza-azulene (Example 59, Step E; 0.1 mmol) using 3,4-dimethoxy-benzaldehyde (0.2 mmol) in place of formaldehyde. MS (ESI): exact mass calculated for $C_{29}H_{30}ClN_3O_2$, 487.20; found, m/z 488.2 [M+H]$^+$. $^1$H NMR (500 MHz, CDCl$_3$): 7.44-7.43 (m, 2H), 7.30-7.29 (m, 2H), 7.25-7.22 (m, 2H), 7.20-7.18 (m, 1H), 7.03-7.02 (m, 2H), 6.86 (d, J=1.7 Hz, 1H), 6.76-6.71 (m, 2H), 5.25 (s, 2H), 3.79 (s, 6H), 3.63 (s, 2H), 2.72 (s, 4H), 2.68-2.66 (m, 4H).

Example 170

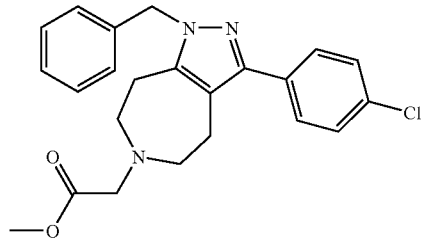

[1-Benzyl-3-(4-chloro-phenyl)-4,5,7,8-tetrahydro-1H-1,2,6-triaza-azulen-6-yl]-acetic acid methyl ester To a solution of 1-benzyl-3-(4-chloro-phenyl)-1,4,5,6,7,8-hexahydro-1,2,6-triaza-azulene (Example 59, Step E; 1 mmol) in acetone (3 mL) was added Na$_2$CO$_3$ (2 mmol) and bromoacetic methyl ester (2 mmol). The mixture was stirred at RT for 1 h. After concentration and purification (SiO$_2$, 2 M NH$_3$ in MeOH/CH$_2$Cl$_2$), the title compound was obtained (60 mg). MS (ESI): exact mass calculated for $C_{23}H_{24}ClN_3O_2$, 409.16; found, m/z 410.1 [M+H]$^+$. $^1$H NMR (500 MHz, CDCl$_3$): 7.44-7.42 (m, 2H), 7.31-7.29 (m, 2H), 7.25-7.23 (br m, 2H), 7.20-7.18 (br m, 1H), 7.02-6.99 (br m, 2H), 5.26 (s, 2H), 3.64 (s, 2H), 3.41 (s, 2H), 2.81-2.79 (br m, 4H), 2.75-2.73 (br m, 2H), 2.70-2.68 (br m, 2H).

Example 171

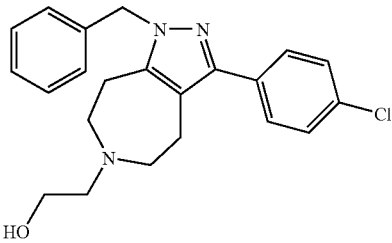

2-[1-Benzyl-3-(4-chloro-phenyl)-4,5,7,8-tetrahydro-1H-1,2,6-triaza-azulen-6-yl]-ethanol To a solution of [1-benzyl-3-(4-chloro-phenyl)-4,5,7,8-tetrahydro-1H-1,2,6-triaza-azulen-6-yl]-acetic acid methyl ester (Example 170, 16 mg) in THF (1 mL) was added lithium aluminum hydride (100 mg). The mixture was stirred at RT for 16 h. The reaction was quenched by the addition of H$_2$O (0.1 mL). Concentration and purification (SiO$_2$, 2 M NH$_3$ in MeOH/CH$_2$Cl$_2$) provided the title compound (5 mg). MS (ESI): exact mass calculated for C$_{22}$H$_{24}$ClN$_3$O, 381.16; found, m/z 382.1 [M+H]$^+$. $^1$H NMR (500 MHz, CDCl$_3$): 7.50-7.20 (m, 7H), 7.04 (d, J=7.2 Hz, 1H), 5.29 (s, 2H), 3.07-3.04 (m, 2H), 2.89-2.77 (m, 10H).

Example 172

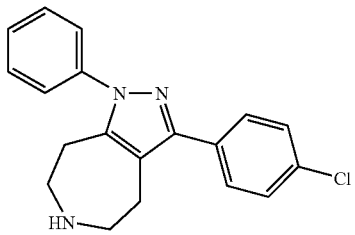

3-(4-Chloro-phenyl)-1-phenyl-1,4,5,6,7,8-hexahydro-1,2,6-triaza-azulene

A solution of 3-(4-chloro-phenyl)-4,5,7,8-tetrahydro-1H-1,2,6-triaza-azulene-6-carboxylic acid tert-butyl ester (Example 59, Step C, 0.3 mmol) in CH$_2$Cl$_2$ (5 mL) was treated with phenylboronic acid (0.6 mmol), pyridine (0.6 mmol), and copper(II) acetate (4.5 mmol). The mixture was stirred at RT for 16 h. After concentration and purification (SiO$_2$, EtOAc/hexanes), 3-(4-chloro-phenyl)-1-phenyl-1,4,5,6,7,8-hexahydro-1,2,6-triaza-azulene-6-carboxylic acid tert-butyl ester was obtained. This intermediate was then diluted with CH$_2$Cl$_2$ (10 mL), and TFA (1 mL) was added. The mixture was stirred at RT for 4 h. The mixture was concentrated and the residue was purified (SiO$_2$, 2 M NH$_3$ in MeOH/CH$_2$Cl$_2$) to provide the title compound (40 mg). MS (ESI): exact mass calculated for C$_{19}$H$_{18}$ClN$_3$, 323.12; found, m/z 324.1 [M+H]$^+$. $^1$H NMR (500 MHz, CDCl$_3$): 7.46-7.40 (m, 4H), 7.36-7.32 (m, 5H), 3.09-3.07 (br m, 4H), 3.00-2.98 (br m, 2H), 3.92-2.90 (br m, 2H).

Example 173

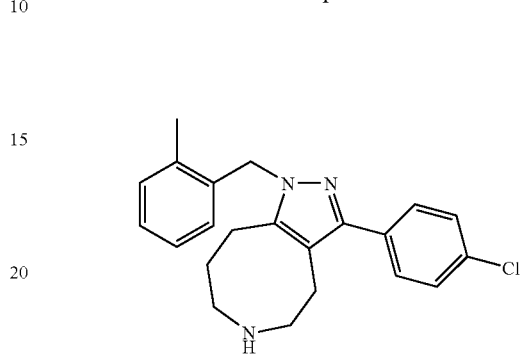

3-(4-Chloro-phenyl)-1-(2-methyl-benzyl)-4,5,6,7,8,9-hexahydro-1H-1,2,6-triaza-cyclopentacyclooctene Step A. 3-(4-Chloro-phenyl)-1,4,5,7,8,9-hexahydro-1,2,6-triaza-cyclopentacyclooctene-6-carboxylic acid tert-butyl ester. To a 0° C. solution of 4-oxo-azepane-1-carboxylic acid tert-butyl ester (Example 59, Step B; 0.915 g) in Et$_2$O (30 mL) was added BF$_3$.Et$_2$O (0.733 mL) followed by a solution of 1-(4-chlorophenyl)-2-diazo-ethanone (Example 103, Step A; 4.5 mmol) in Et$_2$O (30 mL). The mixture was warmed to 25° C. and stirred for 1 h. Satd. aq. NaHCO$_3$ (40 mL) was added, and the organic layer was separated and concentrated. The resulting residue was diluted with MeOH (50 mL) and treated with hydrazine (1.5 mL). The reaction mixture was stirred at 25° C. for 16 h. Concentration and purification by flash chromatography (SiO$_2$, EtOAc/CH$_2$Cl$_2$) provided the desired ester.

Step B. 3-(4-Chloro-phenyl)-1-(2-methyl-benzyl)-1,4,5,7,8,9-hexahydro-1,2,6-triaza-cyclopentacyclooctene-6-carboxylic acid tert-butyl ester. A solution of the product from Step A (0.2 mmol) in DMF (2 mL) was treated with 2-methylbenzyl chloride (0.3 mmol) followed by Cs$_2$CO$_3$ (0.3 mmol). The mixture was stirred at 25° C. for 16 h. Concentration and purification by chromatography (SiO$_2$, EtOAc/hexanes) provided the target intermediate.

Step C. A solution of the product from Step B in MeOH (20 mL) was treated with HCl (2 M in Et$_{2O}$, 1 mL) for 16 h. After concentration and purification by chromatography (SiO$_2$, 2 M NH$_3$ in MeOH/CH$_2$Cl$_2$), the title compound was obtained (24 mg). The reaction sequence also yielded 3-(4-chloro-phenyl)-1-(2-methyl-benzyl)-4,5,6,7,8,9-hexahydro-1H-1,2,7-triaza-cyclopentacyclooctene (20 mg). MS (ESI): exact mass calculated for C$_{22}$H$_{24}$ClN$_3$, 365.17; found, m/z 366.2 [M+H]$^+$. $^1$H NMR (500 MHz, CD$_3$OD): 7.51-7.50 (m, 2H), 7.42-7.40 (m, 2H), 7.14-7.05 (m, 3H), 6.58 (d, J=7.6 Hz, 1H), 5.42 (s, 2H), 3.25 (t, J=5.6 Hz, 2H), 3.13 (t, J=5.6 Hz, 2H), 3.01 (t, J=5.6 Hz, 2H), 2.89 (t, J=5.6 Hz, 2H), 2.30 (s, 3H), 1.78-1.76 (m, 2H).

Example 174

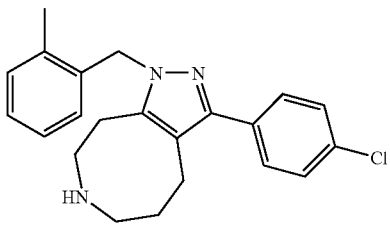

3-(4-Chloro-phenyl)-1-(2-methyl-benzyl)-4,5,6,7,8,
9-hexahydro-1H-1,2,7-triaza-cyclopentacyclooctene The title compound (20 mg) was obtained as in Example 173. MS (ESI): exact mass calculated for $C_{22}H_{24}ClN_3$, 365.17; found, m/z 366.2 $[M+H]^+$. $^1H$ NMR (500 MHz, $CD_3OD$): 7.48-7.46 (m, 2H), 7.39-7.36 (m, 2H), 7.14-7.05 (m, 3H), 6.55-6.54 (m, 1H), 5.39 (s, 2H), 3.02-3.00 (m, 2H), 2.98-2.96 (m, 4H), 2.80-2.78 (m, 2H), 2.30-2.28 (s, 3H), 1.99-1.97 (m, 2H).

Example 175

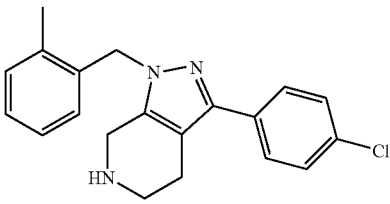

3-(4-Chloro-phenyl)-1-(2-methyl-benzyl)-4,5,6,7-tetrahydro-1H-pyrazolo[3,4-c]pyridine The title compound (22 mg) was prepared from 3-oxo-pyrrolidine-1-carboxylic acid tert-butyl ester (0.858 g) and 1-(4-chlorophenyl)-2-diazo-ethanone (Example 103, Step A; 5.79 mmol) as in Example 173. MS (ESI): exact mass calculated for $C_{17}H_{22}ClN_3O$, 337.13; found, m/z 338.2 $[M+H]^+$. $^1H$ NMR (500 MHz, $CD_3OD$): 7.62-7.60 (m, 2H), 7.36-7.34 (m, 2H), 7.14-7.06 (m, 3H), 6.76 (d, J=7.5 Hz, 1H), 5.33 (s, 2H), 4.09 (s, 2H), 3.38 (t, J=6.1 Hz, 2H), 3.10 (t, J=6.1 Hz, 2H), 2.25 (s, 3H).

Example 176

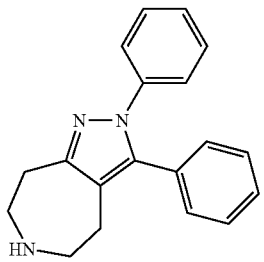

2,3-Diphenyl-2,4,5,6,7,8-hexahydro-1,2,6-triaza-azulene

Step A. 3-Oxo-2-phenyl-2,3,4,5,7,8-hexahydro-1H-1,2,6-triaza-azulene-6-carboxylic acid tert-butyl ester. To a solution of the compound (3.13 g) from Example 59, Step A in 80 mL of EtOH was added 1.2 mL of phenylhydrazine. The resulting solution was heated at reflux for 3 days and then was cooled to RT and the solvent was removed in vacuo. The residue was chromatographed on $SiO_2$ (0 to 80% EtOAc/hexanes) to afford 3.13 g of the desired compound. MS (ESI): exact mass calculated for $C_{18}H_{23}N_3O_3$, 329.17; found, m/z 330.2 $[M+H]^+$.

Step B. 2-Phenyl-3-trifluoromethanesulfonyloxy-4,5,7,8-tetrahydro-2H-1,2,6-triaza-azulene-6-carboxylic acid tert-butyl ester. To a stirred solution of the above compound (1.79 g) in 35 mL of $CH_2Cl_2$ was added 3.0 mL of i-$Pr_2NEt$ and 3.05 g of N-phenyltrifluoromethanesulfonimide. The mixture was heated at reflux for 24 h and then was concentrated in vacuo. Chromatography on $SiO_2$ (0 to 75% EtOAc/hexanes) afforded 1.88 g of the desired compound. MS (ESI): exact mass calculated for $C_{19}H_{22}F_3N_3O_5S$, 461.12; found, m/z 407.1 $[M+H]^+$.

Step C. 2,3-Diphenyl-4,5,7,8-tetrahydro-2H-1,2,6-triaza-azulene-6-carboxylic acid tert-butyl ester. To a solution of the above compound (0.28 g) in 5 mL of 1,4-dioxane was added 0.29 g of $K_3PO_4$, 104.3 mg of phenylboronic acid and 43.0 mg of $PdCl_2dppf$. The mixture was heated at 80° C. for 3 h. More phenylboronic acid (0.10 g) and $PdCl_2dppf$ (26 mg) were added and the temperature was increased to 100° C. After an additional 12 h, the mixture was poured into water (100 mL) and extracted with $CH_2Cl_2$ (3×20 mL). The combined organic layers were filtered through diatomaceous earth and the filtrate was concentrated in vacuo. Chromatography on $SiO_2$ (0 to 20% EtOAc/hexanes) afforded 158.8 mg of the desired compound. MS (ESI): exact mass calculated for $C_{24}H_{27}N_3O_2$, 389.21; found, m/z 390.2 $[M+H]^+$.

Step D. To a stirred solution of the above compound (158.8 mg) in 5 mL of EtOH was added 2 mL of 1.0 M HCl in $Et_2O$. The mixture was stirred at RT for 12 h and concentrated in vacuo to give 75.6 mg of the title compound. MS (ESI): exact mass calculated for $C_{19}H_{19}N_3$, 289.16; found, m/z 290.2 $[M+H]^+$. $^1H$ NMR (500 MHz, $CD_3OD$): 7.41-7.38 (m, 3H), 7.36-7.32 (m, 3H), 7.23-7.18 (m, 4H), 3.49-3.45 (m, 2H), 3.38-3.34 (m, 2H), 3.26-3.23 (m, 2H), 2.96-2.93 (m, 2H).

Example 177

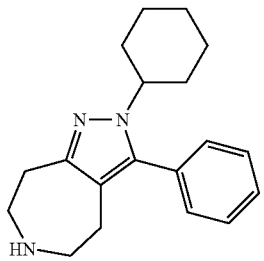

2-Cyclohexyl-3-phenyl-2,4,5,6,7,8-hexahydro-1,2,6-triaza-azulene

Step A. Cyclohexyl-hydrazine hydrochloride. To a solution of cyclohexanone (1.25 mL) in hexanes (8 mL) was added 1.59 g of tert-butyl carbazate. The mixture was heated at reflux for 10 min and then allowed to cool to RT. The white precipitate that had formed was removed by filtration and washed with cold hexanes. The white solid was then treated with $BH_3$ (1.0 M in THF, 12 mL). After stirring at RT for 20 min, the mixture was treated with 16 mL of 6 N HCl. The mixture was heated at 110° C. for 20 min and then was concentrated in vacuo. The residue was treated with 30 mL of THF. The title compound (1.82 g), a white solid, was collected from this mixture by filtration. MS (ESI): exact mass calculated for $C_6H_{14}N_2$, 114.12; found, m/z 115.1 [M+H]$^+$. $^1$H NMR (500 MHz, CDCl$_3$): 3.05-2.99 (m, 1H), 2.11-2.09 (m, 2H), 1.88-1.86 (m, 2H), 1.72-1.69 (m, 1H), 1.37-1.19 (m, 5H).

Step B. 2-Cyclohexyl-3-trifluoromethanesulfonyloxy-4,5, 7,8-tetrahydro-2H-1,2,6-triaza-azulene-6-carboxylic acid tert-butyl ester. The desired compound was made as in Steps A and B of Example 176, with cyclohexylhydrazine hydrochloride from Step A in place of phenylhydrazine. The hydrazine salt was neutralized with Dowex® 550 resin prior to use.

Step C. 2-Cyclohexyl-3-phenyl-4,5,7,8-tetrahydro-2H-1, 2,6-triaza-azulene-6-carboxylic acid tert-butyl ester. To a solution of 126 mg of the compound from Step A in 3 mL of 1,4-dioxane were added 229 mg of K$_3$PO$_4$, 131 mg of phenylboronic acid, and 7.5 mg of dppf. PdCl$_2$dppf (22 mg) was then added and the mixture was heated at reflux overnight. The mixture was concentrated in vacuo and the residue was dissolved in toluene. The solution was filtered through diatomaceous earth and the filtrate was concentrated to afford 202 mg of an oil. Chromatography on SiO$_2$ (5 to 25% EtOAc/hexanes) provided 98.7 mg of the desired compound. MS (ESI): exact mass calculated for $C_{24}H_{33}N_3O_2$, 395.26; found, m/z 396.2 [M+H]$^+$.

Step D. The above compound (98.7 mg) was converted to the title compound (71.0 mg) as in Example 43, Step E, and the crude product was chromatographed on SiO$_2$ (2 to 8% 2 M NH$_3$ in MeOH/EtOAc). MS (ESI): exact mass calculated for $C_{19}H_{25}N_3$, 295.20; found, m/z 296.2 [M+H]$^+$. $^1$H NMR (500 MHz, CDCl$_3$): 7.59-7.49 (m, 3H), 7.35-7.29 (m, 2H), 3.97-3.88 (m, 1H), 3.44-3.38 (m, 2H), 3.34-3.27 (m, 2H), 3.20-3.14 (m, 2H), 2.81-2.73 (m, 2H), 1.99-1.76 (m, 6H), 1.65 (br s, 1H), 1.28-1.17 (m, 3H).

Example 178

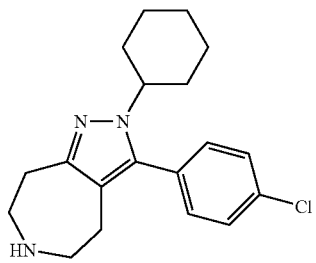

3-(4-Chloro-phenyl)-2-cyclohexyl-2,4,5,6,7,8-hexahydro-1,2,6-triaza-azulene

The title compound (48 mg) was prepared as in Example 177, Steps C and D, using 129 mg of 2-cyclohexyl-3-trifluoromethanesulfonyloxy-4,5,7,8-tetrahydro-2H-1,2,6-triaza-azulene-6-carboxylic acid tert-butyl ester (Example 177, Step B) and 173 mg of 4-chlorophenylboronic acid. MS (ESI): exact mass calculated for $C_{19}H_{24}ClN_3$, 329.17; found, m/z 330.1 [M+H]$^+$. $^1$H NMR (500 MHz, CDCl$_3$): 7.60-7.53 (m, 2H), 7.36-7.27 (m, 2H), 3.94-3.83 (m, 1H), 3.43-3.36 (m, 2H), 3.34-3.26 (m, 2H), 3.2-3.12 (m, 2H), 2.80-2.72 (m, 2H), 1.98-1.76 (m, 6H), 1.67 (br s, 1H), 1.32-1.17 (m, 3H).

Example 179

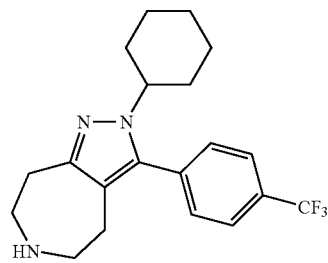

2-Cyclohexyl-3-(4-trifluoromethyl-phenyl)-2,4,5,6,7,8-hexahydro-1,2,6-triaza-azulene The title compound (68 mg) was prepared as in Example 177, Steps C and D, using 130 mg of 2-cyclohexyl-3-trifluoromethanesulfonyloxy-4,5,7,8-tetrahydro-2H-1,2,6-triaza-azulene-6-carboxylic acid tert-butyl ester (Example 177, Step B) and 132 mg of 4-trifluoromethylphenylboronic acid. MS (ESI): exact mass calculated for $C_{20}H_{24}F_3N_3$, 363.19; found, m/z 364.2 [M+H]$^+$. $^1$H NMR (500 MHz, CDCl$_3$): 7.90-7.84 (m, 2H), 7.57-7.50 (m, 2H), 4.64 (br s, 2H), 3.94-3.85 (m, 1H), 3.33-3.05 (m, 4H), 2.93-2.72 (m, 2H), 2.00-1.76 (m, 6H), 1.67 (br s, 1H), 1.38-1.17 (m, 3H).

Example 180

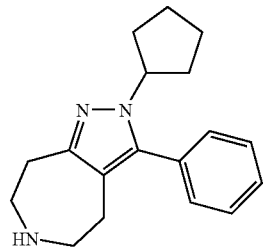

2-Cyclopentyl-3-phenyl-2,4,5,6,7,8-hexahydro-1,2,6-triaza-azulene

Step A. 2-Cyclopentyl-3-trifluoromethanesulfonyloxy-4, 5,7,8-tetrahydro-2H-1,2,6-triaza-azulene-6-carboxylic acid tert-butyl ester. The desired triflate was prepared as in Steps A and B of Example 176, using cyclopentylhydrazine hydrochloride (made according to the procedure of Example 177, Step A using cyclopentanone in place of cyclohexanone) in place of phenylhydrazine, t-butanol in place of EtOH, with the addition of 3 equiv. of triethylamine.

Step B. The title compound (52 mg) was prepared from the product of Step A (101 mg) according to the procedure of Example 177, Steps C and D, using 109 mg of phenylboronic acid. MS (ESI): exact mass calculated for $C_{18}H_{23}N_3$, 281.19; found, m/z 282.1 [M+H]$^+$. $^1$H NMR (500 MHz, CDCl$_3$): 7.58-7.48 (m, 3H), 7.36-7.30 (m, 2H), 4.50 (m, 1H), 3.44-

3.38 (m, 2H), 3.34-3.27 (m, 2H), 3.22-3.16 (m, 2H), 2.81-2.75 (m, 2H), 2.06-1.84 (m, 6H), 1.65-1.54 (m, 2H).

Example 181

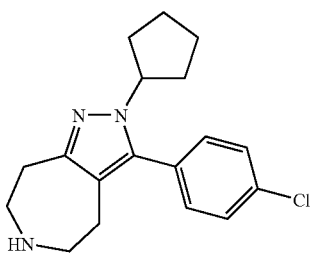

3-(4-Chloro-phenyl)-2-cyclopentyl-2,4,5,6,7,8-hexahydro-1,2,6-triaza-azulene

The title compound (74 mg) was prepared as in Example 177, Steps C and D, using 215 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 296 mg of 4-chlorophenylboronic acid. MS (ESI): exact mass calculated for $C_{18}H_{22}ClN_3$, 315.15; found, m/z 316.1 [M+H]$^+$. $^1$H NMR (500 MHz, CDCl$_3$): 7.59-7.53 (m, 2H), 7.36-7.30 (m, 2H), 4.48 (m, 1H), 3.44-3.37 (m, 2H), 3.34-3.27 (m, 2H), 3.22-3.15 (m, 2H), 2.81-2.74 (m, 2H), 2.06-1.84 (m, 6H), 1.65-155 (m, 2H).

Example 182

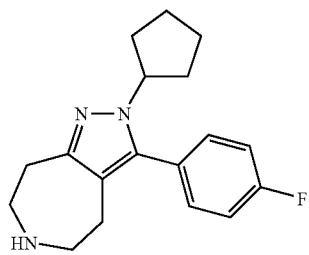

2-Cyclopentyl-3-(4-fluoro-phenyl)-2,4,5,6,7,8-hexahydro-1,2,6-triaza-azulene

The title compound (113 mg) was prepared as in Example 177, Steps C and D, using 200 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 185 mg of 4-fluorophenylboronic acid. MS (ESI): exact mass calculated for $C_{18}H_{22}FN_3$, 299.18; found, m/z 300.5 [M+H]$^+$. $^1$H NMR (500 MHz, CDCl$_3$): 7.45-7.39 (m, 2H), 7.35-7.29 (m, 2H), 4.53 (m, 1H), 3.48-3.42 (m, 2H), 3.36-3.28 (m, 2H), 3.28-3.23 (m, 2H), 2.84-2.78 (m, 2H), 2.08-1.85 (m, 6H), 1.67-1.56 (m, 2H).

Example 183

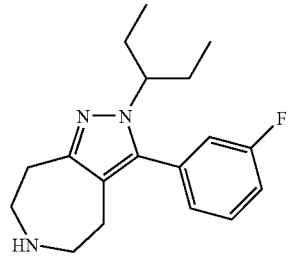

2-(1-Ethyl-propyl)-3-(3-fluoro-phenyl)-2,4,5,6,7,8-hexahydro-1,2,6-triaza-azulene Step A. 2-(1-Ethyl-propyl)-3-trifluoromethanesulfonyloxy-4,5,7,8-tetrahydro-2H-1,2,6-triaza-azulene-6-carboxylic acid tert-butyl ester. The desired triflate was prepared as in Steps A and B of Example 176, using (1-ethyl-propyl)-hydrazine hydrochloride (made from 3-pentanone as described in Example 177, Step A) in place of phenylhydrazine. The hydrazine was neutralized with NaH in DMF prior to use.

Step B. The title compound (82 mg) was prepared as in Example 177, Steps C and D, using 150 mg of the triflate from Step A and 138 mg of 3-fluorophenylboronic acid. MS (ESI): exact mass calculated for $C_{18}H_{24}FN_3$, 301.20; found, m/z 302.4 [M+H]$^+$. $^1$H NMR (500 MHz, CDCl$_3$): 7.61-7.55 (m, 1H), 7.31-7.25 (m, 1H), 7.16-7.12 (m, 1H), 7.10-7.05 (m, 1H), 3.85-3.77 (m, 1H), 3.45-3.40 (m, 2H), 3.35-3.29 (m, 2H), 3.23-3.18 (m, 2H), 2.82-2.76 (m, 2H), 1.97-1.80 (m, 2H), 1.79-1.70 (m, 2H), 0.71 (t, J=7.4 Hz, 3H).

Example 184

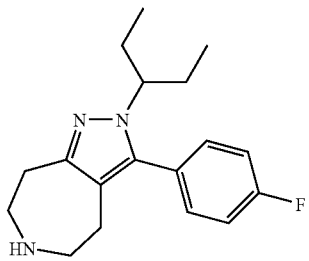

2-(1-Ethyl-propyl)-3-(4-fluoro-phenyl)-2,4,5,6,7,8-hexahydro-1,2,6-triaza-azulene The title compound (93 mg) was prepared as in Example 177, Steps C and D, using 150 mg of 2-(1-ethyl-propyl)-3-trifluoromethanesulfonyloxy-4,5,7,8-tetrahydro-2H-1,2,6-triaza-azulene-6-carboxylic acid tert-butyl ester (Example 183, Step A) and 138 mg of 3-fluorophenylboronic acid. MS (ESI): exact mass calculated for $C_{18}H_{24}FN_3$, 301.20; found, m/z 302.5 [M+H]$^+$. $^1$H NMR (500 MHz, CDCl$_3$): 7.44-7.30 (m, 4H), 3.92-3.85 (m, 1H), 3.51-3.43 (m, 2H), 3.38-3.33 (m, 2H), 3.30-3.24 (m, 2H), 2.86-2.78 (m, 2H), 1.98-1.85 (m, 2H), 1.84-1.73 (m, 2H), 0.73 (t, J=7.4 Hz, 3H).

Example 185

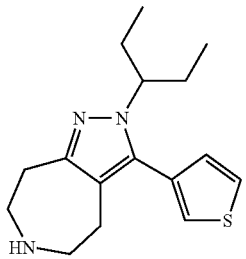

2-(1-Ethyl-propyl)-3-thiophen-3-yl-2,4,5,6,7,8-hexahydro-1,2,6-triaza-azulene

The title compound (95 mg) was prepared as in Example 177, Steps C and D, using 150 mg of 2-(1-ethyl-propyl)-3-trifluoromethanesulfonyloxy-4,5,7,8-tetrahydro-2H-1,2,6-triaza-azulene-6-carboxylic acid tert-butyl ester (Example 183, Step A) and 126 mg of 3-thiopheneboronic acid. MS (ESI): exact mass calculated for $C_{16}H_{23}N_3S$, 289.16; found, m/z 290.4 [M+H]+. 1H NMR (500 MHz, CDCl3): 7.68-7.64 (m, 1H), 7.52-7.48 (m, 1H), 7.12-7.07 (m, 1H), 3.93-3.86 (m, 1H), 3.44-3.39 (m, 2H), 3.34-3.28 (m, 2H), 3.22-3.17 (m, 2H), 2.85-2.79 (m, 2H), 1.95-1.84 (m, 2H), 1.79-1.69 (m, 2H), 0.71 (t, J=7.4 Hz, 3H).

Example 186

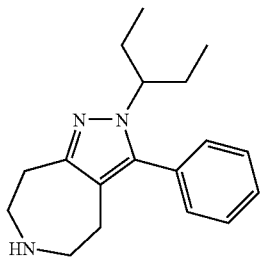

2-(1-Ethyl-propyl)-3-phenyl-2,4,5,6,7,8-hexahydro-1,2,6-triaza-azulene

The title compound (40 mg) was prepared as in Example 177, Steps C and D, using 150 mg of 2-(1-ethyl-propyl)-3-trifluoromethanesulfonyloxy-4,5,7,8-tetrahydro-2H-1,2,6-triaza-azulene-6-carboxylic acid tert-butyl ester (Example 183, Step A) and 120 mg of phenylboronic acid. MS (ESI): exact mass calculated for $C_{18}H_{25}N_3$, 283.20; found, m/z 284.4 [M+H]+. 1H NMR (500 MHz, CDCl3): 7.48-7.38 (m, 3H), 7.24-7.19 (m, 2H), 3.77-3.70 (m, 1H), 3.36-3.31 (m, 2H), 3.24-3.19 (m, 2H), 3.14-3.09 (m, 2H), 2.71-2.65 (m, 2H), 1.85-1.75 (m, 2H), 1.68-1.58 (m, 2H), 0.61 (t, J=7.4 Hz, 3H).

Example 187

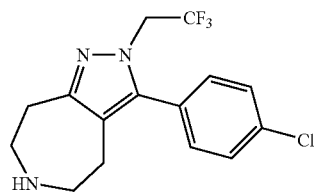

3-(4-Chloro-phenyl)-2-(2,2,2-trifluoro-ethyl)-2,4,5,6,7,8-hexahydro-1,2,6-triaza-azulene Step A. 2-(2,2,2-Trifluoro-ethyl)-3-trifluoromethanesulfonyloxy-4,5,7,8-tetrahydro-2H-1,2,6-triaza-azulene-6-carboxylic acid tert-butyl ester. The desired triflate was prepared as in Steps A and B of Example 176, using 2,2,2-trifluoroethylhydrazine in place of phenylhydrazine.

Step B. The title compound (40 mg) was prepared as in Example 177, Steps C and D, using 304 mg of the triflate from Step A and 407 mg of 4-chlorophenylboronic acid. MS (ESI): exact mass calculated for $C_{15}H_{15}ClF_3N_3$, 329.09; found, m/z 330.0 [M+H]+. 1H NMR (500 MHz, CDCl3): 7.62-7.52 (m, 2H), 7.40-7.29 (m, 2H), 4.70 (q, J=8.6 Hz, 2H), 3.44-3.37 (m, 2H), 3.36-3.25 (m, 2H), 3.22-3.13 (m, 2H), 2.83-2.73 (m, 2H).

Example 188

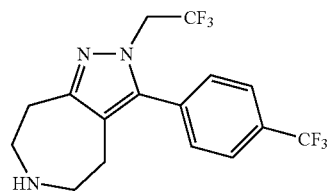

2-(2,2,2-Trifluoro-ethyl)-3-(4-trifluoromethyl-phenyl)-2,4,5,6,7,8-hexahydro-1,2,6-triaza-azulene The title compound (128 mg) was prepared as in Example 177, Steps C and D, using 288 mg of 2-(2,2,2-trifluoro-ethyl)-3-trifluoromethanesulfonyloxy-4,5,7,8-tetrahydro-2H-1,2,6-triaza-azulene-6-carboxylic acid tert-butyl ester (Example 187, Step A) and 468 mg of 4-trifluoromethylphenylboronic acid. MS (ESI): exact mass calculated for $C_{16}H_{15}F_6N_3$, 363.12; found, m/z 364.0 [M+H]+. 1H NMR (500 MHz, CDCl3): 7.93-7.83 (m, 2H), 7.62-7.54 (m, 2H), 4.75 (q, J=8.6 Hz, 2H), 3.47-3.39 (m, 2H), 3.38-3.27 (m, 2H), 3.24-3.15 (m, 2H), 2.87-2.76 (m, 2H).

Example 189

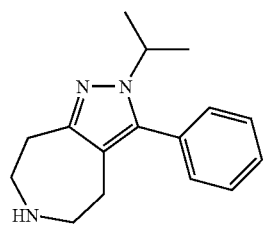

2-Isopropyl-3-phenyl-2,4,5,6,7,8-hexahydro-1,2,6-triaza-azulene

Step A. 2-Isopropyl-3-trifluoromethanesulfonyloxy-4,5,7,8-tetrahydro-2H-1,2,6-triaza-azulene-6-carboxylic acid tert-butyl ester. The desired triflate was prepared as in Steps A and B of Example 176, using isopropylhydrazine hydrochloride in place of phenylhydrazine, t-butanol in place of EtOH, with the addition of 3 equiv. of triethylamine.

Step B. The title compound (93 mg) was prepared as in Example 177, Steps C and D, using 172 mg of the triflate from Step A and 147 mg of phenylboronic acid. MS (ESI): exact mass calculated for $C_{16}H_{21}N_3$, 255.17; found, m/z 256.5 [M+H]$^+$. $^1$H NMR (500 MHz, CDCl$_3$): 7.58-7.49 (m, 3H), 7.36-7.30 (m, 2H), 4.40 (m, 1H), 3.45-3.40 (m, 2H), 3.34-3.28 (m, 2H), 3.23-3.18 (m, 2H), 2.82-2.75 (m, 2H), 1.40 (d, J=6.9 Hz, 6H).

Example 190

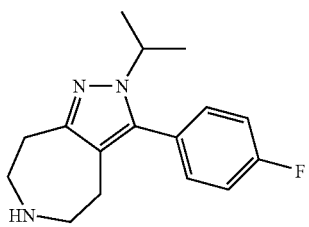

3-(4-Fluoro-phenyl)-2-isopropyl-2,4,5,6,7,8-hexahydro-1,2,6-triaza-azulene

The title compound (92 mg) was prepared as in Example 177, Steps C and D, using 159 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 156 mg of 4-fluorophenylboronic acid. MS (ESI): exact mass calculated for $C_{16}H_{20}FN_3$, 273.16; found, m/z 274.4 [M+H]$^+$. $^1$H NMR (500 MHz, CDCl$_3$): 7.42-7.35 (m, 2H), 7.33-7.27 (m, 2H), 4.37 (m, 1H), 3.46-3.39 (m, 2H), 3.34-3.28 (m, 2H), 3.23-3.18 (m, 2H), 2.81-2.74 (m, 2H), 1.41 (d, J=6.9 Hz, 6H).

Example 191

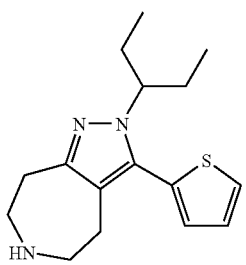

2-(1-Ethyl-propyl)-3-thiophen-2-yl-2,4,5,6,7,8-hexahydro-1,2,6-triaza-azulene

The title compound (35 mg) was prepared as in Example 177, Steps C and D, using 148 mg of 2-(1-ethyl-propyl)-3-trifluoromethanesulfonyloxy-4,5,7,8-tetrahydro-2H-1,2,6-triaza-azulene-6-carboxylic acid tert-butyl ester (Example 183, Step A) and 122 mg of 2-thiopheneboronic acid. MS (ESI): exact mass calculated for $C_{16}H_{23}N_3S$, 289.16; found, m/z 290.5 [M+H]$^+$. $^1$H NMR (500 MHz, CDCl$_3$): 7.72-7.67 (m, 1H), 7.25-7.21 (m, 1H), 7.13-7.09 (m, 1H), 4.01-3.94 (m, 1H), 3.43-3.38 (m, 2H), 3.34-3.28 (m, 2H), 3.20-3.14 (m, 2H), 2.86-2.80 (m, 2H), 1.95-1.85 (m, 2H), 1.79-1.69 (m, 2H), 0.71 (t, J=7.4 Hz, 3H).

Example 192

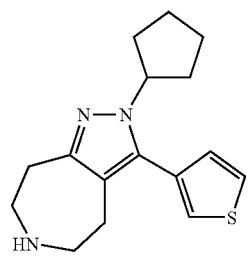

2-Cyclopentyl-3-thiophen-3-yl-2,4,5,6,7,8-hexahydro-1,2,6-triaza-azulene

The title compound (114 mg) was prepared as in Example 177, Steps C and D, using 200 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 169 mg of 3-thiopheneboronic acid. MS (ESI): exact mass calculated for $C_{16}H_{21}N_3S$, 287.15; found, m/z 288.4 [M+H]$^+$. $^1$H NMR (500 MHz, CDCl$_3$): 7.68-7.63 (m, 1H), 7.56-7.51 (m, 1H), 7.17-7.12 (m, 1H), 4.58 (m, 1H), 3.43-3.37 (m, 2H), 3.34-3.28 (m, 2H), 3.19-3.14 (m, 2H), 2.86-2.80 (m, 2H), 2.04-1.85 (m, 6H), 1.67-1.57 (m, 2H).

Example 193

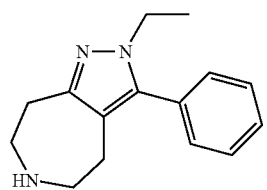

2-Ethyl-3-phenyl-2,4,5,6,7,8-hexahydro-1,2,6-triaza-azulene

Step A. 2-Ethyl-3-trifluoromethanesulfonyloxy-4,5,7,8-tetrahydro-2H-1,2,6-triaza-azulene-6-carboxylic acid tert-butyl ester. The desired triflate was prepared as in Steps A and B of Example 176, using ethylhydrazine oxalate in place of phenylhydrazine, t-butanol in place of EtOH, with the addition of 3 equiv. of triethylamine.

Step B. The title compound (106 mg) was prepared as in Example 177, Steps C and D, using 198 mg of the triflate from Step A and 122 mg of phenylboronic acid. MS (ESI): exact mass calculated for $C_{15}H_{19}N_3$, 241.16; found, m/z 242.4 [M+H]$^+$. $^1$H NMR (500 MHz, CDCl$_3$): 7.61-7.54 (m, 3H), 7.43-7.39 (m, 2H), 4.11 (q, J=7.1 Hz, 2H), 3.49-3.44 (m, 2H), 3.37-3.32 (m, 2H), 3.28-3.22 (m, 2H), 2.89-2.82 (m, 2H), 1.33 (t, J=7.1 Hz, 3H).

Example 194

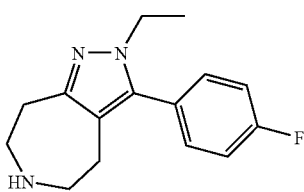

2-Ethyl-3-(4-fluoro-phenyl)-2,4,5,6,7,8-hexahydro-1,2,6-triaza-azulene

The title compound (114 mg) was prepared as in Example 177, Steps C and D, using 208 mg of 2-ethyl-3-trifluoromethanesulfonyloxy-4,5,7,8-tetrahydro-2H-1,2,6-triaza-azulene-6-carboxylic acid tert-butyl ester (Example 193, Step A) and 211 mg of 4-fluorophenylboronic acid. MS (ESI): exact mass calculated for $C_{15}H_{18}FN_3$, 259.15; found, m/z 260.4 [M+H]$^+$. $^1$H NMR (500 MHz, CDCl$_3$): 7.41-7.35 (m, 2H), 7.32-7.26 (m, 2H), 3.99 (q, J=7.1 Hz, 2H), 3.43-3.38 (m, 2H), 3.33-3.28 (m, 2H), 3.18-3.12 (m, 2H), 2.80-2.75 (m, 2H), 1.27 (t, J=7.1 Hz, 3H).

Example 195

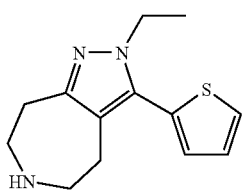

2-Ethyl-3-thiophen-2-yl-2,4,5,6,7,8-hexahydro-1,2,6-triaza-azulene

The title compound (101 mg) was prepared as in Example 177, Steps C and D, using 148 mg of 2-ethyl-3-trifluoromethanesulfonyloxy-4,5,7,8-tetrahydro-2H-1,2,6-triaza-azulene-6-carboxylic acid tert-butyl ester (Example 193, Step A) and 306 mg of 2-thiopheneboronic acid. MS (ESI): exact mass calculated for $C_{13}H_{17}N_3S$, 247.11; found, m/z 248.4 [M+H]$^+$. $^1$H NMR (500 MHz, CDCl$_3$): 7.62-7.57 (m, 1H), 7.16-7.11 (m, 1H), 7.10-7.05 (m, 1H), 3.98 (q, J=7.1 Hz, 2H), 3.33-3.27 (m, 2H), 3.24-3.18 (m, 2H), 3.07-3.01 (m, 2H), 2.80-2.73 (m, 2H), 1.22 (t, J=7.1 Hz, 3H).

Example 196

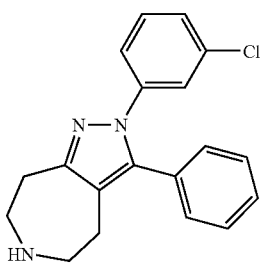

2-(3-Chloro-phenyl)-3-phenyl-2,4,5,6,7,8-hexahydro-1,2,6-triaza-azulene

Step A. 2-(3-Chloro-phenyl)-3-phenyl-4,5,7,8-tetrahydro-2H-1,2,6-triaza-azulene-6-carboxylic acid tert-butyl ester. The desired compound (53.9 mg) was prepared from 142.7 mg of 2-(3-chloro-phenyl)-3-trifluoromethanesulfonyloxy-4,5,7,8-tetrahydro-2H-1,2,6-triaza-azulene-6-carboxylic acid tert-butyl ester (made as in Example 176, Steps A and B) replacing phenylhydrazine with (3-chloro-phenyl)-hydrazine, as described in Example 43, Step D, using 102.1 mg of phenylboronic acid. MS (ESI): exact mass calculated for $C_{24}H_{26}ClN_3O_2$, 423.17; found, m/z 424.1 [M+H]$^+$.

Step B. The above compound (53.9 mg) was converted to the title compound (37.6 mg) as in Example 26, Step B. MS (ESI): exact mass calculated for $C_{19}H_{18}ClN_3$, 323.12; found, m/z 324.1 [M+H]$^+$. $^1$H NMR (500 MHz, CDCl$_3$): 7.38-7.32 (m, 4H), 7.16-7.09 (m, 4H), 6.96-6.93 (m, 1H), 3.09-3.05 (m, 2H), 3.02-2.98 (m, 2H), 2.97-2.94 (m, 2H), 2.65-2.62 (m, 2H), 2.07 (br s, 1H).

Example 197

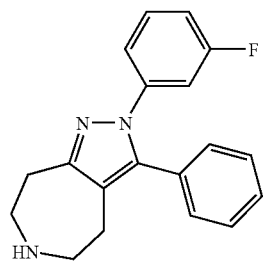

2-(3-Fluoro-phenyl)-3-phenyl-2,4,5,6,7,8-hexahydro-1,2,6-triaza-azulene

The title compound (37.6 mg) was prepared from 339.2 mg of 2-(3-fluoro-phenyl)-3-trifluoromethanesulfonyloxy-4,5,7,8-tetrahydro-2H-1,2,6-triaza-azulene-6-carboxylic acid tert-butyl ester (made as in Example 176, Steps A and B from (3-fluoro-phenyl)-hydrazine) as described in Example 196, using 1,4-dioxane as the solvent. MS (ESI): exact mass calculated for $C_{19}H_{18}FN_3$, 307.15 307.15; found, m/z 308.1 [M+H]$^+$. $^1$H NMR (400 MHz, CDCl$_3$): 7.39-7.35 (m, 3H), 7.20-7.14 (m, 3H), 7.00-6.96 (m, 1H), 6.94-6.86 (m, 2H), 3.13-3.09 (m, 2H), 3.06-3.02 (m, 2H), 3.01-2.96 (m, 2H), 2.69-2.66 (m, 2H).

Example 198

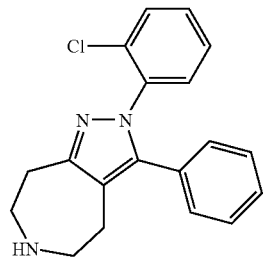

2-(2-Chloro-phenyl)-3-phenyl-2,4,5,6,7,8-hexahydro-1,2,6-triaza-azulene

The title compound (17.2 mg) was prepared from 199.8 mg of 2-(2-chloro-phenyl)-3-trifluoromethanesulfonyloxy-4,5,7,8-tetrahydro-2H-1,2,6-triaza-azulene-6-carboxylic acid tert-butyl ester (made from (2-chloro-phenyl)-hydrazine as in Example 176, Steps A and B), as described in Example 196 using 1,4-dioxane as the solvent. MS (ESI): exact mass calculated for $C_{19}H_{18}ClN_3$, 323.12; found, m/z 324.1 [M+H]$^+$. $^1$H NMR (500 MHz, CDCl$_3$): 7.37-7.34 (m, 2H), 7.29-7.24 (m, 5H), 7.14-7.10 (m, 2H), 3.12-3.09 (m, 2H), 3.04-2.99 (m, 4H), 2.74-2.71 (m, 2H), 2.13 (br s, 1H).

Example 199

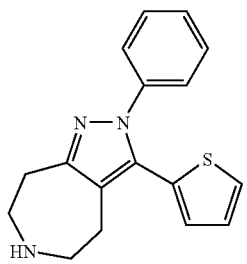

2-Phenyl-3-thiophen-2-yl-2,4,5,6,7,8-hexahydro-1,2,6-triaza-azulene

Step A. 2-Phenyl-3-thiophen-2-yl-4,5,7,8-tetrahydro-2H-1,2,6-triaza-azulene-6-carboxylic acid tert-butyl ester. To a solution of 199.8 mg of 2-phenyl-3-trifluoromethanesulfonyloxy-4,5,7,8-tetrahydro-2H-1,2,6-triaza-azulene-6-carboxylic acid tert-butyl ester (Example 176, Step B) in 3.5 mL of DMF were added 0.6 mL of 2 M aq. Na$_2$CO$_3$ and 75.6 mg of thiophene-2-boronic acid. PdCl$_2$dppf (20.2 mg) was added and the mixture was heated at 80° C. for 16 h. The mixture was poured into water (50 mL) and extracted with CH$_2$Cl$_2$ (3×15 mL) and the combined organic layers were concentrated in vacuo. Chromatography on SiO$_2$ (0 to 50% EtOAc/hexanes) afforded 58.9 mg of the desired compound as a white solid. MS (ESI): exact mass calculated for $C_{22}H_{25}N_3O_2S$, 395.17; found, m/z 396.1 [M+H]$^+$.

Step B. The above compound (58.9 mg) was converted to the title compound (28.1 mg) as in Example 26, Step B. MS (ESI): exact mass calculated for $C_{17}H_{17}N_3S$, 295.11; found, m/z 296.1 [M+H]$^+$. $^1$H NMR (500 MHz, CDCl$_3$): 7.36 (dd, J=5.2, 1.3 Hz, 1H), 7.32-7.23 (m, 5H), 7.01 (dd, J=5.2, 3.3 Hz, 1H), 6.85 (dd, J=3.3, 1.3 Hz, 1H), 3.11-3.08 (m, 2H), 3.03-2.99 (m, 4H), 2.76-2.73 (m, 2H), 2.12 (br s, 1H).

Example 200

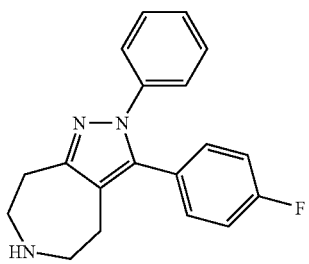

3-(4-Fluoro-phenyl)-2-phenyl-2,4,5,6,7,8-hexahydro-1,2,6-triaza-azulene

The title compound (70.0 mg) was prepared from 207.0 mg of 2-phenyl-3-trifluoromethanesulfonyloxy-4,5,7,8-tetrahydro-2H-1,2,6-triaza-azulene-6-carboxylic acid tert-butyl ester (Example 176, Step B) and 98.5 mg of 4-fluorophenylboronic acid as in Example 199. MS (ESI): exact mass calculated for $C_{19}H_{18}FN_3$, 307.15; found, m/z 308.2 [M+H]$^+$. $^1$H NMR (500 MHz, CDCl$_3$): 7.28-7.24 (m, 2H), 7.22-7.16 (m, 3H), 7.13-7.10 (m, 2H), 7.05-7.01 (m, 2H), 3.12-3.08 (m, 2H), 3.05-3.02 (m, 2H), 3.01-2.98 (m, 2H), 2.68-2.64 (m, 2H).

Example 201

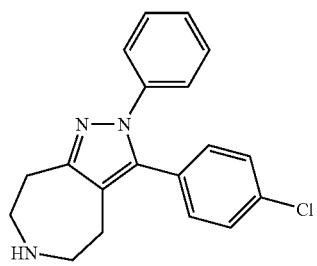

3-(4-Chloro-phenyl)-2-phenyl-2,4,5,6,7,8-hexahydro-1,2,6-triaza-azulene

The title compound (9.3 mg) was prepared from 164.0 mg of 2-phenyl-3-trifluoromethanesulfonyloxy-4,5,7,8-tetrahydro-2H-1,2,6-triaza-azulene-6-carboxylic acid tert-butyl ester (Example 176, Step B) and 63.8 mg of 4-chlorophenylboronic acid as in Example 196. MS (ESI): exact mass calculated for $C_{19}H_{18}ClN_3$, 323.12; found, m/z 324.1 [M+H]$^+$. $^1$H NMR (500 MHz, CDCl$_3$): 7.33-7.25 (m, 4H), 7.23-7.16 (m, 3H), 7.09-7.06 (m, 2H), 3.10-3.07 (m, 2H), 3.03-3.00 (m, 2H), 2.99-2.96 (m, 2H), 2.66-2.63 (m, 2H).

Example 202

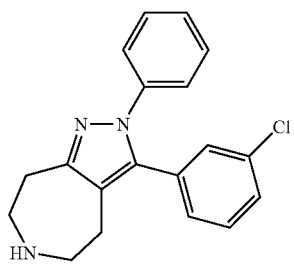

3-(3-Chloro-phenyl)-2-phenyl-2,4,5,6,7,8-hexahydro-1,2,6-triaza-azulene

The title compound (37.5 mg) was prepared from 192.3 mg of 2-phenyl-3-trifluoromethanesulfonyloxy-4,5,7,8-tetrahydro-2H-1,2,6-triaza-azulene-6-carboxylic acid tert-butyl ester (Example 176, Step B) and 84.7 mg of 3-chlorophenylboronic acid as in Example 199. MS (ESI): exact mass calculated for $C_{19}H_{18}ClN_3$, 323.12; found, m/z 324.1 [M+H]$^+$. $^1$H NMR (500 MHz, CDCl$_3$): 7.32-7.16 (m, 8H), 7.01-6.98 (m, 1H), 3.12-3.08 (m, 2H), 3.05-3.02 (m, 2H), 3.01-2.98 (m, 2H), 2.69-2.66 (m, 2H).

Example 203

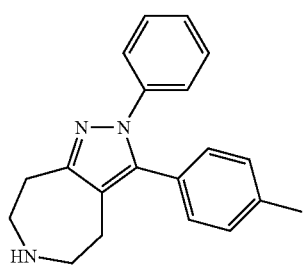

2-Phenyl-3-p-tolyl-2,4,5,6,7,8-hexahydro-1,2,6-triaza-azulene

The title compound (17.5 mg) was prepared from 188.9 mg of 2-phenyl-3-trifluoromethanesulfonyloxy-4,5,7,8-tetrahydro-2H-1,2,6-triaza-azulene-6-carboxylic acid tert-butyl ester (Example 176, Step B) and 93.3 mg of p-tolylboronic acid as in Example 199, using DME as the solvent. MS (ESI): exact mass calculated for $C_{20}H_{21}N_3$, 303.17; found, m/z 304.2 [M+H]$^+$. $^1$H NMR (500 MHz, CDCl$_3$): 7.26-7.23 (m, 2H), 7.21-7.16 (m, 3H), 7.15-7.12 (m, 2H), 7.04-7.01 (m, 2H), 3.11-3.07 (m, 2H), 3.04-3.00 (m, 2H), 2.98-2.96 (m, 2H), 2.68-2.65 (m, 2H), 2.35 (s, 3H).

Example 204

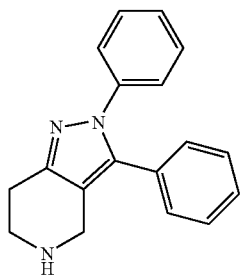

2,3-Diphenyl-4,5,6,7-tetrahydro-2H-pyrazolo[4,3-c]pyridine

Step A. 2,3-Diphenyl-2,4,6,7-tetrahydro-pyrazolo[4,3-c]pyridine-5-carboxylic acid tert-butyl ester. To a solution of 156.6 mg of 2-phenyl-3-trifluoromethanesulfonyloxy-2,4,6,7-tetrahydro-pyrazolo[4,3-c]pyridine-5-carboxylic acid tert-butyl ester (made from 4-oxo-piperidine-1,3-dicarboxylic acid 1-tert-butyl ester 3-methyl ester as in Example 176, Steps A and B) in THF/H$_2$O (10:1, 4 mL) were added 148.4 mg of K$_2$CO$_3$ and 56.2 mg of phenylboronic acid. PdCl$_2$dppf (23.4 mg) was added and the mixture was heated at reflux for 16 h. The mixture was concentrated in vacuo. The residue was chromatographed on SiO$_2$ (0 to 75% EtOAc/hexanes) to afford 45.6 mg of the desired ester as an off-white solid. MS (ESI): exact mass calculated for $C_{23}H_{25}N_3O_2$, 375.19; found, m/z 376.2 [M+H]$^+$.

Step B. The above compound (45.6 mg) was converted to the title compound (24.5 mg) as in Example 26, Step B. MS (ESI): exact mass calculated for $C_{18}H_{17}N_3$, 275.14; found, m/z 276.2 [M+H]$^+$. $^1$H NMR (500 MHz, CDCl$_3$): 7.34-7.22 (m, 8H), 7.16-7.12 (m, 2H), 3.96 (s, 2H), 3.23 (t, J=6.0 Hz, 2H), 2.88 (t, J=6.0 Hz, 2H).

Example 205

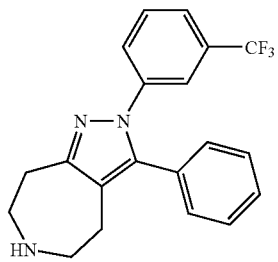

3-Phenyl-2-(3-trifluoromethyl-phenyl)-2,4,5,6,7,8-hexahydro-1,2,6-triaza-azulene Step A. 3-Phenyl-2-(3-trifluoromethyl-phenyl)-4,5,7,8-tetrahydro-2H-1,2,6-triaza-azulene-6-carboxylic acid tert-butyl ester. The desired compound (172.0 mg) was prepared from 279.1 of mg of 3-trifluoromethanesulfonyloxy-2-(3-trifluoromethyl-phenyl)-4,5,7,8-tetrahydro-2H-1,2,6-triaza-azulene-6-carboxylic acid tert-butyl ester (made from (3-trifluoromethyl-phenyl)-hydrazine as in Example 176, Steps A and B) and 0.21 g of phenylboronic acid, as described in Example 177, Step C. MS (ESI): exact mass calculated for $C_{25}H_{26}F_3N_3O_2$, 457.20; found, m/z 458.1 [M+H]$^+$.

Step B. The above compound (172.0 mg) was converted to the title compound (106.4 mg) as in Example 26, Step B. MS (ESI): exact mass calculated for $C_{20}H_{18}F_3N_3$, 357.15; found, m/z 358.1 [M+H]$^+$. $^1$H NMR (500 MHz, CDCl$_3$): 7.53 (s, 1H), 7.44-7.41 (m, 1H), 7.39-7.29 (m, 5H), 7.17-7.13 (m, 2H), 3.12-3.09 (m, 2H), 3.06-3.02 (m, 2H), 3.00-2.97 (m, 2H), 2.69-2.66 (m, 2H).

Example 206

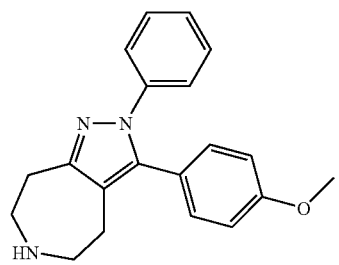

3-(4-Methoxy-phenyl)-2-phenyl-2,4,5,6,7,8-hexahydro-1,2,6-triaza-azulene

The title compound (43.6 mg) was prepared from 198.3 mg of 2-phenyl-3-trifluoromethanesulfonyloxy-4,5,7,8-tetrahydro-2H-1,2,6-triaza-azulene-6-carboxylic acid tert-butyl ester (Example 176, Step B) and 94.7 mg of 4-methoxyphenylboronic acid as described in Example 199. MS (ESI): exact mass calculated for $C_{20}H_{21}N_3O$, 319.17; found, m/z 320.2 [M+H]$^+$. $^1$H NMR (500 MHz, CDCl$_3$): 7.28-7.24 (m, 2H), 7.21-7.17 (m, 3H), 7.07 (d, J=8.8 Hz, 2H), 6.87 (d, J=8.8 Hz, 2H), 3.81 (s, 3H), 3.11-3.08 (m, 2H), 3.04-3.01 (m, 2H), 3.00-2.97 (m, 2H), 2.68-2.65 (m, 2H).

Example 207

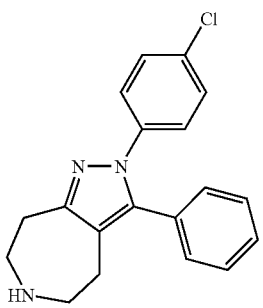

2-(4-Chloro-phenyl)-3-phenyl-2,4,5,6,7,8-hexahydro-1,2,6-triaza-azulene

The title compound (50.4 mg) was prepared from 201.1 mg of 2-(4-chloro-phenyl)-3-trifluoromethanesulfonyloxy-4,5,7,8-tetrahydro-2H-1,2,6-triaza-azulene-6-carboxylic acid tert-butyl ester (made from (4-chloro-phenyl)-hydrazine as in Example 176, Steps A and B), and 65.1 mg of phenylboronic acid as described in Example 204. MS (ESI): exact mass calculated for $C_{19}H_{18}ClN_3$, 323.12; found, m/z 324.1 [M+H]$^+$. $^1$H NMR (500 MHz, CDCl$_3$): 7.39-7.34 (m, 3H), 7.22-7.19 (m, 2H), 7.15-7.11 (m, 4H), 3.11-3.07 (m, 2H), 3.04-3.00 (m, 2H), 2.99-2.96 (m, 2H), 2.67-2.64 (m, 2H).

Example 208

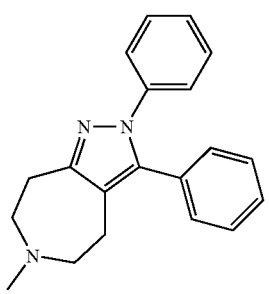

6-Methyl-2,3-diphenyl-2,4,5,6,7,8-hexahydro-1,2,6-triaza-azulene

To a solution of 33.5 mg of 2,3-diphenyl-2,4,5,6,7,8-hexahydro-1,2,6-triaza-azulene (Example 176, Step D) in 5 mL of CH$_2$Cl$_2$ were added 0.15 g of paraformaldehyde and 0.15 g of NaBH(OAc)$_3$. The mixture was stirred at RT for 12 h and was diluted with 20 mL of 1 M NaOH. After stirring for 3 h, the mixture was extracted with CH$_2$Cl$_2$ (2×10 mL) and the combined organic layers were concentrated. Chromatography on SiO$_2$ (0 to 5% 2 M NH$_3$ in MeOH/CH$_2$Cl$_2$) gave 22.3 mg of the title compound as a white solid. MS (ESI): exact mass calculated for $C_{20}H_{21}N_3$, 303.17; found, m/z 304.2 [M+H]$^+$. $^1$H NMR (500 MHz, CDCl$_3$): 7.35-7.30 (m, 3H), 7.27-7.21 (m, 2H), 7.20-7.16 (m, 3H), 7.15-7.12 (m, 2H), 3.06-3.02 (m, 2H), 2.83-2.79 (m, 2H), 2.72-2.67 (m, 4H), 2.50 (s, 3H).

Example 209

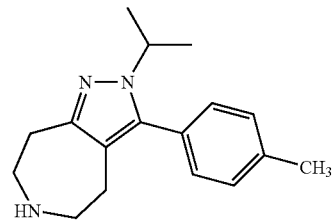

2-Isopropyl-3-p-tolyl-2,4,5,6,7,8-hexahydro-1,2,6-triaza-azulene

The title compound (129 mg) was prepared as in Example 177, Steps C and D, using 204 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 194 mg of 4-methylphenylboronic acid. MS (ESI): exact mass calculated for $C_{17}H_{23}N_3$, 269.19; found, m/z 270.5 [M+H]$^+$. $^1$H NMR (500 MHz, CD$_3$OD): 7.28 (d, J=7.7 Hz, 2H), 7.12 (d, J=7.7 Hz, 2H), 4.32 (m, 1H), 3.34-3.33 (m, 2H), 3.12-3.10 (m, 2H), 2.70-2.68 (m, 2H), 2.33 (s, 3H), 1.30 (d, J=6.6 Hz, 6H).

Example 210

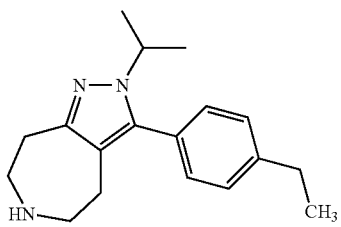

3-(4-Ethyl-phenyl)-2-isopropyl-2,4,5,6,7,8-hexahydro-1,2,6-triaza-azulene

The title compound (134 mg) was prepared as in Example 177, Steps C and D, using 202 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 212 mg of 4-ethylphenylboronic acid. MS (ESI): exact mass calculated for $C_{18}H_{25}N_3$, 283.20; found, m/z 284.5 [M+H]$^+$. $^1$H NMR (500 MHz, CD$_3$OD): 7.44 (d, J=7.7 Hz, 2H), 7.31 (d, J=7.7 Hz, 2H), 4.52 (m, 1H), 3.50-3.48 (m, 2H), 3.36-3.34 (m, 2H), 2.85-2.83 (m, 2H), 2.75 (q, J=7.7 Hz, 2H), 1.47 (d, J=6.6 Hz, 6H), 1.29 (t, J=7.7 Hz, 3H).

Example 211

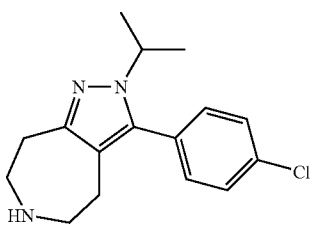

3-(4-Chloro-phenyl)-2-isopropyl-2,4,5,6,7,8-hexahydro-1,2,6-triaza-azulene

The title compound (82 mg) was prepared as in Example 177, Steps C and D, using 205 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 332 mg of 2-(4-chloro-phenyl)-benzo[1,3,2]dioxaborole. MS (ESI): exact mass calculated for $C_{16}H_{20}ClN_3$, 289.13; found, m/z 290.4 [M+H]$^+$, 292.4 [M+H]$^+$. $^1$H NMR (500 MHz, CD$_3$OD): 7.57 (d, J=8.5 Hz, 2H), 7.33 (d, J=8.5 Hz, 2H), 4.36 (m, 1H), 3.44-3.40 (m, 2H), 3.20-3.18 (m, 2H), 2.81-2.76 (m, 2H), 1.40 (d, J=6.6 Hz, 6H).

Example 212

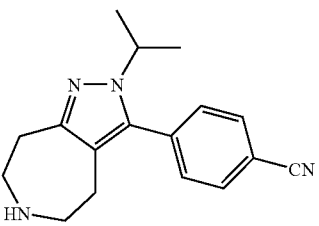

4-(2-Isopropyl-2,4,5,6,7,8-hexahydro-1,2,6-triaza-azulen-3-yl)-benzonitrile

The title compound (95 mg) was prepared as in Example 177, Steps C and D, using 205 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 211 mg of 4-cyanophenylboronic acid. MS (ESI): exact mass calculated for $C_{17}H_{20}N_4$, 280.17; found, m/z 281.4 [M+H]$^+$. $^1$H NMR (500 MHz, CD$_3$OD): 7.57 (d, J=8.5 Hz, 2H), 7.33 (d, J=8.5 Hz, 2H), 4.36 (m, 1H), 3.42-3.40 (m, 2H), 3.19-3.17 (m, 2H), 2.79-2.77 (m, 2H), 1.40 (d, J=6.6 Hz, 6H).

Example 213

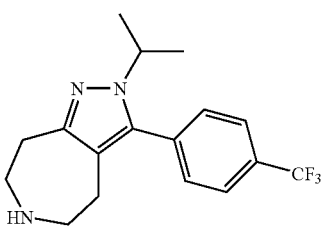

2-Isopropyl-3-(4-trifluoromethyl-phenyl)-2,4,5,6,7,8-hexahydro-1,2,6-triaza-azulene The title compound (103 mg) was prepared as in Example 177, Steps C and D, using 199 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 265 mg of 4-trifluoromethylphenylboronic acid. MS (ESI): exact mass calculated for $C_{17}H_{20}F_3N_3$, 323.16; found, m/z 324.4 [M+H]$^+$. $^1$H NMR (500 MHz, CD$_3$OD): 7.86 (d, J=8.0 Hz, 2H), 7.55 (d, J=8.0 Hz, 2H), 4.34 (m, 1H), 3.43-3.40 (m, 2H), 3.20-3.18 (m, 2H), 2.80-2.78 (m, 2H), 1.40 (d, J=6.6 Hz, 6H).

Example 214

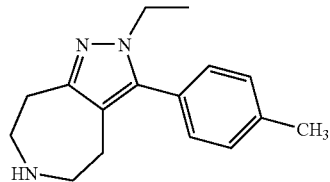

2-Ethyl-3-p-tolyl-2,4,5,6,7,8-hexahydro-1,2,6-triaza-azulene

The title compound (136 mg) was prepared as in Example 177, Steps C and D, using 201 mg of 2-ethyl-3-trifluoromethanesulfonyloxy-4,5,7,8-tetrahydro-2H-1,2,6-triaza-azulene-6-carboxylic acid tert-butyl ester (Example 193, Step A) and 198 mg of 4-methylphenylboronic acid. MS (ESI): exact mass calculated for $C_{16}H_{21}N_3$, 255.17; found, m/z 256.5 [M+H]$^+$. $^1$H NMR (500 MHz, CD$_3$OD): 7.38 (d, J=8.0 Hz, 2H), 7.25 (d, J=8.0 Hz, 2H), 4.67 (br s, 1H), 4.05 (q, J=7.1 Hz, 2H), 3.92-3.41 (m, 2H), 3.28-3.18 (m, 3H), 2.89-2.80 (m, 2H), 2.43 (s, 3H), 1.29 (t, J=7.1 Hz, 3H).

Example 215

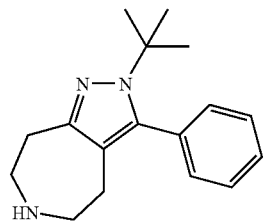

2-tert-Butyl-3-phenyl-2,4,5,6,7,8-hexahydro-1,2,6-triaza-azulene

Step A. 2-(tert-Butyl)-3-trifluoromethanesulfonyloxy-4,5,7,8-tetrahydro-2H-1,2,6-triaza-azulene-6-carboxylic acid tert-butyl ester. The desired triflate was prepared as in Steps A and B of Example 176, using tert-butyl hydrazine hydrochloride in place of phenylhydrazine, t-butanol in place of EtOH, with the addition of 3 equiv. of triethylamine.

Step B. The title compound (53 mg) was prepared as in Example 177, Steps C and D, using 200 mg of the triflate from Step A and 166 mg of phenylboronic acid. MS (ESI): exact mass calculated for $C_{17}H_{23}N_3$, 269.19; found, m/z 270.5 [M+H]$^+$, 214.4 [M-$^t$Bu]$^+$. $^1$H NMR (500 MHz, CD$_3$OD):

7.49-7.47 (m, 3H), 7.32-7.30 (m, 2H), 3.41-3.39 (m, 2H), 3.25-3.23 (m, 2H), 3.18-3.15 (m, 2H), 2.52-2.520 (m, 2H), 1.41 (s, 9H).

Example 216

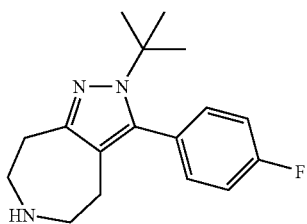

2-tert-Butyl-3-(4-fluoro-phenyl)-2,4,5,6,7,8-hexahydro-1,2,6-triaza-azulene

The title compound (88 mg) was prepared as in Example 177, Steps C and D, using 204 mg of 2-(tert-butyl)-3-trifluoromethanesulfonyloxy-4,5,7,8-tetrahydro-2H-1,2,6-triaza-azulene-6-carboxylic acid tert-butyl ester (Example 215 Step A) and 194 mg of 4-fluorophenylboronic acid. MS (ESI): exact mass calculated for $C_{17}H_{22}FN_3$, 287.18; found, m/z 288.4 $[M+H]^+$, 232.4 $[M-^tBu]^+$. $^1H$ NMR (500 MHz, $CD_3OD$): 7.37-7.33 (m, 2H), 7.26-7.22 (m, 2H), 3.41-3.38 (m, 2H), 3.26-3.24 (m, 2H), 3.18-3.15 (m, 2H), 2.53-2.51 (m, 2H), 1.42 (s, 9H).

Example 217

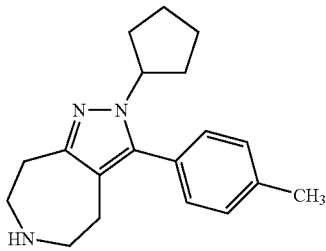

2-Cyclopentyl-3-p-tolyl-2,4,5,6,7,8-hexahydro-1,2,6-triaza-azulene

The title compound (70.4 mg) was prepared as in Example 177, Steps C and D, using 204.3 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 204.1 mg of 4-methylphenylboronic acid. MS (ESI): exact mass calculated for $C_{19}H_{25}N_3$, 295.42; found, m/z 296.5 $[M+H]^+$. $^1H$ NMR (500 MHz, $CD_3OD$): 7.37 (d, J=7.9 Hz, 2H), 7.21 (d, J=7.9 Hz, 2H), 4.50 (m, 1H), 3.43-3.40 (m, 2H), 3.32-3.28 (m, 2H), 3.20-3.17 (m, 2H), 2.80-2.77 (m, 2H), 2.43 (s, 3H), 2.04-1.86 (m, 6H), 1.64-1.55 (m, 2H).

Example 218

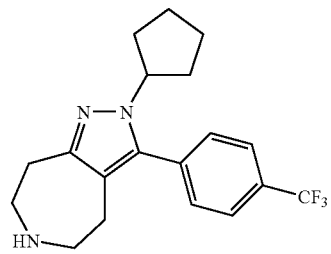

2-Cyclopentyl-3-(4-trifluoromethyl-phenyl)-2,4,5,6,7,8-hexahydro-1,2,6-triaza-azulene The title compound (45.2 mg) was prepared as in Example 177, Steps C and D, using 269.2 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 359.2 mg of 4-trifluoromethylphenylboronic acid. MS (ESI): exact mass calculated for $C_{19}H_{22}F_3N_3$, 349.49; found, m/z 350.3 $[M+H]^+$. $^1H$ NMR (500 MHz, $CD_3OD$): 7.87 (d, J=7.9 Hz, 2H), 7.55 (d, J=7.9 Hz, 2H), 4.48 (m, 1H), 3.43-3.40 (m, 2H), 3.21-3.17 (m, 2H), 2.81-2.77 (m, 2H), 2.07-1.86 (m, 6H), 1.66-1.57 (m, 2H).

Example 219

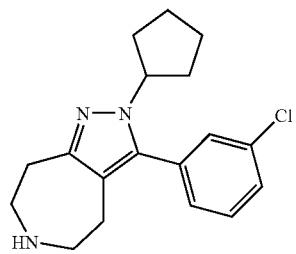

3-(3-Chloro-phenyl)-2-cyclopentyl-2,4,5,6,7,8-hexahydro-1,2,6-triaza-azulene

The title compound (34.9 mg) was prepared as in Example 177, Steps C and D, using 204.4 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 234.5 mg of 3-chlorophenylboronic acid. MS (ESI): exact mass calculated for $C_{18}H_{22}ClN_3$, 315.84; found, m/z 316.4 $[M+H]^+$. $^1H$ NMR (500 MHz, $CD_3OD$): 7.57-7.52 (m, 2H), 7.37-7.35 (m, 1H), 7.29-7.26 (m, 1H), 4.46 (m, 1H), 3.43-3.39 (m, 2H), 3.20-3.16 (m, 2H), 2.80-2.76 (m, 2H), 2.06-1.86 (m, 6H), 1.66-1.57 (m, 2H).

Example 220

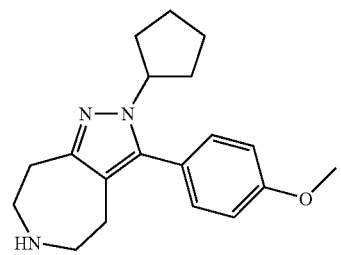

2-Cyclopentyl-3-(4-methoxy-phenyl)-2,4,5,6,7,8-hexahydro-1,2,6-triaza-azulene The title compound (34.9 mg) was prepared as in Example 177, Steps C and D, using 299.2 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 329.2 mg of 4-methoxyphenylboronic acid. MS (ESI): exact mass calculated for $C_{19}H_{25}N_3O$, 311.42; found, m/z 312.3 $[M+H]^+$. $^1H$ NMR (500 MHz, $CD_3OD$): 7.26-7.23 (m, 2H), 7.11-7.08 (m, 2H), 4.51 (m, 1H), 3.87 (s, 3H), 3.43-3.40 (m, 2H), 3.20-3.16 (m, 2H), 2.80-2.76 (m, 2H), 2.02-1.86 (m, 6H), 1.64-1.55 (m, 2H).

Example 221

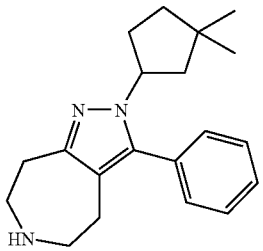

2-(3,3-Dimethyl-cyclopentyl)-3-phenyl-2,4,5,6,7,8-hexahydro-1,2,6-triaza-azulene Step A. 2-(3,3-Dimethyl-cyclopentyl)-3-trifluoromethanesulfonyloxy-4,5,7,8-tetrahydro-2H-1,2,6-triaza-azulene-6-carboxylic acid tert-butyl ester. The desired triflate was prepared as in Steps A and B of Example 176, using (3,3-dimethyl-cyclopentyl)-hydrazine hydrochloride in place of phenylhydrazine, t-butanol in place of EtOH, with the addition of 3 equiv. of triethylamine.

Step B. The title compound (92.8 mg) was prepared as in Example 177, Steps C and D, using 197.5 mg of the triflate from Step A and 150 mg of phenylboronic acid. MS (ESI): exact mass calculated for $C_{20}H_{27}N_3$, 309.45; found, m/z 310.5 $[M+H]^+$. $^1H$ NMR (500 MHz, $CD_3OD$): 7.58-7.50 (m, 3H), 7.34-7.31 (m, 2H), 4.66-4.58 (m, 1H), 3.44-3.40 (m, 2H), 3.32-3.28 (m, 2H), 3.21-3.17 (m, 2H), 2.81-2.77 (m, 2H), 2.21-2.03 (m, 2H), 2.01-1.95 (m, 1H), 1.80-1.73 (m, 2H), 1.48-1.39 (m, 1H), 1.16 (s, 3H), 0.92 (s, 3H).

Example 222

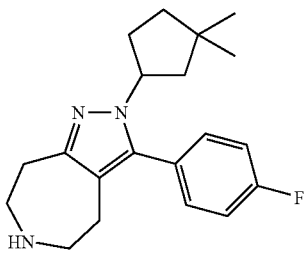

2-(3,3-Dimethyl-cyclopentyl)-3-(4-fluoro-phenyl)-2,4,5,6,7,8-hexahydro-1,2,6-triaza-azulene The title compound (52.6 mg) was prepared as in Example 177, Steps C and D, using 201.7 mg of 2-(3,3-dimethyl-cyclopentyl)-3-trifluoromethanesulfonyloxy-4,5,7,8-tetrahydro-2H-1,2,6-triaza-azulene-6-carboxylic acid tert-butyl ester (Example 221, Step A) and 180 mg of 4-fluorophenylboronic acid. MS (ESI): exact mass calculated for $C_{20}H_{26}FN_3$, 327.44; found, m/z 328.5 $[M+H]^+$. $^1H$ NMR (500 MHz, $CD_3OD$): 7.39-7.34 (m, 2H), 7.33-7.28 (m, 2H), 4.62-4.53 (m, 1H), 3.44-3.39 (m, 2H), 3.31-3.29 (m, 2H), 3.21-3.17 (m, 2H), 2.80-2.75 (m, 2H), 2.20-2.03 (m, 2H), 2.00-1.94 (m, 1H), 1.80-1.73 (m, 2H), 1.49-1.41 (m, 1H), 1.16 (s, 3H), 0.93 (s, 3H).

Example 223

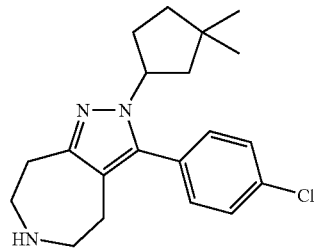

3-(4-Chloro-phenyl)-2-(3,3-dimethyl-cyclopentyl)-2,4,5,6,7,8-hexahydro-1,2,6-triaza-azulene The title compound (25.6 mg) was prepared as in Example 177, Steps C and D, using 203.3 mg of 2-(3,3-dimethyl-cyclopentyl)-3-trifluoromethanesulfonyloxy-4,5,7,8-tetrahydro-2H-1,2,6-triaza-azulene-6-carboxylic acid tert-butyl ester (Example 221 Step A) and 204.1 mg of 4-chlorophenylboronic acid. MS (ESI): exact mass calculated for $C_{20}H_{26}ClN_3$, 343.89; found, m/z 344.5 $[M+H]^+$. $^1H$ NMR (500 MHz, $CD_3OD$): 7.57 (d, J=8.5 Hz, 2H), 7.32 (d, J=8.5 Hz, 2H), 4.62-4.54 (m, 1H), 3.43-3.39 (m, 2H), 3.32-3.28 (m, 2H), 3.20-3.16 (m, 2H), 2.79-2.75 (m, 2H), 2.19-2.03 (m, 2H), 1.99-1.94 (m, 1H), 1.80-1.73 (m, 2H), 1.49-1.40 (m, 1H), 1.16 (s, 3H), 0.94 (s, 3H).

Example 224

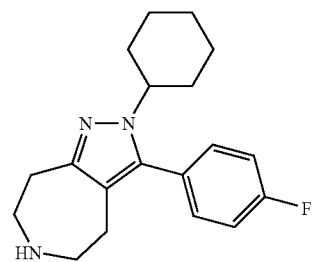

2-Cyclohexyl-3-(4-fluoro-phenyl)-2,4,5,6,7,8-hexahydro-1,2,6-triaza-azulene The title compound (17.2 mg) was prepared as in Example 177, Steps C and D, using 206.5 mg of 2-cyclohexyl-3-trifluoromethanesulfonyloxy-4,5,7,8-tetrahydro-2H-1,2,6-triaza-azulene-6-carboxylic acid tert-butyl ester (Example 177, Step B) and 193.2 mg of 4-fluorophenylboronic acid. MS (ESI): exact mass calculated for $C_{19}H_{24}FN_3$, 313.41; found, m/z 314.5 $[M+H]^+$. $^1H$ NMR (500 MHz, $CD_3OD$):

7.37-7.28 (m, 4H), 3.91-3.84 (m, 1H), 3.43-3.38 (m, 2H), 3.32-3.27 (m, 2H), 3.18-3.14 (m, 2H), 2.78-2.74 (m, 2H), 1.96-1.79 (m, 6H), 1.69-1.63 (m, 1H), 1.30-1.19 (m, 3H).

Example 225

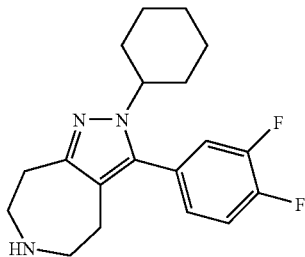

2-Cyclohexyl-3-(3,4-difluoro-phenyl)-2,4,5,6,7,8-hexahydro-1,2,6-triaza-azulene

The title compound (42.7 mg) was prepared as in Example 177, Steps C and D, using 205.2 mg of 2-cyclohexyl-3-trifluoromethanesulfonyloxy-4,5,7,8-tetrahydro-2H-1,2,6-triaza-azulene-6-carboxylic acid tert-butyl ester (Example 177, Step B) and 224.9 mg of 3,4-difluorophenylboronic acid. MS (ESI): exact mass calculated for $C_{19}H_{23}F_2N_3$, 331.40; found, m/z 332.5 [M+H]$^+$. $^1$H NMR (500 MHz, CD$_3$OD): 7.51-7.44 (m, 1H), 7.34-7.28 (m, 1H), 7.17-7.13 (m, 1H), 3.91-3.84 (m, 1H), 3.42-3.38 (m, 2H), 3.18-3.14 (m, 2H), 2.78-2.74 (m, 2H), 1.96-1.78 (m, 6H), 1.70-1.64 (m, 1H), 1.32-1.19 (m, 3H).

Example 226

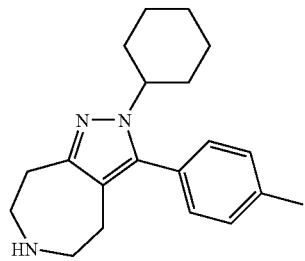

2-Cyclohexyl-3-p-tolyl-2,4,5,6,7,8-hexahydro-1,2,6-triaza-azulene

The title compound (60.2 mg) was prepared as in Example 177, Steps C and D, using 203.8 mg of 2-cyclohexyl-3-trifluoromethanesulfonyloxy-4,5,7,8-tetrahydro-2H-1,2,6-triaza-azulene-6-carboxylic acid tert-butyl ester (Example 177, Step B) and 181.6 mg of 4-methylphenylboronic acid. MS (ESI): exact mass calculated for $C_{20}H_{27}N_3$, 309.45; found, m/z 310.5 [M+H]$^+$. $^1$H NMR (500 MHz, CD$_3$OD): 7.37 (d, J=7.7 Hz, 2H), 7.19 (d, J=7.7 Hz, 2H), 3.97-3.89 (m, 1H), 3.44-3.39 (m, 2H), 3.31-3.26 (m, 2H), 3.20-3.15 (m, 2H), 2.80-2.75 (m, 2H), 1.96-1.78 (m, 6H), 1.70-1.62 (m, 1H), 1.28-1.18 (m, 3H).

Example 227

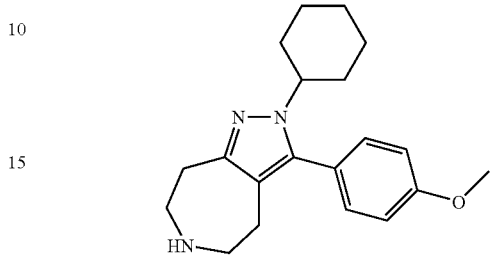

2-Cyclohexyl-3-(4-methoxy-phenyl)-2,4,5,6,7,8-hexahydro-1,2,6-triaza-azulene

The title compound (96.8 mg) was prepared as in Example 177, Steps C and D, using 207 mg of 2-cyclohexyl-3-trifluoromethanesulfonyloxy-4,5,7,8-tetrahydro-2H-1,2,6-triaza-azulene-6-carboxylic acid tert-butyl ester (Example 177, Step B) and 224.1 mg of 4-methoxyphenylboronic acid. MS (ESI): exact mass calculated for $C_{20}H_{27}N_3O$, 325.45; found, m/z 326.5 [M+H]$^+$. $^1$H NMR (500 MHz, CD$_3$OD): 7.25 (d, J=8.7 Hz, 2H), 7.11 (d, J=8.7 Hz, 2H), 4.00-3.92 (m, 1H), 3.87 (s, 3H), 3.45-3.40 (m, 2H), 3.22-3.17 (m, 2H), 2.81-2.75 (m, 2H), 1.96-1.65 (m, 7H), 1.29-1.19 (m, 3H).

Example 228

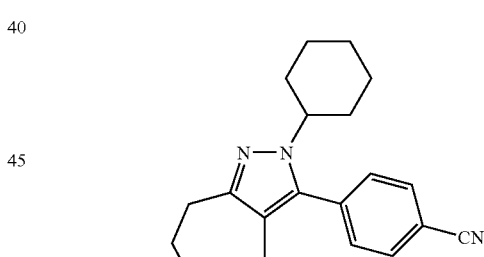

4-(2-Cyclohexyl-2,4,5,6,7,8-hexahydro-1,2,6-triaza-azulen-3-yl)-benzonitrile

The title compound (135.4 mg) was prepared as in Example 177, Steps C and D, using 203.8 mg of 2-cyclohexyl-3-trifluoromethanesulfonyloxy-4,5,7,8-tetrahydro-2H-1,2,6-triaza-azulene-6-carboxylic acid tert-butyl ester (Example 177, Step B) and 198 mg of 4-cyanophenylboronic acid. MS (ESI): exact mass calculated for $C_{20}H_{24}N_4$, 320.43; found, m/z 321.5 [M+H]$^+$. $^1$H NMR (500 MHz, CD$_3$OD): 7.93 (d, J=8.5 Hz, 2H), 7.53 (d, J=8.5 Hz, 2H), 3.92-3.84 (m, 1H), 3.43-3.38 (m, 2H), 3.19-3.15 (m, 2H), 2.80-2.75 (m, 2H), 1.98-1.80 (m, 6H), 1.71-1.64 (m, 1H), 1.32-1.20 (m, 3H).

Example 229

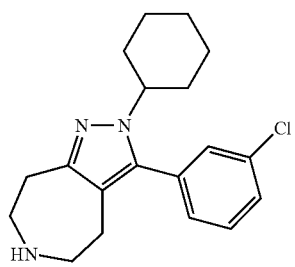

3-(3-Chloro-phenyl)-2-cyclohexyl-2,4,5,6,7,8-hexahydro-1,2,6-triaza-azulene

The title compound (14.4 mg) was prepared as in Example 177, Steps C and D, using 199.3 mg of 2-cyclohexyl-3-trifluoromethanesulfonyloxy-4,5,7,8-tetrahydro-2H-1,2,6-triaza-azulene-6-carboxylic acid tert-butyl ester (Example 177, Step B) and 216.2 mg of 3-chlorophenylboronic acid. MS (ESI): exact mass calculated for $C_{19}H_{24}ClN_3$, 329.87; found, m/z 330.5 [M+H]$^+$. $^1$H NMR (500 MHz, CD$_3$OD): 7.57-7.54 (m, 2H), 7.35 (s, 1H), 7.28-7.25 (m, 1H), 3.91-3.84 (m, 1H), 3.43-3.38 (m, 2H), 3.19-3.14 (m, 2H), 2.79-2.74 (m, 2H), 1.97-1.80 (m, 6H), 1.71-1.64 (m, 1H), 1.28-1.19 (m, 3H).

Example 230

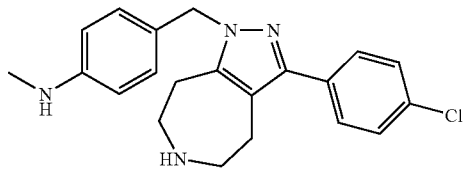

{4-[3-(4-Chloro-phenyl)-5,6,7,8-tetrahydro-4H-1,2,6-triaza-azulen-1-ylmethyl]-phenyl}-methyl-amine A mixture of 1-(4-bromo-benzyl)-3-(4-chloro-phenyl)-4,5,7,8-tetrahydro-1H-1,2,6-triaza-azulene-6-carboxylic acid tert-butyl ester (Example 113; 0.04 mmol), tert-butyl carbamate (0.05 mmol), sodium phenoxide trihydrate (0.05 mmol), tris(dibenzylideneacetone)dipalladium(0) (0.001 mmol), and tri-tert-butylphosphine (0.05 mmol) in anhydrous toluene (3 mL) was heated under N$_2$ at 100° C. for 6 h, 70° C. for 15 h and 100° C. for 2.5 h. After cooling to RT, the reaction mixture was purified directly by preparative TLC (2:1 hexanes/EtOAc) to yield 0.008 g of 1-(4-tert-butoxycarbonylamino-benzyl)-3-(4-chloro-phenyl)-4,5,7,8-tetrahydro-1H-1,2,6-triaza-azulene-6-carboxylic acid tert-butyl ester, which was then diluted with DMF (1 mL) and treated with NaH (60%, 1.5 equiv.). After 15 min, methyl iodide (1.5 equiv.) was added. After 1 h, the reaction was quenched with H$_2$O and the mixture was extracted with EtOAc (2×). The combined organic layers were dried over Na$_2$SO$_4$ and concentrated. The resulting semi-solid was then dissolved in CH$_2$Cl$_2$/MeOH (9:1, 1 mL) and treated with HCl (1 N in Et$_2$O, 4 mL). The mixture was stirred at RT for 3 h, then was concentrated. The resulting oil was purified by preparative TLC (10% 2 M NH$_3$ in MeOH/CH$_2$Cl$_2$) to yield 0.002 mg of the title compound as a white solid. MS (ESI): exact mass calculated for $C_{21}H_{23}ClN_4$, 366.16; found, m/z 367.1 [M+H]$^+$. $^1$H NMR (500 MHz, CD$_3$OD): 7.39-7.32 (m, 4H), 6.84 (d, J=8.6 Hz, 1H), 6.48-6.45 (m, 2H), 5.12 (s, 2H), 2.84-2.81 (m, 4H), 2.79-2.77 (m, 2H), 2.69-2.66 (m, 2H), 2.63 (s, 3H).

Example 231

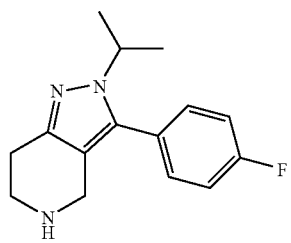

3-(4-Fluoro-phenyl)-2-isopropyl-4,5,6,7-tetrahydro-2H-pyrazolo[4,3-c]pyridine

Step A. 2-Isopropyl-3-trifluoromethanesulfonyloxy-2,4,6,7-tetrahydro-pyrazolo[4,3-c]pyridine-5-carboxylic acid tert-butyl ester. The desired triflate was prepared according to Example 189, Step A, starting with 4-oxo-piperidine-1,3-dicarboxylic acid 1-tert-butyl ester 3-methyl ester.

Step B. The title compound (26 mg) was prepared as in Example 177, Steps C and D, using 221 mg of the triflate from Step A and 140 mg of 4-fluorophenylboronic acid. MS (ESI): exact mass calculated for $C_{15}H_{18}FN_3$, 259.32; found, m/z 260.4 [M+H]$^+$. $^1$H NMR (500 MHz, CD$_3$OD): 7.44-7.39 (m, 2H), 7.33-7.28 (m, 2H), 4.48 (m, 1H), 4.15 (s, 2H), 3.58 (t, J=6.3 Hz, 2H), 3.08 (t, J=6.3 Hz, 2H), 1.42 (d, J=6.6 Hz, 6H).

Example 232

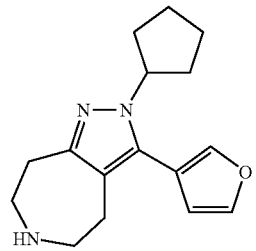

2-Cyclopentyl-3-furan-3-yl-2,4,5,6,7,8-hexahydro-1,2,6-triaza-azulene

The title compound (101 mg) was prepared according to Example 180 using 202 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 149 mg of 3-furanboronic acid. MS (ESI): exact mass calculated for $C_{16}H_{21}N_3O$, 271.17; found, m/z 272.5 [M+H]$^+$. $^1$H NMR (500 MHz, CD$_3$OD): 7.73-7.72 (m, 2H), 6.57-6.56 (m, 1H), 4.64 (m, 1H), 3.40-3.38 (m, 2H), 3.16-3.14 (m, 2H), 2.86-2.84 (m, 2H), 2.03-1.91 (m, 6H), 1.66-1.64 (m, 2H).

Example 233

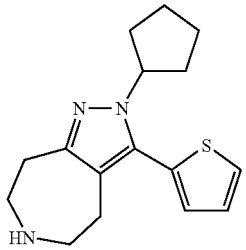

2-Cyclopentyl-3-thiophen-2-yl-2,4,5,6,7,8-hexahydro-1,2,6-triaza-azulene

The title compound (83 mg) was prepared according to Example 180 using 200 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 282 mg of 2-thiopheneboronic acid. MS (ESI): exact mass calculated for $C_{16}H_{21}N_3S$, 287.15; found, m/z 288.4 [M+H]$^+$. $^1$H NMR (500 MHz, CD$_3$OD): 7.70-7.68 (m, 1H), 7.24-7.22 (m, 1H), 7.15-7.14 (m, 1H), 4.64 (m, 1H), 3.41-3.39 (m, 2H), 3.16-3.15 (m, 2H), 2.85-2.83 (m, 2H), 2.01-1.88 (m, 6H), 1.64-1.60 (m, 2H).

Example 234

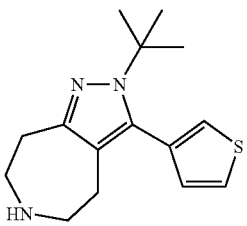

2-tert-Butyl-3-thiophen-3-yl-2,4,5,6,7,8-hexahydro-1,2,6-triaza-azulene

The title compound (83 mg) was prepared according to Example 215 using 204 mg of 2-(tert-butyl)-3-trifluoromethanesulfonyloxy-4,5,7,8-tetrahydro-2H-1,2,6-triaza-azulene-6-carboxylic acid tert-butyl ester (Example 215, Step A) and 177 mg of 3-thiopheneboronic acid. MS (ESI): exact mass calculated for $C_{15}H_{21}N_3S$, 275.15; found, m/z 276.4 [M+H]$^+$. $^1$H NMR (500 MHz, CD$_3$OD): 7.59-7.57 (m, 1H), 7.43-7.42 (m, 1H), 7.08-7.06 (m, 1H), 3.38-3.36 (m, 2H), 3.25-3.23 (m, 2H), 3.13-3.11 (m, 2H), 2.56-2.54 (m, 2H), 1.43 (s, 9H).

Example 235

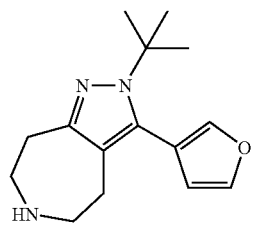

2-tert-Butyl-3-furan-3-yl-2,4,5,6,7,8-hexahydro-1,2,6-triaza-azulene

The title compound (60 mg) was prepared according to Example 215 using 203 mg of 2-(tert-butyl)-3-trifluoromethanesulfonyloxy-4,5,7,8-tetrahydro-2H-1,2,6-triaza-azulene-6-carboxylic acid tert-butyl ester (Example 215, Step A) and 154 mg of 3-furanboronic acid. MS (ESI): exact mass calculated for $C_{15}H_{21}N_3O$, 259.17; found, m/z 260.5 [M+H]$^+$. $^1$H NMR (500 MHz, CD$_3$OD): 7.69-7.68 (m, 1H), 7.61 (br s, 1H), 6.50-6.49 (m, 1H), 3.38-3.36 (m, 2H), 3.27-3.25 (m, 2H), 3.13-3.11 (m, 2H), 2.63-2.61 (m, 2H), 1.50 (s, 9H).

Example 236

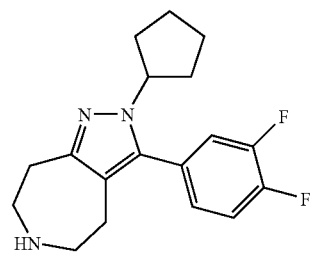

2-Cyclopentyl-3-(3,4-difluoro-phenyl)-2,4,5,6,7,8-hexahydro-1,2,6-triaza-azulene The title compound (70 mg) was prepared according to Example 180 using 209 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 218 mg of 3,4-difluorophenylboronic acid. MS (ESI): exact mass calculated for $C_{18}H_{21}F_2N_3$, 317.17; found, m/z 318.4 [M+H]$^+$. $^1$H NMR (500 MHz, CD$_3$OD): 7.50-7.45 (m, 1H), 7.36-7.32 (m, 1H), 7.18-7.17 (m, 1H), 4.49 (m, 1H), 3.43-3.41 (m, 2H), 3.21-3.19 (m, 2H), 2.80-2.78 (m, 2H), 2.15-1.87 (m, 6H), 1.66-1.61 (m, 2H).

Example 237

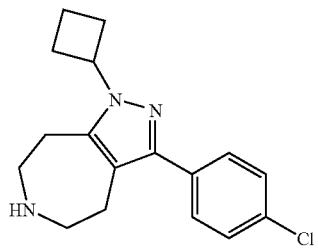

3-(4-Chloro-phenyl)-1-cyclobutyl-1,4,5,6,7,8-hexahydro-1,2,6-triaza-azulene

The title compound (0.01 g) was prepared from 3-(4-chloro-phenyl)-1-cyclobutyl-1,4,5,6,7,8-hexahydro-1,2,6-triaza-azulene-6-carboxylic acid tert-butyl ester (Example 238) according to Example 103, Step C. (MS (ESI): exact mass calculated for $C_{17}H_{20}ClN_3$, 301.13; found, m/z 302.4 [M+H]$^+$. $^1$H NMR (500 MHz, CD$_3$OD): 7.54-7.48 (m, 4H), 5.15-5.05 (m, 1H), 3.47-3.46 (m, 2H), 3.35-3.30 (m, 4H), 3.22-3.21 (m, 2H), 2.70-2.60 (m, 2H), 2.50-2.40 (m, 2H), 1.90-1.80 (m, 2H).

Example 238

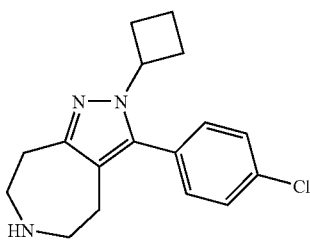

3-(4-Chloro-phenyl)-2-cyclobutyl-2,4,5,6,7,8-hexahydro-1,2,6-triaza-azulene

To a solution of 3-(4-chloro-phenyl)-4,5,7,8-tetrahydro-1H-1,2,6-triaza-azulene-6-carboxylic acid tert-butyl ester (Example 103, Step B; 0.40 mmol) in DMF (2 mL) was added NaH (60% dispersion in oil, 60 mg) at 25° C. After 10 min, the mixture was heated to 80° C., and chloro-cyclobutane (1.5 mmol) was added. The mixture was heated at this temperature for 16 h. The mixture was concentrated and purified by chromatography (SiO$_2$, EtOAc/hexanes) to provide 3-(4-chloro-phenyl)-2-cyclobutyl-2,4,5,6,7,8-hexahydro-1,2,6-triaza-azulene-6-carboxylic acid tert-butyl ester. The title compound (0.030 mg) was obtained from this ester according to the deprotection method in Example 103, Step C. The reaction sequence also yielded 3-(4-chloro-phenyl)-1-cyclobutyl-2,4,5,6,7,8-hexahydro-1,2,6-triaza-azulene-6-carboxylic acid tert-butyl ester in the alkylation step. MS (ESI): exact mass calculated for $C_{17}H_{20}ClN_3$, 301.13; found, m/z 302.4 [M+H]$^+$. $^1$H NMR (500 MHz, CD$_3$OD): 7.52-7.51 (m, 2H), 7.30-7.29 (m, 2H), 4.70-4.60 (m, 1H), 3.40-3.89 (m, 2H), 3.27-3.21 (m, 4H), 2.79-2.76 (m, 2H), 2.60-2.50 (m, 2H), 2.30-2.20 (m, 2H), 1.81-1.65 (m, 2H).

Example 239

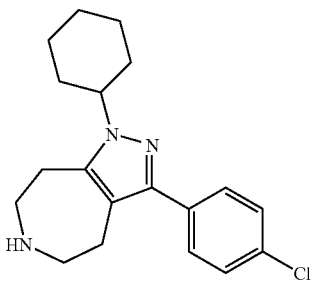

3-(4-Chloro-phenyl)-1-cyclohexyl-1,4,5,6,7,8-hexahydro-1,2,6-triaza-azulene

The title compound (15 mg) was prepared from 3-(4-chloro-phenyl)-4,5,7,8-tetrahydro-1H-1,2,6-triaza-azulene-6-carboxylic acid tert-butyl ester (Example 103, Step B; 0.40 mmol) using bromo-cyclohexane (1.5 mmol) in place of chloro-cyclobutane according to Example 238. MS (ESI): exact mass calculated for $C_{19}H_{24}ClN_3$, 329.17; found, m/z 330.4 [M+H]$^+$. $^1$H NMR (500 MHz, CD$_3$OD): 7.45-7.41 (m, 4H), 4.30-4.27 (m, 1H), 3.44-3.42 (m, 2H), 3.31-3.26 (m, 4H), 2.98-2.96 (m, 2H), 1.93-1.84 (m, 5H), 1.70-1.65 (m, 1H), 1.46-1.40 (m, 2H), 1.24-1.89 (m, 2H).

Example 240

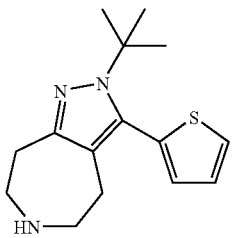

2-tert-Butyl-3-thiophen-2-yl-2,4,5,6,7,8-hexahydro-1,2,6-triaza-azulene

The title compound (83 mg) was prepared according to Example 215 using 203 mg of 2-(tert-butyl)-3-trifluoromethanesulfonyloxy-4,5,7,8-tetrahydro-2H-1,2,6-triaza-azulene-6-carboxylic acid tert-butyl ester (Example 215, Step A) and 176 mg of 2-thiopheneboronic acid. MS (ESI): exact mass calculated for $C_{15}H_{21}N_3S$, 275.15; found, m/z 276.4 [M+H]$^+$. $^1$H NMR (500 MHz, CD$_3$OD): 7.57-7.56 (m, 1H), 7.08-7.06 (m, 1H), 7.01-7.00 (m, 1H), 3.29-3.27 (m, 2H), 3.17-3.14 (m, 2H), 2.51-2.48 (m, 2H), 1.37 (s, 9H).

Example 241

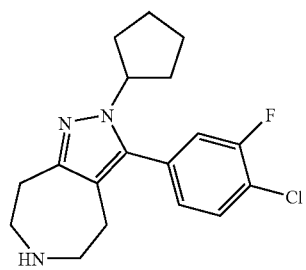

3-(4-Chloro-3-fluoro-phenyl)-2-cyclopentyl-2,4,5,6,7,8-hexahydro-1,2,6-triaza-azulene The title compound (31 mg) was prepared according to Example 180 using 146 mg of 2-cyclopentyl-3-trifluoromethanesulfonyloxy-4,5,7,8-tetrahydro-2H-1,2,6-triaza-azulene-6-carboxylic acid tert-butyl ester (Example 180, Step A) and 168 mg of 3-chloro-4-fluorophenylboronic acid. MS (ESI): exact mass calculated for $C_{18}H_{21}ClFN_3$, 333.14; found, m/z 334.4 [M+H]$^+$, 336.4 [M+H]$^+$. $^1$H NMR (500 MHz, CD$_3$OD): 7.39-7.31 (m, 2H), 7.22-7.18 (m, 1H), 4.37 (m, 1H), 3.31-3.28 (m, 2H), 3.07-3.03 (m, 2H), 2.67-2.64 (m, 2H), 2.11-1.78 (m, 6H), 1.56-1.47 (m, 2H).

Example 242

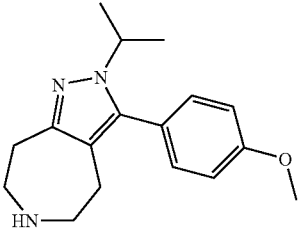

2-Isopropyl-3-(4-methoxy-phenyl)-2,4,5,6,7,8-hexahydro-1,2,6-triaza-azulene

The title compound (148 mg) was prepared according to Example 189 using 206 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 219 mg of 4-methoxyphenylboronic acid. MS (ESI): exact mass calculated for $C_{17}H_{23}N_3O$, 285.18; found, m/z 286.5 [M+H]$^+$. $^1$H NMR (500 MHz, CD$_3$OD): 7.30-7.28 (m, 2H), 7.13-7.11 (m, 2H), 4.68 (m, 1H), 4.47 (m, 1H), 3.87 (s, 3H), 3.47-3.44 (m, 1H), 3.25-3.23 (m, 1H), 2.89-2.81 (m, 2H), 1.43 (d, J=6.6 Hz, 6H).

Example 243

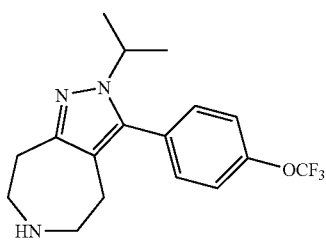

2-Isopropyl-3-(4-trifluoromethoxy-phenyl)-2,4,5,6,7,8-hexahydro-1,2,6-triaza-azulene The title compound (196 mg) was prepared according to Example 189 using 278 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 402 mg of 4-trifluoromethoxyphenylboronic acid. MS (ESI): exact mass calculated for $C_{17}H_{20}F_3N_3O$, 339.36; found, m/z 340.5 [M+H]$^+$. $^1$H NMR (500 MHz, CD$_3$OD): 7.53-7.45 (m, 4H), 4.66 (br s, 1H), 4.40 (J=6.68 Hz, 1H), 3.45-3.43 (m, 1H), 3.23-3.21 (m, 1H), 2.88-2.79 (m, 2H), 1.42 (d, J=6.7 Hz, 6H).

Example 244

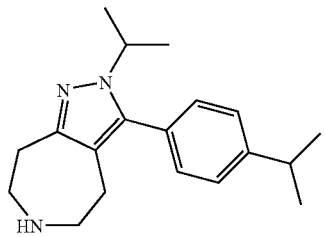

2-Isopropyl-3-(4-isopropyl-phenyl)-2,4,5,6,7,8-hexahydro-1,2,6-triaza-azulene

The title compound (177 mg) was prepared according to Example 189 using 270 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 311 mg of 4-isopropylphenylboronic acid. MS (ESI): exact mass calculated for $C_{19}H_{27}N_3$, 297.44; found, m/z 298.5 [M+H]$^+$. $^1$H NMR (500 MHz, CD$_3$OD): 7.35-7.34 (m, 2H), 7.19-7.17 (m, 2H), 4.57 (br s, 1H), 4.38-4.32 (m, 1H), 3.36-3.34 (m, 1H), 3.15-3.13 (m, 1H), 2.90 (m, 1H), 2.79-2.70 (m, 2H), 1.31 (d, J=13.3 Hz, 6H), 1.20 (d, J=6.9 Hz, 6H).

Example 245

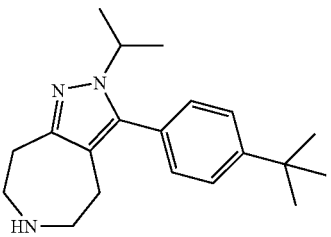

3-(4-tert-Butyl-phenyl)-2-isopropyl-2,4,5,6,7,8-hexahydro-1,2,6-triaza-azulene

The title compound (28 mg) was prepared according to Example 189 using 215 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 268 mg of 4-tert-butylphenylboronic acid. MS (ESI): exact mass calculated for $C_{20}H_{29}N_3$, 311.24; found, m/z 312.5 [M+H]$^+$. $^1$H NMR (500 MHz, CD$_3$OD): 7.61-7.59 (m, 2H), 7.27-7.25 (m, 2H), 4.40 (m, 1H), 3.43-3.40 (m, 2H), 3.19-3.17 (m, 2H), 2.79-2.77 (m, 2H), 1.50-1.25 (m, 15H).

Example 246

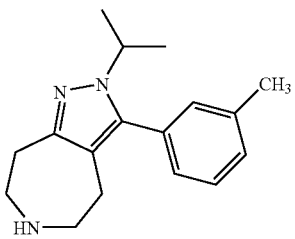

2-Isopropyl-3-m-tolyl-2,4,5,6,7,8-hexahydro-1,2,6-triaza-azulene

The title compound (24 mg) was prepared according to Example 189 using 219 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 209 mg of 3-methylphenylboronic acid. MS (ESI): exact mass calculated for $C_{17}H_{23}N_3$, 269.19; found, m/z 270.5 [M+H]$^+$. $^1$H NMR (500 MHz, CD$_3$OD): 7.44-7.41 (m, 1H), 7.34-7.33 (m, 1H), 7.13-7.10 (m, 2H), 4.37 (m, 1H), 3.42-3.40 (m, 2H), 3.19-3.17 (m, 2H), 2.78-2.76 (m, 2H), 2.42 (s, 3H), 1.38 (d, J=6.7 Hz, 6H).

Example 247

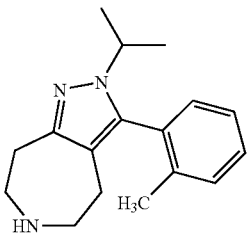

2-Isopropyl-3-o-tolyl-2,4,5,6,7,8-hexahydro-1,2,6-triaza-azulene

The title compound (80 mg) was prepared according to Example 189 using 207 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 198 mg of 2-methylphenylboronic acid. MS (ESI): exact mass calculated for $C_{17}H_{23}N_3$, 269.19; found, m/z 270.5 [M+H]$^+$. $^1$H NMR (500 MHz, CD$_3$OD): 7.45-7.40 (m, 2H), 7.36-7.33 (m, 1H), 7.19-7.18 (m, 1H), 4.66 (br s, 2H), 4.10 (m, 1H), 4.00-3.66 (m, 2H), 2.76-2.61 (m, 2H), 2.13 (s, 3H), 1.45-1.29 (m, 6H).

Example 248

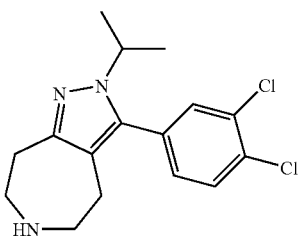

3-(3,4-Dichloro-phenyl)-2-isopropyl-2,4,5,6,7,8-hexahydro-1,2,6-triaza-azulene

The title compound (60 mg) was prepared according to Example 189 using 200 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 268 mg of 3,4-dichlorophenylboronic acid. MS (ESI): exact mass calculated for $C_{16}H_{19}Cl_2N_3$, 323.10; found, m/z 324.4 [M+H]$^+$, 326.4 [M+H]$^+$. $^1$H NMR (500 MHz, CD$_3$OD): 7.72-7.71 (m, 1H), 7.53-7.52 (m, 1H), 7.29-7.27 (m, 1H), 4.64 (br s, 2H), 4.32 (m, 1H), 3.86-3.57 (m, 2H), 3.31-3.08 (m, 2H), 2.84-2.75 (m, 2H), 1.39 (d, J=6.6 Hz, 6H).

Example 249

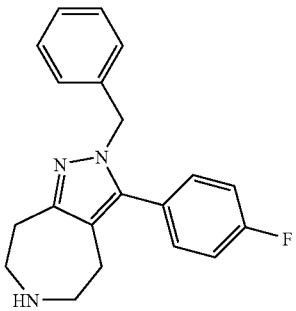

2-Benzyl-3-(4-fluoro-phenyl)-2,4,5,6,7,8-hexahydro-1,2,6-triaza-azulene

Step A. 2-Benzyl-3-trifluoromethanesulfonyloxy-4,5,7,8-tetrahydro-2H-1,2,6-triaza-azulene-6-carboxylic acid tert-butyl ester. The desired triflate was prepared according to Example 189, Step A, using benzylhydrazine hydrochloride in place of isopropylhydrazine hydrochloride.

Step B. The title compound (29 mg) was prepared as in Example 177, Steps C and D, using 230 mg of the triflate from Step A and 234 mg of 4-fluorophenylboronic acid. MS (ESI): exact mass calculated for $C_{20}H_{20}FN_3$, 321.39; found, m/z 322.4 [M+H]$^+$. $^1$H NMR (500 MHz, CD$_3$OD): 7.31-7.19 (m, 7H), 6.97-6.93 (m, 2H), 5.20 (s, 2H), 3.45-3.40 (m, 2H), 3.35-3.30, (m, 2H), 3.20-3.15 (m, 2H), 2.83-2.78 (m, 2H).

Example 250

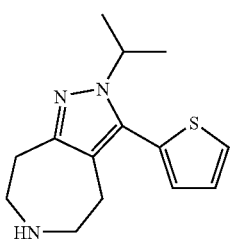

2-Isopropyl-3-thiophen-2-yl-2,4,5,6,7,8-hexahydro-1,2,6-triaza-azulene

The title compound (46 mg) was prepared according to Example 189 using 208 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 187 mg of 2-thiopheneboronic acid. MS (ESI): exact mass calculated for $C_{14}H_{19}N_3S$, 261.13; found, m/z 262.4 [M+H]$^+$. $^1$H NMR (500 MHz, CD$_3$OD): 7.70-7.69 (m, 1H), 7.25-7.23 (m, 1H), 7.15-7.14 (m, 1H), 4.65 (br s, 2H), 4.55-4.49 (m, 1H), 3.8-3.6 (m, 2H), 3.23-3.10 (m, 2H), 2.93-2.83 (m, 2H), 1.44-1.36 (m, 6H).

Example 251

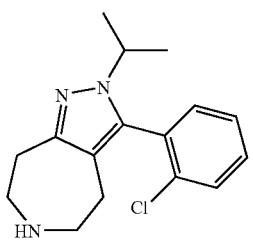

3-(2-Chloro-phenyl)-2-isopropyl-2,4,5,6,7,8-hexahydro-1,2,6-triaza-azulene

The title compound (90 mg) was prepared according to Example 189 using 266 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 292 mg of 2-chlorophenylboronic acid. MS (ESI): exact mass calculated for $C_{16}H_{20}ClN_3$, 289.13; found, m/z 290.4 [M+H]$^+$, 292.4 [M+H]$^+$. $^1$H NMR (500 MHz, CD$_3$OD): 7.65-7.63 (m, 1H), 7.58-7.49 (m, 2H), 7.41-7.39 (m, 1H), 4.66 (br s, 2H), 4.16 (m, 1H), 4.00-3.44 (m, 2H), 3.0-2.6 (m, 2H), 1.47-1.38 (m, 6H).

Example 252

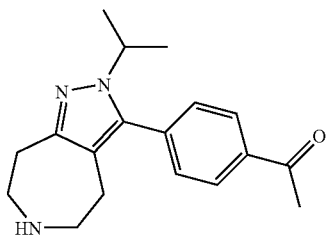

1-[4-(2-Isopropyl-2,4,5,6,7,8-hexahydro-1,2,6-triaza-azulen-3-yl)-phenyl]-ethanone The title compound (168 mg) was prepared according to Example 189 using 255 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 341 mg of 4-acetylphenylboronic acid. MS (ESI): exact mass calculated for $C_{18}H_{23}N_3O$, 297.18; found, m/z 298.5 [M+H]$^+$. $^1$H NMR (500 MHz, CD$_3$OD): 8.17-8.15 (m, 1H), 7.69-7.67 (m, 1H), 7.51-7.49 (m, 1H), 7.37-7.35 (m, 1H), 4.65 (br s, 1H), 4.46-4.38 (m, 1H), 4.00-3.50 (m, 2H), 3.48-3.42 (m, 1H), 3.25-3.17 (m, 1H), 3.13-2.81 (m, 2H), 2.67 (s, 1.5H), 1.55 (s, 1.5H), 1.44-1.40 (m, 6H).

Example 253

2-Isopropyl-3-(4-nitro-phenyl)-2,4,5,6,7,8-hexahydro-1,2,6-triaza-azulene

The title compound (34 mg) was prepared according to Example 189 using 274 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 321 mg of 4-nitrophenylboronic acid. MS (ESI): exact mass calculated for $C_{16}H_{20}N_4O_2$, 300.16; found, m/z 301.4 [M+H]$^+$. $^1$H NMR (500 MHz, CD$_3$OD): 8.42-8.40 (m, 2H), 7.62-7.60 (m, 2H), 4.37 (m, 1H), 3.43-3.41 (m, 2H), 3.21-3.18 (m, 2H), 2.82-2.79 (m, 2H), 1.41 (d, J=8.2 Hz, 6H).

Example 254

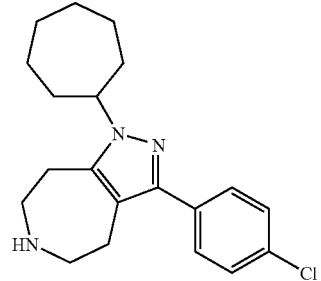

3-(4-Chloro-phenyl)-1-cycloheptyl-1,4,5,6,7,8-hexahydro-1,2,6-triaza-azulene

The title compound (22 mg) was prepared from 3-(4-chloro-phenyl)-4,5,7,8-tetrahydro-1H-1,2,6-triaza-azulene-6-carboxylic acid tert-butyl ester (Example 103, Step B; 0.30 mmol) using chloro-cycloheptane (1.0 mmol) in place of chloro-cyclobutane according to Example 238. The reaction sequence also yielded 3-(4-chloro-phenyl)-2-cycloheptyl-1,4,5,6,7,8-hexahydro-1,2,6-triaza-azulene-6-carboxylic acid tert-butyl ester in the alkylation step. MS (ESI): exact mass calculated for $C_{20}H_{26}ClN_3$, 343.18; found, m/z 344.4 [M+H]$^+$. $^1$H NMR (500 MHz, CD$_3$OD): 7.40-7.34 (m, 4H), 4.31-4.27 (m, 1H), 3.39-3.37 (m, 2H), 3.28-3.26 (m, 2H), 3.17-3.16 (m, 2H), 2.95-2.92 (m, 2H), 2.04-2.01 (m, 2H), 1.92-1.90 (m, 2H), 1.77-1.75 (m, 2H), 1.63-1.53 (m, 6H).

Example 255

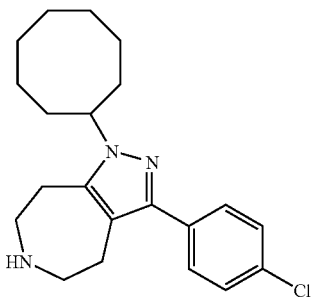

3-(4-Chloro-phenyl)-1-cyclooctyl-1,4,5,6,7,8-hexahydro-1,2,6-triaza-azulene

The title compound (47 mg) was prepared from 3-(4-chloro-phenyl)-4,5,7,8-tetrahydro-1H-1,2,6-triaza-azulene-6-carboxylic acid tert-butyl ester (Example 103, Step B; 0.30 mmol) using chloro-cyclooctane (1.0 mmol) in place of chloro-cyclobutane according to Example 238. The reaction sequence also yielded 3-(4-chloro-phenyl)-2-cyclooctyl-1,4,5,6,7,8-hexahydro-1,2,6-triaza-azulene-6-carboxylic acid tert-butyl ester in the alkylation step. MS (ESI): exact mass calculated for $C_{21}H_{28}ClN_3$, 357.20; found, m/z 358.5 [M+H]$^+$. $^1$H NMR (500 MHz, CD$_3$OD): 7.50-7.44 (m, 4H), 4.49-4.45 (m, 1H), 3.51-3.48 (m, 2H), 3.38-3.36 (m, 2H), 3.33-3.32 (m, 2H), 3.05-3.04 (m, 2H), 2.21-2.18 (m, 2H), 1.97-1.88 (m, 4H), 1.72-1.64 (m, 8H).

Example 256

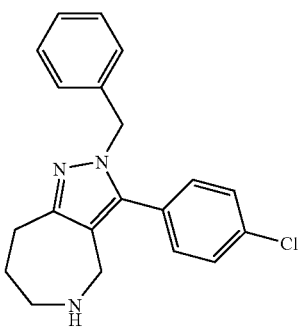

2-Benzyl-3-(4-chloro-phenyl)-2,4,5,6,7,8-hexahydro-1,2,5-triaza-azulene

The title compound (0.023 g) was prepared from 3-(4-chloro-phenyl)-4,6,7,8-tetrahydro-1H-1,2,5-triaza-azulene-5-carboxylic acid tert-butyl ester (Example 59, Step C, 0.1 g), as described in Example 60. MS (ESI): exact mass calculated for $C_{20}H_{20}ClN_3$, 337.13; found, m/z 338.4 [M+H]$^+$. $^1$H NMR (500 MHz, CD$_3$OD): 7.47-7.44 (m, 2H), 7.25-7.19 (m, 5H), 6.94-6.92 (m, 2H), 5.17 (s, 2H), 3.66 (s, 2H), 3.21-3.19 (m, 2H), 2.93-2.90 (m, 2H), 1.93-1.84 (s, 2H).

Example 257

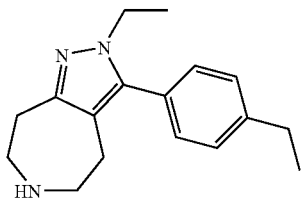

2-Ethyl-3-(4-ethyl-phenyl)-2,4,5,6,7,8-hexahydro-1,2,6-triaza-azulene

The title compound (140 mg) was prepared according to Example 193 using 213 mg of 2-ethyl-3-trifluoromethane-sulfonyloxy-4,5,7,8-tetrahydro-2H-1,2,6-triaza-azulene-6-carboxylic acid tert-butyl ester (Example 193, Step A) and 232 mg of 4-ethylphenylboronic acid. MS (ESI): exact mass calculated for $C_{17}H_{23}N_3$, 269.19; found, m/z 270.5 [M+H]$^+$. $^1$H NMR (500 MHz, CD$_3$OD): 7.40-7.39 (m, 2H), 7.27-7.26 (m, 2H), 4.65 (br s, 2H), 4.05-4.00 (m, 2H), 3.8-3.6 (m, 2H), 3.18-3.00 (m, 2H), 2.88-2.81 (m, 2H), 2.76-2.71 (m, 2H), 1.32-1.24 (m, 6H).

Example 258

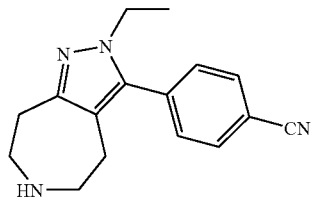

4-(2-Ethyl-2,4,5,6,7,8-hexahydro-1,2,6-triaza-azulen-3-yl)-benzonitrile

The title compound (47 mg) was prepared according to Example 193 using 205 mg of 2-ethyl-3-trifluoromethane-sulfonyloxy-4,5,7,8-tetrahydro-2H-1,2,6-triaza-azulene-6-carboxylic acid tert-butyl ester (Example 193, Step A) and 218 mg of 4-cyanophenylboronic acid. MS (ESI): exact mass calculated for $C_{16}H_{18}N_4$, 266.15; found, m/z 267.5 [M+H]$^+$. $^1$H NMR (500 MHz, CD$_3$OD): 7.93-7.91 (m, 2H), 7.58-7.56 (m, 2H), 4.03 (q, J=7.2 Hz, 2H), 3.43-3.40 (m, 2H), 3.18-3.16 (m, 2H), 2.82-2.80 (m, 2H), 1.29 (t, J=7.2 Hz, 3H).

Example 259

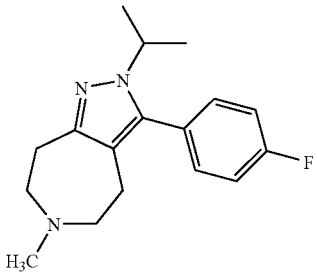

3-(4-Fluoro-phenyl)-2-isopropyl-6-methyl-2,4,5,6,7,8-hexahydro-1,2,6-triaza-azulene The title compound (113 mg) was prepared from 3-(4-fluoro-phenyl)-2-isopropyl-2,4,5,6,7,8-hexahydro-1,2,6- triaza-azulene (Example 190) and paraformaldehyde as in Example 35. MS (ESI): exact mass calculated for $C_{17}H_{22}FN_3$, 287.18; found, m/z 288.5 [M+H]$^+$. $^1$H NMR (500 MHz, CD$_3$OD): 7.42-7.40 (m, 2H), 7.34-7.30 (m, 2H), 4.42 (m, 1H), 3.77-3.74 (m, 1H), 3.67-3.62 (m, 2H), 3.36-3.34 (m, 1H), 3.27-3.21 (m, 3H), 3.03 (s, 3H), 2.92-2.89 (m, 1H), 2.80-2.76 (m, 1H), 1.49-1.29 (m, 6H).

Example 260

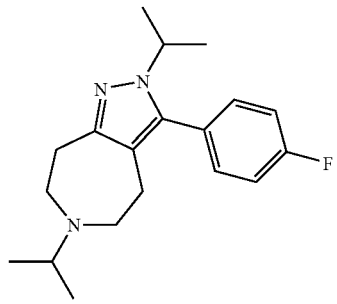

3-(4-Fluoro-phenyl)-2,6-diisopropyl-2,4,5,6,7,8-hexahydro-1,2,6-triaza-azulene

The title compound (92 mg) was prepared from 3-(4-fluoro-phenyl)-2-isopropyl-2,4,5,6,7,8-hexahydro-1,2,6-triaza-azulene (Example 190) and acetone as in Example 35. MS (ESI): exact mass calculated for $C_{19}H_{26}FN_3$, 315.21; found, m/z 316.5 [M+H]$^+$. $^1$H NMR (500 MHz, CD$_3$OD): 7.42-7.39 (m, 2H), 7.33-7.30 (m, 2H), 4.40 (m, 1H), 3.78-3.74 (m, 2H), 3.68-3.63 (m, 1H), 3.36-3.21 (m, 4H), 2.99-2.94 (m, 1H), 2.80-2.76 (m, 1H), 1.54-1.37 (m, 12H).

Example 261

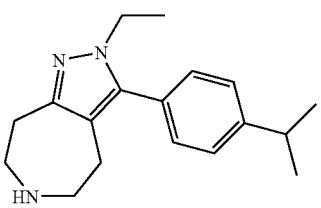

2-Ethyl-3-(4-isopropyl-phenyl)-2,4,5,6,7,8-hexahydro-1,2,6-triaza-azulene

The title compound (131 mg) was prepared according to Example 193 using 205 mg of 2-ethyl-3-trifluoromethanesulfonyloxy-4,5,7,8-tetrahydro-2H-1,2,6-triaza-azulene-6-carboxylic acid tert-butyl ester (Example 193, Step A) and 245 mg of 4-isopropylphenylboronic acid. MS (ESI): exact mass calculated for $C_{18}H_{25}N_3$, 283.20; found, m/z 284.5 [M+H]$^+$. $^1$H NMR (500 MHz, CD$_3$OD): 7.48-7.46 (m, 2H), 7.34-7.33 (m, 2H), 4.12 (q, J=7.3 Hz, 2H), 3.50-3.45 (m, 2H), 3.36-3.33 (m, 2H), 3.27-3.25 (m, 2H), 3.01 (m, 1H), 2.87-2.85 (m, 2H), 1.34 (t, J=7.3 Hz, 3H), 1.31 (d, J=6.9 Hz, 6H).

Example 262

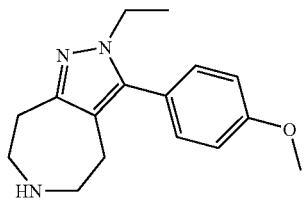

2-Ethyl-3-(4-methoxy-phenyl)-2,4,5,6,7,8-hexahydro-1,2,6-triaza-azulene

The title compound (134 mg) was prepared according to Example 193 using 219 mg of 2-ethyl-3-trifluoromethanesulfonyloxy-4,5,7,8-tetrahydro-2H-1,2,6-triaza-azulene-6-carboxylic acid tert-butyl ester (Example 193, Step A) and 241 mg of 4-methoxyphenylboronic acid. MS (ESI): exact mass calculated for $C_{16}H_{21}N_3O$, 271.17; found, m/z 272.5 [M+H]$^+$. $^1$H NMR (500 MHz, CD$_3$OD): 7.36-7.33 (m, 2H), 7.15-7.12 (m, 2H), 4.12 (q, J=7.3 Hz, 2H), 3.88 (s, 3H), 3.49-3.47 (m, 2H), 3.36-3.34 (m, 2H), 3.28-3.25 (m, 2H), 2.88-2.85 (m, 2H), 1.35 (t, J=7.3 Hz, 3H).

Example 263

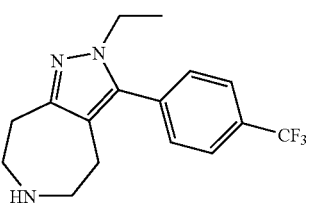

2-Ethyl-3-(4-trifluoromethyl-phenyl)-2,4,5,6,7,8-hexahydro-1,2,6-triaza-azulene

Step A. 2-Ethyl-3-(4-trifluoromethyl-phenyl)-4,5,7,8-tetrahydro-2H-1,2,6-triaza-azulene-6-carboxylic acid tert-butyl ester. To a 25 mL round bottom flask was added 216 mg of 2-ethyl-3-trifluoromethanesulfonyloxy-4,5,7,8-tetrahydro-2H-1,2,6-triaza-azulene-6-carboxylic acid tert-butyl ester (Example 193, Step A), 139 mg of 4-trifluoromethylphenylboronic acid, 17 mg of Bu$_4$N$^+$Br$^-$, 6 mg of dppf and 17 mg of PdCl$_2$(dppf). Toluene (5 mL) was added, followed by 0.8 mL of 2 M aq. Na$_2$CO$_3$, and the mixture was heated at 120° C. for 12 h under N$_2$. The mixture was filtered through diatomaceous earth and the filtrate was concentrated in vacuo to afford 294 mg of dark brown viscous oil. Chromatography on SiO$_2$ (0 to 25% EtOAc/hexanes) provided 177 mg of the desired product. MS (ESI): exact mass calculated for $C_{21}H_{26}F_3N_3O_2$, 409.20; found, m/z 410.5 [M+H]$^+$.

Step B. The title compound (149 mg) was prepared according to Example 43, Step E. MS (ESI): exact mass calculated for $C_{16}H_{18}F_3N_3$, 309.15; found, m/z 310.5 [M+H]$^+$. $^1$H NMR (500 MHz, CD$_3$OD): 7.90-7.89 (m, 2H), 7.65-7.63 (m, 2H), 4.67 (br s, 2H), 4.10 (q, J=7.2 Hz, 2H), 4.00-3.56 (m, 2H), 3.36-3.24 (m, 2H), 2.95-2.85 (m, 2H), 1.33 (t, J=7.2 Hz, 3H).

Example 264

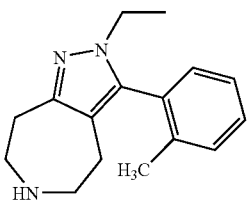

2-Ethyl-3-o-tolyl-2,4,5,6,7,8-hexahydro-1,2,6-triaza-azulene

The title compound (138 mg) was prepared according to Example 263 using 206 mg of 2-ethyl-3-trifluoromethanesulfonyloxy-4,5,7,8-tetrahydro-2H-1,2,6-triaza-azulene-6-carboxylic acid tert-butyl ester (Example 193, Step A) and 95 mg of 2-methylphenylboronic acid. MS (ESI): exact mass calculated for $C_{16}H_{21}N_3$, 255.17; found, m/z 256.5 [M+H]$^+$. $^1$H NMR (500 MHz, CD$_3$OD): 7.49-7.42 (m, 2H), 7.38-7.35 (m, 1H), 7.25-7.24 (m, 1H), 4.69 (br s, 2H), 4.03-3.17 (m, 5H), 2.76-2.68 (m, 2H), 2.15 (s, 3H), 1.28 (t, J=7.2 Hz, 3H).

Example 265

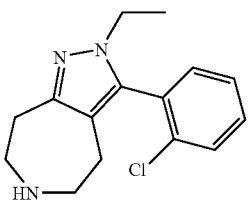

3-(2-Chloro-phenyl)-2-ethyl-2,4,5,6,7,8-hexahydro-1,2,6-triaza-azulene

The title compound (73 mg) was prepared according to Example 263 using 227 mg of 2-ethyl-3-trifluoromethanesulfonyloxy-4,5,7,8-tetrahydro-2H-1,2,6-triaza-azulene-6-carboxylic acid tert-butyl ester (Example 193, Step A) and 120 mg of 2-chlorophenylboronic acid. MS (ESI): exact mass calculated for $C_{15}H_{18}ClN_3$, 275.12; found, m/z 276.4 [M+H]$^+$, 278.4 [M+H]$^+$. $^1$H NMR (500 MHz, CD$_3$OD): 7.64-7.62 (m, 1H), 7.58-7.48 (m, 2H), 7.41-7.39 (m, 1H), 3.97-3.86 (m, 2H), 3.44-3.42 (m, 2H), 3.20-3.17 (m, 2H), 2.70-2.63 (m, 2H), 1.26 (t, J=7.2 Hz, 3H).

Example 266

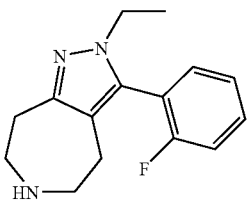

2-Ethyl-3-(2-fluoro-phenyl)-2,4,5,6,7,8-hexahydro-1,2,6-triaza-azulene

The title compound (121 mg) was prepared according to Example 263 using 205 mg of 2-ethyl-3-trifluoromethanesulfonyloxy-4,5,7,8-tetrahydro-2H-1,2,6-triaza-azulene-6-carboxylic acid tert-butyl ester (Example 193, Step A) and 97 mg of 2-fluorophenylboronic acid. MS (ESI): exact mass calculated for $C_{15}H_{18}FN_3$, 259.15; found, m/z 260.4 [M+H]$^+$. $^1$H NMR (500 MHz, CD$_3$OD): 7.61-7.55 (m, 1H), 7.39-7.30 (m, 3H), 4.01-3.91 (m, 2H), 3.43-3.41 (m, 2H), 3.18-3.16 (m, 2H), 2.79-2.73 (m, 2H), 1.28 (t, J=9.0 Hz, 3H).

Example 267

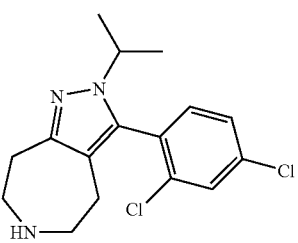

3-(2,4-Dichloro-phenyl)-2-isopropyl-2,4,5,6,7,8-hexahydro-1,2,6-triaza-azulene

The title compound (37 mg) was prepared according to Example 189 using 230 mg of 2-isopropyl-3-trifluoromethanesulfonyloxy-4,5,7,8-tetrahydro-2H-1,2,6-triaza-azulene-6-carboxylic acid tert-butyl ester (Example 189, Step A) and 308 mg of 2,4-dichlorophenylboronic acid. MS (ESI): exact mass calculated for $C_{16}H_{19}Cl_2N_3$, 323.10; found, m/z 324.4 [M+H]$^+$, 326.4 [M+H]$^+$. $^1$H NMR (500 MHz, CD$_3$OD): 7.73-7.72 (m, 1H), 7.54-7.51 (m, 1H), 7.37-7.35 (m, 1H), 4.65 (br s, 1H), 4.11-4.05 (m, 1H), 3.43-3.40 (m, 2H), 3.29-3.16 (m, 3H), 2.70-2.63 (m, 2H), 1.39-1.32 (m, 6H).

Example 268

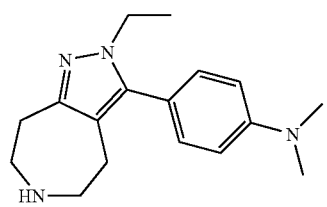

[4-(2-Ethyl-2,4,5,6,7,8-hexahydro-1,2,6-triaza-azulen-3-yl)-phenyl]-dimethyl-amine The title compound (57 mg) was prepared according to Example 263 using 205 mg of 2-ethyl-3-trifluoromethanesulfonyloxy-4,5,7,8-tetrahydro-2H-1,2,6-triaza-azulene-6-carboxylic acid tert-butyl ester (Example 193, Step A) and 115 mg of 4-dimethylaminophenylboronic acid. MS (ESI): exact mass calculated for $C_{17}H_{24}N_4$, 284.20; found, m/z 285.5 [M+H]$^+$. $^1$H NMR (500 MHz, CD$_3$OD): 7.87-7.85 (m, 2H), 7.65-7.63 (m, 2H), 4.67 (br s, 2H), 4.06 (q, J=9.0 Hz, 2H), 4.00-3.62 (m, 2H), 3.36 (s, 6H), 3.32-3.29 (m, 2H), 3.18-2.81 (m, 2H), 1.31 (t, J=9.0 Hz, 3H).

Example 269

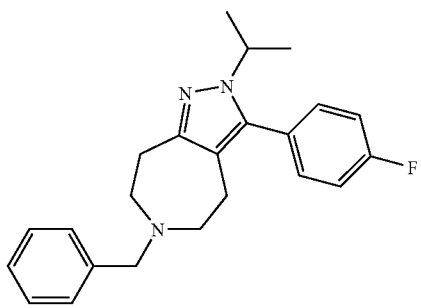

6-Benzyl-3-(4-fluoro-phenyl)-2-isopropyl-2,4,5,6,7,8-hexahydro-1,2,6-triaza-azulene The title compound (115 mg) was prepared from 3-(4-fluoro-phenyl)-2-isopropyl-2,4,5,6,7,8-hexahydro-1,2,6-triaza-azulene (Example 190) and benzaldehyde as in Example 35. MS (ESI): exact mass calculated for $C_{23}H_{26}FN_3$, 363.21; found, m/z 364.5 [M+H]$^+$. $^1$H NMR (500 MHz, CD$_3$OD): 7.58-7.55 (m, 2H), 7.53-7.51 (m, 3H), 7.37-7.33 (m, 2H), 7.31-7.27 (m, 2H), 4.52 (s, 2H), 4.34 (m, 1H), 3.80-3.75 (m, 1H), 3.68-3.64 (m, 1H), 3.35-3.16 (m, 4H), 2.83-2.80 (m, 2H), 1.38 (t, J=6.7 Hz, 6H).

Example 270

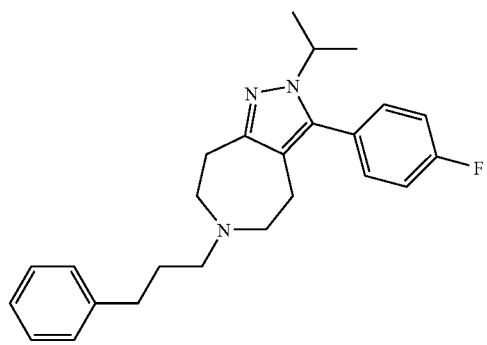

3-(4-Fluoro-phenyl)-2-isopropyl-6-(3-phenyl-propyl)-2,4,5,6,7,8-hexahydro-1,2,6-triaza-azulene The title compound (142 mg) was prepared from 3-(4-fluoro-phenyl)-2-isopropyl-2,4,5,6,7,8-hexahydro-1,2,6-triaza-azulene (Example 190) and 3-phenyl-propionaldehyde as in Example 35. MS (ESI): exact mass calculated for $C_{25}H_{30}FN_3$, 391.24; found, m/z 392.5 [M+H]$^+$. $^1$H NMR (500 MHz, CD$_3$OD): 7.45-7.41 (m, 2H), 7.35-7.26 (m, 6H), 7.22-7.19 (m, 1H), 4.46 (m, 1H), 3.79-3.76 (m, 1H), 3.67-3.63 (m, 1H), 3.46-3.43 (m, 1H), 3.35-3.29 (m, 5H), 2.90-2.87 (m, 1H), 2.83-2.73 (m, 3H), 2.19-2.12 (m, 2H), 1.44 (t, J=6.7 Hz, 6H).

Example 271

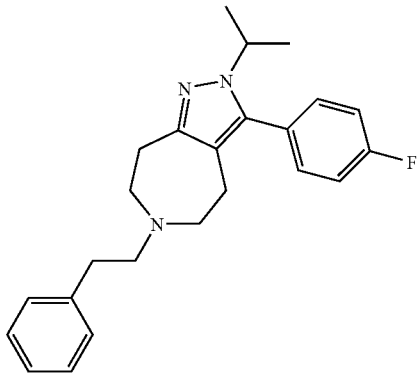

3-(4-Fluoro-phenyl)-2-isopropyl-6-phenethyl-2,4,5,6,7,8-hexahydro-1,2,6-triaza-azulene The title compound (104 mg) was prepared from 3-(4-fluoro-phenyl)-2-isopropyl-2,4,5,6,7,8-hexahydro-1,2,6-triaza-azulene (Example 190) and phenylacetaldehyde as in Example 35. MS (ESI): exact mass calculated for $C_{24}H_{28}FN_3$, 377.23; found, m/z 378.5 [M+H]$^+$. $^1$H NMR (500 MHz, CD$_3$OD): 7.41-7.27 (m, 9H), 4.39 (m, 1H), 3.88-3.84 (m, 1H), 3.73-3.71 (m, 1H), 3.56-3.52 (m, 3H), 3.45-3.20 (m, 3H), 3.17-3.14 (m, 2H), 2.89-2.84 (m, 2H), 1.41 (t, J=6.6 Hz, 6H).

Example 272

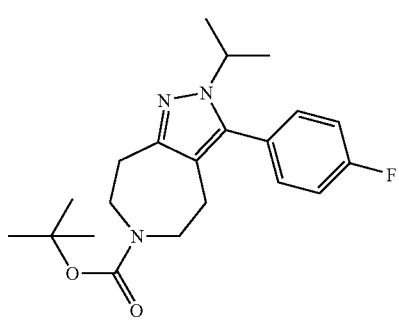

3-(4-Fluoro-phenyl)-2-isopropyl-4,5,7,8-tetrahydro-2H-1,2,6-triaza-azulene-6-carboxylic acid tert-butyl ester This compound was obtained as an intermediate in the sequence described for Example 190. MS (ESI): exact mass calculated for $C_{21}H_{28}FN_3O_2$, 373.46; found, m/z 374.5 [M+H]$^+$. $^1$H NMR (500 MHz, CDCl$_3$): 7.24-7.13 (m, 4H), 4.24 (m, 1H), 3.62-3.55 (m, 2H), 3.49-3.42 (m, 2H), 3.01-2.93 (m, 2H), 2.52-2.44 (m, 2H), 1.50-1.45 (m, 9H), 1.39 (d, J=6.9 Hz, 6H).

Example 273

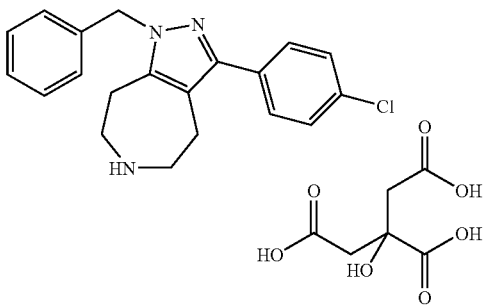

1-Benzyl-3-(4-chloro-phenyl)-1,4,5,6,7,8-hexahydro-1,2,6-triaza-azulene citrate salt Step A. 5-Oxo-azepane-1,4-dicarboxylic acid 1-tert-butyl ester 4-ethyl ester. A dried, $N_2$-flushed, 500-mL, three-necked, round-bottomed flask equipped with a magnetic stir bar, was charged with 4-oxo-piperidine-1-carboxylic acid tert-butyl ester (20 g, 0.10 mol) and $BF_3 \cdot Et_2O$ (14 mL, 0.11 mol) in $Et_2O$ (200 mL) and the mixture was chilled to −5° C. Slowly, ethyl diazoacetate (13.7 mL, 0.13 mol) was added over a period of 1 h causing vigorous gas evolution. The internal temperature was maintained between 0° C. and −5° C. during the addition. The reaction was stirred for 1 h at 0° C., then slowly quenched with 30% aq. $Na_2CO_3$ at 0° C. The pH was adjusted to between 7 and 8 and then $H_2O$ (30 mL) was added to the mixture. The organic layer was extracted with EtOAc (2×75 mL), dried with $Na_2SO_4$, filtered, and concentrated to an orange oil. The crude oil was purified by filtration chromatography ($SiO_2$: 14 cm OD, 8 cm in height; 10 to 30% EtOAc/hexanes) to recover the title compound as light yellow oil (85%). MS (ESI): exact mass calculated for $C_{14}H_{23}NO_5$; found, m/z none, unstable. HPLC (Method B): $R_t$=8.53 min. $^1$H NMR (400 MHz, $CDCl_3$): 4.25-2.03 (m, 11H), 1.47-1.45 (d, J=7.8 Hz, 9H), 1.31-1.24 (m, 3H).

Step B. 3-Oxo-2,3,4,5,7,8-hexahydro-1H-1,2,6-triaza-azulene-6-carboxylic acid tert-butyl ester. In a 1-L, one-necked, round-bottomed flask equipped with a magnetic stir bar was combined 5-oxo-azepane-1,4-dicarboxylic acid 1-tert-butyl ester 4-ethyl ester (24.42 g, 85.0 mmol) and hydrazine (3.0 mL, 0.095 mol) in EtOH (250 mL). The resulting reaction mixture was heated at reflux for 4 h, then was concentrated to provide the desired pyrazole as a white solid in 95% crude yield. The crude pyrazole was used in the next step without further purification. MS (ESI): exact mass calculated for $C_{12}H_{19}N_3O_3$, 253.14; found, m/z 254.1 [M+H]$^+$. HPLC (Method B): $R_t$=6.48 min. $^1$H NMR (400 MHz, $CDCl_3$): 3.64-3.54 (m, 4H), 2.91-2.86 (m, 2H), 2.70-2.65 (m, 2H), 1.49 (s, 9H).

Step C. 3-Trifluoromethanesulfonyloxy-4,5,7,8-tetrahydro-1H-1,2,6-triaza-azulene-6-carboxylic acid tert-butyl ester. In a 250-mL, one-necked, round-bottomed flask equipped with a magnetic stirring bar, N-phenyltrifluoromethanesulfonimide (50 g, 0.14 mol) was suspended in 100 mL pyridine and then 3-oxo-2,3,4,5,7,8-hexahydro-1H-1,2,6-triaza-azulene-6-carboxylic acid tert-butyl ester (35.4 g, 0.14 mol) was added as a solid at rt. The reaction mixture formed a homogeneous solution after 1 h and stirring was continued at rt overnight (15 h). The solvent was evaporated under vacuum and then the residue was partitioned between $Et_2O$ (500 mL) and 1 M aq. $K_2CO_3$ (300 mL). The organic layer was separated and washed with aq. $K_2CO_3$ (1 mol/L, 300 mL) three times and then with brine (200 mL) once, dried over $MgSO_4$, and evaporated to afford the product as a white solid (50.2 g, 0.13 mol, 93%), which was used on next reaction without further purification. MS (ESI): exact mass calculated for $C_{13}H_{18}F_3N_3O_5S$, 385.09; m/z found, 384.0 [M−H]$^-$. HPLC (Method B): $R_t$=9.55 min. $^1$H NMR (500 MHz, $CDCl_3$): 9.52 (s, 1H), 3.70-3.50 (m, 4H), 3.00-2.85 (m, 2H), 2.70-2.60 (m, 2H), 1.49 (s, 9H).

Step D. 1-Benzyl-3-trifluoromethanesulfonyloxy-4,5,7,8-tetrahydro-1H-1,2,6-triaza-azulene-6-carboxylic acid tert-butyl ester. In a 1-L, three-necked, round-bottomed flask containing a magnetic stirring bar, 3-trifluoromethanesulfonyloxy-4,5,7,8-tetrahydro-1H-1,2, 6-triaza-azulene-6-carboxylic acid tert-butyl ester (48 g, 0.125 mol) was dissolved in 500 mL of dry THF under $N_2$. The solution was cooled to 0° C. and potassium t-butoxide (15.4 g, 0.137 mol) was added portion-wise as solid. The reaction mixture was stirred for 10 min to form a clear, homogeneous solution. Benzyl bromide (23.4 g, 0.137 mol) was added through an addition funnel over 10 min. The resulting mixture was stirred at rt overnight (15 h). The solvent was evaporated and the residue was re-dissolved in EtOAc (300 mL). The organic layer was washed with $H_2O$ (2×200 mL) and then with brine (200 mL), dried over $MgSO_4$, filtered, and concentrated. The crude product was purified by pad-filtration through a plug of $SiO_2$ to afford the pure product as a white solid (44.5 g, 94 mmol, 75%). MS (ESI): exact mass calculated for $C_{20}H_{24}F_3N_3O_5S$, 475.14; found, m/z 476.2 [M+H]$^+$. HPLC (Method B): $R_t$=10.90 min. $^1$H NMR (500 MHz, $CDCl_3$): 7.40-7.25 (m, 5H), 7.10-7.05 (m, 2H), 5.22-5.15 (m, 2H), 3.60-3.50 (m, 4H), 2.80-2.60 (m, 4H), 1.47-1.42 (m, 9H).

Step E. 2-(4-Chloro-phenyl)-benzo[1,3,2]dioxaborole. In a 250-mL, one-necked, round-bottomed flask equipped with a Dean-Stark trap and a condenser, the reaction solution of 4-chlorophenylboronic acid (17.5 g, 0.112 mol) and catechol (12.3 g, 0.112 mol) in toluene (150 mL) was heated at reflux for 4 h. The solution was cooled to rt and a white solid precipitated. The solvent was evaporated and the crude product (25.8 g, 0.112 mol, 100%) was used as such in the next reaction without further purification. HPLC (Method B): $R_t$=6.00 and 7.50 min. $^1$H NMR (500 MHz, $CDCl_3$): 8.01 (d, J=8.1 Hz, 2H), 7.47 (d, J=8.1 Hz, 2H), 7.34-7.29 (m, 2H), 7.15-7.11 (m, 2H).

Step F. 1-Benzyl-3-(4-chloro-phenyl)-4,5,7,8-tetrahydro-1H-1,2,6-triaza-azulene-6-carboxylic acid tert-butyl ester. To a 1-L, three-necked, round-bottomed flask was added Pd(dppf)$Cl_2$ (2.8 g, 3.4 mmol), 1,1'-bis(diphenylphosphino)ferrocene (0.96 g, 1.73 mmol), Bu$_4$N$^+$Br$^-$ (2.78 g, 8.6 mmol), $Na_2CO_3$ (36.5 g, 344 mmol) and 2-(4-chloro-phenyl)-benzo[1,3,2]dioxaborole (23.8 g, 103 mmol), under $N_2$. A solution of 1-benzyl-3-trifluoromethanesulfonyloxy-4,5,7,8-tetrahydro-1H-1,2,6-triaza-azulene-6-carboxylic acid tert-butyl ester (41 g, 86 mmol) in toluene (250 mL) was added, followed by the addition of $H_2O$ (250 mL) via syringe. The reaction mixture was stirred at reflux for 3 h and then was cooled to rt. The organic layer was diluted with EtOAc (200 mL) and then was washed with 1 M aq. $K_2CO_3$ until the color of the aqueous layer stabilized. The organic layer was washed with brine (200 mL), dried over $MgSO_4$, filtered, and concentrated. The crude product thus obtained was pad-filtered through a short plug of $SiO_2$ to afford the title compound (34.5 g, 79 mmol, 92%) as a white solid. MS (ESI): exact mass calculated for $C_{25}H_{28}ClN_3O_2$, 437.19; found, m/z 438.1, [M+H]$^+$. HPLC (Method B): $R_t$=10.89 min. $^1$H NMR (400 MHz, $CDCl_3$): 7.50-7.45 (m, 2H), 7.40-7.36 (m, 2H), 7.36-7.25 (m, 3H), 7.13-7.10 (m, 2H), 5.35-5.33 (m, 2H), 3.56-3.50 (m, 4H), 2.83-2.75 (m, 4H), 1.28-1.25 (m, 9H).

Step G. 1-Benzyl-3-(4-chloro-phenyl)-1,4,5,6,7,8-hexahydro-1,2,6-triaza-azulene. In a 500-mL, one-necked, round-bottomed flask, 1-benzyl-3-(4-chloro-phenyl)-4,5,7, 8-tetrahydro-1H-1,2,6-triaza-azulene-6-carboxylic acid tert-butyl ester (34 g, 77 mmol) was dissolved in CH$_2$Cl$_2$ (100 mL). Trifluoroacetic acid (70 mL) was added carefully. The reaction mixture was stirred at rt for 2 h. The solvent was evaporated and the residue was re-dissolved in CH$_2$Cl$_2$ (200 mL). Sat. aq. NaHCO$_3$ solution was added slowly until CO$_2$ evolution ceased. The aqueous layer was extracted with CH$_2$Cl$_2$ (2×200 mL). The organic layers were combined, dried over MgSO$_4$, filtered, and concentrated. The crude product was recrystallized from hot EtOAc to afford the pure product as a white solid (24 g, 71 mmol, 91%). MS (ESI): exact mass calculated for C$_{20}$H$_{20}$ClN$_3$, 337.13; found, m/z 338.3 [M+H]$^+$. HPLC (Method B): R$_t$=7.53 min. $^1$H NMR (400 MHz, CDCl$_3$): 7.48-7.44 (m, 2H), 7.44-7.38 (m, 3H), 7.38-7.27 (m, 3H), 7.14-7.06 (m, 2H), 5.36 (s, 2H), 3.30-3.16 (m, 4H), 3.10-2.98 (m, 4H).

Step H. 1-Benzyl-3-(4-chloro-phenyl)-1,4,5,6,7,8-hexahydro-1,2,6-triaza-azulene citrate salt. In a 500-mL, one-necked, round-bottomed flask, 1-benzyl-3-(4-chloro-phenyl)-1,4,5,6,7,8-hexahydro-1,2,6-triaza-azulene 7 (10 g, 30 mmol) was suspended in MeOH (70 mL), and the mixture was heated until a homogeneous solution formed. A solution of citric acid monohydrate (7.5 g, 36 mmol) in MeOH (10 mL) was added dropwise. The resulting homogeneous solution was heated at reflux for 20 min and then was cooled to rt. The solvent was evaporated to form an oil. The oil was diluted with EtOAc (200 mL) and the mixture was heated to reflux. To this hot solution MeOH was slowly added to form a slurry. The slurry was cooled to rt and the precipitated solids were collected by filtration, washed with EtOAc, and dried under vacuum to afford the citrate salt (1:1 ratio based on $^1$H NMR analysis, 9.1 g). The filtrate was concentrated and the above procedure to form the citrate salt was repeated by adding another 0.5 equivalents of citric acid to afford another 2 g of product. The combined yield was 71%. $^1$H NMR (500 MHz, D$_2$O): 7.35-7.22 (m, 4H), 7.22-7.15 (m, 3H), 7.0-6.92 (m, 2H), 5.22 (s, 2H), 3.22-3.14 (m, 4H), 3.0-2.92 (m, 2H), 2.88-2.80 (m, 2H), 2.69 (d, J=15 Hz, 2H), 2.57 (d, J=15 Hz, 2H).

Example 274

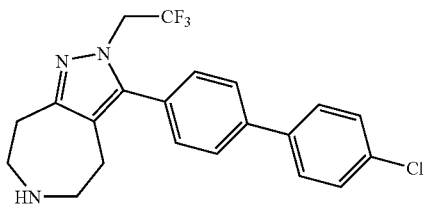

3-(4'-Chloro-biphenyl-4-yl)-2-(2,2,2-trifluoro-ethyl)-2,4,5,6,7,8-hexahydro-1,2,6-triaza-azulene The title compound (18 mg) was also obtained from Example 187, Step B. MS (ESI): exact mass calculated for C$_{21}$H$_{19}$ClF$_3$N$_3$, 405.12; found, m/z 406.1 [M+H]$^+$, 408.0 [M+H]$^+$. $^1$H NMR (500 MHz, CD$_3$OD): 7.74-7.72 (m, 2H), 7.61-7.59 (m, 2H), 7.41-7.35 (m, 4H), 4.70-4.55 (m, 3H), 3.85-3.30 (m, 3H), 3.25-3.05 (m, 2H), 2.82-2.74 (m, 2H).

Example 275

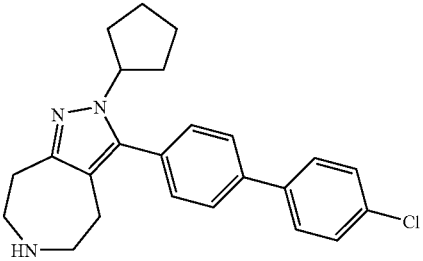

3-(4'-Chloro-biphenyl-4-yl)-2-cyclopentyl-2,4,5,6,7,8-hexahydro-1,2,6-triaza-azulene The title compound (33 mg) was also obtained from Example 181. MS (ESI): exact mass calculated for C$_{24}$H$_{26}$ClN$_3$, 391.18; found, m/z 392.1 [M+H]$^+$, 394.1 [M+H]$^+$. $^1$H NMR (500 MHz, CD$_3$OD): 7.81-7.80 (m, 2H), 7.70-7.68 (m, 2H), 7.50-7.41 (m, 4H), 4.65-4.53 (m, 3H), 3.85-3.67 (m, 2H), 3.30-3.10 (m, 2H), 2.88 (br s, 2H), 2.01-1.91 (m, 6H), 1.63-1.60 (m, 2H).

Example 276

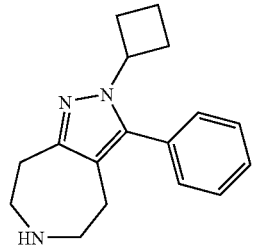

2-Cyclobutyl-3-phenyl-2,4,5,6,7,8-hexahydro-1,2,6-triaza-azulene

Step A. 2-Cyclobutyl-3-trifluoromethanesulfonyloxy-4,5,7,8-tetrahydro-2H-1,2,6-triaza-azulene-6-carboxylic acid tert-butyl ester. The desired triflate was prepared as in Steps A and B of Example 176, using cyclobutylhydrazine hydrochloride (made from cyclobutanone as shown in Example 177, Step A) in place of phenylhydrazine and t-butanol in place of EtOH, with the addition of 3 equiv of triethylamine.

Step B. The title compound (118 mg) was prepared according to Example 263 using 189 mg of the product from Step A and 73 mg of phenylboronic acid. MS (ESI): exact mass calculated for C$_{17}$H$_{21}$N$_3$, 267.17; found, m/z 268.5 [M+H]$^+$. $^1$H NMR (500 MHz, CD$_3$OD): 7.60-7.50 (m, 3H), 7.34-7.30 (m, 2H), 4.71-4.63 (m, 2H), 4.00-3.40 (m, 2H), 3.24-3.22 (m, 3H), 3.00-2.80 (m, 2H), 2.68-2.59 (m, 2H), 2.30-2.24 (m, 2H), 2.30-2.24 (m, 2H), 1.84-1.71 (m, 2H).

Example 277

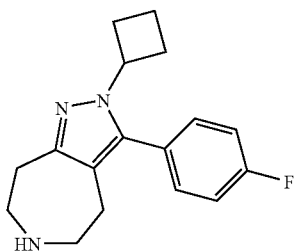

2-Cyclobutyl-3-(4-fluoro-phenyl)-2,4,5,6,7,8-hexahydro-1,2,6-triaza-azulene

The title compound (122 mg) was prepared according to Example 263 using 198 mg of 2-cyclobutyl-3-trifluoromethanesulfonyloxy-4,5,7,8-tetrahydro-2H-1,2,6-triaza-azulene-6-carboxylic acid tert-butyl ester (Example 276, Step A) and 88 mg of 4-fluorophenylboronic acid. MS (ESI): exact mass calculated for $C_{17}H_{20}FN_3$, 285.16; found, m/z 286.4 [M+H]$^+$. $^1$H NMR (500 MHz, $CD_3OD$): 7.35-7.27 (m, 4H), 4.65-4.59 (m, 2H), 3.95-3.3.40 (m, 2H), 3.32-3.05 (m, 3H), 3.00-2.75 (m, 2H), 2.67-2.59 (m, 2H), 2.29-2.23 (m, 2H), 1.84-1.73 (m, 2H).

Example 278

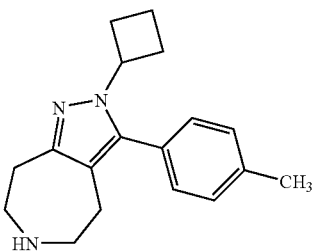

2-Cyclobutyl-3-p-tolyl-2,4,5,6,7,8-hexahydro-1,2,6-triaza-azulene

The title compound (117 mg) was prepared according to Example 263 using 192 mg of 2-cyclobutyl-3-trifluoromethanesulfonyloxy-4,5,7,8-tetrahydro-2H-1,2,6-triaza-azulene-6-carboxylic acid tert-butyl ester (Example 276, Step A) and 83 mg of 4-methylphenylboronic acid. MS (ESI): exact mass calculated for $C_{18}H_{23}N_3$, 281.19; found, m/z 282.5 [M+H]$^+$. $^1$H NMR (500 MHz, $CD_3OD$): 7.41-7.32 (m, 2H), 7.23-7.13 (m, 2H), 4.71-4.65 (m, 2H), 4.00-3.41 (m, 2H), 3.32-3.05 (m, 3H), 2.95-2.79 (m, 2H), 2.67-2.58 (m, 2H), 2.43 (s, 3H), 2.28-2.23 (m, 2H), 1.84-1.71 (m, 2H).

Example 279

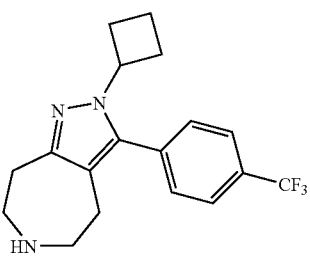

2-Cyclobutyl-3-(4-trifluoromethyl-phenyl)-2,4,5,6,7,8-hexahydro-1,2,6-triaza-azulene The title compound (73 mg) was prepared according to Example 263 using 201 mg of 2-cyclobutyl-3-trifluoromethanesulfonyloxy-4,5,7,8-tetrahydro-2H-1,2,6-triaza-azulene-6-carboxylic acid tert-butyl ester (Example 276, Step A) and 122 mg of 4-trifluoromethylphenylboronic acid. MS (ESI): exact mass calculated for $C_{18}H_{20}F_3N_3$, 335.16; found, m/z 336.4 [M+H]$^+$. $^1$H NMR (500 MHz, $CD_3OD$): 7.86-7.85 (m, 2H), 7.52-7.50 (m, 2H), 4.65-4.58 (m, 1H), 3.45-3.41 (m, 2H), 3.22-3.20 (m, 2H), 2.81-2.79 (m, 2H), 2.67-2.62 (m, 2H), 2.30-2.24 (m, 2H), 1.84-1.74 (m, 2H).

Example 280

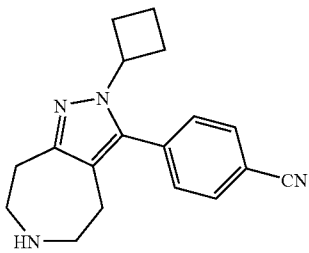

4-(2-Cyclobutyl-2,4,5,6,7,8-hexahydro-1,2,6-triaza-azulen-3-yl)-benzonitrile

The title compound (28 mg) was prepared according to Example 263 using 172 mg of 2-cyclobutyl-3-trifluoromethanesulfonyloxy-4,5,7,8-tetrahydro-2H-1,2,6-triaza-azulene-6-carboxylic acid tert-butyl ester (Example 276, Step A) and 172 mg of 4-cyanophenylboronic acid. MS (ESI): exact mass calculated for $C_{18}H_{20}N_4$, 292.17; found, m/z 293.5 [M+H]$^+$. $^1$H NMR (500 MHz, $CD_3OD$): 7.92-7.90 (m, 2H), 7.50-7.48 (m, 2H), 4.65-4.58 (m, 1H), 3.42-3.40 (m, 2H), 3.21-3.19 (m, 2H), 2.81-2.78 (m, 2H), 2.66-2.62 (m, 2H), 2.30-2.25 (m, 2H), 1.85-1.74 (m, 2H).

Example 281

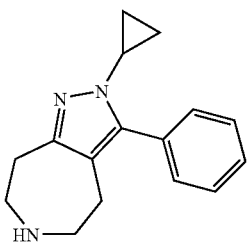

2-Cyclopropyl-3-phenyl-2,4,5,6,7,8-hexahydro-1,2,6-triaza-azulene

Step A. N'-cyclopropyl-hydrazinecarboxylic acid tert-butyl ester. To a solution of 1.37 g of 3-(4-cyano-phenyl)-oxaziridine-2-carboxylic acid tert-butyl ester in $Et_2O$ (8 mL) was added 1.2 mL of cyclopropylamine. The mixture was aged for 2 h and then concentrated in vacuo. Chromatography on $SiO_2$ (0 to 25% EtOAc/hexanes) provided an impure pale yellow solid that was sublimed under high vacuum in a 50° C. oil bath to afford 641 mg of the desired compound. $^1$H NMR (500 MHz, $CDCl_3$): 6.31 (br s, 1H), 3.49 (br s, 1H), 2.74 (br s, 1H), 1.48 (s, 9H), 0.52-0.48 (m, 4H).

Step B. Cyclopropyl-hydrazine hydrochloride. To a solution of the product from Step A (636 mg) in $CH_2Cl_2$ (10 mL) was added 9 mL of 4.0 M HCl in 1,4-dioxane. The mixture was aged for 12 h and then concentrated in vacuo to provide 507 mg of the title compound. $^1$H NMR (500 MHz, CD$_3$OD): 2.61-2.57 (m, 1H), 0.71-0.59 (m, 4H).

Step C. 2-Cyclopropyl-3-trifluoromethanesulfonyloxy-4,5,7,8-tetrahydro-2H-1,2,6-triaza-azulene-6-carboxylic acid tert-butyl ester. The desired triflate was prepared as in Steps A and B of Example 176, using cyclopropyl-hydrazine hydrochloride in place of phenylhydrazine and t-butanol in place of EtOH, with the addition of 3 equiv. of triethylamine.

Step D. The title compound (128 mg) was prepared according to Example 263 using 208 mg of 2-cyclopropyl-3-trifluoromethanesulfonyloxy-4,5,7,8-tetrahydro-2H-1,2,6-triaza-azulene-6-carboxylic acid tert-butyl ester and 84 mg of phenylboronic acid. MS (ESI): exact mass calculated for C$_{16}$H$_{19}$N$_3$, 253.16; found, m/z 254.4 [M+H]$^+$. $^1$H NMR (500 MHz, CD$_3$OD): 7.57-7.44 (m, 5H), 3.57-3.54 (m, 1H), 3.42-3.40 (m, 2H), 3.17-3.14 (m, 2H), 2.93-2.84 (m, 2H), 0.91-0.85 (m, 4H).

Example 282

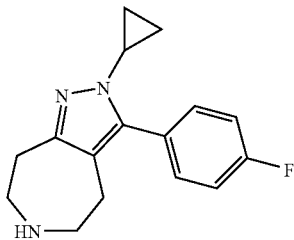

2-Cyclopropyl-3-(4-fluoro-phenyl)-2,4,5,6,7,8-hexahydro-1,2,6-triaza-azulene

The title compound (134 mg) was prepared according to Example 281 using 200 mg of 2-cyclopropyl-3-trifluoromethanesulfonyloxy-4,5,7,8-tetrahydro-2H-1,2,6-triaza-azulene-6-carboxylic acid tert-butyl ester (Example 281, Step C) and 92 mg of 4-fluorophenylboronic acid. MS (ESI): exact mass calculated for C$_{16}$H$_{18}$FN$_3$, 271.15; found, m/z 272.5 [M+H]$^+$. $^1$H NMR (500 MHz, CD$_3$OD): 7.51-7.47 (m, 2H), 7.31-7.27 (m, 2H), 3.55-3.51 (m, 1H), 3.41-3.39 (m, 2H), 3.23-3.14 (m, 2H), 3.00-2.83 (m, 2H), 0.93-0.084 (m, 4H).

Example 283

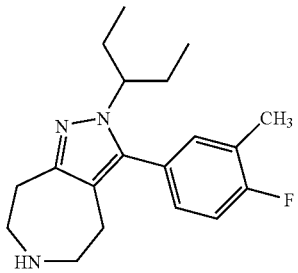

2-(1-Ethyl-propyl)-3-(4-fluoro-3-methyl-phenyl)-2,4,5,6,7,8-hexahydro-1,2,6-triaza-azulene The title compound (34 mg) was prepared according to Example 183 using 59 mg of 2-(1-ethyl-propyl)-3-trifluoromethanesulfonyloxy-4,5,7,8-tetrahydro-2H-1,2,6-triaza-azulene-6-carboxylic acid tert-butyl ester (Example 183, Step A) and 19 mg of 4-fluoro-3-methylphenylboronic acid. MS (ESI): exact mass calculated for C$_{19}$H$_{26}$FN$_3$, 315.21; found, m/z 316.5 [M+H]$^+$. $^1$H NMR (500 MHz, CD$_3$OD): 7.27-7.18 (m, 3H), 4.69-4.65 (m, 1H), 3.93-3.89 (m, 1H), 3.50-3.27 (m, 5H), 3.00-2.80 (m, 2H), 2.35 (s, 3H), 1.95-1.87 (m, 2H), 1.83-1.76 (m, 2H), 0.81-0.68 (m, 6H).

Example 284

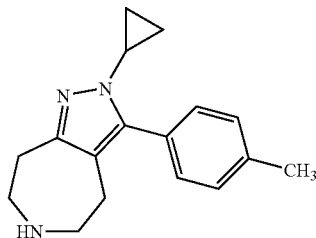

2-Cyclopropyl-3-p-tolyl-2,4,5,6,7,8-hexahydro-1,2,6-triaza-azulene

The title compound (133 mg) was prepared according to Example 281 using 200 mg of 2-cyclopropyl-3-trifluoromethanesulfonyloxy-4,5,7,8-tetrahydro-2H-1,2,6-triaza-azulene-6-carboxylic acid tert-butyl ester (Example 281, Step C) and 90 mg of 4-methylphenylboronic acid. MS (ESI): exact mass calculated for C$_{17}$H$_{21}$N$_3$, 267.17; found, m/z 268.5 [M+H]$^+$. $^1$H NMR (500 MHz, CD$_3$OD): 7.42-7.34 (m, 4H), 4.68-4.65 (m, 2H), 3.80-3.30 (m, 6H), 2.97 (br s, 2H), 2.44 (s, 3H), 0.94-0.91 (m, 4H).

Example 285

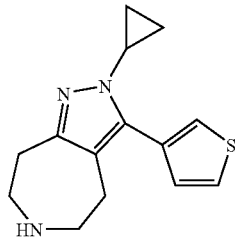

2-Cyclopropyl-3-thiophen-3-yl-2,4,5,6,7,8-hexahydro-1,2,6-triaza-azulene

The title compound (134 mg) was prepared according to Example 281 using 200 mg of 2-cyclopropyl-3-trifluoromethanesulfonyloxy-4,5,7,8-tetrahydro-2H-1,2,6-triaza-azulene-6-carboxylic acid tert-butyl ester (Example 281, Step C) and 84 mg of 3-thiopheneboronic acid. MS (ESI): exact mass calculated for C$_{14}$H$_{17}$N$_3$S, 259.11; found, m/z 260.4 [M+H]$^+$. $^1$H NMR (500 MHz, CD$_3$OD): 7.64-7.63 (m, 2H), 7.31-7.29 (m, 1H), 4.65 (br s, 1H), 3.70-3.60 (br s, 1H), 3.57-3.52 (m, 1H), 3.40-3.38 (m, 1H), 3.19 (br s, 1H), 3.13-3.11 (m, 1H), 2.99-2.96 (m, 1H), 2.91-2.89 (m, 1H), 0.93-0.88 (m, 4H).

Example 286

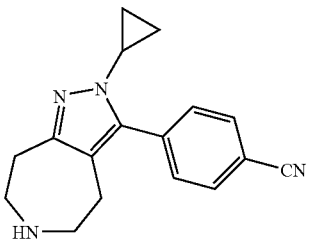

4-(2-Cyclopropyl-2,4,5,6,7,8-hexahydro-1,2,6-triaza-azulen-3-yl)-benzonitrile

The title compound (91 mg) was prepared according to Example 281 using 200 mg of 2-cyclopropyl-3-trifluoromethanesulfonyloxy-4,5,7,8-tetrahydro-2H-1,2,6-triaza-azulene-6-carboxylic acid tert-butyl ester (Example 281, Step C) and 97 mg of 4-cyanophenylboronic acid. MS (ESI): exact mass calculated for $C_{17}H_{18}N_4$, 278.15; found, m/z 279.4 [M+H]$^+$. $^1$H NMR (500 MHz, CD$_3$OD): 7.94-7.92 (m, 2H), 7.71-7.70 (m, 2H), 4.66 (br s, 1H), 3.71-3.68 (m, 1H), 3.47 (br s, 1H), 3.39-3.19 (m, 4H), 3.01-2.88 (m, 2H), 0.96-0.90 (m, 4H).

Example 287

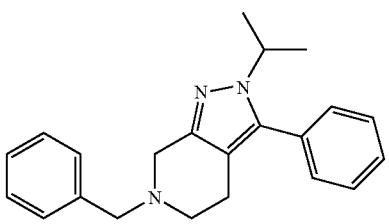

6-Benzyl-2-isopropyl-3-phenyl-4,5,6,7-tetrahydro-2H-pyrazolo[3,4-c]pyridine

Step A. Trifluoro-methanesulfonic acid 6-benzyl-2-isopropyl-4,5,6,7-tetrahydro-2H-pyrazolo[3,4-c]pyridin-3-yl ester. The desired triflate was prepared as in Step A of Example 189, using 1-benzyl-3-oxo-piperidine-4-carboxylic acid ethyl ester in place of the product from Example 59, Step A.

Step B. The title compound (54 mg) was prepared as in Example 263 using 200 mg of trifluoro-methanesulfonic acid 6-benzyl-2-isopropyl-4,5,6,7-tetrahydro-2H-pyrazolo[3,4-c]pyridin-3-yl ester and 85 mg of phenylboronic acid. MS (ESI): exact mass calculated for $C_{22}H_{25}N_3$, 331.20; found, m/z 332.5 [M+H]$^+$. $^1$H NMR (500 MHz, CD$_3$OD): 7.60-7.48 (m, 7H), 7.39-7.37 (m, 2H), 4.59-4.48 (m, 3H), 4.44-4.34 (m, 2H), 3.81-3.79 (m, 1H), 3.46-3.40 (m, 1H), 2.94-2.84 (m, 2H), 1.46-1.29 (m, 6H).

Example 288

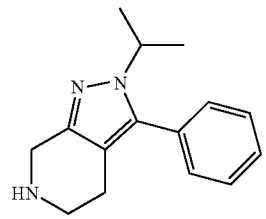

2-Isopropyl-3-phenyl-4,5,6,7-tetrahydro-2H-pyrazolo[3,4-c]pyridine

To a solution of the compound (98 mg) from Example 287, Step B in 5 mL of EtOH was added 98 mg of 10% Pd/C followed by 0.14 mL of 1,4-cyclohexadiene. The mixture was placed under N$_2$ and heated in an 80° C. oil bath for 5 h. The mixture was filtered and the filtrate was concentrated in vacuo to provide 67 mg of viscous colorless oil. Chromatography on SiO$_2$ (0 to 8% 2 M NH$_3$ in MeOH/EtOAc) afforded 59 mg of the title compound. The product (59 mg) was dissolved in Et$_2$O and treated with excess 1.0 M HCl in Et$_2$O for 30 min. The solvent was removed in vacuo to afford 68 mg of the corresponding HCl salt. MS (ESI): exact mass calculated for $C_{15}H_{19}N_3$, 241.16; found, m/z 242.4 [M+H]$^+$. $^1$H NMR (500 MHz, CD$_3$OD): 7.57-7.48 (m, 3H), 7.38-7.36 (m, 2H), 4.53 (m, 1H), 4.40-4.32 (m, 2H), 3.47 (t, J=6.2 Hz, 2H), 2.82 (t, J=6.2 Hz, 2H), 1.41 (d, J=6.7 Hz, 6H).

Example 289

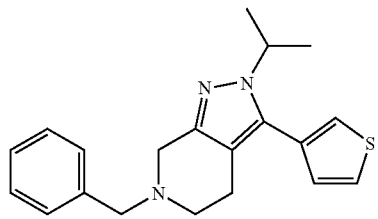

6-Benzyl-2-isopropyl-3-thiophen-3-yl-4,5,6,7-tetrahydro-2H-pyrazolo[3,4-c]pyridine The title compound (69 mg) was prepared according to Example 287 using 300 mg of trifluoro-methanesulfonic acid 6-benzyl-2-isopropyl-4,5,6,7-tetrahydro-2H-pyrazolo[3,4-c]pyridin-3-yl ester and 133 mg of 3-thiopheneboronic acid. MS (ESI): exact mass calculated for $C_{20}H_{23}N_3S$, 337.16; found, m/z 338.5 [M+H]$^+$. $^1$H NMR (500 MHz, CD$_3$OD): 7.66-7.65 (m, 1H), 7.60-7.57 (m, 3H), 7.55-7.53 (m, 3H), 7.21-7.20 (m, 1H), 4.65-4.52 (m, 3H), 4.42-4.33 (m, 2H), 3.82-3.79 (m, 1H), 3.44-3.40 (m, 1H), 2.94-2.91 (m, 2H), 1.46-1.35 (m, 6H).

Example 290

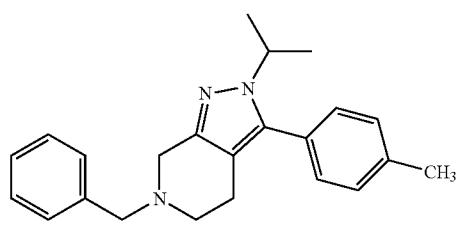

6-Benzyl-2-isopropyl-3-p-tolyl-4,5,6,7-tetrahydro-2H-pyrazolo[3,4-c]pyridine The title compound (67 mg) was prepared according to Example 287 using 300 mg of trifluoro-methanesulfonic acid 6-benzyl-2-isopropyl-4,5,6,7-tetrahydro-2H-pyrazolo[3,4-c]pyridin-3-yl ester and 141 mg of 4-methylphenylboronic acid. MS (ESI): exact mass calculated for $C_{23}H_{27}N_3$, 345.22; found, m/z 346.5 [M+H]$^+$. $^1$H NMR (500 MHz, $CD_3OD$): 7.60-7.58 (m, 2H), 7.54-7.53 (m, 3H), 7.37-7.35 (m, 2H), 7.28-7.24 (m, 2H), 4.58-4.49 (m, 3H), 4.42-4.33 (m, 2H), 3.81-3.78 (m, 1H), 3.45-3.41 (m, 1H), 2.90-2.82 (m, 2H), 2.41 (s, 3H), 1.42-1.29 (m, 6H).

Example 291

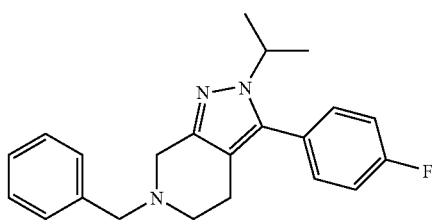

6-Benzyl-3-(4-fluoro-phenyl)-2-isopropyl-4,5,6,7-tetrahydro-2H-pyrazolo[3,4-c]pyridine The title compound (72 mg) was prepared according to Example 287 using 300 mg of trifluoro-methanesulfonic acid 6-benzyl-2-isopropyl-4,5,6,7-tetrahydro-2H-pyrazolo[3,4-c]pyridin-3-yl ester and 146 mg of 4-fluorophenylboronic acid. MS (ESI): exact mass calculated for $C_{22}H_{24}FN_3$, 349.20; found, m/z 350.5 [M+H]$^+$. $^1$H NMR (500 MHz, $CD_3OD$): 7.60-7.57 (m, 2H), 7.55-7.53 (m, 3H), 7.43-7.40 (m, 2H), 7.32-7.27 (m, 2H), 4.59-4.34 (m, 5H), 3.81-3.79 (m, 1H), 3.46-3.40 (m, 1H), 2.90-2.85 (m, 2H), 1.43-1.36 (m, 6H).

Example 292

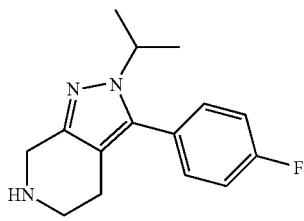

3-(4-Fluoro-phenyl)-2-isopropyl-4,5,6,7-tetrahydro-2H-pyrazolo[3,4-c]pyridine The title compound (101 mg) was prepared according to Example 288 using 153 mg of 6-benzyl-3-(4-fluoro-phenyl)-2-isopropyl-4,5,6,7-tetrahydro-2H-pyrazolo[3,4-c]pyridine in place of the product of Example 287, Step B. MS (ESI): exact mass calculated for $C_{15}H_{18}FN_3$, 259.15; found, m/z 260.4 [M+H]$^+$. $^1$H NMR (500 MHz, $CD_3OD$): 7.42-7.28 (m, 4H), 4.50-4.47 (m, 1H), 4.35 (br s, 2H), 3.49-3.46 (m, 2H), 2.81-2.79 (m, 2H), 1.42-1.36 (m, 6H).

Example 293

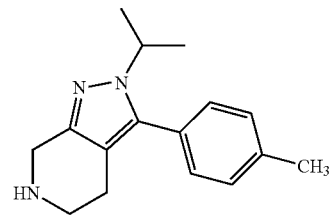

2-Isopropyl-3-p-tolyl-4,5,6,7-tetrahydro-2H-pyrazolo[3,4-c]pyridine

The title compound (114 mg) was prepared according to Example 288 using 163 mg of 6-benzyl-2-isopropyl-3-p-tolyl-4,5,6,7-tetrahydro-2H-pyrazolo[3,4-c]pyridine in place of the product of Example 287, Step B. MS (ESI): exact mass calculated for $C_{16}H_{21}N_3$, 255.17; found, m/z 256.4 [M+H]$^+$. $^1$H NMR (500 MHz, $CD_3OD$): 7.43-7.32 (m, 2H), 7.30-7.20 (m, 2H), 4.52 (m, 1H), 4.39-4.31 (m, 2H), 3.47 (t, J=6.2 Hz, 2H), 2.80 (t, J=6.2 Hz, 2H), 1.42 (d, J=6.6 Hz, 6H).

Example 294

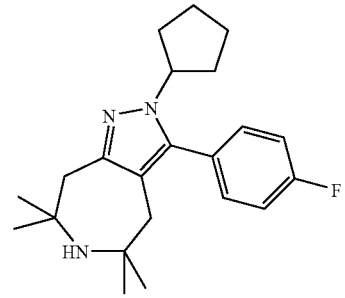

2-Cyclopentyl-3-(4-fluoro-phenyl)-5,5,7,7-tetramethyl-2,4,5,6,7,8-hexahydro-1,2,6-triaza-azulene Step A. Trifluoro-methanesulfonic acid 2-cyclopentyl-5,5,7,7-tetramethyl-2,4,5,6,7,8-hexahydro-1,2,6-triaza-azulen-3-yl ester. The desired triflate was prepared as in Step A of Example 180 using 2,2,7,7-tetramethyl-5-oxo-azepane-4-carboxylic acid ethyl ester (made from 2,2,6,6-tetramethyl-piperidin-4-one as shown in Step A of Example 59) in place of 5-oxo-azepane-1,4-dicarboxylic acid tert-butyl ester 4-ethyl ester.

Step B. The title compound was prepared as in Step A of Example 263, using 216 mg of trifluoro-methanesulfonic acid 2-cyclopentyl-5,5,7,7-tetramethyl-2,4,5,6,7,8-hexahydro-1,2,6-triaza-azulen-3-yl ester and 103 mg of 4-fluorophenylboronic acid. The product (134 mg) was dissolved in $Et_2O$ and treated with excess 1.0 M HCl in $Et_2O$ for 30 min. The solvent was removed in vacuo to afford 146 mg of the corresponding HCl salt. MS (ESI): exact mass calculated for $C_{22}H_{30}FN_3$, 355.24; found, m/z 356.5 [M+H]$^+$. $^1$H NMR (500 MHz, $CD_3OD$): 7.36-7.26 (m, 4H), 4.47-4.41 (m, 1H), 3.15 (s, 2H), 2.71 (s, 2H), 2.03-1.88 (m, 6H), 1.61-1.57 (m, 2H), 1.44 (s, 6H), 1.35 (s, 6H).

Example 295

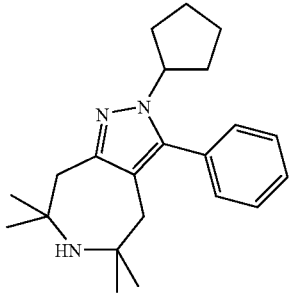

2-Cyclopentyl-5,5,7,7-tetramethyl-3-phenyl-2,4,5,6,7,8-hexahydro-1,2,6-triaza-azulene The title compound (129 mg) was prepared as in Example 294, using 263 mg of trifluoro-methanesulfonic acid 2-cyclopentyl-5,5,7,7-tetramethyl-2,4,5,6,7,8-hexahydro-1,2,6-triaza-azulen-3-yl ester and 110 mg of phenylboronic acid. MS (ESI): exact mass calculated for $C_{22}H_{31}N_3$, 337.25; found, m/z 338.5 [M+H]$^+$. $^1$H NMR (500 MHz, CD$_3$OD): 7.56-7.49 (m, 3H), 7.32-7.30 (m, 2H), 4.51-4.44 (m, 1H), 3.12 (s, 2H), 2.72 (s, 2H), 2.03-1.88 (m, 6H), 1.61-1.57 (m, 2H), 1.45 (s, 6H), 1.35 (s, 6H).

Example 296

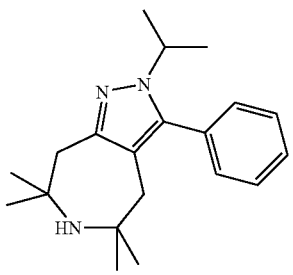

2-Isopropyl-5,5,7,7-tetramethyl-3-phenyl-2,4,5,6,7,8-hexahydro-1,2,6-triaza-azulene Step A. Trifluoro-methanesulfonic acid 2-isopropyl-5,5,7,7-tetramethyl-2,4,5,6,7,8-hexahydro-1,2,6-triaza-azulen-3-yl ester. The desired triflate was prepared as in Step A of Example 294 using isopropylhydrazine in place of cyclopentylhydrazine.

Step B. The title compound (98 mg) was prepared as in Step B of Example 294 using 196 mg trifluoro-methanesulfonic acid 2-isopropyl-5,5,7,7-tetramethyl-2,4,5,6,7,8-hexahydro-1,2,6-triaza-azulen-3-yl ester and 87 mg of phenylboronic acid. MS (ESI): exact mass calculated for $C_{20}H_{29}N_3$, 311.24; found, m/z 312.5 [M+H]$^+$. $^1$H NMR (500 MHz, CD$_3$OD): 7.57-7.52 (m, 3H), 7.32-7.31 (m, 2H), 4.34 (m, 1H), 3.11 (s, 2H), 2.71 (s, 2H), 1.49-1.34 (m, 18H).

Example 297

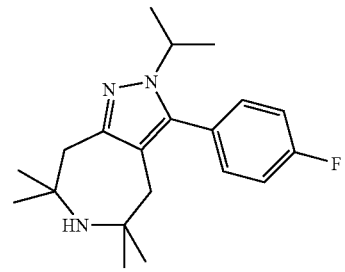

3-(4-Fluoro-phenyl)-2-isopropyl-5,5,7,7-tetramethyl-2,4,5,6,7,8-hexahydro-1,2,6-triaza-azulene The title compound (100 mg) was prepared as in Example 296 using 196 mg of trifluoro-methanesulfonic acid 2-isopropyl-5,5,7,7-tetramethyl-2,4,5,6,7,8-hexahydro-1,2,6-triaza-azulen-3-yl ester and 100 mg of 4-fluorophenylboronic acid. MS (ESI): exact mass calculated for $C_{20}H_{28}FN_3$, 329.23; found, m/z 330.5 [M+H]$^+$. $^1$H NMR (500 MHz, CD$_3$OD): 7.36-7.27 (m, 4H), 4.31 (m, 1H), 3.10 (s, 2H), 2.70 (s, 2H), 1.47-1.34 (m, 18H).

Example 298

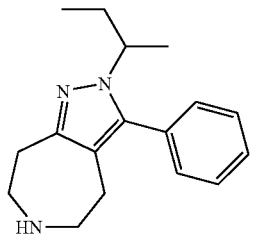

2-sec-Butyl-3-phenyl-2,4,5,6,7,8-hexahydro-1,2,6-triaza-azulene

Step A. 2-sec-Butyl-3-trifluoromethanesulfonyloxy-4,5,7,8-tetrahydro-2H-1,2,6-triaza-azulene-6-carboxylic acid tert-butyl ester. The desired triflate was prepared according to Example 189, Step A, using sec-butylhydrazine hydrochloride (made from 2-butanone as shown in Example 177, Step A) in place of isopropylhydrazine hydrochloride.

Step B. The title compound (97 mg) was prepared as in Example 263 using 216 mg of the triflate from Step A and 106 mg of phenylboronic acid. MS (ESI): exact mass calculated for $C_{17}H_{23}N_3$, 269.38; found, m/z 270.5 [M+H]$^+$. $^1$H NMR (500 MHz, CD$_3$OD): 7.58-7.50 (m, 3H), 7.35-7.31 (m, 2H), 4.15-4.07 (m, 1H), 3.50-3.18 (m, 6H), 2.88-2.73 (m, 2H), 1.97-1.86 (m, 1H), 1.74-1.65 (m, 1H), 1.43 (d, J=6.8 Hz, 3H), 0.64 (t, J=7.4 Hz, 3H).

Example 299

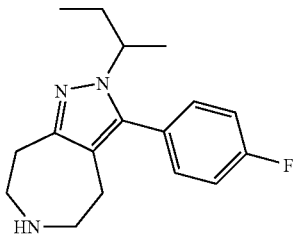

2-sec-Butyl-3-(4-fluoro-phenyl)-2,4,5,6,7,8-hexahydro-1,2,6-triaza-azulene

The title compound (71 mg) was prepared as in Example 263 using 245 mg of the triflate from Example 298, Step A, and 153 mg of 4-fluorophenylboronic acid. MS (ESI): exact mass calculated for $C_{17}H_{22}FN_3$, 287.38; found, m/z 288.5 [M+H]+. 1H NMR (500 MHz, CD3OD): 7.41-7.35 (m, 2H), 7.34-7.28 (m, 2H), 4.12-4.03 (m, 1H), 3.51-3.20 (m, 6H), 2.90-2.73 (m, 2H), 1.97-1.87 (m, 1H), 1.75-1.65 (m, 1H), 1.44 (d, J=6.6 Hz, 3H), 0.66 (t, J=7.4 Hz, 3H).

Example 300

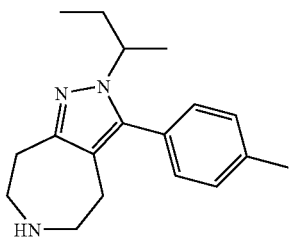

2-sec-Butyl-3-p-tolyl-2,4,5,6,7,8-hexahydro-1,2,6-triaza-azulene

The title compound (116 mg) was prepared as in Example 263 using 249 mg of the triflate from Example 298, Step A, and 129 mg of 4-methylphenylboronic acid. MS (ESI): exact mass calculated for $C_{18}H_{25}N_3$, 283.41; found, m/z 284.5 [M+H]+. 1H NMR (500 MHz, CD3OD): 7.42-7.37 (m, 2H), 7.27-7.21 (m, 2H), 4.23-4.12 (m, 1H), 3.55-3.23 (m, 6H), 2.92-2.75 (m, 2H), 2.43 (s, 3H), 1.98-1.88 (m, 1H), 1.77-1.68 (m, 1H), 1.46 (d, J=6.6 Hz, 3H), 0.67 (t, J=7.4 Hz, 3H).

Example 301

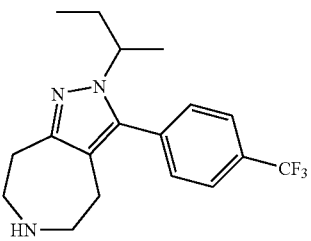

2-sec-Butyl-3-(4-trifluoromethyl-phenyl)-2,4,5,6,7,8-hexahydro-1,2,6-triaza-azulene The title compound (71 mg) was prepared as in Example 263 using 257 mg of the triflate from Example 298, Step A, and 175 mg of 4-trifluoromethylphenylboronic acid. MS (ESI): exact mass calculated for $C_{18}H_{22}F_3N_3$, 337.38; found, m/z 338.5 [M+H]+. 1H NMR (500 MHz, CD3OD): 7.91-7.85 (m, 2H), 7.61-7.54 (m, 2H), 4.11-4.03 (m, 1H), 3.52-3.20 (m, 6H), 2.93-2.75 (m, 2H), 1.99-1.88 (m, 1H), 1.75-1.65 (m, 1H), 1.45 (d, J=6.6 Hz, 3H), 0.65 (t, J=7.4 Hz, 3H).

Example 302

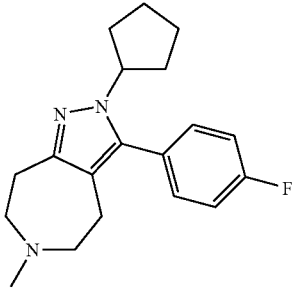

2-Cyclopentyl-3-(4-fluoro-phenyl)-6-methyl-2,4,5,6,7,8-hexahydro-1,2,6-triaza-azulene The title compound (186 mg) was prepared from 216 mg of the product of Example 182 according to Example 208. The product was dissolved in Et2O and treated with excess 1.0 M HCl in Et2O to afford the corresponding HCl salt. MS (ESI): exact mass calculated for $C_{19}H_{24}FN_3$, 313.41; found, m/z 314.4 [M+H]+. 1H NMR (500 MHz, CD3OD): 7.38-7.34 (m, 2H), 7.31-7.26 (m, 2H), 4.47 (m, 1H), 3.75-3.69 (m, 1H), 3.64-3.57 (m, 1H), 3.33-3.15 (m, 4H), 3.02 (s, 3H), 2.91-2.83 (m, 1H), 2.78-2.71 (m, 1H), 2.04-1.84 (m, 6H), 1.65-1.54 (m, 2H).

Example 303

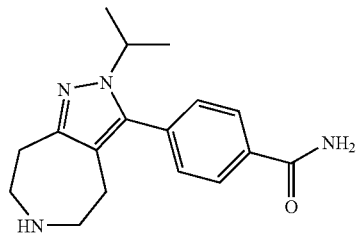

4-(2-Isopropyl-2,4,5,6,7,8-hexahydro-1,2,6-triaza-azulen-3-yl)-benzamide

The title compound (26 mg) was prepared as in Example 263 using 206 mg of the triflate from Example 189, Step A, and 135 mg of 4-benzamide boronic acid. MS (ESI): exact mass calculated for $C_{17}H_{22}N_4O$, 298.38; found, m/z 299.5 [M+H]+. 1H NMR (500 MHz, CDCl3): 7.93-7.89 (m, 2H), 7.37-7.34 (m, 2H), 6.16 (br s, 1H), 5.81 (br s, 1H), 4.27 (m, 1H), 3.05-3.00 (m, 2H), 2.97-2.88 (m, 4H), 2.51-2.46 (m, 2H), 1.41 (d, J=6.6 Hz, 6H).

Example 304

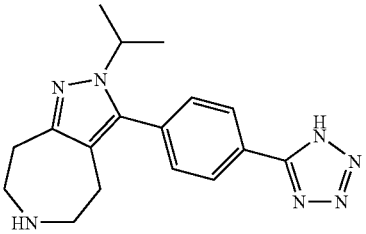

2-Isopropyl-3-[4-(1H-tetrazol-5-yl)-phenyl]-2,4,5,6,7,8-hexahydro-1,2,6-triaza-azulene Step A. 2-Isopropyl-3-[4-(1H-tetrazol-5-yl)-phenyl]-4,5,7,8-tetrahydro-2H-1,2,6-triaza-azulene-6-carboxylic acid tert-butyl ester. A toluene solution of 3-(4-cyano-phenyl)-2- isopropyl-4,5,7,8-tetrahydro-2H-1,2,6-triaza-azulene-6-carboxylic acid tert-butyl ester (intermediate in Example 212) and tributyltin azide was heated at reflux for 48 h. The mixture was concentrated and the residue was purified on SiO$_2$ (0 to 75% EtOAc/hexanes) to afford 89 mg of desired tetrazole as a glass.

Step B. The product from Step A was dissolved in dioxane and treated with HCl (4 M in dioxane, 1 mL) and mixture was stirred at RT. After 48 h, the liquid was decanted and the solids washed with dioxane and dried under vacuum to afford 60 mg of the title compound. MS (ESI): exact mass calculated for C$_{17}$H$_{21}$N$_7$, 323.40; found, m/z 324.4 [M+H]$^+$. $^1$H NMR (500 MHz, CD$_3$OD): 8.24-8.20 (m, 2H), 7.58-7.55 (m, 2H), 4.42 (m, 1H), 3.44-3.40 (m, 2H), 3.34-3.30 (m, 2H), 3.21-3.17 (m, 2H), 2.84-2.80 (m, 2H), 1.42 (d, J=6.8, 6H).

Example 305

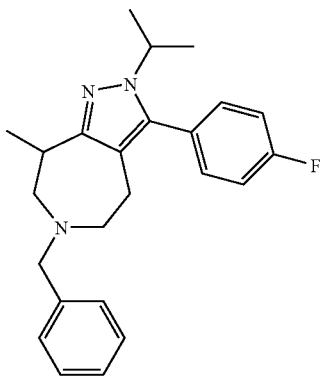

6-Benzyl-3-(4-fluoro-phenyl)-2-isopropyl-8-methyl-2,4,5,6,7,8-hexahydro-1,2,6-triaza-azulene Step A. Trifluoro-methanesulfonic acid 6-benzyl-2-isopropyl-8-methyl-2,4,5,6,7,8-hexahydro-1,2,6-triaza-azulen-3-yl ester. The desired triflate was prepared as in Step A of Example 189 using 1-benzyl-6-methyl-5-oxo-azepane-4-carboxylic acid ethyl ester (made from 1-benzyl-3-methyl-piperidin-4-one as shown in Step A of Example 59) in place of 5-oxo-azepane-1,4-dicarboxylic acid tert-butyl ester 4-ethyl ester.

Step B. The title compound (29 mg) was prepared as in Example 287, Step B, from 151 mg of the triflate from Step A and 110 mg of 4-fluorophenylboronic acid. MS (ESI): exact mass calculated for C$_{24}$H$_{28}$FN$_3$, 377.50; found, m/z 378.5 [M+H]$^+$. $^1$H NMR (500 MHz, CDCl$_3$): 7.41-7.37 (m, 2H), 7.33-7.29 (m, 2H), 7.27-7.18 (m, 3H), 7.16-7.10 (m, 2H), 4.24 (m, 1H), 3.78 (d, J=13.4 Hz, 1H), 3.70 (d, J=13.4 Hz, 1H), 3.19-3.12 (m, 1H), 2.78-2.68 (m, 3H), 2.55-2.43 (m, 3H), 1.40 (d, J=6.6, 3H), 1.37 (d, J=6.6, 3H), 1.33 (d, J=7.1, 3H).

Example 306

3-(4-Fluoro-phenyl)-2-isopropyl-8-methyl-2,4,5,6,7,8-hexahydro-1,2,6-triaza-azulene Step A. 3-Methyl-4-oxo-piperidine-1-carboxylic acid tert-butyl ester. To a −78° C. solution of 4-oxo-piperidine-1-carboxylic acid tert-butyl ester in THF (100 mL) was added LDA (50 mL, 1.8 M in THF) with stirring over 1 h. Methyl iodide was then added (5 mL) and the mixture was allowed to warm slowly to RT and was stirred for 24 h. The reaction was quenched by the addition of satd. aq. NH$_4$Cl (20 mL). The mixture was poured into H$_2$O (800 mL), extracted with EtOAc, and concentrated. Purification on SiO$_2$ (120 g, 0 to 10% EtOAc/hexanes) gave 3.83 g of the desired product as an off-white solid. $^1$H NMR (500 MHz, CDCl$_3$): 4.23-4.14 (m, 2H), 3.31-3.21 (m, 1H), 2.61-2.37 (m, 4H), 1.50 (s, 9H), 1.05 (d, J=6.6 Hz, 3H).

Step B. 2-Isopropyl-8-methyl-3-trifluoromethanesulfonyloxy-4,5,7,8-tetrahydro-2H-1,2,6-triaza-azulene-6-carboxylic acid tert-butyl ester. The product from Step A (2.01 g) was treated with ethyl diazoacetate (1.5 mL) as in Step A of Example 59. The resulting material (2.90 g) was then transformed to the desired triflate (2.68 g) as shown in Step A of Example 189. The reaction sequence also produced 0.60 g of 2-isopropyl-4-methyl-3-trifluoromethanesulfonyloxy-4,5,7,8-tetrahydro-2H-1,2,6-triaza-azulene-6-carboxylic acid tert-butyl ester.

Step C. The title compound (1.62 g) was prepared as in Step A of Example 263 from 2.68 g of the triflate of Step B and 1.36 g of 4-fluorophenylboronic acid. The coupling product was treated with TFA (20 mL) in 50 mL of CH$_2$Cl$_2$ for 16 h. The mixture was concentrated and the residue was diluted with 1 M NaOH (50 mL) and extracted with CH$_2$Cl$_2$ (50 mL, 3×). The combined organic layers were dried over Na$_2$SO$_4$ and concentrated to provide the desired material. MS (ESI): exact mass calculated for C$_{17}$H$_{22}$FN$_3$, 287.18; found, m/z 288.4 [M+H]$^+$. $^1$H NMR (500 MHz, CDCl$_3$): 7.18-7.05 (m, 4H), 4.16 (m, 1H), 3.08-2.97 (m, 2H), 2.96-2.83 (m, 2H), 2.78-2.71 (m, 1H), 2.49-2.31 (m, 2H), 1.34 (d, J=6.6 Hz, 3H), 1.31 (d, J=6.6 Hz, 3H), 1.29 (d, J=7.3 Hz, 3H).

Example 307

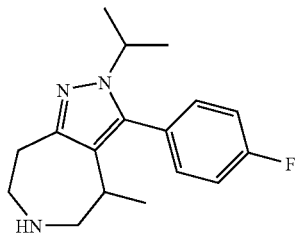

3-(4-Fluoro-phenyl)-2-isopropyl-4-methyl-2,4,5,6,7,8-hexahydro-1,2,6-triaza-azulene The title compound (154 mg) was prepared as in Example 177, Steps C and D, from 0.60 g of the triflate of Example 306, Step B, and 0.57 g of 4-fluorophenylboronic acid. MS (ESI): exact mass calculated for C$_{17}$H$_{22}$FN$_3$, 287.18; found, m/z 288.4 [M+H]$^+$. $^1$H NMR (500 MHz, CDCl$_3$): 7.25-7.20 (m, 2H), 7.17-7.12 (m, 2H), 4.15 (m, 1H), 3.35-3.30 (m, 1H), 3.08-3.03 (m, 1H), 3.00-2.85 (m, 3H), 2.77-2.71 (m, 1H), 2.57-2.51 (m, 1H), 1.39 (d, J=6.6 Hz, 3H), 1.36 (d, J=6.6 Hz, 3H), 1.15 (d, J=7.3 Hz, 3H).

Example 308

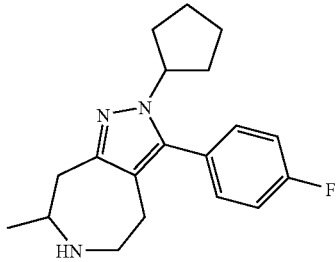

2-Cyclopentyl-3-(4-fluoro-phenyl)-7-methyl-2,4,5,6,
7,8-hexahydro-1,2,6-triaza-azulene Step A. 2-Methyl-4-oxo-piperidine-1-carboxylic acid tert-butyl ester. A solution of 1,4-dioxa-8-aza-spiro[4.5]decane-8-carboxylic acid tert-butyl ester (2.97 g) in TMEDA (2.2 mL) was cooled to −78° C. and sec-BuLi (1.8 M in THF, 13 mL) was added dropwise. The resulting yellow solution was aged at −78° C. for 1 h. Methyl iodide (1.5 mL) was added and the mixture was warmed from −78° C. to RT over 16 h. The reaction mixture was poured into water (800 mL) and extracted with EtOAc. The combined organic extracts were washed with $H_2O$, brine, and dried over $Na_2SO_4$. Purification on $SiO_2$ (330 g, 5 to 20% EtOAc/hexanes) provided 1.65 g of 7-methyl-1,4-dioxa-8-aza-spiro[4.5]decane-8-carboxylic acid tert-butyl ester. Multiple aliquots of this ester were combined (2.29 g), treated with 5 mL of conc. HCl in 10 mL of dioxane, and heated at 65° C. for 6 h. The solvent was removed and the residue was dissolved in $CH_2Cl_2$ and treated with di-tert-butyldicarbonate (1.0 g). After 5 d, the mixture was diluted with satd. aq. $NaHCO_3$ and $H_2O$, and extracted with $CH_2Cl_2$. Purification on $SiO_2$ (120 g, 5 to 15% EtOAc/hexanes) provided 1.40 g of the desired product as a white solid. $^1$H NMR (500 MHz, $CDCl_3$): 4.69-4.59 (m, 1H), 4.21-4.12 (m, 1H), 3.30-3.20 (m, 1H), 2.66-2.57 (m, 1H), 2.47-2.36 (m, 1H), 2.32-2.23 (m, 1H), 2.22-2.15 (m, 1H), 1.42 (s, 9H), 1.11 (d, J=7.1 Hz, 3H).

Step B. 2-Cyclopentyl-7-methyl-3-trifluoromethanesulfonyloxy-4,5,7,8-tetrahydro-2H-1,2,6-triaza-azulene-6-carboxylic acid tert-butyl ester. The product from Step A (1.40 g) was treated with ethyl diazoacetate as in Step A of Example 59. The resulting material (1.0 g) was transformed to the desired triflate (0.78 g) as outlined in Step A of Example 180. The reaction sequence also produced 2-cyclopentyl-5-methyl-3-trifluoromethanesulfonyloxy-4,5,7,8-tetrahydro-2H-1,2,6-triaza-azulene-6-carboxylic acid tert-butyl ester.

Step C. The title compound (160.4 mg) was prepared as in Example 263 from 301 mg of the triflate from Step B and 185 mg of 4-fluorophenylboronic acid. The sequence also produced 2-cyclopentyl-3-(4-fluoro-phenyl)-5-methyl-2,4,5,6,7,8-hexahydro-1,2,6-triaza-azulene. The isomers were separated by SFC chromatography. MS (ESI): exact mass calculated for $C_{19}H_{24}FN_3$, 313.41; found, m/z 314.4 [M+H]$^+$. $^1$H NMR (500 MHz, $CD_3OD$): 7.25-7.21 (m, 2H), 7.18-7.12 (m, 2H), 4.22 (m, 1H), 3.24-3.18 (m, 1H), 3.03-2.92 (m, 2H), 2.76-2.67 (m, 2H), 2.60-2.52 (m, 1H), 2.45-2.39 (m, 1H), 2.16-1.82 (m 6H), 1.59-1.47 (m, 2H), 1.25 (d, J=6.3 Hz, 3H).

Example 309

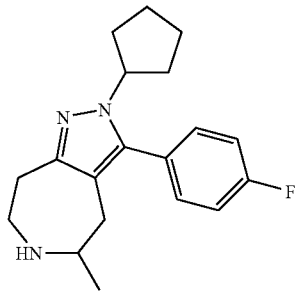

2-Cyclopentyl-3-(4-fluoro-phenyl)-5-methyl-2,4,5,6,
7,8-hexahydro-1,2,6-triaza-azulene The title compound (3.8 mg) was prepared as outlined in Example 308. MS (ESI): exact mass calculated for $C_{19}H_{24}FN_3$, 313.41; found, m/z 314.4 [M+H]$^+$. $^1$H NMR (500 MHz, $CDCl_3$): 7.24-7.19 (m, 2H), 7.18-7.13 (m, 2H), 4.31 (m, 1H), 3.42-3.35 (m, 1H), 3.09-2.90 (m, 4H), 2.57-2.45 (m, 2H), 2.14-1.80 (m 6H), 1.58-1.48 (m, 2H), 1.22 (d, J=6.3 Hz, 3H).

Example 310

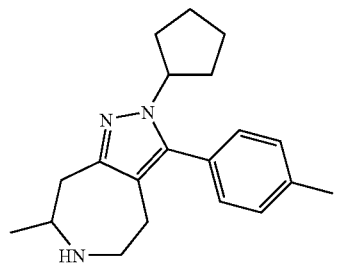

2-Cyclopentyl-7-methyl-3-p-tolyl-2,4,5,6,7,8-
hexahydro-1,2,6-triaza-azulene

The title compound (64 mg) was prepared from 193 mg of the triflate from Example 308, Step B, and 117 mg of 4-methylphenylboronic acid. MS (ESI): exact mass calculated for $C_{20}H_{27}N_3$, 309.45; found, m/z 310.4 [M+H]$^+$. $^1$H NMR (500 MHz, $CDCl_3$): 7.28-7.25 (m, 2H), 7.17-7.13 (m, 2H), 4.39 (m, 1H), 3.21-3.16 (m, 1H), 3.03-2.92 (m, 2H), 2.74-2.67 (m, 2H), 2.59-2.52 (m, 1H), 2.49-2.43 (m, 1H), 2.40 (s, 3H), 2.17-1.82 (m, 6H), 1.59-1.47 (m, 2H), 1.24 (d, J=6.3 Hz, 3H).

Example 311

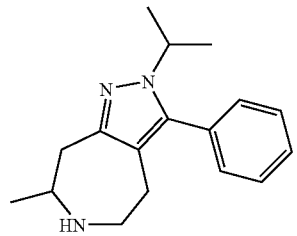

2-Isopropyl-7-methyl-3-phenyl-2,4,5,6,7,8-hexahydro-1,2,6-triaza-azulene

The title compound (102 mg) was prepared as in Example 263 using 260 mg of 2-isopropyl-7-methyl-3-trifluoromethanesulfonyloxy-4,5,7,8-tetrahydro-2H-1,2,6-triaza-azulene-6-carboxylic acid tert-butyl ester (as outlined in Example 308 replacing cyclopentyl hydrazine with isopropyl hydrazine) and 101 mg of phenylboronic acid. The reaction sequence also yielded 2-isopropyl-5-methyl-3-phenyl-2,4,5,6,7,8-hexahydro-1,2,6-triaza-azulene. MS (ESI): exact mass calculated for $C_{17}H_{23}N_3$, 269.19; found, m/z 270.5 [M+H]$^+$. $^1$H NMR (600 MHz, CD$_3$OD): 7.58-7.52 (m, 3H), 7.36-7.35 (m, 2H), 4.43 (m, 1H), 3.65-3.57 (m, 1H), 3.51-3.48 (m, 1H), 3.23-3.11 (m, 3H), 2.87-2.82 (m, 2H), 2.76-2.73 (m, 1H), 1.48 (d, J=6.4 Hz, 3H), 1.43-1.40 (m, 6H).

Example 312

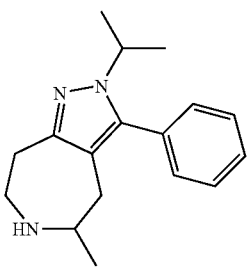

2-Isopropyl-5-methyl-3-phenyl-2,4,5,6,7,8-hexahydro-1,2,6-triaza-azulene

The title compound (28 mg) was prepared as in Example 311 and purified by SFC chromatography. MS (ESI): exact mass calculated for $C_{17}H_{23}N_3$, 269.19; found, m/z 270.4 [M+H]$^+$. $^1$H NMR (600 MHz, CD$_3$OD): 7.58-7.52 (m, 3H), 7.35-7.33 (m, 2H), 4.40 (m, 1H), 3.63-3.59 (m, 1H), 3.5-3.47 (m, 1H), 3.31-3.19 (m, 3H), 2.80-2.68 (m, 2H), 1.43-1.39 (m, 6H), 1.34 (d, J=6.6 Hz, 3H).

Example 313

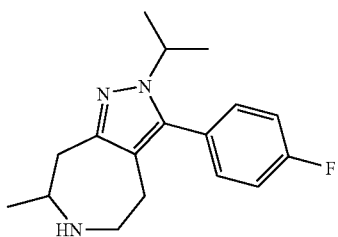

3-(4-Fluoro-phenyl)-2-isopropyl-7-methyl-2,4,5,6,7,8-hexahydro-1,2,6-triaza-azulene The title compound (127 mg) was prepared as in Example 311 using 260 mg of 2-isopropyl-7-methyl-3-trifluoromethanesulfonyloxy-4,5,7,8-tetrahydro-2H-1,2,6-triaza-azulene-6-carboxylic acid tert-butyl ester and 115 of 4-fluorophenylboronic acid. The reaction sequence also yielded 3-(4-fluoro-phenyl)-2-isopropyl-5-methyl-2,4,5,6,7,8-hexahydro-1,2,6-triaza-azulene. MS (ESI): exact mass calculated for $C_{17}H_{22}FN_3$, 287.18; found, m/z 288.5 [M+H]$^+$. $^1$H NMR (600 MHz, CD$_3$OD): 7.39-7.37 (m, 2H), 7.32-7.28 (m, 2H), 4.36 (m, 1H), 3.61-3.56 (m, 1H), 3.50-3.47 (m, 1H), 3.20-3.08 (m, 3H), 2.85-2.80 (m, 1H), 2.73-2.69 (m, 1H), 1.46 (d, J=6.6 Hz, 3H), 1.41-1.38 (m, 6H).

Example 314

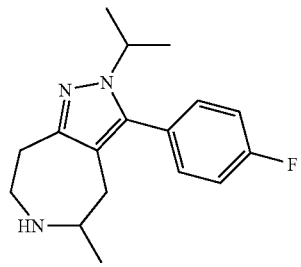

3-(4-Fluoro-phenyl)-2-isopropyl-5-methyl-2,4,5,6,7,8-hexahydro-1,2,6-triaza-azulene The title compound (36 mg) was prepared as in Example 311 and purified by chromatography on SFC. MS (ESI): exact mass calculated for $C_{17}H_{22}FN_3$, 287.18; found, m/z 288.5 [M+H]$^+$. $^1$H NMR (600 MHz, CD$_3$OD): 7.37-7.35 (m, 2H), 7.31-7.28 (m, 2H), 4.33 (m, 1H), 3.61-3.58 (m, 1H), 3.48-3.45 (m, 1H), 3.27-3.13 (m, 3H), 2.77-2.65 (m, 2H), 1.41-1.37 (m, 6H), 1.34 (d, J=6.6 Hz, 3H).

Example 315

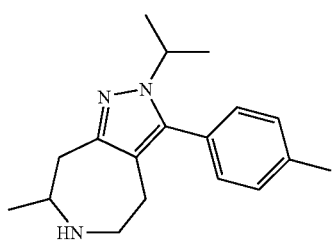

2-Isopropyl-7-methyl-3-p-tolyl-2,4,5,6,7,8-hexahydro-1,2,6-triaza-azulene

The title compound (127 mg) was prepared as in Example 311 using 260 mg of 2-isopropyl-7-methyl-3-trifluoromethanesulfonyloxy-4,5,7,8-tetrahydro-2H-1,2,6-triaza-azulene-6-carboxylic acid tert-butyl ester and 112 mg of 4-methylphenylboronic acid. The reaction sequence also yielded 2-isopropyl-5-methyl-3-p-tolyl-2,4,5,6,7,8-hexahydro-1,2,6-triaza-azulene. MS (ESI): exact mass calculated for $C_{18}H_{25}N_3$, 283.20; found, m/z 284.5 [M+H]$^+$. $^1$H NMR (600 MHz, CD$_3$OD): 7.38-7.36 (m, 2H), 7.22-7.20 (m, 2H), 4.41 (m, 1H), 3.60-3.56 (m, 1H), 3.50-3.45 (m, 1H), 3.21-3.06 (m, 3H), 2.84-2.70 (m, 2H), 1.46 (d, J=6.6 Hz, 3H), 1.42-1.37 (m, 6H).

Examples 316 through 323 were prepared as described in Example 238, with adjustments as noted.

Example 316

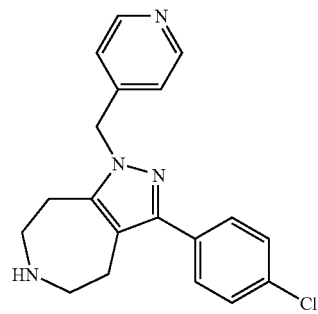

3-(4-Chloro-phenyl)-1-pyridin-4-ylmethyl-1,4,5,6,7,8-hexahydro-1,2,6-triaza-azulene The title compound (0.02 g) was prepared from 3-(4-chloro-phenyl)-4,5,7,8-tetrahydro-1H-1,2,6-triaza-azulene-6-carboxylic acid tert-butyl ester (Example 103, Step B; 0.3 mmol) using 4-chloromethyl-pyridine hydrogen chloride (0.5 mmol) in place of 2-chloromethyl-thiophene. MS (ESI): exact mass calculated for $C_{19}H_{19}ClN_4$, 338.13; found, m/z 339.3 [M+H]$^+$. $^1$H NMR (500 MHz, CDCl$_3$): 8.49-8.48 (m, 2H), 7.43-7.41 (m, 2H), 7.33-7.31 (m, 2H), 6.90-6.89 (m, 2H), 5.28 (s, 2H), 2.92-2.87 (m, 2H), 2.75-2.73 (m, 1H), 2.66-2.64 (m, 1H).

Example 317

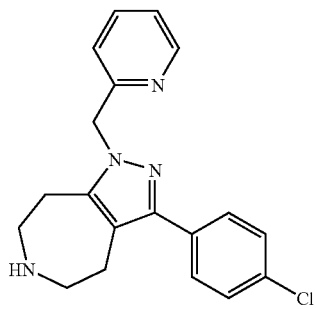

3-(4-Chloro-phenyl)-1-pyridin-2-ylmethyl-1,4,5,6,7,8-hexahydro-1,2,6-triaza-azulene The title compound (0.01 g) was prepared from 3-(4-chloro-phenyl)-4,5,7,8-tetrahydro-1H-1,2,6-triaza-azulene-6-carboxylic acid tert-butyl ester (Example 103, Step B; 0.4 mmol) using 2-chloromethyl-pyridine hydrogen chloride (0.5 mmol) in place of 2-chloromethyl-thiophene. The reaction sequence also yielded 3-(4-chloro-phenyl)-2-pyridin-2-ylmethyl-4,5,7,8-tetrahydro-2H-1,2,6-triaza-azulene-6-carboxylic acid tert-butyl ester in the alkylation step. MS (ESI): exact mass calculated for $C_{19}H_{19}ClN_4$, 338.13; found, m/z 339.3 [M+H]$^+$. $^1$H NMR (500 MHz, CDCl$_3$): 8.49-8.48 (m, 1H), 7.56-7.54 (m, 1H), 7.44-7.42 (m, 2H), 7.32-7.30 (m, 2H), 7.19-7.11 (m, 1H), 6.84-6.82 (m, 1H), 5.39 (s, 2H), 2.93-2.87 (m, 4H), 2.76-2.74 (m, 4H).

Example 318

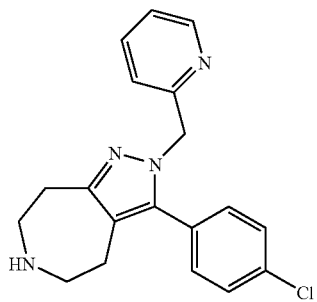

3-(4-Chloro-phenyl)-2-pyridin-2-ylmethyl-1,4,5,6,7,8-hexahydro-1,2,6-triaza-azulene The title compound (0.011 g) was prepared from 3-(4-chloro-phenyl)-2-pyridin-2-ylmethyl-4,5,7,8-tetrahydro-2H-1,2,6-triaza-azulene-6-carboxylic acid tert-butyl ester (Example 317) according to Example 103, Step C. MS (ESI): exact mass calculated for $C_{19}H_{19}ClN_4$, 338.13; found, m/z 339.3 [M+H]$^+$. $^1$H NMR (500 MHz, CDCl$_3$): 8.44-8.43 (m, 1H), 7.56-7.55 (m, 1H), 7.32-7.27 (m, 2H), 7.11-7.07 (m, 3H), 6.81-6.77 (m, 1H), 5.20 (s, 2H), 2.98-2.96 (m, 2H), 2.89-2.86 (m, 4H), 2.48-2.46 (m, 2H).

Example 319

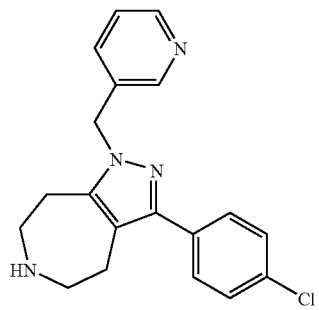

3-(4-Chloro-phenyl)-1-pyridin-3-ylmethyl-1,4,5,6,7,8-hexahydro-1,2,6-triaza-azulene The title compound was prepared from 3-(4-chloro-phenyl)-4,5,7,8-tetrahydro-1H-1,2,6-triaza-azulene-6-carboxylic acid tert-butyl ester (Example 103, Step B; 0.3 mmol) using 3-chloromethyl-pyridine hydrogen chloride (0.5 mmol) in place of 2-chloromethyl-thiophene. The title compound was obtained as a 2:1 mixture (25 mg) with 3-(4-chloro-phenyl)-2-pyridin-3-ylmethyl-2,4,5,6,7,8-hexahydro-1,2,6-triaza-azulene. Data for the mixture: MS (ESI): exact mass calculated for $C_{19}H_{19}ClN_4$, 338.13; found, m/z 339.4 [M+H]$^+$. $^1$H NMR (500 MHz, CDCl$_3$): 8.47-8.14 (m, 2H), 7.42-7.03 (m, 6H), 5.39-5.07 (two s, 2H), 2.97-2.84 (m, 2H), 2.72-2.43 (m, 2H).

Example 320

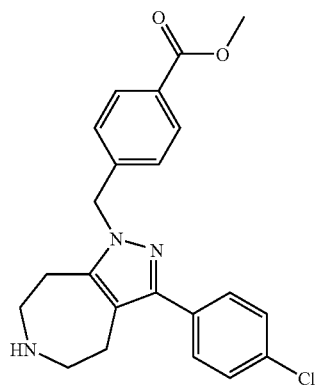

4-[3-(4-Chloro-phenyl)-5,6,7,8-tetrahydro-4H-1,2,6-triaza-azulen-1-ylmethyl]-benzoic acid methyl ester The title compound (0.03 g) was prepared from 3-(4-chloro-phenyl)-4,5,7,8-tetrahydro-1H-1,2,6-triaza-azulene-6-carboxylic acid tert-butyl ester (Example 103, Step B; 0.3 mmol) using 4-bromomethyl-benzoic acid methyl ester (0.5 mmol) in place of 2-chloromethyl-thiophene. MS (ESI): exact mass calculated for $C_{22}H_{22}ClN_3O_2$, 395.14; found, m/z 396.4 [M+H]⁺. ¹H NMR (500 MHz, CDCl₃): 7.63-7.19 (m, 7H), 7.03-7.02 (m, 2H), 5.27 (s, 2H), 3.15 (s, 2H), 2.79-2.67 (m, 8H).

Example 321

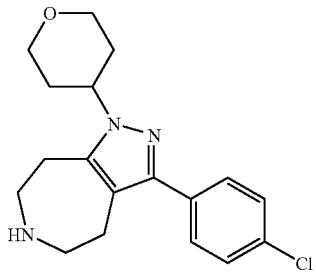

3-(4-Chloro-phenyl)-1-(tetrahydro-pyran-4-yl)-1,4,5,6,7,8-hexahydro-1,2,6-triaza-azulene The title compound was prepared from 3-(4-chloro-phenyl)-4,5,7,8-tetrahydro-1H-1,2,6-triaza-azulene-6-carboxylic acid tert-butyl ester (Example 103, Step B; 0.40 mmol) using 4-chloro-tetrahydro-pyran (1.5 mmol) in place of chloro-cyclobutane. The title compound was obtained as a 2:1 mixture (10 mg) with 3-(4-chloro-phenyl)-2-(tetrahydro-pyran-4-yl)-1,4,5,6,7,8-hexahydro-1,2,6-triaza-azulene. Data for the mixture: MS (ESI): exact mass calculated for C₁₈H₂₂ClN₃O, 331.15; found, m/z 332.4 [M+H]⁺. ¹H NMR (500 MHz, CD₃OD): 7.44-7.42 (m, 1H), 7.36-7.30 (m, 4H), 7.20-7.18 (m, 1H), 4.36-4.33 (m, 1H), 3.97-3.94 (m, 3H), 3.87-3.86 (m, 1H), 3.51-3.49 (m, 3H), 3.28-3.25 (m, 1H), 2.90-2.75 (m, 8H), 2.66-2.64 (m, 2H), 2.39-2.37 (m, 1H), 2.19-2.10 (m, 3H), 1.74-1.71 (m, 2H), 1.65-1.62 (m, 1H).

Example 322

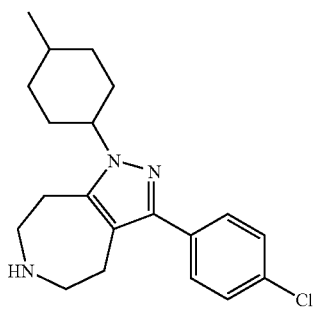

3-(4-Chloro-phenyl)-1-(4-methyl-cyclohexyl)-1,4,5,6,7,8-hexahydro-1,2,6-triaza-azulene The title compound (11 mg) was prepared from 3-(4-chloro-phenyl)-4,5,7,8-tetrahydro-1H-1,2,6-triaza-azulene-6-carboxylic acid tert-butyl ester (Example 103, Step B; 0.30 mmol) using 1-bromo-4-methyl-cyclohexane (1.0 mmol) in place of chloro-cyclobutane. The reaction sequence also yielded 3-(4-chloro-phenyl)-2-(4-methyl-cyclohexyl)-1,4,5,6,7,8-hexahydro-1,2,6-triaza-azulene-6-carboxylic acid tert-butyl ester in the alkylation step. MS (ESI): exact mass calculated for C₂₀H₂₆ClN₃, 343.18; found, m/z 344.4 [M+H]⁺. ¹H NMR (500 MHz, CD₃OD): 7.40-7.34 (m, 4H), 4.10-4.06 (m, 1H), 3.39-3.37 (m, 2H), 3.28-3.26 (m, 2H), 3.17-3.15 (m, 2H), 2.94-2.91 (m, 2H), 1.96-1.89 (m, 2H), 1.83-1.76 (m, 4H), 1.52-1.10 (m, 2H), 0.91-0.87 (m, 4H).

Example 323

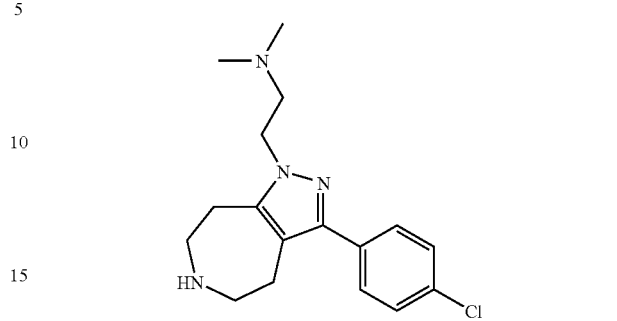

{2-[3-(4-Chloro-phenyl)-5,6,7,8-tetrahydro-4H-1,2,6-triaza-azulen-1-yl]-ethyl}-dimethyl-amine The title compound was prepared from 3-(4-chloro-phenyl)-4,5,7,8-tetrahydro-1H-1,2,6-triaza-azulene-6-carboxylic acid tert-butyl ester (Example 103, Step B; 0.33 mmol) using (2-chloro-ethyl)-dimethyl-amine hydrogen chloride (0.66 mmol) in place of chloro-cyclobutane. The title compound was obtained as a 2:1 mixture (10 mg) with {2-[3-(4-chloro-phenyl)-5,6,7,8-tetrahydro-4H-1,2,6-triaza-azulen-2-yl]-ethyl}-dimethyl-amine. Data for the mixture: MS (ESI): exact mass calculated for C₁₇H₂₃ClN₄, 318.16; found, m/z 319.4 [M+H]⁺. ¹H NMR (500 MHz, CD₃OD): 7.50-7.45 (m, 2H), 7.37-7.33 (m, 2H), 4.51-4.49 (m, 1.3H), 4.27-4.26 (m, 0.7H), 3.63-3.61 (m, 1.3H), 3.48-3.42 (m, 2H), 3.33-3.29 (m, 2H), 3.24-3.23 (m, 2H), 3.14-3.12 (m, 0.7H), 3.00-2.98 (m, 1.3H), 2.91 (s, 4H), 2.84 (s, 2H), 2.75-2.73 (m, 0.7H).

Example 324

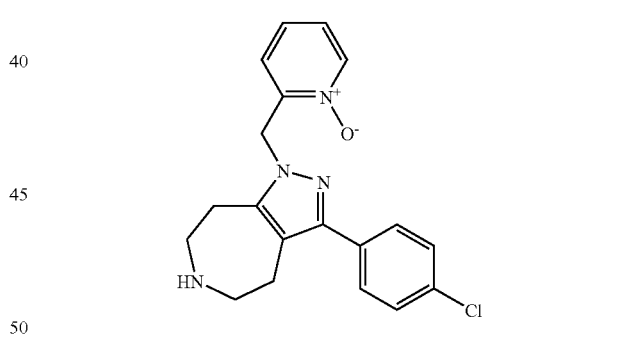

3-(4-Chloro-phenyl)-1-(1-oxy-pyridin-2-ylmethyl)-1,4,5,6,7,8-hexahydro-1,2,6-triaza-azulene A mixture of 3-(4-chloro-phenyl)-2-pyridin-2-ylmethyl-1,4,5,6,7,8-hexahydro-1,2,6-triaza-azulene-6-carboxylic acid tert-butyl ester (Example 317; 0.1 mmol) and mCPBA (0.1 g) in dichloroethane (10 mL) was heated at 80° C. for 1 h. Satd. aq. NaHCO₃ (20 mL) was added, and the layers were separated. The organic layer was concentrated, and the residue was diluted with MeOH (5 mL). Hydrogen chloride (1 M, 2 mL) was added and the mixture was stirred at 25° C. for 16 h. After concentration, purification by flash chromatography (2 M NH₃/MeOH in CH₂Cl₂) provided the desired compound (34 mg). MS (ESI): exact mass calculated for C₁₉H₁₉ClN₄O, 354.12; found, m/z 355.2 [M+H]⁺. ¹H NMR (500 MHz, CDCl₃): 8.20-8.19 (m, 1H), 7.41-7.39 (m, 2H), 7.33-7.31 (m, 2H), 7.18-7.15 (m, 2H), 6.69-6.67 (m, 1H), 5.50 (s, 2H), 3.10-3.03 (m, 2H), 2.93-2.86 (m, 2H).

Example 325

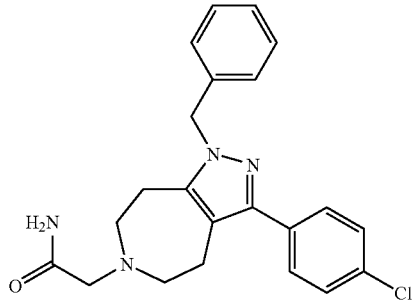

2-[1-Benzyl-3-(4-chloro-phenyl)-4,5,7,8-tetrahydro-1H-1,2,6-triaza-azulen-6-yl]-acetamide A mixture of 1-benzyl-3-(4-chloro-phenyl)-1-pyridin-3-ylmethyl-1,4,5,6,7,8-hexahydro-1,2,6-triaza-azulene (Example 59, Step E; 0.05 mmol), 2-bromo-acetamide (8 mg), and $Na_2CO_3$ (15 mg) in acetone (2 mL) was stirred at 25° C. for 16 h. After concentration, purification by flash chromatography (2 M $NH_3$/MeOH in $CH_2Cl_2$) provided the desired compound (6 mg). MS (ESI): exact mass calculated for $C_{22}H_{23}ClN_4O$, 394.16; found, m/z 395.3 [M+H]$^+$. $^1$H NMR (500 MHz, CDCl$_3$): 8.49-8.48 (m, 1H), 7.56-7.54 (m, 1H), 7.44-7.42 (m, 2H), 7.32-7.30 (m, 2H), 7.19-7.11 (m, 1H), 6.84-6.82 (m, 1H), 5.39 (s, 2H), 2.93-2.87 (m, 2H), 2.76-2.74 (m, 2H).

Example 326

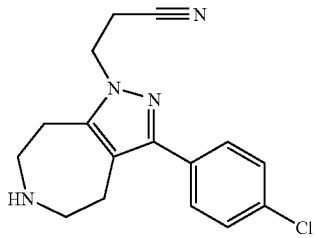

3-[3-(4-Chloro-phenyl)-5,6,7,8-tetrahydro-4H-1,2,6-triaza-azulen-1-yl]-propionitrile To a mixture of 3-(4-chloro-phenyl)-4,5,7,8-tetrahydro-1H-1,2,6-triaza-azulene-6-carboxylic acid tert-butyl ester (Example 103, Step B; 0.05 mmol), NaOH (50% aq., 0.2 mL), and Bu$_4$NHSO$_4$ (0.005 mmol) in dichloroethane (5 mL) was added 3-bromo-propionitrile (0.1 mmol). The mixture was stirred at 25° C. for 16 h and then was heated at 80° C. for 1 h. After concentration, purification by flash chromatography (EtOAc/hexanes) provided 3-[3-(4-chloro-phenyl)-5,6,7,8-tetrahydro-4H-1,2,6-triaza-azulen-1-yl]-propionitrile-6-carboxylic acid tert-butyl ester. Deprotection of this ester according to the deprotection method in Example 103, Step C, gave the title compound (9 mg). The reaction sequence also yielded 3-[3-(4-chloro-phenyl)-5,6,7,8-tetrahydro-4H-1,2,6-triaza-azulen-2-yl]-propionitrile-6-carboxylic acid tert-butyl ester in the alkylation step. MS (ESI): exact mass calculated for $C_{16}H_{17}ClN_4$, 300.11; found, m/z 301.4 [M+H]$^+$. $^1$H NMR (500 MHz, CD$_3$OD): 7.44-7.37 (m, 4H), 4.39-4.37 (t, J=6.1 Hz, 2H), 3.41-3.39 (m, 2H), 3.29-3.27 (m, 2H), 3.24-3.22 (m, 2H), 2.99-2.96 (m, 2H), 2.95-2.92 (t, J=6.1 Hz, 2H).

Example 327

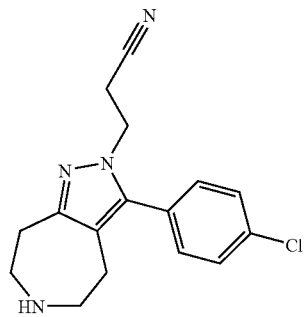

3-[3-(4-Chloro-phenyl)-5,6,7,8-tetrahydro-4H-1,2,6-triaza-azulen-2-yl]-propionitrile The title compound (0.004 g) was prepared from 3-[3-(4-chloro-phenyl)-5,6,7,8-tetrahydro-4H-1,2,6-triaza-azulen-2-yl]-propionitrile-6-carboxylic acid tert-butyl ester (Example 326) according to the deprotection method in Example 103, Step C. MS (ESI): exact mass calculated for $C_{16}H_{17}ClN_4$, 300.11; found, m/z 301.4 [M+H]$^+$. $^1$H NMR (500 MHz, CD$_3$OD): 7.50-7.48 (m, 2H), 7.31-7.30 (m, 2H), 4.14-4.11 (t, J=6.1 Hz, 2H), 3.32-3.31 (m, 2H), 3.23-3.21 (m, 2H), 3.09-3.07 (m, 2H), 2.86-2.84 (t, J=6.1 Hz, 2H), 2.72-2.70 (m, 2H).

Example 328

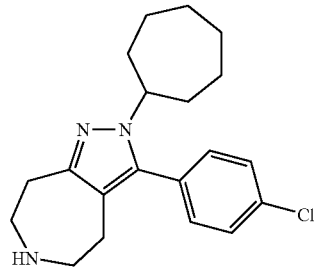

3-(4-Chloro-phenyl)-2-cycloheptyl-2,4,5,6,7,8-hexahydro-1,2,6-triaza-azulene

The title compound (0.010 g) was prepared from 3-(4-chloro-phenyl)-2-cycloheptyl-2,4,5,6,7,8-hexahydro-1,2,6-triaza-azulene-6-carboxylic acid tert-butyl ester (Example 254, Step C) according to the deprotection method in Example 103, Step C. MS (ESI): exact mass calculated for $C_{20}H_{26}ClN_3$, 343.18; found, m/z 344.5 [M+H]$^+$. $^1$H NMR (500 MHz, CD$_3$OD): 7.60-7.58 (m, 2H), 7.33-7.31 (m, 2H), 4.10-4.06 (m, 1H), 3.41-3.39 (m, 2H), 3.31-3.29 (m, 2H), 3.18-3.16 (m, 2H), 2.78-2.75 (m, 2H), 2.10-2.05 (m, 2H), 1.91-1.87 (m, 2H), 1.80-1.76 (m, 2H), 1.60-1.58 (m, 4H), 1.40-1.39 (m, 2H).

Example 329

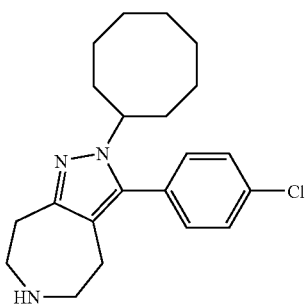

3-(4-Chloro-phenyl)-2-cyclooctyl-2,4,5,6,7,8-hexahydro-1,2,6-triaza-azulene

The title compound (0.017 g) was prepared from 3-(4-chloro-phenyl)-2-cyclooctyl-2,4,5,6,7,8-hexahydro-1,2,6-triaza-azulene-6-carboxylic acid tert-butyl ester (Example 255, Step C) according to the deprotection method in Example 103, Step C. MS (ESI): exact mass calculated for $C_{21}H_{28}ClN_3$, 357.20; found, m/z 358.5 [M+H]$^+$. $^1$H NMR (500 MHz, CD$_3$OD): 7.61-7.58 (m, 2H), 7.34-7.32 (m, 2H), 4.24-4.21 (m, 1H), 3.41-3.39 (m, 2H), 3.31-3.29 (m, 2H), 3.18-3.16 (m, 2H), 2.78-2.76 (m, 2H), 2.15-2.11 (m, 2H), 1.81-1.77 (m, 4H), 1.57-1.46 (m, 6H), 1.31-1.29 (m, 2H).

Example 330

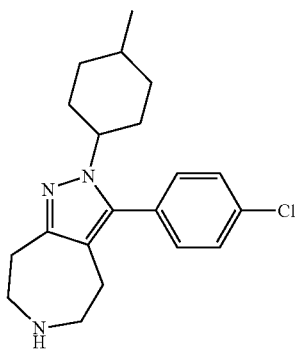

3-(4-Chloro-phenyl)-2-(4-methyl-cyclohexyl)-2,4,5,6,7,8-hexahydro-1,2,6-triaza-azulene The title compound (0.007 g) was prepared from 3-(4-chloro-phenyl)-2-(4-methyl-cyclohexyl)-2,4,5,6,7,8-hexahydro-1,2,6-triaza-azulene-6-carboxylic acid tert-butyl ester (Example 322, Step C) according to the deprotection method in Example 103, Step C. MS (ESI): exact mass calculated for $C_{20}H_{26}ClN_3$, 343.18; found, m/z 344.4 [M+H]$^+$. $^1$H NMR (500 MHz, CD$_3$OD): 7.59-7.57 (m, 2H), 7.33-7.31 (m, 2H), 3.95-3.92 (m, 1H), 3.37-3.35 (m, 2H), 3.31-3.29 (m, 2H), 3.18-3.16 (m, 2H), 2.78-2.75 (m, 2H), 2.10-1.95 (m, 2H), 1.90-1.77 (m, 4H), 1.05-0.91 (m, 6H),

Example 331

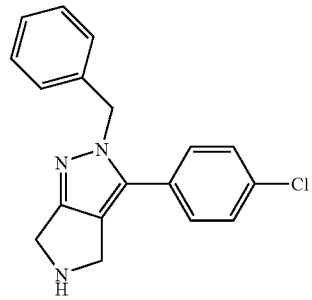

2-Benzyl-3-(4-chloro-phenyl)-2,4,5,6-tetrahydro-pyrrolo[3,4-c]pyrazole

To a solution of LDA (1.80 M in THF, 20 mmol) in THF (100 mL) at −78° C., was added a solution of 3-oxo-pyrrolidine-1-carboxylic acid tert-butyl ester (10 mmol) in THF (10 mL) dropwise. After 20 min, a solution of 4-chlorobenzyl chloride (15 mmol) in THF (10 mL) was added. Then the mixture was warmed to 25° C. and stirred for 16 h. Satd. aq. NaHCO$_3$ (100 mL) was added, and the organic layer was separated and concentrated to give 3-(4-chloro-benzyl)-4-oxo-pyrrolidine-1-carboxylic acid tert-butyl ester. This residue (⅛ portion, approx. 1.25 mmol) was diluted with EtOH (10 mL) and treated with benzyl hydrazine hydrogen chloride (1.5 mmol) and K$_2$CO$_3$ (5 mmol). The mixture was stirred at 25° C. for 16 h. Concentration and purification by flash chromatography (EtOAc/CH$_2$Cl$_2$) provided 2-benzyl-3-(4-chloro-phenyl)-2,6-dihydro-4H-pyrrolo[3,4-c]pyrazole-5-carboxylic acid tert-butyl ester. A solution of the ester and TFA (2 mL) in CH$_2$Cl$_2$ (10 mL) was stirred at 25° C. for 4 h. Concentration and purification by flash chromatography (2 M NH$_3$ in MeOH/CH$_2$Cl$_2$) provided the desired compound (10 mg). MS (ESI): exact mass calculated for $C_{18}H_{16}ClN_3$, 309.10; found, m/z 310.4 [M+H]$^+$. $^1$H NMR (500 MHz, CDCl$_3$): 7.37-7.21 (m, 7H), 7.08-7.05 (m, 2H), 5.29 (s, 2H), 4.09 (s, 2H), 4.04 (s, 2H).

Example 332

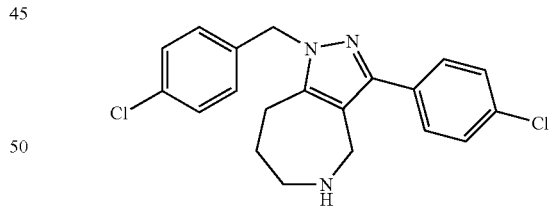

1-(4-Chloro-benzyl)-3-(4-chloro-phenyl)-1,4,5,6,7,8-hexahydro-1,2,5-triaza-azulene The title compound (0.017 g), as a hydrochloride salt, was prepared from 3-(4-chloro-phenyl)-4,6,7,8-tetrahydro-1H-1,2,5-triaza-azulene-5-carboxylic acid tert-butyl ester (Example 59, Step C, 0.15 g) using 4-chlorobenzyl bromide (0.1 g) in place of benzyl chloride in Example 59, Step D. MS (ESI): exact mass calculated for $C_{20}H_{19}Cl_2N_3$, 371.10; found, m/z 372.1 [M+H]$^+$. $^1$H NMR (500 MHz, CD$_3$OD): 7.57-7.50 (m, 4H), 7.41-7.33 (m, 2H), 7.27-7.19 (m, 2H), 5.45 (s, 2H), 4.34 (s, 2H), 3.57-3.53 (m, 2H), 3.08-3.03 (m, 2H), 2.08-2.02 (m, 2H).

Example 333

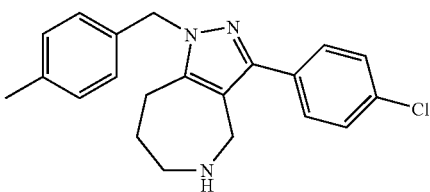

3-(4-Chloro-phenyl)-1-(4-methyl-benzyl)-1,4,5,6,7,8-hexahydro-1,2,5-triaza-azulene The title compound (0.011 g), as a hydrochloride salt, was prepared from 3-(4-chloro-phenyl)-4,6,7,8-tetrahydro-1H-1,2,5-triaza-azulene-5-carboxylic acid tert-butyl ester (Example 59, Step C, 0.15 g) using 4-methylbenzyl bromide (0.09 g) in place of benzyl chloride in Example 59, Step D. MS (ESI): exact mass calculated for $C_{21}H_{22}ClN_3$, 351.15; found, m/z 352.2 [M+H]$^+$. $^1$H NMR (500 MHz, CD$_3$OD): 7.46-7.39 (m, 2H), 7.21-7.18 (m, 2H), 6.98-6.95 (m, 2H), 6.77-6.74 (m, 2H), 5.08 (s, 2H), 3.97 (s, 2H), 3.46-3.43 (m, 2H), 2.96-2.92 (m, 2H), 2.17 (s, 3H), 2.01-1.97 (m, 2H).

Example 334

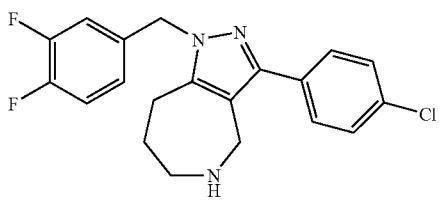

3-(4-Chloro-phenyl)-1-(3,4-difluoro-benzyl)-1,4,5,6,7,8-hexahydro-1,2,5-triaza-azulene The title compound (0.005 g) was prepared from 3-(4-chloro-phenyl)-4,6,7,8-tetrahydro-1H-1,2,5-triaza-azulene-5-carboxylic acid tert-butyl ester (Example 59, Step C, 0.07 g) using 3,4-difluorobenzyl bromide (0.06 g) in place of benzyl chloride in Example 59, Step D. MS (ESI): exact mass calculated for $C_{20}H_{18}ClF_2N_3$, 373.12; found, m/z 374.1 [M+H]$^+$. $^1$H NMR (500 MHz, CD$_3$OD): 7.39-7.34 (m, 4H), 7.16-7.10 (m, 1H), 6.98-6.97 (m, 1H), 6.89-6.88 (m, 1H), 5.27 (s, 2H), 3.81 (s, 2H), 3.09-3.06 (m, 2H), 2.80-2.76 (m, 2H), 1.75-1.70 (m, 2H).

Example 335

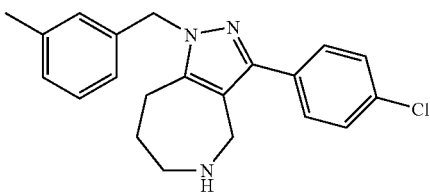

3-(4-Chloro-phenyl)-1-(3-methyl-benzyl)-1,4,5,6,7,8-hexahydro-1,2,5-triaza-azulene The title compound (0.012 g) was prepared from 3-(4-chloro-phenyl)-4,6,7,8-tetrahydro-1H-1,2,5-triaza-azulene-5-carboxylic acid tert-butyl ester (Example 59, Step C, 0.1 g) using 3-methylbenzyl bromide (0.06 g) in place of benzyl chloride in Example 59, Step D. MS (ESI): exact mass calculated for $C_{21}H_{22}ClN_3$, 351.15; found, m/z 352.2 [M+H]$^+$. $^1$H NMR (500 MHz, CD$_3$OD): 7.49-7.43 (m, 4H), 7.19 (t, J=7.6 Hz, 1H), 7.08 (d, J=7.6 Hz, 1H), 7.00 (s, 1H), 6.92 (d, J=7.3 Hz, 1H), 5.34 (s, 2H), 3.88 (s, 2H), 3.16-3.13 (m, 2H), 2.88-2.85 (m, 2H), 2.30 (s, 3H), 1.80-1.77 (m, 2H).

Example 336

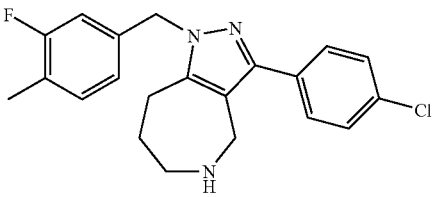

3-(4-Chloro-phenyl)-1-(3-fluoro-4-methyl-benzyl)-1,4,5,6,7,8-hexahydro-1,2,5-triaza-azulene The title compound (0.002 g) was prepared from 3-(4-chloro-phenyl)-4,6,7,8-tetrahydro-1H-1,2,5-triaza-azulene-5-carboxylic acid tert-butyl ester (Example 59, Step C, 0.1 g) using 3-fluoro-4-methylbenzyl bromide (0.09 g) in place of benzyl chloride in Example 59, Step D. MS (ESI): exact mass calculated for $C_{21}H_{21}ClFN_3$, 369.14; found, m/z 370.1 [M+H]$^+$. $^1$H NMR (500 MHz, CD$_3$OD): 7.49-7.43 (m, 4H), 7.19 (t, J=7.9 Hz, 1H), 6.88-6.80 (m, 2H), 5.34 (s, 2H), 3.88 (s, 2H), 3.16-3.13 (m, 2H), 2.87-2.85 (m, 2H), 2.23 (d, J=1.5 Hz, 3H), 1.81-1.78 (m, 2H).

Example 337

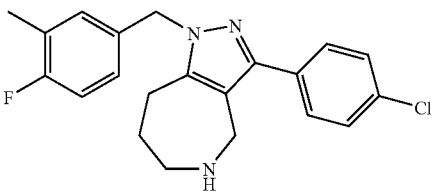

3-(4-Chloro-phenyl)-1-(4-fluoro-3-methyl-benzyl)-1,4,5,6,7,8-hexahydro-1,2,5-triaza-azulene The title compound (0.001 g) was prepared from 3-(4-chloro-phenyl)-4,6,7,8-tetrahydro-1H-1,2,5-triaza-azulene-5-carboxylic acid tert-butyl ester (Example 59, Step C, 0.1 g) using 4-fluoro-3-methylbenzyl bromide (0.09 g) in place of benzyl chloride in Example 59, Step D. MS (ESI): exact mass calculated for $C_{21}H_{21}ClFN_3$, 369.14; found, m/z 370.1 [M+H]$^+$. $^1$H NMR (500 MHz, CD$_3$OD): 7.48-7.43 (m, 4H), 7.08-7.06 (m, 1H), 6.99-6.97 (m, 2H), 5.32 (s, 2H), 3.88 (s, 2H), 3.16-3.14 (m, 2H), 2.89-2.86 (m, 2H), 2.22 (d, J=1.6 Hz, 3H), 1.80 (m, 2H).

Example 338

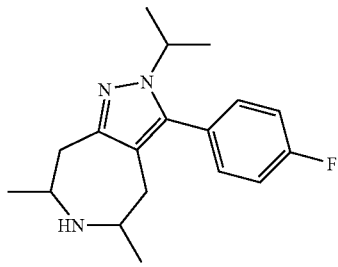

3-(4-Fluoro-phenyl)-2-isopropyl-5,7-dimethyl-2,4,5,6,7,8-hexahydro-1,2,6-triaza-azulene The title compound was prepared in a manner analogous to those described above.

Assay Methods

In Vitro Pharmacology

1. Affinity for 5-HT$_7$ Receptor Binding Sites

The affinity of the compounds described in this invention for the 5-HT$_7$ receptor binding site was evaluated by single competition radioligand binding assay. The assay was performed on membranes prepared from HEK-293 cells that had been subjected to stable transfection with the rat 5-HT$_{7a}$ receptor (GB: NM022938). Cells were scraped from the culture plates, suspended in Tris-HCl 50 mM pH 7.5 and collected through centrifugation (1000 rpm for 5 min). The cell pellets were homogenized (Polytron, 15 s, setting 5) in 50 mM Tris-HCl (pH 7.5), 5 mM EDTA. Following centrifugation (15,000 rpm for 25 min), membranes (135 µg protein/mL) were resuspended in the same buffer and incubated for 60 min at RT with 1 nM [$^3$H]5-CT in the presence of increasing concentration of test compounds. Nonspecific binding was defined in the presence of 10 µM 5-HT. Incubation was stopped by rapid filtration using the cell harvester (Packard). Radioactivity was counted in a TopCount-NXT (Packard).

Sigmoidal inhibition curves were generated and fitted by nonlinear regression analysis (GraphPad Prism). IC$_{50}$ values (concentration producing 50% inhibition of specific radioligand binding) were calculated. K$_i$ values were derived according to Cheng and Prussoff (*Biochem. Pharmacol.* (1973) 22: 3099-3108). Experiments were conducted in triplicate.

Stock drug solutions (10 mM) were prepared in DMSO (the final assay concentration of DMSO not exceeding 0.4%). Drug dilutions were prepared in assay buffer. Data are shown in Table 1 below.

2. Effect on Adenylyl Cyclase Activity

In vitro functional properties of the compounds described in this invention were evaluated in an adenylyl cyclase assay. HEK-293 cells stably transfected with the rat 5-HT$_7$ receptor were plated into 96-well plates. Cells were washed with 200 µL DNEM/F12 and incubated for 10 min with 80 µL of 2 mM 3-isobutyl-1-methylxanthine. Compounds (10 µL) were added for another 10 min. Subsequently, 5-CT (10 µL) was added. After 20 min the incubation was stopped by the addition of 20 µL of 0.5 N HCl. Plates were incubated at 4° C. for 30 min. Twenty µL of the supernatant were assayed for cAMP content with a commercially available kit (Perkin Elmer) using $^{125}$I-cAMP. Sigmoidal curves of best fit were calculated by nonlinear regression analysis using GrapPad Prism.

5-CT-stimulated adenylyl cyclase activity in r5-HT$_{7a}$/HEK-293 cells was inhibited by Example 59 with an estimated pK$_B$~8 in good agreement with the K$_i$ value determined from [$^3$H]5-CT binding studies.

3. Affinity for 5-HT$_{2A}$ Receptor Binding Sites

The affinity of the compounds for the rat 5-HT$_{2A}$ receptor was evaluated by competitive radioligand binding assay using [$^3$H]ketanserine as the radioligand. The assay was performed on membranes from rat cortex as previously described (Schotte, A. et al., *Psychopharmacology* (1996) 124: 57-73). Briefly, brain tissue (rat cortex) was homogenized in 20 volumes per wet weight tissue of Tris-HCl buffer (50 mM, pH 7.4). The total membrane fraction was collected by centrifugation and washed by subsequent centrifugation runs (25 min at 25,000 g at 4° C.). Membranes were re-suspended in Tris-HCl buffer (50 mM, pH 7.4) containing 1 nM [$^3$H]ketanserin. Non-specific binding was estimated in the presence of 10 µM risperidone. The incubation was terminated by rapid filtration over Whatman GF/B filters pre-soaked in 0.1% polyethylenimine, and one washing step with 1 mL ice-cold Tris-HCl buffer, pH 7.4. pK$_i$ values for all compounds were calculated by pK$_i$=–log K$_i$ where K$_i$ was calculated according to the method of Cheng and Prusoff (*Biochem Pharmacol.* (1973) 22: 3099-3108) (IC$_{50}$/(1+[S]/K$_d$) were [S]=1 nM; K$_d$=0.42 nM). All values in Table 1 are listed in nM units. Data are shown in Table 1 below.

4. Affinity for 5HT2 Receptor Binding Sites

Receptor binding was performed using the human recombinant 5-HT$_{2A}$ (GB: X57830), 5-HT$_{2B}$ (GB: Z36748) and 5-HT$_{2C}$ (GB: M81778) receptors. The affinity of the compounds for the 3 different human 5-HT$_2$ receptor subtypes was evaluated by competitive radioligand binding assays using [$^3$H]ketanserin (h5-HT$_{2A}$) or [$^3$H]mesulergine (h5-HT$_{2B}$ and h5-HT$_{2C}$). The assays were performed on membranes prepared from NIH3T3 stably transfected with h5-HT$_{2A}$ or CHO stably transfected with h5-HT$_{2B}$ and h5-HT$_{2C}$. K$_i$ values for all compounds were calculated according to Cheng and Prusoff equation (Cheng and Prusoff, Biochem. Pharmacol. (1973) 22:3099-3108) (IC$_{50}$/(1+[S]/K$_d$) where [S]=1 nM (5-HT$_{2A}$), 4 nM (5-HT$_{2B}$) and 3 nM (5-HT$_{2C}$); K$_d$=0.4 nM (5-HT$_{2A}$), 3.5 nM (5-HT$_{2B}$) and 3 nM (5-HT$_{2C}$). Data are shown in Table 1 below.

5. In Vitro Functional Assay for 5-HT2 Receptor (Intracellular Calcium)

In vitro functional properties of these compounds on the different 5-HT$_2$ receptor subtypes were determined using fluorometric imaging plate reader (FLIPR) based calcium assay as previously described (Porter et al., 1999, Jerman, J. C. et al. Eur. J. Pharmacol. (2001)-414:23-30). The 5-HT$_2$ receptors are linked to the Gq family of G proteins and to subsequent activation of phospholipase C, induction of phosphoinositide metabolism and to an increase in intracellular calcium concentration. The same cell lines as described in the previous section (receptor binding) were used for the FLIPR experiments.

TABLE 1

| | Binding Affinities (nM) | | | |
|---|---|---|---|---|
| EX | K$_i$ 5-HT$_7$ | K$_i$ 5-HT$_{2A}$ | K$_i$ 5-HT$_{2B}$ | K$_i$ 5-HT$_{2C}$ |
| 1 | 120 | NT | NT | NT |
| 17 | 70 | NT | NT | NT |
| 18 | 25 | NT | NT | NT |
| 22 | 45 | NT | NT | NT |
| 26 | 18 | NT | NT | NT |
| 38 | pK$_b$ 7.8 | NT | NT | NT |
| 47 | 7 | 9 | 64 | 24 |
| 57 | 15 | NT | NT | NT |
| 59 | 6 | 280 | 160 | 74 |
| 64 | 19 | 18 | NT | NT |
| 74 | 5 | 100 | 94 | 180 |
| 75 | 7 | 200 | 100 | 320 |
| 76 | 8 | 210 | 350 | 690 |
| 87 | 33 | NT | NT | NT |
| 98 | 40 | NT | NT | NT |
| 100 | 30 | NT | NT | NT |
| 103 | 7.7 | 60 | 44 | 150 |
| 104 | 9 | 80 | 52 | 360 |
| 108 | 9 | NT | 100 | 800 |
| 111 | 17 | NT | NT | NT |
| 114 | 32 | NT | 90 | 400 |
| 117 | 20 | NT | NT | NT |
| 118 | 8 | 20 | NT | NT |
| 119 | 39 | NT | NT | NT |
| 120 | 40 | NT | NT | NT |
| 131 | 120 | 7 | 4.2 | 50 |
| 133 | 125 | 2.3 | 3.5 | 10 |
| 160 | 7 | 300 | 350 | 3500 |
| 165 | 4 | 100 | 310 | 180 |
| 166 | 8 | 80 | 560 | 590 |
| 167 | 75 | NT | 350 | 10000 |
| 172 | 37 | NT | NT | NT |
| 174 | 40 | NT | NT | NT |
| 177 | 80 | 7 | 7 | 110 |
| 178 | 85 | 3 | 3 | NT |
| 180 | 10 | 1.5 | 1.4 | 12 |

TABLE 1-continued

| | Binding Affinities (nM) | | | |
|---|---|---|---|---|
| EX | $K_i$ 5-HT$_7$ | $K_i$ 5-HT$_{2A}$ | $K_i$ 5-HT$_{2B}$ | $K_i$ 5-HT$_{2C}$ |
| 181 | 37 | 1.5 | 1.8 | 11 |
| 182 | 90 | 0.74 | 1.4 | 18 |
| 183 | 240 | 7 | 54 | 70 |
| 184 | 120 | 1 | 17 | 15 |
| 186 | 61 | 1 | 24 | 20 |
| 190 | 16 | 10 | 22 | 51 |
| 191 | 30 | NT | NT | NT |
| 192 | 20 | 2.5 | 0.9 | 15 |
| 209 | 6 | 1.1 | 1.4 | 12 |
| 210 | 7 | 2 | 0.75 | 20 |
| 211 | 8.5 | 5 | 0.5 | 18 |
| 212 | 93 | 25 | 12 | 425 |
| 213 | 12 | 7.5 | 4.7 | 80 |
| 214 | 5 | NT | 2 | 170 |
| 215 | 30 | 8 | 95 | NT |
| 216 | 70 | 6 | 20 | 17 |
| 217 | 25 | 1 | 0.65 | 10 |
| 218 | 75 | 1.7 | 1.8 | 15 |
| 220 | 55 | 1.3 | 0.55 | 6.8 |
| 232 | 20 | 25 | 0.50 | 66 |
| 233 | 15 | 4 | 25 | 16 |
| 236 | 950 | 7 | 4.5 | 32 |
| 238 | 40 | 1 | 0.50 | 13 |
| 241 | 310 | 9 | 9.5 | 38 |
| 242 | 21 | 8 | 1.3 | 45 |
| 253 | 75 | NT | 25 | 625 |
| 255 | 60 | NT | NT | NT |
| 257 | 9 | NT | 2 | 110 |
| 273 | 5 | 400 | NT | NT |
| 276 | 90 | 3 | 2.5 | 90 |
| 277 | 150 | 0.9 | 3 | 40 |
| 278 | 35 | 0.1 | 0.2 | 10 |
| 279 | 80 | 0.8 | 1 | 45 |
| 280 | 3300 | 1.5 | 6 | 120 |
| 282 | 100 | 6 | 20 | 200 |
| 283 | 5000 | 10 | 60 | 150 |
| 284 | 10 | 1 | 2 | 60 |
| 285 | 29 | 60 | 6 | 500 |
| 286 | 335 | 50 | 80 | 5000 |
| 298 | 50 | 5 | 6.5 | 60 |
| 299 | 35 | 1.7 | 9 | 26 |
| 300 | 10 | 0.3 | 0.8 | 12 |
| 301 | 40 | 1.6 | 3 | 100 |
| 302 | 100 | 0.2 | 1.3 | 21.5 |
| 305 | 600 | 20 | 60 | 2200 |
| 306 | 120 | 1 | 22 | 39 |
| 308 | 5200 | 2 | 3 | 162 |
| 309 | 130 | 30 | 15 | 130 |
| 310 | 475 | 0.2 | 0.4 | 30 |
| 311 | 80 | 140 | 100 | 3000 |
| 313 | 30 | 100 | 40 | 1000 |
| 315 | 12 | 9 | 3 | 300 |
| 316 | 9.1 | 60 | 530 | 5000 |

NT = not tested

What is claimed is:

1. A compound which is any one of 3-(4-Fluoro-phenyl)-2-isopropyl-2,4,5,6,7,8-hexahydro-1,2,6-triaza-azulene and pharmaceutically acceptable salts thereof.

2. A pharmaceutical composition of claim 1, where the compound is any one of 3-(4-Fluoro-phenyl)-2-isopropyl-2,4,5,6,7,8-hexahydro-1,2,6-triaza-azulene and pharmaceutically acceptable salts thereof.

* * * * *